(12) United States Patent
Gummadi et al.

(10) Patent No.: US 12,410,193 B2
(45) Date of Patent: *Sep. 9, 2025

(54) BICYCLIC HETEROCYCLYL DERIVATIVES AS IRAK4 INHIBITORS

(71) Applicant: Aurigene Oncology Limited, Bangalore (IN)

(72) Inventors: Venkateshwar Rao Gummadi, Bangalore (IN); Susanta Samajdar, Bangalore (IN)

(73) Assignee: Aurigene Oncology Limited, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/629,313

(22) Filed: Apr. 8, 2024

(65) Prior Publication Data

US 2024/0294547 A1   Sep. 5, 2024

Related U.S. Application Data

(63) Continuation of application No. 18/141,008, filed on Apr. 28, 2023, now Pat. No. 11,981,685, which is a continuation of application No. 17/245,611, filed on Apr. 30, 2021, now Pat. No. 11,691,987, which is a continuation of application No. 16/795,394, filed on Feb. 19, 2020, now Pat. No. 10,995,100, which is a continuation of application No. 16/054,512, filed on Aug. 3, 2018, now Pat. No. 10,640,517, which is a continuation of application No. 15/667,173, filed on Aug. 2, 2017, now Pat. No. 10,047,104, which is a continuation of application No. 15/111,000, filed as application No. PCT/IB2015/050217 on Jan. 12, 2015, now Pat. No. 9,732,095.

(30) Foreign Application Priority Data

Jan. 13, 2014  (IN) .............................. 158/CHE/2014
Jun. 20, 2014  (IN) ........................... 3000/CHE/2014

(51) Int. Cl.
*C07D 498/04*   (2006.01)
*C07D 513/04*   (2006.01)
*C07D 519/00*   (2006.01)

(52) U.S. Cl.
CPC ......... *C07D 513/04* (2013.01); *C07D 498/04* (2013.01); *C07D 519/00* (2013.01)

(58) Field of Classification Search
CPC .......................... C07D 498/04; C07D 513/04
See application file for complete search history.

(56) References Cited

U.S. PATENT DOCUMENTS 5,494,911 A   2/1996 Bartlett et al.
7,338,950 B2  3/2008 Kelly et al.
9,732,095 B2  8/2017 Gummadi et al.
9,855,273 B2  1/2018 Starczynowski et al.
10,047,104 B2 8/2018 Gummadi et al.
10,160,753 B2 12/2018 Gummadi et al.
10,640,517 B2 5/2020 Gummadi et al.
10,758,518 B2 9/2020 Booher
10,995,100 B2 5/2021 Gummadi et al.
11,419,875 B2 8/2022 Gummadi et al.
11,691,987 B2 7/2023 Gummadi et al.
11,981,685 B2 5/2024 Gummadi et al.
12,178,821 B2 12/2024 von Roemeling et al.
(Continued)

FOREIGN PATENT DOCUMENTS

CN  103608017 A   2/2014
EP    1627869 A1   2/2006
(Continued)

OTHER PUBLICATIONS

D'Angelo, "Targeting IRAK4 as Novel Therapy in Primary CNS Lymphoma," University of Nebraska Medical Center, Published Aug. 7, 2024: 13 slides.

(Continued)

*Primary Examiner* — Rebecca L Anderson
(74) *Attorney, Agent, or Firm* — Foley Hoag LLP; David P. Halstead; Alexander J. Chatterley

(57) ABSTRACT

The present invention provides bicyclic heterocyclyl kinase enzyme inhibitor compounds of formula (I), which are therapeutically useful as kinase inhibitors, particularly IRAK4 inhibitors.

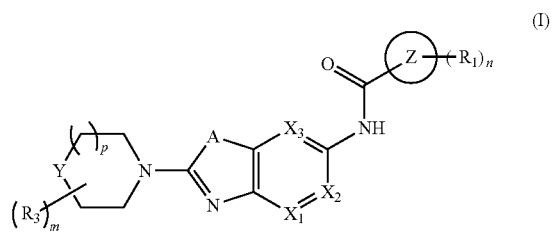

wherein A, Y, Z, $X_1$, $X_2$, $X_3$, $R_1$, $R_3$, 'm', 'n' and 'p' have the meanings given in the specification and pharmaceutically acceptable salts or stereoisomers thereof that are useful in the treatment and prevention of diseases or disorders, in particular their use in diseases or disorders mediated by kinase enzyme, particularly IRAK4 enzyme. The present invention also provides pharmaceutical compositions comprising at least one of the compounds of compound of formula (I) together with a pharmaceutically acceptable carrier, diluent or excipient therefor.

9 Claims, No Drawings

(56) References Cited

U.S. PATENT DOCUMENTS

| | | |
|---|---|---|
| 2005/0192293 A1 | 9/2005 | Kelly et al. |
| 2006/0014747 A1 | 1/2006 | Krueger et al. |
| 2006/0160861 A1 | 7/2006 | Bohlmann et al. |
| 2009/0069288 A1 | 3/2009 | Breinlinger et al. |
| 2010/0160388 A1 | 6/2010 | Brotherton-Pleiss et al. |
| 2010/0210619 A1 | 8/2010 | Bombrun et al. |
| 2011/0224137 A1 | 9/2011 | Ting et al. |
| 2012/0015962 A1 | 1/2012 | Arora et al. |
| 2012/0053345 A1 | 3/2012 | Ericson et al. |
| 2013/0035326 A1 | 2/2013 | Abraham et al. |
| 2015/0094315 A1 | 4/2015 | Choi et al. |
| 2016/0326151 A1 | 11/2016 | Gummadi et al. |
| 2017/0152263 A1 | 6/2017 | Gummadi et al. |
| 2018/0022758 A1 | 1/2018 | Gummadi et al. |
| 2018/0201609 A1 | 7/2018 | Gummadi et al. |
| 2018/0208605 A1 | 7/2018 | Gummadi et al. |
| 2018/0289685 A1 | 10/2018 | Bothe et al. |
| 2020/0069668 A1 | 3/2020 | Lannutti et al. |
| 2020/0190112 A1 | 6/2020 | Gummadi et al. |
| 2021/0290628 A1 | 9/2021 | Gummadi et al. |
| 2022/0056046 A1 | 2/2022 | Gummadi et al. |
| 2022/0331330 A1 | 10/2022 | von Roemeling et al. |
| 2022/0339161 A1 | 10/2022 | Gummadi et al. |
| 2023/0310444 A1 | 10/2023 | von Roemeling et al. |
| 2023/0331740 A1 | 10/2023 | Gummadi et al. |
| 2023/0414582 A1 | 12/2023 | von Roemeling et al. |
| 2025/0082644 A1 | 3/2025 | von Roemeling et al. |

FOREIGN PATENT DOCUMENTS

| | | |
|---|---|---|
| GB | 2406856 A | 4/2005 |
| JP | 2008/239617 A | 10/2008 |
| JP | 2013/531018 A | 8/2013 |
| KR | 2013/0128693 A | 11/2013 |
| WO | WO-2004/007457 A2 | 1/2004 |
| WO | WO-2004/007458 A1 | 1/2004 |
| WO | WO-2004/098518 A2 | 11/2004 |
| WO | WO-2004/103954 A1 | 12/2004 |
| WO | WO-2004/108133 A2 | 12/2004 |
| WO | WO-2005/032493 A2 | 4/2005 |
| WO | WO-2005/107460 A1 | 11/2005 |
| WO | WO-2006/048249 A1 | 5/2006 |
| WO | WO-2006/053227 A2 | 5/2006 |
| WO | WO-2006/066173 A2 | 6/2006 |
| WO | WO-2006/066174 A1 | 6/2006 |
| WO | WO-2006/066795 A1 | 6/2006 |
| WO | WO-2007/058626 A1 | 5/2007 |
| WO | WO-2007/095124 A2 | 8/2007 |
| WO | WO-2007/112914 A2 | 10/2007 |
| WO | WO-2007/117465 A2 | 10/2007 |
| WO | WO-2007/121154 A2 | 10/2007 |
| WO | WO-2008/030579 A2 | 3/2008 |
| WO | WO-2008/030584 A2 | 3/2008 |
| WO | WO-2008/061109 A2 | 5/2008 |
| WO | WO-2008/073825 A1 | 6/2008 |
| WO | WO-2008/156614 A2 | 12/2008 |
| WO | WO-2009/012312 A1 | 1/2009 |
| WO | WO-2009/019167 A1 | 2/2009 |
| WO | WO-2009/102468 A1 | 8/2009 |
| WO | WO-2010/008847 A2 | 1/2010 |
| WO | WO-2010/071819 A1 | 6/2010 |
| WO | WO-2011/046954 A1 | 4/2011 |
| WO | WO-2011/133750 A1 | 10/2011 |
| WO | WO-2011/137219 A1 | 11/2011 |
| WO | WO-2011/163640 A1 | 12/2011 |
| WO | WO-2012/007375 A1 | 1/2012 |
| WO | WO-2012/068546 A1 | 5/2012 |
| WO | WO-2012/084704 A1 | 6/2012 |
| WO | WO-2012/142125 A2 | 10/2012 |
| WO | WO-2013/042137 A1 | 3/2013 |
| WO | WO-2013/056070 A2 | 4/2013 |
| WO | WO-2013/059587 A1 | 4/2013 |
| WO | WO-2013/068458 A1 | 5/2013 |
| WO | WO-2014/003483 A1 | 1/2014 |
| WO | WO-2014/011902 A1 | 1/2014 |
| WO | WO-2014/070979 A1 | 5/2014 |
| WO | WO-2014/190163 A2 | 11/2014 |
| WO | WO-2015/038503 A1 | 3/2015 |
| WO | WO-2015/091426 A1 | 6/2015 |
| WO | WO-2015/104662 A1 | 7/2015 |
| WO | WO-2015/104688 A1 | 7/2015 |
| WO | WO-2015/119998 A1 | 8/2015 |
| WO | WO-2015/193846 A1 | 12/2015 |
| WO | WO-2016/083433 A1 | 6/2016 |
| WO | WO-2017/009798 A1 | 1/2017 |
| WO | WO-2017/009806 A1 | 1/2017 |
| WO | WO-2017/023941 A1 | 2/2017 |
| WO | WO-2018/081738 A1 | 5/2018 |
| WO | WO-2018/178947 A2 | 10/2018 |
| WO | WO-2019/089580 A1 | 5/2019 |
| WO | WO-2020/113233 A1 | 6/2020 |
| WO | WO-2020/264499 A1 | 12/2020 |
| WO | WO-2022/031330 A1 | 2/2022 |
| WO | WO-2022/108996 A1 | 5/2022 |
| WO | WO-2022/216379 A1 | 10/2022 |
| WO | WO-2023/220227 A1 | 11/2023 |
| WO | WO-2024/249837 A1 | 12/2024 |
| WO | WO-2024/249839 A1 | 12/2024 |

OTHER PUBLICATIONS

Extended European Search Report for EP Application No. 21895491.5 dated Aug. 27, 2024.

Extended European Search Report for EP Application No. 21852519.4 dated Aug. 1, 2024.

Giménez et al., "Targeting IRAK4 disrupts inflammatory pathways and delays tumor development in chronic lymphocytic leukemia." Leukemia 34.1 (2020): 100-114.

International Search Report and Written Opinion for International Application No. PCT/US24/31970 dated Jul. 18, 2024.

International Search Report and Written Opinion for International Application No. PCT/US24/31972 dated Aug. 26, 2024.

Wiese et al., "Investigational IRAK-4 inhibitors for the treatment of rheumatoid arthritis." Expert opinion on investigational drugs 29.5 (2020): 475-482.

Abu-Duhier et al., "FLT3 internal tandem duplication mutations in adult acute myeloid leukemia define a high-risk group," British Journal of Haematology, 111: 190-195 (2000).

Alder, C. M. et al., "Identification of a Novel and Selective Series of Itk Inhibitors via a Template-Hopping Strategy", *Med. Chem. Lett.*, 4:948-952 (American Chemical Society, 2013).

Anonymous, "Chronic myelomonocytic leukaemia", Leukaemia Foundation, Retrieved from the Internet: https://www.leukaemia.org.au/blood-cancer/myelodysplastic-syndromes/chronic-myelomonocytic-leukaemia/, pp. 1-2 (2019).

Bains et al., "FLT3 and NPM1 Mutations in Myelodysplastic Syndromes: Frequency and Potential Value for Predicting Progression to Acute Myeloid Leukemia," American Journal of Clinical Pathology, 135(1): 62-69 (2011).

Balasubramanian et al., "Abstract 3646: Novel IRAK-4 inhibitors exhibit highly potent anti-proliferative activity in DLBCL cell lines with activating MYD88 L265P mutation," Cancer Research, 75(15 Suppl):Abstract 3646 (2015).

Bennett et al., "IRAK1 and IRAK4 as emerging therapeutic targets in hematologic malignancies." Current Opinion in Hematology, vol. 29, No. 1, p. 8 (2022).

Bhagat et al., "Abstract 2570: IMO-8400, a selective antagonist of TLRs 7, 8 and 9, inhibits MYD88 L265P mutation-driven signaling and cell survival: A potential novel approach for treatment of B-cell lymphomas harboring MYD88 L265P mutation," Cancer Res, 74(19): 2570 (3 pages) (2014).

Blackmon et al., "Test then erase? Current status and future opportunities for Measurable Residual Disease testing in Acute Myeloid Leukemia", Acta Haematologica, pp. 1-14, (2023).

Booher et al., "Combination of IRAK4 (CA-4948) and BTK (Vecabrutinib) Inhibitors Show Superior Efficacy in Preclinical Models of Abc Dlbcl Tumors Containing MYD88-L265P Mutations," Hematological Oncology, 37(S2): 512- 512 (2019).

(56) References Cited

OTHER PUBLICATIONS

Booher et al., "Combination of IRAK4 Inhibitor CA-4948 with BCL2 Inhibitor Venetoclax Induces Tumor Regression in an ABC-DLBCL Xenograft Model", Blood, 130(1): 1534, (2017).
Booher et al., "Preclinical activity of IRAK4 kinase inhibitor CA-4948 alone or in combination with targeted therapies and preliminary phase 1 clinical results in non-Hodgkin lymphoma." Blood, vol. 132, No. 4168 (2018).
Burguera et al., "Trial in Progress: A Phase 1b Single-Arm, Open-Label Study of Emavusertib (CA-4948) in Combination with Azacitidine and Venetoclax in Acute Myeloid Leukemia Patients in Complete Response with Measurable Residual Disease." Blood 142 (2023): 5975.
Chen et al., "Design and Synthesis of a Series of Non-Peptide High-Affinity Human Corticotropin-Releasing Factor1 Receptor Antagonists," J Med Chem, 39:4358-4360 (1996).
Chen et al., "Design and synthesis of Imidazo[1,2-b]pyridazine IRAK4 inhibitors for the treatment of mutant MYD88 L265P diffuse large B-cell lymphoma," Eur J Med Chem, 190: 11209 (33 pages) (2020).
Choudhary et al., "Abstract 127: Efficacy of novel IRAK4 inhibitor CA4948 in AML and MDS," Proceedings of the American Association for Cancer Research Annual Meeting 2017; Apr. 1-5, 2017; Washington, DC. Philadelphia (PA): AACR; Cancer Res 2017;77(13 Suppl):Abstract 127 (2017).
Choudhary et al., "SF3B1 Mutations Induce Oncogenetic IRAK4 Isoforms and Activate Targetable Innate Immune Pathways in MDS and AML," Blood, 134(Supplement 1): 4224 (5 pages) (2019).
Clinical study NCT04278768 (V3), "An Open Label Dose Escalation Trial of CA-4948 in Patients With Acute Myelogenous Leukemia or Myelodysplastic Syndrome," Clinical Trials (6 pages) (2020).
Curis Corporate Presentation, NASDAQ:CRIS, Jul. 1, 2020.
Curis Inc. First Quarter 2020 Financial Results, May 12, 2020.
Curis, "Dec. 2020 Key Opinion Leader Event," (22 pages) (2020).
Dadabayev, "DAKA nVision+ System, Peroxidase," Biocompare, (7 pages) (2004).
Das et al., "Effects of Positional and Geometrical isomerism on the Biological Activity of Some Novel Oxazolidinones," Bioorg Med Chem Lett, 15:337-343 (2005).
Das et al., "Impact Analysis of SARS-COV2 on Signaling Pathways During COVID19 Pathogenesis Using Codon Usage Assisted Host-Viral Protein Interactions," BioRxiv, (27 pages) (2020).
Davids et al., "Phase I First-in-Human Study of Venetoclax in Patients With Relapsed or Refractory Non-Hodgkin Lymphoma," J Clin Oncol, 35(8): 826-833 (2015).
De la Fuente et al. "A phase 1 single-arm, open-label study of emavusertib (CA-4948) in combination with azacitidine and venetoclax in patients (pts) with acute myeloid leukemia (AML) in complete response (CR) with measurable residual disease (MRD)." Poster at 2024 American Society of Clinical Oncology Meeting. Published Jun. 3, 2024.
Doonan et al., "CA-4948 for the treatment of melanoma brain metastasis," Central Nervous System Tumors: 1 page (Published Apr. 16, 2022).
Ex Parte Cao, Decision rendered by the Board of Patent Appeals and Interferences in U.S. Appl. No. 10/696,862, filed Sep. 21, 2011.
Extended European Search Report for EP Application No. 18777745.3 mailed Jul. 27, 2020.
Extended European Search Report for EP Application No. 18873778.7 dated Jul. 23, 2021.
Extended European Search Report for EP Application No. 20211096.1 dated Feb. 12, 2021.
Extended European Search Report for EP Application No. 23173240.5 dated Nov. 11, 2023.
Extended European Search Report for EP Application No. 23214923.7 dated Jun. 5, 2024.
Extended European Search Report for EP Application No. EP 16823968, mailed Dec. 10, 2018.
Extended European Search Report for EP Application No. EP 16823970 issued Jun. 25, 2019.
Extended European Search Report for EP Application No. EP 18190333 issued Mar. 13, 2019.
Extended European Search Report issued by the European Patent Office in corresponding Application No. PCT/IB2015054620 dated Jan. 16, 2018.
Extended European Search Report issued by the European Patent Office in corresponding International Application No. PCT/IB2015/050217, dated May 2, 2017.
Faison, "Curis: Differentiated IRAK4 Inhibitor To Drive Value Creation in the Near Term," Seeking Alpha, Mar. 1, 2021.
Fathi et al., "Treatment of FLT3-ITD acute myeloid leukemia," Am. J. Blood. Res., 1(2): 175-189 (2011).
Gao et al., "Inhibition of IL-1 Receptor-Associated Kinase 1 Decreases Murine Acute Graft-versus-Host Disease While Preserving the Graft-versus-Lymphoma Effect." Transplantation and Cellular Therapy, vol. 28, No. 3, pp. 134-e1.(2022).
Garcia-Manero et al., "2863 A Phase 1, Open Label Dose Escalation Trial Evaluating the Safety, Pharmacokinetics, Pharmacodynamics, and Clinical Activity of Orally Administered CA-4948 in Patients with Acute Myelogenous Leukemia or Myelodysplastic Syndrome," Abstract, ASH Annual Meeting (4 pages) (2020).
Garcia-Manero et al., "A Phase 1, Dose Escalation Trial With Novel Oral IRAK4 Inhibitor CA-4948 In Patients With Acute Myelogenous Leukemia or Myelodysplastic Syndrome—Interim Report," Curis Inc. Presentation published Jun. 11, 2021 (22 pages).
Garcia-Manero., "Spliceosome Mutations, IRAK4 and CA-4948 in MDS and AML," Curis Inc. Presentation published Apr. 24, 2021 (22 pages).
Genung et al., "Chapter Four—Small Molecule Inhibition of Interleukin-1 Receptor-Associated Kinase 4 (IRAK4)," Progress in Medicinal Chemistry, 56: 117-163 (2017).
Gerecitano et al., "A Phase 1 Study of Venetoclax (ABT-199/GDC-0199) Monotherapy in Patients with Relapsed/Refractory Non-Hodgkin Lymphoma," Blood, 126(23):254 (2015).
Golub et al., "Molecular classification of cancer: Class discovery and class prediction by gene expression monitoring," Science, 286: 531-537 (1999).
Grommes et al., "Emavusertib (CA-4948) in Combination with Ibrutinib in Relapsed/Refractory Primary Central Nervous System Lymphoma (R/R PCNSL) patients." American Society of Clinical Oncology. (2024).
Gupta et al., "Interleukin-1-receptor kinase 4 inhibition: achieving immunomodulatory synergy to mitigate the impact of COVID-19." Frontiers in Immunology, vol. 12, No. 693085. (2021).
Huang et al., "Posttranslational modifications of NF-kappaB: another layer of regulation for NF-kappaB signaling pathway," Cell Signalling, 22(9): 1282-90 (2010).
International Preliminary Report on Patentability for Application No. PCT/US2021/059668 dated Feb. 24, 2022.
International Search Report and Written Opinion for Application No. PCT/US2022/017902 dated Aug. 3, 2022.
International Search Report and Written Opinion for Application No. PCT/US2023/021812 dated Aug. 6, 2023.
International Search Report and Written Opinion for International Application No. PCT/IB2015/050119 dated Mar. 19, 2015.
International Search Report and Written Opinion for International Application No. PCT/IB2015/050217 dated Apr. 29, 2015.
International Search Report and Written Opinion for International Application No. PCT/IB2015/054620 dated Oct. 19, 2015.
International Search Report and Written Opinion for International Application No. PCT/IB2016/054203 mailed Sep. 23, 2016.
International Search Report and Written Opinion for International Application No. PCT/IB2016/054229 mailed Nov. 15, 2016.
International Search Report and Written Opinion for International Application No. PCT/US/2018/058194 mailed Feb. 3, 2019.
International Search Report and Written Opinion for International Application No. PCT/US2021/030192 mailed Jun. 25, 2021.
International Search Report and Written Opinion for International Application No. PCT/US2021/059668 mailed Feb. 24, 2022.
Iqbal et al., "Preliminary safety and efficacy data on two patients with relapsed/refractory CNS lymphoma treated with emavusertib

(56) References Cited

OTHER PUBLICATIONS (CA-4948) and ibrutinib combination: a subset analysis of TakeAim Lymphoma trial," CURIS Presentation: 1 pg (Nov. 17, 2022).
Issue Notice for U.S. Appl. No. 17/245,611 dated Jun. 14, 23.
Issue Notification for U.S. Appl. No. 16/498,866 dated Aug. 3, 2022.
Kelly et al., "Selective interleukin-1 receptor-associated kinase 4 inhibitors for the treatment of autoimmune disorders and lymphoid malignancy," J Exp Med, 212(13):2189-2201 (2015).
Knapper et al., "An evaluation of the tyrosine kinase inhibitor pacritinib in patients with relapsed FLT3-mutated acute myeloid leukaemia (the UK NCRI AML17 study)," Haematologica, 101(1): 40 (2016).
Lala at al., "Role of nitric oxide in tumor progression: Lessons from experimental tumors," Cancer and Metastasis Reviews, 17(1):91-106 (1998).
Landgren et al., "MYD88 and beyond: novel opportunities for diagnosis, prognosis and treatment in Waldenstroöm's Macroglobulinemia," Leukemia, 28(9): 1799-1803 (2014).
Lane, "IRAK4 inhibition in AML, MDS and B cell Cancers," Curis Presentation Published Sep. 29, 2021.
Lange et al., "Preclinical evaluation of a novel interleukin-I receptor-associated kinase 4 (IRAK.4) inhibitor in combination with PBK inhibitor copanlisib or BTK inhibitors in ABC-DLBCL" [abstract]. In: Proceedings of the American Association for Cancer Research Annual Meeting 2018; Apr. 14-18, 2018; Chicago, IL. Philadelphia (PA): AACR; Cancer Res 2018; 78(13 Suppl):Abstract nr 1887.
Li et al., "Inhibition of IRAK1/4 sensitizes T cell acute lymphoblastic leukemia to chemotherapies," Journal of Clinical Investigation, 125(3): 1081-1097 (2015).
Li et al., "Synergistic induction of apoptosis in high-risk DLBCL by BCL2 inhibition with ABT-199 combined with pharmacologic loss of MCL1," Leukemia, 29:1702-1712 (2015).
Martell, "Discovery and Development of IRAK4 Inhibitor Emavusertib", Curis Presentation: 36 pages (Sep. 29, 2022).
Martell, "Emavusertib," Curis Presentation: 15 pages (Oct. 7, 2022).
McElroy, "Interleukin-1 receptor-associated kinase 4 (IRAK4) inhibitors: an updated patent review (2016-2018)." Expert opinion on therapeutic patents, vol. 29, No. 4, pp. 243-259.(2019).
Metzeler et al., "ASH Poster #4077: Molecular characterization of clinical response in relapsed/refractory acute myeloid leukemia and high-risk myelodysplastic syndrome patients treated with single agent emavusertib," Pre-ASH Meeting Slideshow, 12 pages (Dec. 1, 2022).
Metzeler et al., "Molecular characterization of clinical response in relapsed/refractory acute myeloid leukemia and high-risk myelodysplastic syndrome patients treated with single agent emavusertib," American Society of Hematology poster, published Nov. 16, 2022 (1 page).
Metzeler et al., "Molecular characterization of clinical response in relapsed/refractory acute myeloid leukemia and high-risk myelodysplastic syndrome patients treated with single agent emavusertib," Curis Inc. Presentation published Nov. 16, 2022 (9 pages).
Metzeler et al., "Predictive biomarkers of response to the IRAK4/FLT3 inhibitor emavusertib in hematological malignancies." American Society of Clinical Oncology. (2024).
Nowakowski et al., "# 2945: A Multi-Center, Dose-Finding Study to Assess Safety, Tolerability, Pharmacokinetics and Preliminary Efficacy of a novel IRAK4 inhibitor CA-4948 in combination with ibrutinib, in Patients with Relapsed or Refractory Hematologic Malignancies," American Society of Hematology, Presentation by Curis Inc. published on Nov. 19, 2020 (12 pages).
Nowakowski et al., "703 Safety, Pharmacokinetics and Activity of CA-4948, an IRAK4 Inhibitor, for Treatment of Patients with Relapsed or Refractory Hematologic Malignancies: Results from the Phase 1 Study," Abstract, ASH Annual Meeting (6 pages) (2020).
Partial Search Report and Written Opinion for EP Patent Application No. EP16823970, mailed Mar. 19, 2019.
Rao et al., "Abstract C191: Efficacy of novel IRAK4 inhibitors in ABC-DLBCL and AML models," Proceedings of the AACR-NCI-EORTC International Conference: Molecular Targets and Cancer Therapeutics; Nov. 5-9, 2015; Boston, MA. Philadelphia (PA): AACR; Mol Cancer Ther, 14(12 Suppl 2): Abstract C191 (2015).
Rao Gummadi et al., "Discovery of CA-4948, an Orally Bioavailable IRAK4 Inhibitor for Treatment of Hematologic Malignancies," ACS Medicinal Chemistry Letters: 8 pages (2020).
Rhyasen., "IRAK family kinases as therapeutic targets for Myelodysplastic Syndrome and Acute Myeloid Leukemia" University of Cincinnati: 132 pages (2014).
Santa Cruz Biotechnology, "p-NFkB p50 (A-8): sc-271908," (1 page) (2012).
STN Registry database entry: [online] 2011, CAS RN 1301085-08-4 (Search date: Feb. 9, 2019).
STN Registry database entry: [online] 2011, CAS RN 1421459-19-9 (Search date: Feb. 9, 2019).
STN Registry database entry: [online] 2011, CAS RN 1421491-68-0 (Search date: Feb. 9, 2019).
STN Registry database entry: [online] 2011, CAS RN 1421497-05-3 (Search date: Feb. 9, 2019).
STN Registry database entry: [online] 2014, CAS RN 1178067-91-8 (Search date: Feb. 9, 2019).
STN Registry database entry: [online] 2014, CAS RN 1184469-61-1 (Search date: Feb. 9, 2019).
STN Registry database entry: [online] 2014, CAS RN 1223638-97-8 (Search date: Feb. 9, 2019).
STN Registry database entry: [online] 2014, CAS RN 1252319-44-0 (Search date: Feb. 9, 2019).
STN Registry database entry: [online] 2014, CAS RN 1274105-18-8 (Search date: Feb. 9, 2019).
STN Registry database entry: [online] 2014, CAS RN 1282974-67-7 (Search date: Feb. 9, 2019).
STN Registry database entry: [online] 2014, CAS RN 1333957-90-6 (Search date: Feb. 9, 2019).
STN Registry database entry: [online] 2014, CAS RN 1346410-97-6 (Search date: Feb. 9, 2019).
STN Registry database entry: [online] 2014, CAS RN 1367793-38-1 (Search date: Feb. 9, 2019).
STN Registry database entry: [online] 2014, CAS RN 1368333-88-3 (Search date: Feb. 9, 2019).
STN Registry database entry: [online] 2014, CAS RN 1369195-81-2 (Search date: Feb. 9, 2019).
STN Registry database entry: [online] 2014, CAS RN 1381262-66-3 (Search date: Feb. 9, 2019).
STN Registry database entry: [online] 2014, CAS RN 1381667-74-0 (Search date: Feb. 9, 2019).
STN Registry database entry: [online] 2014, CAS RN 1396710-33-0 (Search date: Feb. 9, 2019).
STN Registry database entry: [online] 2014, CAS RN 1405289-53-3 (Search date: Feb. 9, 2019).
STN Registry database entry: [online] 2014, CAS RN 1414842-47-9 (Search date: Feb. 9, 2019).
STN Registry database entry: [online] 2014, CAS RN 1414842-48-0 (Search date: Feb. 9, 2019).
STN Registry database entry: [online] 2014, CAS RN 1421504-43-9 (Search date: Feb. 9, 2019).
STN Registry database entry: [online] 2014, CAS RN 1421508-39-5 (Search date: Feb. 9, 2019).
STN Registry database entry: [online] 2014, CAS RN 1423498-44-5 (Search date: Feb. 9, 2019).
STN Registry database entry: [online] 2014, CAS RN 1522249-43-9 (Search date: Feb. 9, 2019).
STN Registry database entry: [online] 2014, CAS RN 1548563-20-7 (Search date: Feb. 9, 2019).
STN Registry database entry: [online] 2014, CAS RN 1570255-99-0 (Search date: Feb. 9, 2019).
STN Registry database entry: [online] 2014, CAS RN 1575185-05-5 (Search date: Feb. 9, 2019).
STN Registry database entry: CAS RN 1181327-83-2 (Entered STN: Sep. 8, 2009). (Year: 2009).

(56) References Cited

OTHER PUBLICATIONS

STN Registry database entry: CAS RN 1301085-08-4 (Entered STN: May 26, 2011). (Year: 2011).
Sun et al., "Synthesis, in Vitro Evaluation and Cocrystal Structure of 4-Oxo-[1]benzopyrano[4,3-c]pyrazole Cryptosporidium parvum Inosine 5'-Monophosphate Dehydrogenase (CpIMPDH) Inhibitors," J Med Chem, 57:10544-10550 (2014).
Takami et al., "Design and synthesis of Rho kinase inhibitors (I)," Bioorg Med Chem, 12:2115-2137 (2004).
Ugolkov et al., "Identification of NF-kappaB phospho-p50 as a predictive biomarker for IRAK4 inhibitor CA-4948 in patients with Non-Hodgkin's lymphoma," American Associates for Cancer Research, published on Nov. 19, 2020 (1 page).
Ugolkov et al., "Identification of NF-kB phospho-p50 as a potential predictive biomarker for IRAK4 inhibitor CA-4948 in patients with Non-Hodgkin's lymphoma," AACR Annual Meeting 2021, Poster No. 385.
Viatour et al., "Phosphorylation of NF-kappaB and IkappaB proteins: implications in cancer and inflammation," Trends Biochem Sci, 30(1): 43-52 (2005).
Von Roemeling et al., "Clinical Activity of IRAK4 Inhibitor, Emavusertib (CA-4948)," Curis Presentation published Oct. 29, 2022 (15 pages).
Von Roemeling et al., "The IRAK4 inhibitor CA-4948 demonstrates antitumor activity in a preclinical model of CNS lymphoma," Molecular Targets and Cancer Therapeutics, Curis Presentation published Oct. 7, 2021 (9 pages).
Von Roemeling, "IRAK-4 as a therapeutic target in primary CNS lymphoma", University of Florida, Curis, Presentation 28 slides (2022).
Wang et al., "Crystal Structures of IRAK-4 Kinase in Complex with Inhibitors: A Serine/Threonine Kinase with Tyrosine as a Gatekeeper," Structure 14, 1835-1844 (2006).
Winer et al., "Preliminary Safety, Efficacy and Molecular Characterization of Emavusertib (CA-4948) in Relapsed/Refractory (R/R) Acute Myeloid Leukemia (AML) Patients with FLT3 Mutation (FLT3m) " American Society of Clinical Oncology. (2024).
Younes et al., "Phase 1 Dose-Finding Study Investigating CA-4948, an IRAK4 Kinase Inhibitor, in Patients with R/R NHL: Report of Initial Efficacy and Updated Safety Information," Blood, 134(1): 5327 (3 pages) (2019).
Yu et al., "Targeting NF-KB pathway for the therapy of diseases: mechanism and clinical study," Sig Transduct Target Ther, 5(209) (23 pages) (2020).
Zhang et al."Canonical NF-kB Signalling Is a Potential Target in FLT3/ITD AML." Blood, vol. 120, No. 21, p. 2447 (2012).
Zhang et al., "Design, synthesis and evaluation of bicyclic benzamides as novel 5-HT1F receptor agonists," Bioorg Med Chem Lett, 14(24):6011-6016 (2004).
Zhang et al., "Innate immune mediator, Interleukin-1 receptor accessory protein (IL1RAP), is expressed and pro-tumorigenic in pancreatic cancer," Journal of Hematology & Oncology, 15: Article 70 pp. 1-5 (2022).
Zhang et al., "Targeting NF-KB pathway for the therapy of diseases: mechanism and clinical study," Sig Transduct Target Ther 5(209): 23 pages (2020).
Bai et al., "The recent advance of Interleukin-1 receptor associated kinase 4 inhibitors for the treatment of inflammation and related diseases," European Journal of Medicinal Chemistry 258 (2023): 15606.
Blood Cancer UK, "Relapse and refractory AML treatments," Retrieved on Nov. 15, 24 from: https://bloodcancer.org.uk/understanding-blood-cancer/leukaemia/acute-myeloid-leukaemia/aml-treatment/relapse-refractory/.
Extended European Search Report for EP Application No. 24168755.7 dated Oct. 10, 2024.
Grommes et al., "Analysis of genetic mutation profile and CNS pharmacokinetics in relapsed/refractory primary CNS lymphoma patients responding to novel emavusertib (IRAK4i) and BTKi combination ," Abstract. Jan. 27, 2025.
Guidetti et al., "Targeting IRAK4 with emavusertib in lymphoma models with secondary resistance to PI3K and BTK inhibitors." Journal of Clinical Medicine 12 (2023): 399.
Pleyer et al., "Azacitidine for Front-Line Therapy of Patients with AML," International Journal of Molecular Sciences 18 (2017): 415 (18 pages).
Smith et al., "Alternative Splice Variants of IRAK4 That Activate Innate Immune Signaling Are Associated with U2AF1 Mutations in Myelodysplastic Syndrome and Acute Myeloid Leukemia," Blood 128.22 (2016): 1531. Abstract.
U.S. Appl. No. 15/110,309, Granted.
U.S. Appl. No. 15/111,000, Granted.
U.S. Appl. No. 15/667,173, Granted.
U.S. Appl. No. 16/054,512, Granted.
U.S. Appl. No. 16/795,394, Granted.
U.S. Appl. No. 17/245,611, Granted.
U.S. Appl. No. 18/141,008, Granted.
U.S. Appl. No. 16/498,866, Granted.
U.S. Appl. No. 17/853,299, Pending.
U.S. Appl. No. 16/176,940, Granted.
U.S. Appl. No. 18/019,400, Pending.
U.S. Appl. No. 18/037,697, Pending.
U.S. Appl. No. 17/680,995, Granted.
U.S. Appl. No. 18/953,879, Pending.
U.S. Appl. No. 18/864,799, Pending.
Arranz et al., "Interleukin-1 [beta] as emerging therapeutic target in hematological malignancies and potentially in their complications." Blood Reviews 31(5) (2017): 306-317.
Chen et al., "Immediate early response 3 gene promotes aggressive progression and autophagy of AML by negatively regulating AKT/mTOR." Translational Oncology 35 (2023): 101711.
Clinical Trial NCT05187182, "CA-4948 in Combination With FOLFOX/PD-1 Inhibitor +/- Trastuzumab for Untreated Unresectable Gastric and Esophageal Cancer," last update posted Jan. 15, 2025. Available at: https://clinicaltrials.gov/study/NCT05187182.
Clinical Trial NCT05669352, "A Study of Oral IRAK-4 Inhibitor CA-4948 in Combination With Pembrolizumab and Stereotactic Radiosurgery in Patients With Melanoma Brain Metastases," last update posted Apr. 4, 2025. Available at: https://clinicaltrials.gov/study/NCT05669352.
Clinical Trial NCT06439836, "Pembrolizumab Plus CA-4948 for the Treatment of Patients With Progressive Metastatic Urothelial Cancer Despite Prior Immunotherapy," last update posted Mar. 10, 2025. Available at: https://clinicaltrials.gov/study/NCT06439836.
Day et al., "Interleukin-1 blockade with anakinra in acute leukaemia patients with severe COVID-19 pneumonia appears safe and may result in clinical improvement." British Journal of Haematology 190(2) (2020): e80.
Doonan, "Novel oral IRAK-4 inhibition plus checkpoint inhibition in metastatic melanoma," Hematology and Oncology 2022. Available at https://web.archive.org/web/20220703052454/https://discovery.education.med.ufl.edu/hematology-and-oncology-2022/.
International Search Report and Written Opinion for International Application No. PCT/US24/52925 dated Feb. 6, 2025.
Parrondo et al., "IRAK-4 inhibition: emavusertib for the treatment of lymphoid and myeloid malignancies." Frontiers in Immunology 14 (2023): 1239082.
Supplementary European Search Report for EP Application No. 22785128.4 dated Jan. 27, 2025.
Ugolkov et al., "IRAK4 inhibitor CA-4948 potentiates antitumor effects of azacitidine and venetoclax in human acute myeloid leukemia", Curis. EHA 2021, Jun. 9-17, 2021.
Ugolkov et al., "IRAK4 inhibitor CA-4948 potentiates antitumor effects of azacitidine and venetoclax in human acute myeloid leukemia", HemaSphere, vol. 5, Suppl. 2, 26th Congress of the European Hematology Association, EHA 2021 20210609 to 20210617, Jul. 1, 2021.
Zhang et al.,. "Constitutive IRAK4 activation underlies poor prognosis and chemoresistance in pancreatic ductal adenocarcinoma." Clinical Cancer Research 23(7) (2017): 1748-1759.

BICYCLIC HETEROCYCLYL DERIVATIVES AS IRAK4 INHIBITORS

RELATED APPLICATIONS

This application is a continuation of U.S. patent application Ser. No. 18/141,008, filed Apr. 28, 2023, which is a continuation of U.S. patent application Ser. No. 17/245,611, filed Apr. 30, 2021, now U.S. Pat. No. 11,691,987, which is a continuation of U.S. patent application Ser. No. 16/795,394, filed Feb. 19, 2020, now U.S. Pat. No. 10,995,100, which is a continuation of U.S. patent application Ser. No. 16/054,512, filed Aug. 3, 2018, now U.S. Pat. No. 10,640,517, which is a continuation of U.S. patent application Ser. No. 15/667,173, filed Aug. 2, 2017, now U.S. Pat. No. 10,047,104, which is a continuation of U.S. patent application Ser. No. 15/111,000, filed on Jul. 12, 2016, now U.S. Pat. No. 9,732,095, issued on Aug. 15, 2017, which is the U.S. national phase of International Patent Application No. PCT/IB2015/050217, filed Jan. 12, 2015, which claims the benefit of Indian provisional applications 158/CHE/2014 filed on Jan. 13, 2014 and 3000/CHE/2014 filed on Jun. 20, 2014, the contents of which are hereby incorporated by reference in their entirety.

FIELD OF THE INVENTION

This invention relates to compounds useful for treatment of cancer and inflammatory diseases associated with interleukin-1 receptor associated kinase (IRAK) and more particularly compounds that modulate the function of IRAK-4. The invention also provides pharmaceutically acceptable compositions comprising compounds of the present invention and methods of using said compositions in the treatment of diseases associated with IRAK-4.

BACKGROUND OF THE INVENTION

Interleukin-1 (IL-1) Receptor-Associated Kinase-4 (IRAK-4) is a serine/threonine kinase enzyme that plays an essential role in signal transduction by Toll/IL-1 receptors (TIRs). Diverse IRAK enzymes are key components in the signal transduction pathways mediated by interleukin-1 receptor (IL-1R) and Toll-like receptors (TLRs) (Janssens, S, et al. Mol. Cell. 11, 2003, 293-302). There are four members in the mammalian IRAK family: IRAK-1, IRAK-2, IRAK-M and IRAK-4. These proteins are characterized by a typical N-terminal death domain that mediates interaction with MyD88-family adaptor proteins and a centrally located kinase domain. The IRAK proteins, as well as MyD88, have been shown to play a role in transducing signals other than those originating from IL-1R receptors, including signals triggered by activation of IL-18 receptors (Kanakaraj, et al. J. Exp. Med. 189(7):1999, 1129-38) and LPS receptors (Yang, et al., J. Immunol. 163, 1999, 639-643). Out of four members in the mammalian IRAK family, IRAK-4 is considered to be the "master IRAK". Under overexpression conditions, all IRAKs can mediate the activation of nuclear factor-kB (NF-kB) and stress-induced mitogen activated protein kinase (MAPK)-signaling cascades. However, only IRAK-1 and IRAK-4 have been shown to have active kinase activity. While IRAK-1 kinase activity could be dispensable for its function in IL-1-induced NF-kB activation (Kanakaraj et al, J. Exp. Med. 187(12), 1998, 2073-2079) and (Xiaoxia Li, et al. Mol. Cell. Biol. 19(7), 1999, 4643-4652), IRAK-4 requires its kinase activity for signal transduction (Li S, et al. Proc. Natl. Acad. Sci. USA 99(8), 2002, 5567-5572) and (Lye, E et al, J. Biol. Chem. 279(39); 2004, 40653-8). Given the central role of IRAK4 in Toll-like/IL-t R signalling and immunological protection, IRAK4 inhibitors have been implicated as valuable therapeutics in inflammatory diseases, sepsis and autoimmune disorders (Wietek C, et al, Mol. Interv. 2: 2002, 212-215).

Mice lacking IRAK-4 are viable and show complete abrogation of inflammatory cytokine production in response to IL-1, IL-18 or LPS (Suzuki et al. Nature, 416(6882), 2002, 750-756). Similarly, human patients lacking IRAK-4 are severely immunocompromised and are not responsive to these cytokines (Medvedev et al. J. Exp. Med., 198(4), 2003, 521-531 and Picard et al. Science 299(5615), 2003, 2076-2079). Knock-in mice containing inactive IRAK4 were completely resistant to lipopolysaccharide- and CpG-induced shock (Kim T W, et al. J Exp Med 204: 2007, 1025-36) and (Kawagoe T, et al. J Exp Med 204(5): 2007, 1013-1024) and illustrated that IRAK4 kinase activity is essential for cytokine production, activation of MAPKs and induction of NF-κB regulated genes in response to TLR ligands (Koziczak-Holbro M, et al. J Biol Chem; 282(18): 2007; 13552-13560). Inactivation of IRAK4 kinase (IRAK4 KI) in mice leads to resistance to EAE due to reduction in infiltrating inflammatory cells into CNS and reduced antigen specific CD4+ T-cell mediated IL-17 production (Kirk A et al. The Journal of Immunology, 183(1), 2009, 568-577).

The crystal structures revealed that IRAK-4 contains characteristic structural features of both serine/threonine and tyrosine kinases, as well as additional novel attributes, including the unique tyrosine gatekeeper residue. Structural analysis of IRAK-4 revealed the underlying similarity with kinase family; ATP-binding cleft sandwiched between a bilobal arrangement. The N-terminal lobe consists of mainly of a twisted five-stranded antiparallel beta-sheet and one alpha-helix and the larger C-terminal lobe are predominantly alpha-helical. Yet, the structure reveals a few unique features for IRAK-4 kinase, including an additional alpha-helix from the N-terminal extension in the N-terminal lobe, a longer loop between helices alpha-D and alpha-E and a significantly moved helix alpha G as well as its adjoining loops. The ATP-binding site in IRAK-4 has no deep pocket in the back but has a featured front pocket. This uniquely shaped binding pocket provides an excellent opportunity for designing IRAK-4 inhibitors.

The development of IRAK-4 kinase inhibitors has generated several novel classes of protein binders which includes thiazole and pyridine amides (George M Buckley, et al. Bioorg. Med. Chem. Lett., 18(11), 2008, 3211-3214), aminobenzimidazoles (Powers J P, et al. Bioorg. Med. Chem. Lett., 16(11), 2006, 2842-2845), Imidazo[1,2-a]pyridines (Buckley G M, et al. Bioorg. Med. Chem. Lett. 18(11), 2008, 3656-3660) and (Buckley G, et al. Bioorg. Med. Chem. Lett. 18(11), 2008, 3291-3295), imidazo[1,2-b]pyridazines and benzimidazole-indazoles (WO2008030579; WO2008030584). Apparently, all of them are still in the early preclinical stage.

Despite various disclosures on different kinase inhibitors, however, with the rise in number of patients affected by kinase enzyme mediated diseases, there appears to be unmet need for newer drugs that can treat such diseases more effectively. There is still need for newer kinase inhibitors including multikinase inhibitors, which may be further useful in treatment of disorders owing to variations in various kinases activity and possessing broader role. They may also be useful as part of other therapeutic regimens for the treatment of disorders, alone or in combination with protein kinase compounds well known by the one skilled in the art.

OBJECTIVES OF THE INVENTION

One objective herein is to provide bicyclic heterocyclyl compounds of formula (I) or a pharmaceutically acceptable salt or a stereoisomer thereof, as kinase inhibitors, particularly IRAK4 inhibitors.

Another objective is to provide a pharmaceutical composition comprising the compound of formula (I) or a pharmaceutically acceptable salt or a stereoisomer thereof and at least one pharmaceutically acceptable excipient such as a pharmaceutically acceptable carrier or diluent.

Yet another objective is to provide a use of bicyclic heterocyclyl derivatives of formula (I) or a pharmaceutically acceptable salt or a stereoisomer thereof, for the treatment and prevention of diseases or disorders, in particular their use in diseases or disorder where there is an advantage in inhibiting kinase enzyme, more particularly IRAK4 enzyme.

SUMMARY OF THE INVENTION

In one aspect according to the present invention, it comprises bicyclic heterocyclyl derivatives of formula (I)

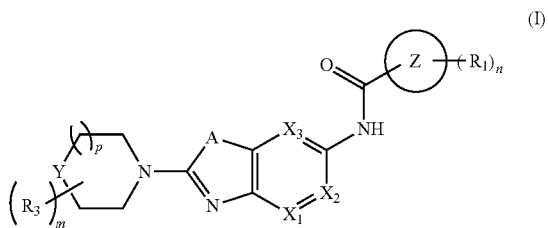

(I)

or a pharmaceutically acceptable salt or a stereoisomer thereof;
wherein,
$X_1$ and $X_3$ independently are CH or N; $X_2$ is $CR_2$ or N; provided one and not more than one of $X_1$, $X_2$ or $X_3$ is N;
A is O or S;
Y is —$CH_2$— or O;
Ring Z is aryl or heterocyclyl;
$R_1$, at each occurrence, is independently halo or optionally substituted heterocyclyl; wherein the substituent is alkyl, alkoxy, aminoalkyl, halo, hydroxyl, hydroxyalkyl or —$NR_aR_b$;
$R_2$ is hydrogen, optionally substituted cycloalkyl, optionally substituted aryl, optionally substituted heterocyclyl or —$NR_aR_b$; wherein the substituent is alkyl, amino, halo or hydroxyl;
$R_3$, at each occurrence, is alkyl or hydroxyl;
$R_a$ and $R_b$ are independently hydrogen, alkyl, acyl or heterocyclyl;
'm' and 'n' are independently 0, 1 or 2;
'p' is 0 or 1.

In yet another aspect, the present invention provides a pharmaceutical composition comprising the compound of formula (I) or a pharmaceutically acceptable salt or a stereoisomer thereof and at least one pharmaceutically acceptable excipient such as a pharmaceutically acceptable carrier or diluent.

In yet another aspect, the present invention relates to the preparation of the compounds of formula (I).

In yet further aspect of the present application, it provides use of bicyclic heterocyclyl derivatives of formula (I) or a pharmaceutically acceptable salt or a stereoisomer thereof, for the treatment and prevention of diseases or disorder mediated by IRAK4 enzyme.

More particularly, the invention relates to the use of bicyclic heterocyclyl derivatives of formula (I) pharmaceutically acceptable salts and stereoisomers thereof, including mixtures thereof in all ratios, as a medicament, by inhibiting IRAK or IRAK4 or other related kinases.

Bicyclic heterocyclyl derivatives of formula (I) of the present invention possess therapeutic role of inhibiting IRAK or IRAK4 or other related kinases useful in the area of diseases and/or disorders include, but are not limited to cancers, allergic diseases and/or disorders, autoimmune diseases and/or disorders, inflammatory diseases and/or disorder and/or conditions associated with inflammation and pain, proliferative diseases, hematopoietic disorders, haematological malignancies, bone disorders, fibrosis diseases and/or disorders, metabolic disorders, muscle diseases and/or disorders, respiratory diseases and/or disorders, pulmonary diseases and/or disorders, genetic developmental diseases and/or, neurological and neurodegenerative diseases and/or disorders, chronic inflammatory demyelinating neuropathies, cardiovascular, vascular or heart diseases and/or disorders, ophthalmic/ocular diseases and/or disorders, wound repair, infection and viral diseases. Therefore, inhibition of one or more kinases would have multiple therapeutic indications.

DETAILED DESCRIPTION OF THE INVENTION

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

As used herein, the terms "optional" or "optionally" mean that the subsequently described event or circumstance may occur or may not occur and that the description includes instances where the event or circumstance occurs as well as instances in which it does not. For example, "optionally substituted alkyl" refers to that 'alkyl' may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: halo, cyano, alkyl, haloalkyl, alkoxy, haloalkoxy, alkenyl, alkynyl, aryl, heterocyclyl, amino, cyano, nitro, alkylamino, arylamino, alkylaminoalkyl, arylaminoalkyl, hydroxyl, hydroxyalkyl, cycloalkyl, aryl, heterocyclic and aliphatic. It is understood that the substituent may be further substituted.

As used herein, the term "alkyl" refers to saturated aliphatic groups, including but not limited $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, t-hexyl, 2-hexyl, 3-hexyl, t-heptyl, 2-heptyl, 3-heptyl, 4-heptyl, 1-octyl, 2-octyl, 3-octyl or 4-octyl and the like. The "alkyl" group may be optionally substituted.

The term "acyl" refers to a group R—CO— wherein R is an alkyl group defined above. Examples of 'acyl' groups are, but not limited to, $CH_3CO$—, $CH_3CH_2CO$—, $CH_3CH_2CH_2CO$— or $(CH_3)_2CHCO$—.

As used herein, the term "alkoxy" refers to a straight or branched, saturated aliphatic $C_1$-$C_{10}$ hydrocarbon radical bonded to an oxygen atom that is attached to a core structure. Preferably, alkoxy groups have one to six carbon atoms. Examples of alkoxy groups include but are not limited to methoxy, ethoxy, propoxy, isopropoxy, butoxy, isobutoxy, tert-butoxy, pentoxy, 3-methyl butoxy and the like.

As used herein, the term "haloalkyl" refers to alkyl group (as defined above) is substituted with one or more halogens. A monohaloalkyl radical, for example, may have a chlorine, bromine, iodine or fluorine atom. Dihalo and polyhaloalkyl radicals may have two or more of the same or different halogen atoms. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl and the like.

As used herein, the term "haloalkoxy" refers to radicals wherein one or more of the hydrogen atoms of the alkoxy groups are substituted with one or more halogens. Representative examples of "haloalkoxy" groups include, but not limited to, difluoromethoxy (—$OCHF_2$), trifluoromethoxy (—$OCF_3$) or trifluoroethoxy (—$OCH_2CF_3$).

As used herein, the term "aryl" alone or in combination with other term(s) means a carbocyclic aromatic system containing one or two rings wherein such rings may be fused. The term "fused" means that the second ring is attached or formed by having two adjacent atoms in common with the first ring. The term "fused" is equivalent to the term "condensed". Examples of aryl groups include but are not limited to phenyl, naphthyl, indanyl and the like. Unless otherwise specified, all aryl groups described herein may be substituted or unsubstituted.

As used herein, "Amino" refers to an —$NH_2$ group.

As used herein, "alkylamino" refers to amino group wherein one of the hydrogen atom of amino group is replaced with alkyl group.

As used herein, "arylamino" refers to amino group wherein one of hydrogen atoms is substituted with aryl group.

As used herein, "alkylaminoalkyl" refers to alkyl group substituted with "alkylamino" group defined above.

As used herein, "arylaminoalkyl" refers to arylamino group, as defined above, substituted with alkyl group.

As used herein, "nitro" refers to an —$NO_2$ group.

As used herein, "alkylamino" or "cycloalkylamino", refer to an —N-group, wherein nitrogen atom of said group being attached to alkyl or cycloalkyl respectively. Representative examples of an "Alkylamino" and "Cycloalkylamino" groups include, but are not limited to —$NHCH_3$ and —NH-cyclopropyl. An amino group can be optionally substituted with one or more of the suitable groups.

"Aminoalkyl" refers to an alkyl group, as defined above, wherein one or more of the alkyl group's hydrogen atom has been replaced with an amino group as defined above. Representative examples of an aminoalkyl group include, but are not limited to —$CH_2NH_2$, —$CH_2CH_2NH_2$, —$CH(CH_3)NH_2$, —$CH_2CH(CH_3)NH_2$. An aminoalkyl group can be unsubstituted or substituted with one or more suitable groups.

As used herein the term "cycloalkyl" alone or in combination with other term(s) means $C_3$-$C_{10}$ saturated cyclic hydrocarbon ring. A cycloalkyl may be a single ring, which typically contains from 3 to 7 carbon ring atoms. Examples of single-ring cycloalkyls include cyclopropyl, cyclobutyl, cyclopentyl, cyclohexyl, cycloheptyl and the like. A cycloalkyl may alternatively be polycyclic or contain more than one ring. Examples of polycyclic cycloalkyls include bridged, fused and spirocyclic carbocyclyls.

As used herein, the term "cyano" refers to —CN group.

As used herein, the term "hydroxy" or "Hydroxyl" refers to —OH group.

As used herein the term "hydroxyalkyl" or "hydroxylalkyl" means alkyl substituted with one or more hydroxyl groups, wherein the alkyl groups are as defined above. Examples of "hydroxyalkyl" include but are not limited to hydroxymethyl, hydroxyethyl, hydroxypropyl, propan-2-ol and the like.

As used herein, the term "halo" or "halogen" alone or in combination with other term(s) means fluorine, chlorine, bromine or iodine.

As used herein, the term "heterocyclyl" includes definitions of "heterocycloalkyl" and "heteroaryl".

The term "heterocycloalkyl" refers to a non-aromatic, saturated or partially saturated, monocyclic or polycyclic ring system of 3 to 15 members having at least one heteroatom or heterogroup selected from O, N, S, S(O), $S(O)_2$, NH or C(O) with the remaining ring atoms being independently selected from the group consisting of carbon, oxygen, nitrogen and sulfur. Examples of "Heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, azepanyl, 2-azabicyclo[2.2.2]octanyl, azocinyl, chromanyl, xanthenyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 4- to 7-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, azepanyl and N-oxides thereof. More preferably, "heterocycloalkyl" includes azetidinyl, pyrrolidinyl, morpholinyl, piperidinyl or azepanyl. All heterocycloalkyl are optionally substituted by one or more aforesaid groups.

The term "heteroaryl" refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. Preferably, "heteroaryl" is a 5- to 6-membered ring. The rings may contain from 1 to 4 heteroatoms selected from N, O and S, wherein the N or S atom is optionally oxidized, or the N atom is optionally quarternized. Any suitable ring position of the heteroaryl moiety may be covalently linked to the defined chemical structure.

Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl; benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and the like. Preferably "heteroaryl" refers to 5- to 6-membered ring selected from the group consisting of furanyl, thiophene, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl and pyridazinyl. More preferably, pyrazolyl, pyridyl, oxazolyl and furanyl. All heteroaryls are optionally substituted by one or more aforesaid groups.

As used herein, the term "including" as well as other forms, such as "include", "includes" and "included" is not limiting.

The phrase "pharmaceutically acceptable" refers to compounds or compositions that are physiologically tolerable and do not typically produce allergic or similar untoward reaction, including but not limited to gastric upset or dizziness when administered to mammal.

The term "pharmaceutically acceptable salt" refers to a product obtained by reaction of the compound of the present invention with a suitable acid or a base. Pharmaceutically acceptable salts of the compounds of this invention include those derived from suitable inorganic bases such as Li, Na, K, Ca, Mg, Fe, Cu, Al, Zn and Mn salts; Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention (compounds of formula (I)) can form pharmaceutically acceptable salts with various organic bases such as lysine, arginine, guanidine, diethanolamine or metformin. Suitable base salts include, but are not limited to, aluminum, calcium, lithium, magnesium, potassium, sodium, or zinc, salts.

As used herein, the term "stereoisomer" is a term used for all isomers of individual compounds of formula (I) that differ only in the orientation of their atoms in space. The term stereoisomer includes mirror image isomers (enantiomers) of compound of formula (I), mixtures of mirror image isomers (racemates, racemic mixtures) compound of formula (I), geometric (cis/trans or E/Z, R/S) isomers compound of formula (I) and isomers of compound of formula (I) with more than one chiral center that are not mirror images of one another (diastereoisomers).

As used herein, the term "composition" is intended to encompass a product comprising the specified ingredients in the specified amounts, as well as any product which results, directly or indirectly, from combination of the specified ingredients in the specified amounts.

As used herein, the term "pharmaceutical composition" refers to a composition(s) containing a therapeutically effective amount of at least one compound of formula (I) or its pharmaceutically acceptable salt; and a conventional pharmaceutically acceptable carrier.

The pharmaceutical composition(s) of the present invention can be administered orally, for example in the form of tablets, coated tablets, pills, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of ointments or creams or transdermals, in the form of patches, or in other ways, for example in the form of aerosols or nasal sprays.

The pharmaceutical composition(s) usually contain(s) about 1% to 99%, for example, about 5% to 75%, or from about 10% to about 30% by weight of the compound of formula (I) or pharmaceutically acceptable salts thereof. The amount of the compound of formula (I) or pharmaceutically acceptable salts thereof in the pharmaceutical composition(s) can range from about 1 mg to about 1000 mg or from about 2.5 mg to about 500 mg or from about 5 mg to about 250 mg or in any range falling within the broader range of 1 mg to 1000 mg or higher or lower than the afore mentioned range.

As used herein, the term "pharmaceutically acceptable carrier" refers to any of the standard pharmaceutical carriers, such as a phosphate buffered saline solution, water, emulsions {e.g., such as an oil/water or water/oil emulsions) and various types of wetting agents. The compositions also can include stabilizers and preservatives. The examples of carriers, stabilizers and adjuvant are mentioned in literature like, Martin, Remington's Pharmaceutical Sciences, 15th Ed., Mack Publ. Co., Easton, PA [1975].

The term "treatment"/"treating" means any treatment of a disease in a mammal, including: (a) Inhibiting the disease, i.e., slowing or arresting the development of clinical symptoms; and/or (b) Relieving the disease, i.e., causing the regression of clinical symptoms and/or (c) alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "subject" refers to an animal, preferably a mammal and most preferably a human.

As used herein, the term, "therapeutically effective amount" refers to an amount of a compound of formula (I) or a pharmaceutically acceptable salt or a stereoisomer thereof; or a composition comprising the compound of formula (I) or a pharmaceutically acceptable salt or a stereoisomer thereof, effective in producing the desired therapeutic response in a particular patient suffering from a disease or disorder mediated by kinase enzymes, particularly IRAK or IRAK4 enzyme. Particularly, the term "therapeutically effective amount" includes the amount of the compound of formula (I) or a pharmaceutically acceptable salt or a stereoisomer thereof, when administered, that induces a positive modification in the disease or disorder to be treated or is sufficient to prevent development of, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed and the particular pharmaceutically acceptable carrier utilized.

In one embodiment, the present invention provides the compound of formula (I);

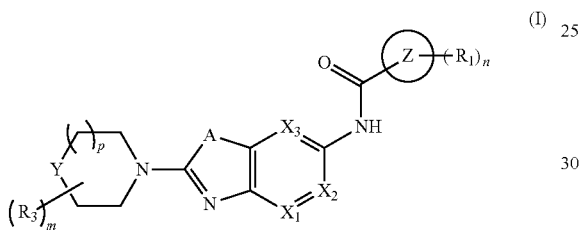

or a pharmaceutically acceptable salt or a stereoisomer thereof;
wherein,
$X_1$ and $X_3$ independently are CH or N; $X_2$ is $CR_2$ or N; provided one and not more than one of $X_1$, $X_2$ or $X_3$ is N;
A is O or S;
Y is —$CH_2$— or O;
Ring Z is aryl or heterocyclyl;
$R_1$, at each occurrence, is independently halo or optionally substituted heterocyclyl; wherein the substituent is alkyl, alkoxy, aminoalkyl, halo, hydroxyl, hydroxyalkyl or —$NR_aR_b$;
$R_2$ is hydrogen, optionally substituted cycloalkyl, optionally substituted aryl, optionally substituted heterocyclyl or —$NR_aR_b$; wherein the substituent is alkyl, amino, halo or hydroxyl;
$R_3$, at each occurrence, is alkyl or hydroxyl;
$R_a$ and $R_b$ are independently hydrogen, alkyl, acyl or heterocyclyl;
'm' and 'n' are independently 0, 1 or 2;
'p' is 0 or 1.

In one embodiment, the compound of formula (I) or a pharmaceutically acceptable salt or a stereoisomer thereof, wherein the group

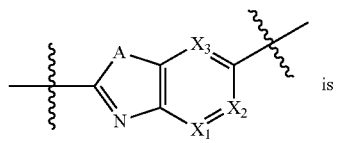 is

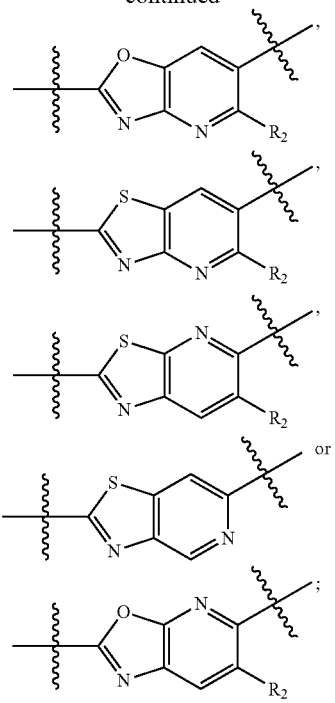

wherein $R_2$ are as defined in compound of formula (I).

In another embodiment, the compound of formula (I) or a pharmaceutically acceptable salt or a stereoisomer thereof, wherein the Ring Z is aryl or 5- or 6-membered heterocyclyl.

In another embodiment, the compound of formula (I) or a pharmaceutically acceptable salt or a stereoisomer thereof, wherein the Ring Z is phenyl, furanyl, thienyl, pyrrolyl, pyrazolyl, imidazolyl, oxazolyl, isoxazolyl, thiazolyl, isothiazolyl, 1H-tetrazolyl, oxadiazolyl, triazolyl, pyridyl, pyrimidinyl, pyrazinyl, pyridazinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl or dihydropyranyl; each of which is optionally substituted with alkyl, alkoxy, halo, hydroxyl, hydroxyalkyl or —$NR_aR_b$; $R_a$ and $R_b$ are independently are hydrogen, alkyl or acyl.

In another embodiment, the compound of formula (I) or a pharmaceutically acceptable salt or a stereoisomer thereof, wherein the Ring Z is phenyl, oxazolyl, furanyl, thienyl or pyridyl; each of which is optionally substituted with one or more $R_1$.

In another embodiment, the compound of formula (I) or a pharmaceutically acceptable salt or a stereoisomer thereof, wherein

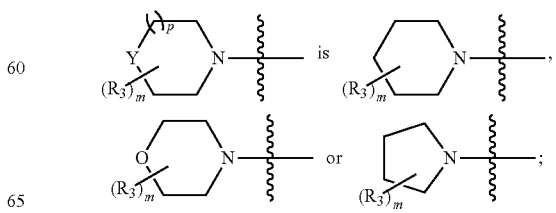

wherein R₃ and 'm' are defined in compound of formula (I).

In another embodiment, the compound of formula (I) is a compound of formula (IA):

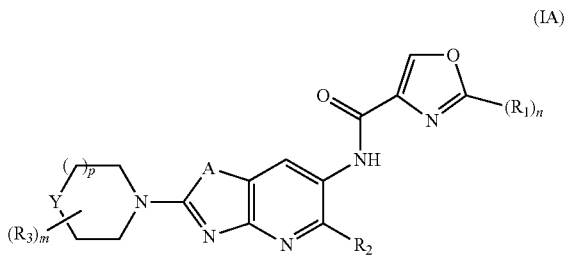

(IA)

or a pharmaceutically acceptable salt or a stereoisomer thereof;
wherein, A, Y, R₁, R₂, R₃, 'm', 'p' and 'n' are same as defined in compound of formula (I).

In another embodiment, the compound of formula (I) is a compound of formula (IB):

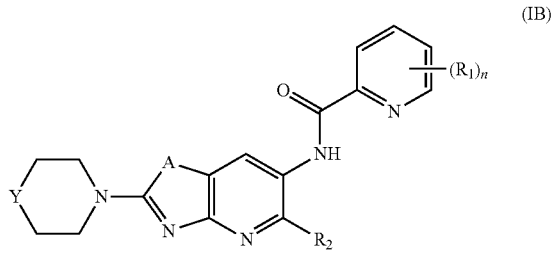

(IB)

or a pharmaceutically acceptable salt or a stereoisomer thereof;
wherein, A, Y, R₁, R₂ and 'n' are same as defined in compound of formula (I).

In yet another embodiment, the compound of formula (I) is a compound of formula (IC):

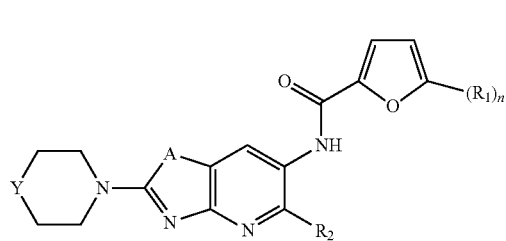

(IC)

or a pharmaceutically acceptable salt or a stereoisomer thereof;
wherein, A, Y, R₁, R₂, R₃ and 'n' are same as defined compounds of formula (I).

The embodiments below are illustrative of the present invention and are not intended to limit the claims to the specific embodiments exemplified.

According to one embodiment, specifically provided are compounds of formula (I) or (IA) or (IB) or (IC), wherein Y is O or $CH_2$.

According to one embodiment, specifically provided are compounds of formula (I) wherein R₁ is optionally substituted heterocyclyl; wherein the substituent is alkyl, alkoxy, aminoalkyl, halo, hydroxyl, hydroxyalkyl or —$NR_aR_b$; $R_a$ and $R_b$ are independently hydrogen, alkyl or acyl.

According to one embodiment, specifically provided are compounds of formula (I) wherein R₁ is pyridyl, pyrazolyl, pyrrolidinyl or piperidinyl; each of which is optionally substituted with alkyl, alkoxy, halo, hydroxyl, hydroxyalkyl or —$NR_aR_b$; $R_a$ and $R_b$ are independently hydrogen or acyl.

According to one embodiment, specifically provided are compounds of formula (I) wherein R₂ is hydrogen.

According to one embodiment, specifically provided are compounds of formula (I) wherein R₂ is optionally substituted cycloalkyl.

According to one embodiment, specifically provided are compounds of formula (I) wherein R₂ is cyclopropyl.

According to one embodiment, specifically provided are compounds of formula (I) wherein R₂ is optionally substituted heterocyclyl; wherein the substituent is alkyl, amino, halo or hydroxyl.

According to one embodiment, specifically provided are compounds of formula (I) wherein R₂ is piperidinyl, pyrrolidinyl, morpholinyl, piperazinyl, azetidinyl, pyrazolyl, furanyl, pyridyl, azepanyl or azabicyclo[3.2.1]octanyl; wherein the substituent is alkyl, amino, halo or hydroxyl.

According to one embodiment, specifically provided are compounds of formula (I) wherein R₂ is optionally substituted aryl; wherein the substituent is halo.

According to one embodiment, specifically provided are compounds of formula (I) wherein R₂ is optionally substituted phenyl; wherein the substituent is fluoro.

According to one embodiment, specifically provided are compounds of formula (I) wherein R₂ is —$NR_aR_b$; wherein $R_a$ and $R_b$ are independently hydrogen or heterocyclyl.

According to one embodiment, specifically provided are compounds of formula (I) wherein R₂ is —$NR_aR_b$; wherein $R_a$ and $R_b$ are independently hydrogen or pyrrolidinyl.

According to one embodiment, specifically provided are compounds of formula (IA) wherein A is O or S; Y is —$CH_2$— or O; R₁ is halo, pyridyl, pyrazolyl, pyrrolidinyl each of which is optionally substituted with alkyl, alkoxy, halo, hydroxyl, hydroxyalkyl or —$NR_aR_b$; R₂ is hydrogen, optionally substituted cycloalkyl, optionally substituted aryl, optionally substituted heterocyclyl or —$NR_aR_b$; wherein the substituent is alkyl, amino, halo or hydroxyl; $R_a$ and $R_b$ are independently hydrogen or alkyl.

According to one embodiment, specifically provided are compounds of formula (IB) wherein A is O or S; Y is —$CH_2$— or O; R₁ is pyridyl, pyrazolyl, pyrrolidinyl; each of which is optionally substituted with alkyl, hydroxyl, hydroxyalkyl or —$NR_aR_b$; $R_a$ and $R_b$ are independently hydrogen; R₂ is hydrogen, optionally substituted cycloalkyl, optionally substituted aryl, optionally substituted heterocyclyl or —$NR_aR_b$; wherein the substituent is alkyl, amino, halo or hydroxyl; $R_a$ and $R_b$ are independently hydrogen, alkyl, acyl or heterocyclyl.

According to one embodiment, specifically provided are compounds of formula (IA), (IB) and (IC), wherein 'n' is 0, 1 or 2.

According to one embodiment, specifically provided are compounds of formula (IA) and (IB), wherein 'p' is 0 or 1.

According to one embodiment, specifically provided are compounds of formula (IA) and (IB), wherein 'm' is 0 or 2.

In yet further embodiment, the present invention relates to a process for preparing bicyclic heterocyclyl derivatives of formula (I).

In yet further embodiment, the present invention relates to a pharmaceutical composition, comprising at least one compound of formula (I), or a pharmaceutically acceptable salt or a stereoisomer thereof and a pharmaceutically acceptable carrier or excipient.

In further embodiment, the present invention provides a method of treating IRAK4 mediated disorders or diseases or condition in a subject comprising administering a therapeutically effective amount of a compound of formula (I).

In further embodiment, the IRAK4-mediated disorder or disease or condition is selected from the group consisting of cancer, an inflammatory disorder, an autoimmune disease, metabolic disorder, a hereditary disorder, a hormone-related disease, immunodeficiency disorders, a condition associated with cell death, a destructive bone disorder, thrombin-induced platelet aggregation, liver disease and a cardiovascular disorder.

In further embodiment, the cancer is selected the group consisting of a solid tumor, benign or malignant tumor, carcinoma of the brain, kidney, liver, stomach, vagina, ovaries, gastric tumors, breast, bladder colon, prostate, pancreas, lung, cervix, testis, skin, bone or thyroid; sarcoma, glioblastomas, neuroblastomas, multiple myeloma, gastrointestinal cancer, a tumor of the neck and head, an epidermal hyperproliferation, psoriasis, prostate hyperplasia, a neoplasia, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, papillary carcinoma, seminoma, melanoma; hematological malignancies selected from leukemia, diffuse large B-cell lymphoma (DLBCL), activated B-cell-like DLBCL, chronic lymphocytic leukemia (CLL), chronic lymphocytic lymphoma, primary effusion lymphoma, Burkitt lymphoma/leukemia, acute lymphocytic leukemia, B-cell pro lymphocytic leukemia, lymphoplasmacytic lymphoma, Waldenstrom's macroglobulinemia (WM), splenic marginal zone lymphoma, intravascular large B-cell lymphoma, plasmacytoma and multiple myeloma.

In further embodiment, the inflammatory disorder is selected from the group consisting of ocular allergy, conjunctivitis, keratoconjunctivitis sicca, vernal conjunctivitis, allergic rhinitis, autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, primary biliary cirrhosis, uveitis (anterior and posterior), Sjogren's syndrome, interstitial lung fibrosis, psoriatic arthritis, systemic juvenile idiopathic arthritis, nephritis, vasculitis, diverticulitis, interstitial cystitis, glomerulonephritis (e.g. including idiopathic nephrotic syndrome or minimal change nephropathy), chronic granulomatous disease, endometriosis, leptospirosis renal disease, glaucoma, retinal disease, headache, pain, complex regional pain syndrome, cardiac hypertrophy, muscle wasting, catabolic disorders, obesity, fetal growth retardation, hypercholesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma, acute lung injury, acute respiratory distress syndrome, eosinophilia, hypersensitivities, anaphylaxis, fibrositis, gastritis, gastroenteritis, nasal sinusitis, ocular allergy, silica induced diseases, chronic obstructive pulmonary disease (COPD), cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, appendicitis, atopic dermatitis, asthma, allergy, blepharitis, bronchiolitis, bronchitis, bursitis, cervicitis, cholangitis, cholecystitis, chronic graft rejection, colitis, conjunctivitis, cystitis, dacryoadenitis, dermatitis, juvenile rheumatoid arthritis, dermatomyositis, encephalitis, endocarditis, endometritis, enteritis, enterocolitis, epicondylitis, epididymitis, fasciitis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, vasculitis, vulvitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acute and chronic gout, chronic gouty arthritis, psoriasis, psoriatic arthritis, rheumatoid arthritis, Cryopyrin Associated Periodic Syndrome (CAPS) and osteoarthritis.

In further embodiment, the present invention provides a compound or a pharmaceutically acceptable salt or a stereoisomer thereof, for use for the treatment of a cancer, an inflammatory disorder, a an autoimmune disease, metabolic disorder, a hereditary disorder, a hormone-related disease, immunodeficiency disorders, a condition associated with cell death, a destructive bone disorder, thrombin-induced platelet aggregation, liver disease and a cardiovascular disorder.

In further embodiment, the present invention relates to a use of the compound of formula (I), or a pharmaceutically acceptable salt or a stereoisomer thereof, in the manufacture of a medicament for the treatment of a cancer, an inflammatory disorder, a an autoimmune disease, metabolic disorder, a hereditary disorder, a hormone-related disease, immunodeficiency disorders, a condition associated with cell death, a destructive bone disorder, thrombin-induced platelet aggregation, liver disease and a cardiovascular disorder.

In further embodiment, the neurodegenerative disease is selected from the group consisting of Alzheimer's disease, Parkinson's disease, amyotrophic lateral sclerosis, Huntington's disease, cerebral ischemia and neurodegenerative disease caused by traumatic injury, glutamate neurotoxicity, hypoxia, epilepsy and graft versus host disease.

An embodiment of the present invention provides the IRAK4 inhibitor compounds according to formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. Moreover, by utilizing the procedures described in detail, one of ordinary skill in the art can prepare additional compounds of the present invention claimed herein. All temperatures are in degrees Celsius (° C.) unless otherwise noted.

In a further embodiment, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compounds are replaced by an atom having the atomic mass or mass number different from the predominant atomic mass or mass number usually found in nature for the atom. All isotopes of any particular atom or element as specified are contemplated within the scope of the compounds of the invention and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically labeled compounds of the present inventions can generally be prepared by following procedures analogous to those disclosed in the Schemes and/or in the Examples herein below, by substituting an isotopically labeled reagent for a non-isotopically labeled reagent.

The MS (Mass Spectral) data provided in the examples were obtained using the equipments—

API 2000 LC/MS/MS/Triplequad,
Agilent (1100) Technologies/LC/MS/DVL/Singlequad and
Shimadzu LCMS-2020/Singlequad.

The NMR data provided in the examples were obtained using the equipment—'$^{1}$H-NMR: Varian—300,400 and 600 MHz.

The abbreviations used in the entire specification may be summarized herein below with their particular meaning.

° C. (degree Celsius); δ (delta); % (percentage); Ac$_2$O (Acetic anhydride); (Boc)$_2$O (boc anhydride); bs (Broad singlet); CDCl$_3$ (Deuteriated chloroform); CH$_2$Cl$_2$/DCM (Dichloromethane); DMF (Dimethyl formamide); DMSO (Dimethyl sulphoxide); DIPEA/DIEA (N, N-Diisopropyl ethylamine); DAST (Diethylaminosulfur trifluoride); DMAP (Dimethyl amino pyridine); DMSO-d$_6$ (Deuteriated DMSO); d (Doublet); dd (Doublet of doublet); EDCI. HCl (1-(3-Dimethyl aminopropyl)-3-carbodiimide hydrochloride); EtOAc (Ethyl acetate); EtOH (Ethanol); Fe (Iron powder); g (gram); H or H$_2$ (Hydrogen); H$_2$O (Water); HATU (1-[Bis(dimethylamino)methylene]-1H-1,2,3-triazolo[4,5-b]pyridinium 3-oxid hexafluorophosphate); HOBt (1-Hydroxy benzotriazole); H$_2$SO$_4$ (Sulphuric acid); HCl (Hydrochloric acid or Hydrochloride salt); h or hr (Hours); Hz (Hertz); HPLC (High-performance liquid chromatography); J (Coupling constant); K$_2$CO$_3$ (Potassium carbonate); KOAc (Potassium Acetate); KNO$_3$ (Potassium nitrate); LiOH (Lithium hydroxide); NaHMDS (Sodiumbis(trimethylsilyl)amide); MeOH/CH$_3$OH (Methanol); mmol (Millimol); M (Molar); ml (Millilitre); mg (Milli gram); m (Multiplet); mm (Millimeter); MHz (Megahertz); MS (ES) (Mass spectroscopy-electro spray); min (Minutes); NaH (Sodium hydride); NaHCO$_3$ (Sodium bicarbonate); Na$_2$SO$_4$ (Sodium sulphate); NH$_4$Cl (Ammonium Chloride); N$_2$ (Nitrogen); NMR (Nuclear magnetic resonance spectroscopy); Pd(PPh$_3$)$_2$Cl$_2$ (Bis(triphenylphosphine)palladium(II) dichloride); Pd(OAc)$_2$ (Palladium diacetate); Pd(dppf)Cl$_2$ (1,1'-Bis(diphenylphosphino)ferrocene) palladium(II) dichloride; RT (Room Temperature); s (Singlet); TBAF (Tetra-n-butylammonium fluoride); TEA (Triethylamine); TFA (Trifluoroacetic acid); TLC (Thin Layer Chromatography); THF (Tetrahydrofuran); TFA (Trifluoro acetic acid); t (Triplet); and Zn(CN)$_2$ (Zinc Cyanide).

Compounds of this invention may be made by synthetic chemical processes, examples of which are shown herein. It is meant to be understood that the order of the steps in the processes may be varied, that reagents, solvents and reaction conditions may be substituted for those specifically mentioned and that vulnerable moieties may be protected and deprotected, as necessary.

A general approach for the synthesis of some of the compounds of general formula (ix) is depicted in below schemes. As used herein the below schemes the terms Z, Y, R$_1$, R$_2$, R$_3$, m, n and p represents all the possible substitutions as disclosed in formula (I).

SCHEME 1

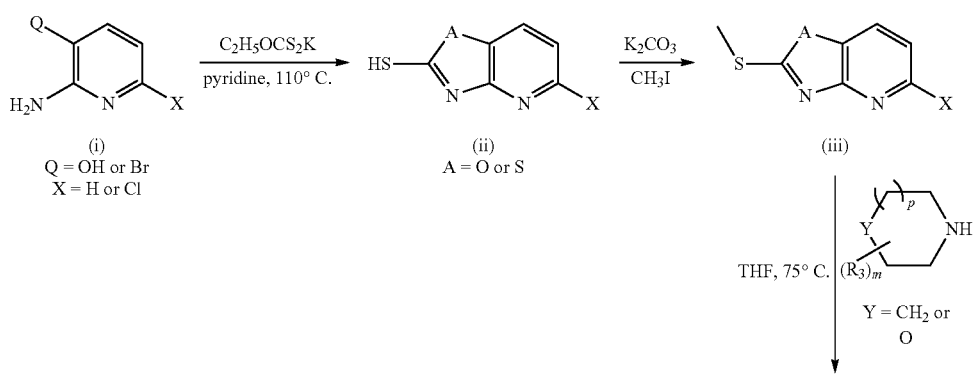

-continued

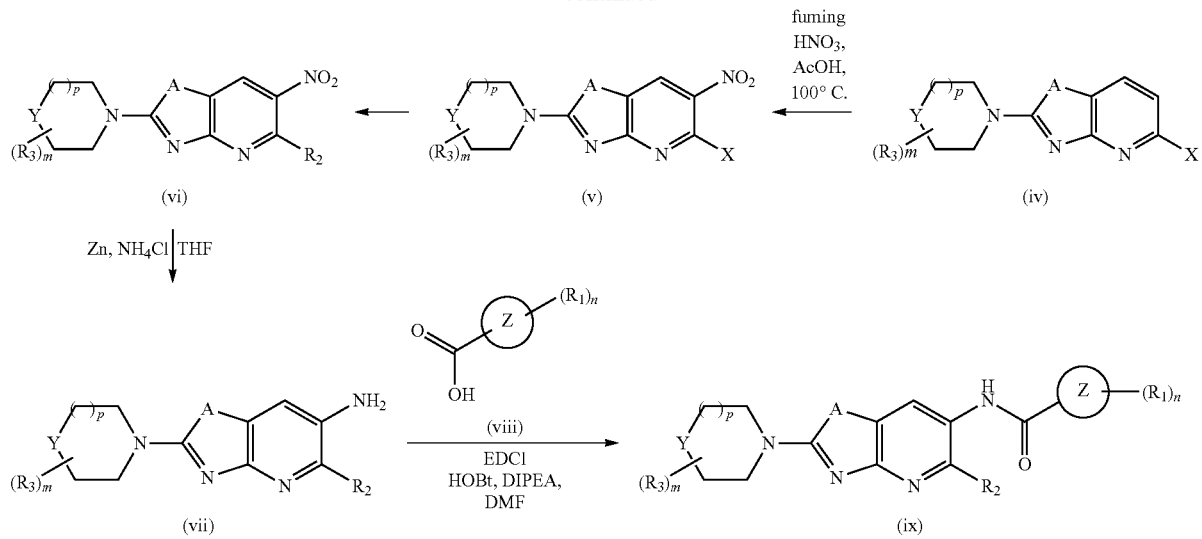

The first general approach for the synthesis of compounds of general formula (ix) is depicted in scheme-1. Compound of formula (ii) can be obtained from compound of formula (i) by reacting with potassium ethyl xanthate in appropriate solvent like pyridine at a higher temperature. Compound of formula (ii) on alkylation with methyl iodide using base like potassium carbonate can give compound of formula (iii) can be subjected to nucleophilic displacement with suitable nucleophile to give compound of formula (iv). Compound of formula (iv) on nitration can give compound of formula (v). Compound of formula (v) can be subjected to Suzuki reaction to give compound of formula (vi) which on reduction with suitable reducing reagents like Zn and ammonium chloride can give compound of formula (vii). Compound of formula vii can be subjected to Amide coupling with a suitable acid of compound of formula (viii) by using a standard amide coupling reagent known in the literature to give compound of formula (ix).

INTERMEDIATES

Intermediate 1: Synthesis of tert-butyl (5-(4,4,5,5-tetramethyl-1,3,2-dioxaborolan-2-yl)pyridin-2-yl)carbamate

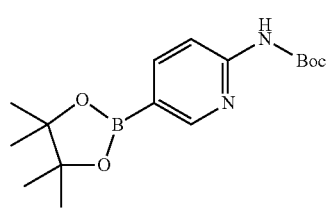 [SMILES: CC(C)(C)OC(=O)Nc1ccc(B2OC(C)(C)C(C)(C)O2)cn1]

Step 1: Preparation of tert-butyl (5-bromopyridin-2-yl)carbamate

To a solution of 5-bromopyridin-2-amine (5.0 g, 28.901 mmol) in DCM (50 mL) was added DMAP (5.28 g, 43.351 mmol) and Boc anhydride (7.56 g, 34.682 mmol) and stirred at RT for overnight. The solvent was distilled out and purified by 60-120 silica gel column chromatography using 30% ethyl acetate in hexane as eluent to obtain the title compound (5.5 g, 69.62%).

$^1$HNMR (CDCl$_3$, 300 MHz): δ 8.327-8.320 (d, 1H), 8.10 (bs, 1H), 7.92-7.89 (d, 1H), 7.76-7.73 (dd, 1H), 1.55 (s, 9H). LCMS: m/z: 217.0 (M-Boc)$^+$.

Step 2: Preparation of tert-butyl (5-(4,4,5,5-tetramethyl-1,3,2-dioxaborolan-2-yl)pyridin-2-yl)carbamate In a sealed tube, tert-butyl (5-bromopyridin-2-yl)carbamate (5.0 g, 0.18315 mmol), 4,4,4',4',5,5,5',5'-octamethyl-2,2'-bi(1,3,2-dioxaborolane) (6.02 g, 23.8 mmol) and potassium acetate (5.38 mg, 54.945 mmol) were taken in 1,4-dioxane (50 mL) and purged argon for 10 min. Added Pd(dppf)Cl$_2$ (669 mg, 0.915 mmol) and heated at 100° C. for 2 h. The solvent was distilled out and purified by 60-120 silica gel column chromatography using 40% ethyl acetate in hexane as eluent to obtain the title compound (5.0 g, 85.32%).

Intermediate 2: Synthesis of tert-butyl (6-carbamoyl-[2,3'-bipyridin]-6'-yl)carbamate

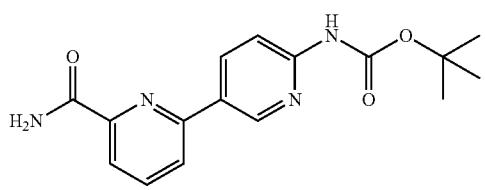 [SMILES: CC(C)(C)OC(=O)Nc1ccc(-c2cccc(C(N)=O)n2)cn1]

Step 1: Preparation of 6-bromopicolinamide

Using the same reaction conditions as described in step 6 of example 1, 6-bromopicolinic acid (2 g, 9.9 mmol) was coupled with ammonium chloride (787 mg, 14.851 mmol) using EDCI·HCl (2.8 g, 14.851 mmol), HOBt (2.0 g, 14.851 mmol) and DIPEA (3.8 g, 29.750 mmol) in DMF (10 mL) to get the crude product. The resultant crude was purified using 60-120 silica-gel column chromatography and compound was eluted using 50% ethyl acetate in hexane as eluent to afford the title compound (2.0 g, 100%).

$^1$HNMR (CDCl$_3$, 300 MHz): δ 8.18-8.16 (d, 1H), 7.7.63-7.5656-7.63 (m, 2H), 5.80-5.60 (bs, 2H).

Step 2: Preparation of tert-butyl (6-carbamoyl-[2,3'-bipyridin]-6'-yl)carbamate Using the same reaction conditions as described in step 7 of example 1, 6-bromopicolinamide (2.0 g, 9.95 mmol) was coupled with tert-butyl (5-(4,4,5,5-tetramethyl-1,3,2-dioxaborolan-2-yl)pyridin-2-yl)carbamate (intermediate 1) (3.8 g, 11.94 mmol) using sodium carbonate (3.2 g, 29.85 mmol) and Pd(PPh$_3$)$_2$Cl$_2$ (363 mg, 0.5 mmol) in 1,2-dimethoxyethane (10 mL) to get the crude product. The resultant crude was purified by 60-120 silica gel column chromatography using 2% methanol in DCM as eluent to obtain the title compound (2.8 g, 90.3%).

$^1$HNMR (CDCl$_3$, 300 MHz): δ 8.908-8.901 (d, 1H), 8.30-8.26 (dd, 1H), 8.18-8.16 (d, 1H), 8.09-8.06 (d, 1H), 7.97-7.68 (m, 3H), 7.26 (s, 1H), 5.70-5.60 (s, 1H), 1.55 (s, 9H). LCMS: m/z: 259.1 (de-t-butyl).$^-$

Intermediate 3: Synthesis of 6-(1-(tetrahydro-2H-pyran-2-yl)-1H-pyrazol-4-yl)picolinic Acid

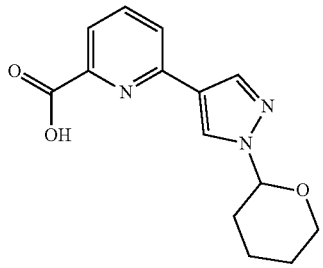 [SMILES: O=C(O)c1cccc(-c2cnn(C3CCCCO3)c2)n1]

Step 1: Preparation of methyl 6-(1-(tetrahydro-2H-pyran-2-yl)-1H-pyrazol-4-yl)picolinate Using the same reaction conditions as described in step 7 of example 1, methyl 6-bromopicolinate (900 mg, 4.166 mmol) was coupled with 1-(tetrahydro-2H-pyran-2-yl)-4-(4, 4,5,5-tetramethyl-1,3,2-dioxaborolan-2-yl)-1H-pyrazole (1.39 g, 5 mmol) using sodium carbonate (1.324 g, 12.49 mmol) and Pd(PPh$_3$)$_2$Cl$_2$ (339 mg, 0.416 mmol) in 1,2-dimethoxyethane (10 mL) to get the crude product. The resultant crude was purified by 60-120 silica gel column chromatography using 30% ethyl acetate in hexane as eluent to obtain the title compound (450 mg, 38%). LCMS: m/z: 288.1 (M+1)$^+$.

Step 2: Preparation of 6-(1-(tetrahydro-2H-pyran-2-yl)-1H-pyrazol-4-yl)picolinic Acid A solution of methyl 6-(1-(tetrahydro-2H-pyran-2-yl)-1H-pyrazol-4-yl)picolinate (450 mg, 1.567 mmol) and lithium hydroxide (500 mg, 7.839 mmol) in THF methanol/ H$_2$O (10 mL/4 ml/1 ml) was stirred at RT for 2 hrs. The reaction mixture was acidified with citric acid and extracted with DCM (2×100 mL) dried over sodium sulphate and distilled out the solvent to get the title compound (300 mg, 70%). LCMS: m/z: 274.3 (M+1)$^+$.

Intermediate 4: Synthesis of 6-(1-methyl-1H-pyrazol-4-yl)picolinic Acid

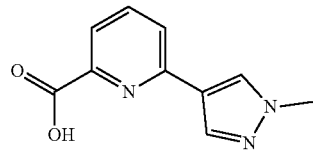

Step 1: Preparation of methyl 6-(1-methyl-1H-pyrazol-4-yl)picolinate

Using the same reaction conditions as described in step 7 of example 1, methyl 6-bromopicolinate (3.5 g, 16.28 mmol) was coupled with 1-methyl-4-(4,4,5,5-tetramethyl-1,3,2-dioxaborolan-2-yl)-1H-pyrazole (4.06 g, 19.53 mmol) using sodium carbonate (5.177 g, 48.846 mmol) and Pd(dppf)Cl$_2$ (1.328 g, 1.628 mmol) in 1,2-dimethoxyethane (20 mL) to get the crude product. The resultant crude was purified by 60-120 silica gel column chromatography using 30% ethyl acetate in hexane as eluent to obtain the title compound (1.2 g, 33.9%). LCMS: m/z: 218.2 (M+1)$^+$.

Step 2: Preparation of 6-(1-methyl-1H-pyrazol-4-yl)picolinic Acid

Using the same reaction conditions as described in step 2 of intermediate 5, 6-(1-methyl-1H-pyrazol-4-yl)picolinic acid (1.2 g, 5.529 mmol) was hydrolysed using lithium hydroxide (696 mg, 16.58 mmol) in THF/methanol (8/2 mL) at RT for 2 h to obtain the title compound (900 mg, 80.3%). LCMS: m/z: 204.0 (M+1)$^+$.

Intermediate 5: Synthesis of 3-(4-(((tert-butoxycarbonyl)amino)methyl)piperidin-1-yl)-5-fluorobenzoic Acid

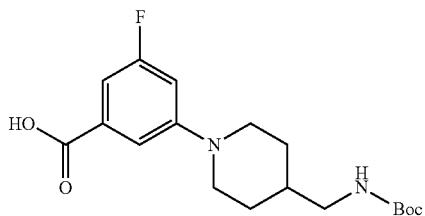 [SMILES: CC(C)(C)OC(=O)NCC1CCN(c2cc(F)cc(C(=O)O)c2)CC1]

Step 1: Preparation of methyl 3-(4-(((tert-butoxycarbonyl)amino)methyl)piperidin-1-yl)-5-fluorobenzoate Using the same reaction conditions as described in step 4 of example 12, methyl 3-bromo-5-fluorobenzoate (100 mg, 0.429 mmol) was coupled with tert-butyl (piperidin-4-ylmethyl)carbamate (110 mg, 0.515 mmol) using cesium carbonate (209 mg, 0.643 mmol), xantphos (14 mg, 0.025 mmol) and Pd$_2$(dba)$_3$ (8 mg, 0.0085 mmol) in toluene (5 mL) to get the crude product. The resultant crude was purified by 60-120 silica gel column chromatography using 2% methanol in DCM as eluent to obtain the title compound (110 mg, 70.06%). LCMS: 94.13%, m/z=367.5 (M+1)⁺.

Step 2: Preparation of 3-(4-(((tert-butoxycarbonyl)amino)methyl)piperidin-1-yl)-5-fluorobenzoic Acid A solution of methyl 3-(4-(((tert-butoxycarbonyl)amino)methyl)piperidin-1-yl)-5-fluorobenzoate (110 mg, 0.02 mmol), lithium hydroxide (5 mg, 0.104 mmol), methanol (3 mL), THF (2 mL) and water (1 mL) was stirred at RT for 1 h., acidified with 2N HCl, distilled the solvent and filtered the solid to get the crude product. This was then purified by prep HPLC to obtain the title compound (105 mg, 100%). LCMS: m/z: 353.4 (M+1)⁺.

Intermediate 6: Synthesis of 2-(4-(((tert-butoxycarbonyl)amino)methyl)piperidin-1-yl)-5-fluorobenzoic Acid

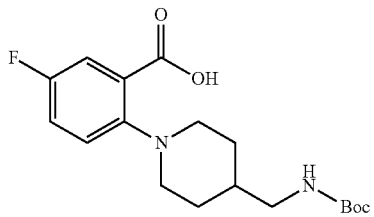 [SMILES: CC(C)(C)OC(=O)NCC1CCN(c2ccc(F)cc2C(=O)O)CC1]

Step 1: Preparation of methyl 2-(4-(((tert-butoxycarbonyl)amino)methyl)piperidin-1-yl)-5-fluorobenzoate Using the same reaction conditions as described in step 1 of example 11, methyl 2,5-difluorobenzoate (1 g, 4.6 mmol), was coupled with tert-butyl (piperidin-4-ylmethyl)carbamate (803 mg, 4.6 mmol) using potassium carbonate (1.289 mg, 9.3 mmol), in DMF (10 mL) at 90° C. overnight to get the crude product. The resultant crude was purified by 60-120 silica gel column chromatography using ethyl acetate in hexane as eluent to obtain the title compound (300 mg, 20%).

¹HNMR (DMSO-$d_6$, 400 MHz): δ 7.38-7.28 (m, 2H), 7.16-7.12 (m, 1H), 6.90-6.85 (t, 1H), 3.80 (s, 3H), 3.13-3.10 (d, 2H), 2.87-2.84 (m, 2H), 2.64-2.58 (t, 2H), 1.67-1.64 (d, 2H), 1.40 (s, 9H), 1.26-1.09 (m, 2H). LCMS: m/z: 367.3 (M+1)⁺.

Step 2: Preparation of 2-(4-(((tert-butoxycarbonyl)amino)methyl)piperidin-1-yl)-5-fluorobenzoic Acid Using the same reaction conditions as described in step 2 of intermediate 5, methyl 2-(4-(((tert-butoxycarbonyl)amino)methyl)piperidin-1-yl)-5-fluorobenzoate (300 mg, 0.819 mmol), was hydrolysed using lithium hydroxide (172 mg, 4.098 mmol) in THF/methanol/H₂O (5 mL/1 ml/0.5 ml) at RT for 2 h to obtain the title compound (220 mg, 77%).

¹HNMR (DMSO-$d_6$, 300 MHz): δ 7.86-7.83 (m, 1H), 7.74-7.70 (m, 1H), 7.55-7.54 (m, 1H), 7.01 (bs, 1H), 3.11-3.08 (m, 4H), 2.93-2.89 (t, 2H), 1.87-1.83 (d, 2H), 1.70-1.60 (bs, 1H), 1.40 (s, 9H), 1.35-1.30 (m, 2H). LCMS: m/z: 353.4 (M+1)⁺.

Intermediate 7: Synthesis of 2-(6-methoxypyridin-3-yl)oxazole-4-carboxylic Acid

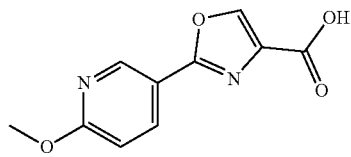 [SMILES: COc1ccc(-c2nc(C(=O)O)co2)cn1]

Step 1: Preparation of ethyl 2-(6-fluoropyridin-3-yl)oxazole-4-carboxylate

Using the same reaction conditions as described in step 7 of example 1, 2-fluoro-5-(4,4,5,5-tetramethyl-1,3,2-dioxaborolan-2-yl)pyridine (200 mg, 1.41 mmol) was coupled with ethyl 2-chlorooxazole-4-carboxylate (298 mg, 1.70 mmol) using sodium carbonate (451 mg, 4.25 mmol) and Pd(PPh₃)₄ (289 mg, 0.332 mmol) in 1,2-dimethoxyethane/water (15/3 mL) to get the crude product. The resultant crude was purified by 60-120 silica gel column chromatography using 20% ethyl acetate in hexane as eluent to obtain the title compound (200 mg, 59.8%).

Step 2: Preparation of 2-(6-methoxypyridin-3-yl)oxazole-4-carboxylic Acid

Using the same reaction conditions as described in step 2 of intermediate 5, ethyl 2-(6-fluoropyridin-3-yl)oxazole-4-carboxylate (300 mg, 0.127 mmol) was hydrolysed using lithium hydroxide (160 mg, 3.91 mmol) in THF/methanol/water (5/1/2 mL) at RT for 2 h to obtain the title compound (160 mg, 57.3%).

¹HNMR (DMSO-$d_6$, 300 MHz): δ 13.5-12.5 (bs, 1H), 8.85 (s, 1H), 8.80-8.79 (d, 1H), 8.26-8.23 (dd, 1H), 7.02-6.99 (dd, 1H), 3.95 (s, 3H). LCMS: m/z=221.1 (M+1)⁺.

Intermediate 8: Synthesis of 2-(2-methylpyridin-3-yl)oxazole-4-carboxylic Acid

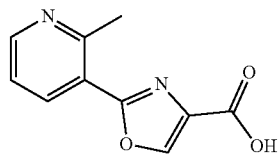

Step 1: Preparation of ethyl 2-(2-methylpyridin-3-yl)oxazole-4-carboxylate

Using the same reaction conditions as described in step 7 of example 1, 2-methyl-3-(4,4,5,5-tetramethyl-1,3,2-dioxaborolan-2-yl)pyridine (1 g, 7.09 mmol) was coupled with ethyl 2-chlorooxazole-4-carboxylate (1.86 g, 0.851 mmol) using sodium carbonate (2.25 g, 21.2 mmol) and Pd(dppf)Cl₂ (289 mg, 0.332 mmol) in 1,2-dimethoxyethane/water (30/6 mL) to get the crude product. The resultant crude was purified by 60-120 silica gel column chromatography using 20% ethyl acetate in hexane as eluent to obtain the title compound (1 g, 59.8%).

Step 2: Preparation of 2-(2-methylpyridin-3-yl)oxazole-4-carboxylic Acid

Using the same reaction conditions as described in step 2 of intermediate 5, ethyl 2-(2-methylpyridin-3-yl)oxazole-4-carboxylate (1 g, 4.3 mmol) was hydrolysed using lithium hydroxide (542 mg, 12.9 mmol) in THF/water (25/4 mL) at RT for 2 h to obtain the title compound (550 mg, 62.5%).

$^1$HNMR (DMSO-$d_6$, 400 MHz): δ 13.3 (s, 1H), 8.96 (s, 1H), 8.64-8.62 (dd, 1H), 8.32-8.03 (dd, 1H), 7.47-7.44 (q, 1H), 2.86 (s, 3H). LCMS: m/z=205.0 (M+1)$^+$.

Intermediate 9: Synthesis of 2-(2-hydroxypyridin-3-yl)oxazole-4-carboxylic Acid

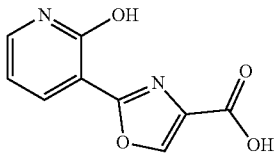 [SMILES: O=C(O)c1coc(-c2cccnc2O)n1]

Step 1: Preparation of ethyl 2-(2-fluoropyridin-3-yl)oxazole-4-carboxylate

Using the same reaction conditions as described in step 7 of example 1, (2-fluoropyridin-3-yl)boronic acid (400 mg, 2.83 mmol) was coupled with ethyl 2-chlorooxazole-4-carboxylate (596 mg, 3.40 mmol) using sodium carbonate (902 mg, 8.51 mmol) and Pd(dppf)Cl$_2$ (115 mg, 0.141 mmol) in 1,2-dimethoxyethane/water (25/4 mL) to get the crude product. The resultant crude was purified by 60-120 silica gel column chromatography using 30% ethyl acetate in hexane as eluent to obtain the title compound (400 mg, 60.6%).

$^1$HNMR (DMSO-$d_6$, 400 MHz): δ 9.11 (s, 1H), 8.64-8.59 (m, 1H), 8.48-8.47 (d, 1H), 7.62-7.59 (m, 1H), 4.38-4.33 (q, 2H), 1.35-1.32 (t, 3H).

Step 2: Preparation of 2-(2-hydroxypyridin-3-yl)oxazole-4-carboxylic Acid

Using the same reaction conditions as described in step 2 of intermediate 5, ethyl 2-(2-fluoropyridin-3-yl)oxazole-4-carboxylate (400 mg, 1.69 mmol) was hydrolysed using lithium hydroxide (213 mg, 5.07 mmol) in THF/water (10/2 mL) at RT for 2 h to obtain the title compound (250 mg, 71.6%).

$^1$HNMR (DMSO-$d_6$, 400 MHz): δ 13.3-12.9 (bs, 1H), 12.4-12.2 (s, 1H), 8.81 (s, 1H), 8.20-8.17 (dd, 1H), 7.68-7.66 (dd, 1H), 6.41-6.37 (t, 1H). LCMS: m/z=207.1 (M+1)$^+$.

Intermediate 10: Synthesis of 2-(2-hydroxypyridin-5-yl)oxazole-4-carboxylic Acid

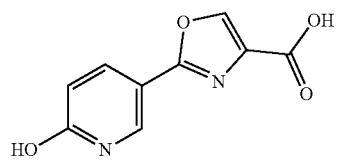 [SMILES: O=C(O)c1coc(-c2ccc(O)nc2)n1]

Using the same reaction conditions as described in step 2 of intermediate 5, ethyl 2-(6-fluoropyridin-3-yl)oxazole-4-carboxylate (product of step 1 of intermediate 7) (400 mg, 1.69 mmol) was hydrolysed using lithium hydroxide (400 mg, 10.3 mmol) in THF/water (2/2 mL) at RT for 2 h to obtain the crude title compound (300 mg). LCMS: m/z=207.1 (M+1)$^+$.

Intermediate 11: Synthesis of 2-(2-methoxypyridin-4-yl)oxazole-4-carboxylic Acid

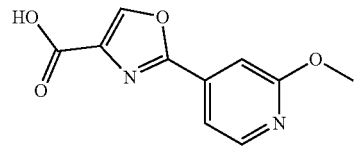 [SMILES: COc1cc(-c2nc(C(=O)O)co2)ccn1]

The title compound was prepared by using the similar conditions and reagents according to the procedure described in the synthesis of Intermediate-7.

$^1$HNMR (DMSO-$d_6$, 300 MHz): δ 8.38 (s, 1H) 8.34-8.32 (d, 1H) 7.53-7.52 (d, 1H) 7.33 (s, 1H) 3.91 (s, 3H). LCMS: m/z=221.1 (M+1)$^+$.

The below intermediates were prepared by using appropriate reagents according to the above protocol depicted in Intermediate 8.

| Intermediate No. | Structure | Characterization Data |
|---|---|---|
| 12 | 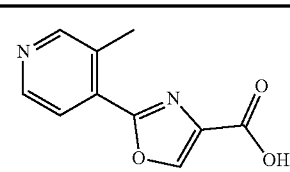 | $^1$HNMR (DMSO-$d_6$, 300 MHz): δ13.3 (bs, 1H) 8.97 (s, 1H) 8.64 (s, 1H) 8.58-8.57 (d, 1H) 7.86-7.84 (d, 1H) 2.62 (s, 3H). LCMS: m/z = 205.0 (M + 1)$^+$, HPLC: 98.44%. |

| Intermediate No. | Structure | Characterization Data |
|---|---|---|
| 13 | 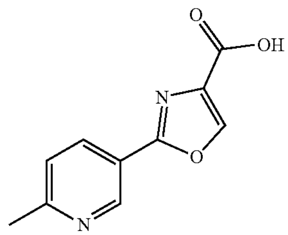 | ¹HNMR (DMSO-d₆, 300 MHz): δ 13.3 (bs, 1H) 9.03 (s, 1H) 8.88 (s, 1H) 8.24-8.20 (d, 1H) 7.46-7.43 (d, 1H) 2.54 (s, 3H). LCMS: m/z = 205.1 (M + 1)⁺, HPLC: 97.33%. |

Intermediate 14: Synthesis of (S)-2-(3-((tert-butoxycarbonyl)amino)pyrrolidin-1-yl)oxazole-4-carboxylic Acid

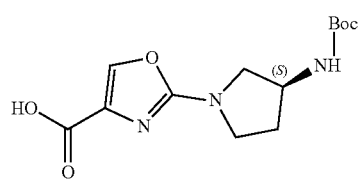

Step 1: Preparation of ethyl (S)-2-(3-((tert-butoxycarbonyl)amino)pyrrolidin-1-yl)oxazole-4-carboxylate The mixture of ethyl 2-chlorooxazole-4-carboxylate (100 mg, 0.5698 mmol), tert-butyl (S)-pyrrolidin-3-ylcarbamate (127 mg, 0.6837 mmol), DIPEA (0.284 mL, 1.4245 mmol) and DMF (5 mL) were heated at 120° C. for 2 h. The reaction mass was quenched with ice water and extracted with DCM. The solvent was distilled out to get the title compound (170 mg, 91.89%).
LCMS: m/z=270.1 (M-t-butyl+1)⁺.

Step 2: Preparation of (S)-2-(3-((tert-butoxycarbonyl)amino)pyrrolidin-1-yl)oxazole-4-carboxylic Acid Using the same reaction conditions as described in step 2 of intermediate 5, ethyl (S)-2-(3-((tert-butoxycarbonyl)amino)pyrrolidin-1-yl)oxazole-4-carboxylate (170 mg, 0.5224 mmol) was hydrolysed using lithium hydroxide (33 mg, 0.7837 mmol) in THF/methanol/water (10/1/2 mL) at RT for 12 h to obtain the title compound (150 mg, 96.77%).
LCMS: m/z=242.0 (M-t-butyl+1)⁺.

Intermediate 15: Synthesis of (S)-2-(3-((tert-butyldimethylsilyl)oxy)pyrrolidin-1-yl)oxazole-4-carboxylic Acid

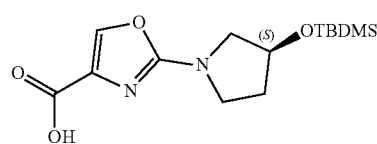

Step 1: Preparation of ethyl (S)-2-(3-hydroxypyrrolidin-1-yl)oxazole-4-carboxylate Using the same reaction conditions as described in step 1 of intermediate 14, ethyl 2-chlorooxazole-4-carboxylate (500 mg, 2.8490 mmol) was reacted with (S)-pyrrolidin-3-ol (298 mg, 3.4188 mmol) using, sodium carbonate (453 mg, 4.2735 mmol) in DMF (10 mL) to get the title compound (535 mg, 83.07%).
LCMS: m/z=227.1 (M+1)⁺.

Step 2: Preparation of ethyl (S)-2-(3-((tert-butyldimethylsilyl)oxy)pyrrolidin-1-yl)oxazole-4-carboxylate Using the same reaction conditions as described in step 2 of example 41, ethyl(S)-2-(3-hydroxypyrrolidin-1-yl)oxazole-4-carboxylate (535 mg, 2.3672 mmol) was protected using TBDMS chloride (429 mg, 2.8407 mmol), imidazole (396 mg, 5.8072 mmol) and DMAP (29 mg, 0.2367 mmol) in DMF (5 mL) at RT for 2 h to get the crude product. The resultant crude was purified by 60-120 silica gel column chromatography using 20% ethyl acetate in hexane as eluent to obtain the title compound (520 mg, 64.5%). LCMS: m/z=341.2 (M+1)⁺.

Step 3: Preparation of (S)-2-(3-((tert-butyldimethylsilyl)oxy)pyrrolidin-1-yl)oxazole-4-carboxylic Acid Using the same reaction conditions as described in step 2 of intermediate 5, ethyl (S)-2-(3-((tert-butyldimethylsilyl)oxy)pyrrolidin-1-yl)oxazole-4-carboxylate (520 mg, 1.5294 mmol) was hydrolysed using lithium hydroxide (97 mg, 2.2941 mmol) in THF/methanol/water (10/5/5 mL) at RT for 2 h to obtain the title compound (350 mg, 73.37%).
¹HNMR (CDCl₃, 400 MHz): δ 7.88 (s, 1H), 4.55-4.50 (s, 1H), 3.75-3.60 (m, 3H), 3.5-3.4 (d, 1H), 2.05-1.90 (m, 2H), 0.9 (s, 9H). LCMS: m/z=313.1 (M+1)⁺.

Intermediate 16: Synthesis of 2-(1-(tetrahydro-2H-pyran-2-yl)-1H-pyrazol-4-yl)oxazole-4-carboxylic Acid

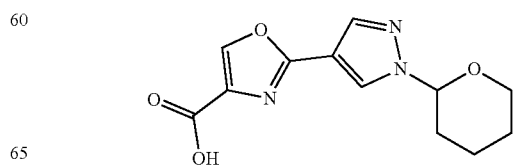

Step 1: Preparation of ethyl 2-(1-(tetrahydro-2H-pyran-2-yl)-1H-pyrazol-4-yl)oxazole-4-carboxylate Using the same reaction conditions as described in step 7 of example 1, 1-(tetrahydro-2H-pyran-2-yl)-4-(4,4,5,5-tetramethyl-1,3,2-dioxaborolan-2-yl)-1H-pyrazole (273 mg, 0.982 mmol) was coupled with ethyl 2-chlorooxazole-4-carboxylate (125 mg, 0.892 mmol) using sodium carbonate (283 mg, 2.676 mmol) and Pd(dppf)Cl$_2$ (65 mg, 0.089 mmol) in 1,2-dimethoxyethane/water (5/1 mL) to get the crude product. The resultant crude was purified by 60-120 silica gel column chromatography using 20% ethyl acetate in hexane as eluent to obtain the title compound (200 mg, 43.9%). LCMS: m/z=292.3 (M+1)$^+$.

Step 2: Preparation of 2-(1-(tetrahydro-2H-pyran-2-yl)-1H-pyrazol-4-yl)oxazole-4-carboxylic Acid Using the same reaction conditions as described in step 2 of intermediate 5, ethyl 2-(1-(tetrahydro-2H-pyran-2-yl)-1H-pyrazol-4-yl)oxazole-4-carboxylate (200 mg, 0.784 mmol) was hydrolysed using lithium hydroxide (50 mg, 1.176 mmol) in THF/methanol/water (5/2/1 mL) at RT for 1 h to obtain the title compound (206 mg, 100%). LCMS: m/z=263.9 (M+1)$^+$.

Intermediate 17: Synthesis of 5-(2-methylpyridin-4-yl)thiophene-2-carboxylic Acid

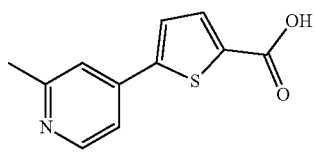

Step 1: Preparation of methyl 5-(2-methylpyridin-4-yl)thiophene-2-carboxylate Using the similar reaction conditions as described in step 7 of example 1, methyl 5-bromothiophene-2-carboxylate (460 mg, 2.08 mmol) was coupled with 2-methyl-4-(4,4,5,5-tetramethyl-1,3,2-dioxaborolan-2-yl)pyridine (680 mg, 3.10 mmol) using potassium carbonate (576 mg, 4.17 mmol) TBAB (100 mg, 0.310 mmol) and Pd(dppf)Cl$_2$ (108 mg, 0.1538 mmol) in dioxane/water (10/3 mL) to get the crude product. The resultant crude was purified by 60-120 silica gel column chromatography using 50% ethyl acetate in hexane as eluent to obtain the title compound (552 mg, 91%). LCMS: m/z=234.0 (M+1)$^+$.

Step 2: Preparation of 5-(2-methylpyridin-4-yl)thiophene-2-carboxylic Acid

Using the same reaction conditions as described in step 2 of intermediate 5, 5-(2-methylpyridin-4-yl)thiophene-2-carboxylate (550 mg, 2.36 mmol) was hydrolysed using lithium hydroxide (200 mg, 4.72 mmol) in THF/methanol/water (10/5/5 mL) at 50° C. for 15 min to obtain the title compound (501 mg, 97%). LCMS: m/z=220.0 (M+1)$^+$.

Intermediate 18: Synthesis of 5-(2-methylpyridin-4-yl)furan-2-carboxylic Acid

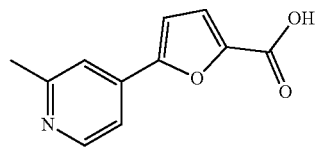

Step 1: Preparation of methyl 5-(2-methylpyridin-4-yl)furan-2-carboxylate

Using the similar reaction conditions as described in step 7 of example 1, methyl 5-bromofuran-2-carboxylate (214 mg, 1.0406 mmol) was coupled with 2-methyl-4-(4,4,5,5-tetramethyl-1,3,2-dioxaborolan-2-yl)pyridine (340 mg, 1.561 mmol) using potassium carbonate (288 mg, 2.08 mmol) TBAB (50 mg, 0.156 mmol) and Pd(dppf)Cl$_2$ (54 mg, 0.078 mmol) in dioxane/water (10/3 mL) to get the crude product. The resultant crude was purified by 60-120 silica gel column chromatography using 50% ethyl acetate in hexane as eluent to obtain the title compound (301 mg, 89%). LCMS: 100%, m/z=217.8 (M+1)$^+$.

Step 2: Preparation of 5-(2-methylpyridin-4-yl)furan-2-carboxylic Acid

Using the same reaction conditions as described in step 2 of intermediate 5, methyl 5-(2-methylpyridin-4-yl)furan-2-carboxylate (300 mg, 1.38 mmol) was hydrolysed using lithium hydroxide (116 mg, 2.76 mmol) in THF/methanol/water (10/5/5 mL) at 50° C. for 0.25 h to obtain the title compound (260 mg, 92.8%). LCMS: 100%, m/z=204.1 (M+1)$^+$.

Intermediate 19: Synthesis of 2-(2-((tert-butoxycarbonyl)amino)pyridin-4-yl)oxazole-4-carboxylic Acid

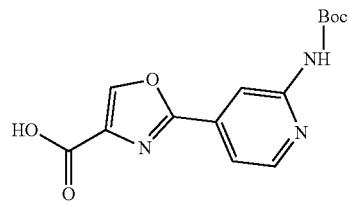 [SMILES: CC(C)(C)OC(=O)Nc1cc(-c2nc(C(=O)O)co2)ccn1]

Step 1: Preparation of ethyl 2-(2-((tert-butoxycarbonyl)amino)pyridin-4-yl)oxazole-4-carboxylate Using the same reaction conditions as described in step 7 of example 1, tert-butyl (5-(4,4,5,5-tetramethyl-1,3,2-dioxaborolan-2-yl)pyridin-2-yl)carbamate (487 mg, 1.5223 mmol) was coupled with ethyl 2-chlorooxazole-4-carboxylate (165 mg, 1.1710 mmol) using sodium carbonate (373 mg, 3.5131 mmol) and Pd(dppf)Cl$_2$ (43 mg, 0.0585 mmol) in 1,2-dimethoxyethane/water (10/5 mL) to get the crude product. The resultant crude was purified by 60-120 silica gel column chromatography using 30% ethyl acetate in hexane as eluent to obtain the title compound (200 mg, 43.9%). LCMS: m/z=278.0 (M+1-t-butyl)⁺.

Step 2: Preparation of 2-(2-((tert-butoxycarbonyl)amino)pyridin-4-yl)oxazole-4-carboxylic Acid Using the same reaction conditions as described in step 2 of intermediate 5, ethyl 2-(2-((tert-butoxycarbonyl)amino)pyridin-4-yl)oxazole-4-carboxylate (145 mg, 0.4349 mmol) was hydrolysed using 10% sodium hydroxide solution (1 mL) in THF/methanol/water (10/5/2 mL) at RT for 10 min to obtain the title compound (75 mg, 56.81%). LCMS: m/z: 250.0 (M+1-de-t-butyl)⁺.

Intermediate 20: Synthesis of 2-(2-acetamidopyridin-4-yl)oxazole-4-carboxylic Acid

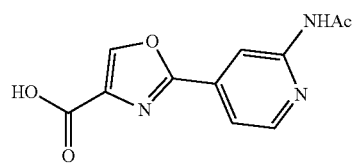 [SMILES: CC(=O)Nc1cc(-c2nc(C(=O)O)co2)ccn1]

Step 1: Preparation of ethyl 2-(2-acetamidopyridin-4-yl)oxazole-4-carboxylate

Using the same reaction conditions as described in step 7 of example 1, N-(5-(4,4,5,5-tetramethyl-1,3,2-dioxaborolan-2-yl)pyridin-2-yl)acetamide (2.78 g, 10.04 mmol) was coupled with ethyl 2-chlorooxazole-4-carboxylate (1 g, 7.09 mmol) using sodium carbonate (106 mg, 21.2 mmol) and Pd(dppf)Cl₂ (259 mg, 0.354 mmol) in 1,2-dimethoxyethane/water (30/5 mL) to get the crude product. The resultant crude was purified by 60-120 silica gel column chromatography using 50% ethyl acetate in hexane as eluent to obtain the title compound (680 mg, 36%). LCMS: m/z: 276.3 (M+1)⁺.

Step 2: Preparation of 2-(2-acetamidopyridin-4-yl)oxazole-4-carboxylic Acid

Using the same reaction conditions as described in step 2 of intermediate 5, ethyl 2-(2-acetamidopyridin-4-yl)oxazole-4-carboxylate (500 mg, 1.81 mmol) was hydrolysed using lithium hydroxide (84 mg, 2 mmol) in THF/methanol/water (10/l/5 mL) at RT for 4 h to obtain the title compound (360 mg, 81.08%). LCMS: m/z: 248.1 (M+1)⁺.

Intermediate 21: Synthesis of 2-(2-aminopyridin-4-yl)oxazole-4-carboxylic Acid

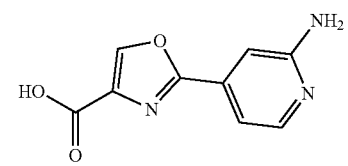 [SMILES: Nc1cc(-c2nc(C(=O)O)co2)ccn1]

Using the same reaction conditions as described in step 2 of intermediate 5, ethyl 2-(2-acetamidopyridin-4-yl)oxazole-4-carboxylate (product of step 1 of intermediate 20) (900 mg, 3.27 mmol) was hydrolysed using lithium hydroxide (329 mg, 7.85 mmol) in THF/methanol/water (30/1/5 mL) at RT for 4 h to obtain the title compound (750 mg, 96%).

LCMS: m/z: 206.2 (M+1)⁺.

Intermediate 22: Synthesis of 5-(2-acetamidopyridin-4-yl)furan-2-carboxylic Acid

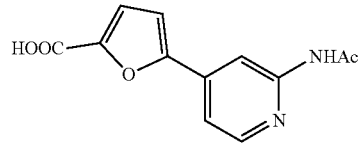 [SMILES: CC(=O)Nc1cc(-c2ccc(C(=O)O)o2)ccn1]

Step 1: Preparation of methyl 5-(2-acetamidopyridin-4-yl)furan-2-carboxylate

Using the same reaction conditions as described in step 7 of example 1, N-(5-(4,4,5,5-tetramethyl-1,3,2-dioxaborolan-2-yl)pyridin-2-yl)acetamide (1.91 g, 7.317 mmol) was coupled with methyl 5-bromofuran-2-carboxylate (1 g, 4.87 mmol) using sodium carbonate (1.54 g, 14.61 mmol) and Pd(dppf)Cl₂ (178 mg, 0.243 mmol) in 1,2-dimethoxyethane/water (20/4 mL) at 80° C. for 3 h to get the crude product. The resultant crude was purified by flash chromatography using 35% ethyl acetate in hexane as eluent to obtain the title compound (451 mg, 35.6%). LCMS: m/z: 261.1 (M+1)⁺.

Step 2: Preparation of 5-(2-acetamidopyridin-4-yl)furan-2-carboxylic Acid

Using the same reaction conditions as described in step 2 of intermediate 5, ethyl 2-(2-acetamidopyridin-4-yl)oxazole-4-carboxylate (450 mg, 1.73 mmol) was hydrolysed using lithium hydroxide (73 mg, 1.73 mmol) in THF/methanol/water (10/5/5 mL) at RT for 2 h to obtain the title compound (396 mg, 93.17%). LCMS: m/z: 247.2 (M+1)⁺.

Intermediate 23: Synthesis of 2-(2-methylpyridin-4-yl)oxazole-4-carboxamide

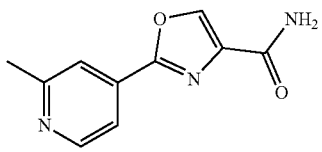

To a solution of 2-(2-methylpyridin-4-yl)oxazole-4-carboxylic acid (WO2011/043371) (0.25 g, 1.22 mmol) in DMF were added ammonium chloride (0.131 g, 2.45 mmol), EDCI·HCl (0.351 g, 1.83 mmol), HOBT (0.248 g, 1.83 mmol) and DIPEA (0.790 g, 6.12 mmol). The reaction mixture was stirred for 12 h at room temperature and was diluted with EtOAc, washed with brine and dried over Na₂SO₄ and concentrated to afford the title compound (0.180 g, 75%) as a white solid.

$^1$H NMR (300 MHz, CDCl$_3$): δ 8.65 (d, 1H), 7.81-7.79 (m, 2H), 7.72 (d, 1H), 7.65 (s, 1H), 2.55 (s, 3H); MS (ES): m/z: 204 (M+1)+; HPLC: 93.5%

EXAMPLES

Example 1

6'-amino-N-(2-morpholinooxazolo[4,5-b]pyridin-6-yl)-[2,3'-bipyridine]-6-carboxamide

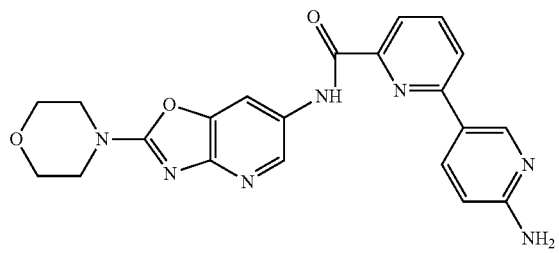 [SMILES: Nc1ccc(-c2cccc(C(=O)Nc3cnc4nc(N5CCOCC5)oc4c3)n2)cn1]

Step 1: Preparation of oxazolo[4,5-b]pyridine-2-thiol

A solution of 2-aminopyridin-3-ol (5.0 g, 45.45 mmol) and potassium ethyl xanthate (8.0 g, 49.99 mmol) in pyridine (50 mL) was heated at 110° C. overnight. The reaction mixture was cooled to 0° C., added ice water and acidified with Conc. HCl. The solid was filtered and dried under vacuum to afford the title compound (6.0 g, 86.95%).
$^1$HNMR (DMSO-d$_6$, 300 MHz): δ 8.24-8.22 (d, 1H), 7.90-7.87 (d, 1H), 7.30-7.26 (m, 1H).
LCMS: m/z: 153.0 (M+1)$^+$.

Step 2: Preparation of 2-(methylthio)oxazolo[4,5-b]pyridine

To a stirred solution of oxazolo[4,5-b]pyridine-2-thiol (3.0 g, 19.73 mmol) in ethyl acetate (30 mL) was added potassium carbonate (3.81 g, 27.62 mmol) and methyl iodide (3.08 g, 21.71 mmol) and stirred at RT overnight. The reaction mixture was diluted with water (100 ml), extracted with ethyl acetate (2×50 mL), dried over sodium sulphate and concentrated to afford the title compound (3.0 g, 93.75%).
$^1$HNMR (CDCl$_3$, 300 MHz): δ 8.46-8.44 (d, 1H), 7.71-7.68 (d, 1H), 7.20-7.15 (m, 1H), 2.81 (s, 3H). LCMS: m/z: 167.0 (M+1)$^+$.

Step 3: Preparation of 2-morpholinooxazolo[4,5-b]pyridine

To a solution of 2-(methylthio)oxazolo[4,5-b]pyridine (2.0 g, 12.12 mmol) in THF (5 mL) was added morpholine (5 mL) and heated at 75° C. overnight. The solvent was distilled off to afford the title compound (2.0 g, 83.3%).
$^1$HNMR (DMSO-d$_6$, 300 MHz): δ 8.20-8.10 (d, 1H), 7.80-7.70 (d, 1H), 7.15-7.00 (m, 1H), 3.75-3.72 (m, 4H), 3.63-3.52 (m, 4H). LCMS: m/z: 206.5 (M+1)$^+$.

Step 4: Preparation of 2-morpholino-6-nitrooxazolo[4,5-b]pyridine

To a solution of 2-morpholinooxazolo[4,5-b]pyridine (1.0 g, 4.854 mmol) in acetic acid (10 mL), was added fuming nitric acid (6 mL) and heated at 100° C. for 4 hrs. The reaction mixture was cooled to 0° C., added ice and filtered the solid to afford the title compound (800 mg, 66.6%).
$^1$HNMR (DMSO-d$_6$, 300 MHz): δ 9.11-9.10 (d, 1H), 8.567-8.560 (d, 1H), 3.75 (s, 8H). LCMS: m/z: 250.9 (M+1)$^+$.

Step 5: Preparation of 2-morpholinooxazolo[4,5-b]pyridin-6-amine

To a solution of 2-morpholino-6-nitrooxazolo[4,5-b]pyridine (700 mg, 2.8 mmol) in THF was added ammonium chloride (2.37 g, 44.80 mmol) in water (5 mL) and zinc dust (1.82 g, 28.0 mmol) and stirred at 50° C. for t hr. The catalyst was filtered through Celite®, extracted with DCM (2×100 mL) and distilled out the solvent to get the title compound (600 mg, 97.4%).
LCMS: m/z: 221.1 (M+1)$^+$.

Step 6: Preparation of 6-bromo-N-(2-morpholinooxazolo[4,5-b]pyridin-6-yl)picolinamide The solution of 2-morpholinooxazolo[4,5-b]pyridin-6-amine (600 mg, 2.727 mmol), 6-bromopicolinic acid (661 mg, 3.27 mmol), EDCI·HCl (797 mg, 4.09 mmol), HOBt (552 mg, 4.09 mmol), DIPEA (1.05 g, 8.181 mmol) in DMF (5 mL) was stirred at RT overnight. Thr reaction mixture was quenched with ice water and extracted the compound in ethyl acetate (2×25 mL), dried over sodium sulphate and concentrated. The resultant crude was filtered by using 60-120 silica-gel column chromatography and compound was eluted using 5% methanol in DCM as eluent to afford the title compound (350 mg, 31.8%).
$^1$HNMR (CDCl$_3$, 300 MHz): δ 9.79 (s, 1H), 8.46-8.45 (d, 1H), 8.32-8.31 (d, 1H), 8.26-8.23 (d, 1H), 7.82-7.68 (m, 2H), 3.85-3.67 (m, 8H). LCMS: m/z: 405.6 (M+1)$^+$.

Step 7: Preparation of tert-butyl (6-((2-morpholinooxazolo[4,5-b]pyridin-6-yl)carbamoyl)-[2,3'-bipyridin]-6'-yl)carbamate To a sealed tube 6-bromo-N-(2-morpholinooxazolo[4,5-b]pyridin-6-yl)picolinamide (350 mg, 0.866 mmol), tert-butyl (5-(4,4,5,5-tetramethyl-1,3,2-dioxaborolan-2-yl)pyridin-2-yl)carbamate (360 mg, 1.126 mmol) (intermediate 1), sodium carbonate (275 mg, 2.598 mmol) in 1,2-dimethoxyethane (10 mL) and water (2 mL) were added. The reaction mixture was purged with argon for 10 min, added Pd(PPh$_3$)$_2$Cl$_2$ (31 mg, 0.043 mmol) and heated at 95° C. overnight. The solvent was distilled out. The resultant crude was purified by 60-120 silica gel column chromatography using 5% methanol in DCM as eluent to obtain the title compound (300 mg, 67.11%). LCMS: m/z: 517.7 (M+1)$^+$.

Step 8: 6'-amino-N-(2-morpholinooxazolo[4,5-b]pyridin-6-yl)-[2,3'-bipyridine]-6-carboxamide TFA (5 mL) was added to the solution of tert-butyl (6-((2-morpholinooxazolo[4,5-b]pyridin-6-yl)carbamoyl)-[2,3'-bipyridin]-6'-yl)carbamate (300 mg, 0.580 mmol) in DCM (1 mL) and stirred at RT for 1 hr. After completion of the reaction, this was then purified by prep. HPLC to obtain the title compound (34 mg, 14.05%).
$^1$HNMR (DMSO-d$_6$, 300 MHz): δ 10.06 (s, 1H), 8.96-8.95 (d, 1H), 8.58-8.44 (d, 1H), 8.44-8.40 (dd, 1H), 8.31-

8.30 (d, 1H), 8.11-7.95 (m, 3H), 6.59-6.56 (d, 1H), 6.38 (s, 2H), 3.75-3.66 (m, 8H). LCMS: 98.20%, m/z=418.1 (M+1)⁺. HPLC: 98.32%.

Example 2

6'-amino-N-(5-cyclopropyl-2-morpholinooxazolo[4,5-b]pyridin-6-yl)-[2,3'-bipyridine]-6-carboxamide Hydrochloride

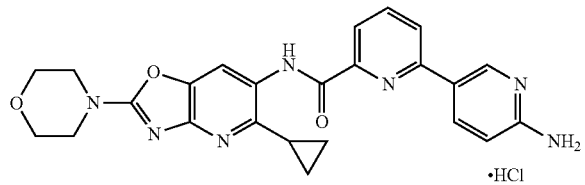 [SMILES: Nc1ccc(-c2cccc(C(=O)Nc3cc4oc(N5CCOCC5)nc4nc3C3CC3)n2)cn1 ; Cl]

Step 1: Preparation of 2-amino-6-chloropyridin-3-ol

Using the same reaction conditions as described in step 5 of example 1, 6-chloro-2-nitropyridin-3-ol (35 mg, 0.201 mmol) was reduced with zinc dust (65 mg, 1.005 mmol) and ammonium chloride (54 mg, 1.005 mmol) in THF (2 mL) to get the title compound (25 mg, 89%).
LCMS: m/z: 145.2 (M+1)⁺.

Step 2: Preparation of 5-chlorooxazolo[4,5-b]pyridine-2-thiol

Using the same reaction conditions as described in step 1 of example 1 2-amino-6-chloropyridin-3-ol (25 mg, 0.173 mmol) was cyclised using potassium ethyl xanthate (33 mg, 0.208 mmol) in pyridine (1 mL) to afford the title compound (25 mg, 78%).
¹HNMR (DMSO-d₆, 300 MHz): δ 7.94-7.90 (d, 1H), 7.38-7.35 (d, 1H). LCMS: m/z: 187.1 (M+1)⁺.

Step 3: Preparation of 5-chloro-2-(methylthio)oxazolo[4,5-b]pyridine

Using the same reaction conditions as described in step 2 of example 1, 5-chlorooxazolo[4,5-b]pyridine-2-thiol (620 mg, 3.33 mmol) was methylated using potassium carbonate (689 mg, 4.99 mmol) and methyl iodide (567 mg, 3.99 mmol) in ethyl acetate (10 mL) to afford the title compound (720 mg, 90%). LCMS: m/z: 201.1 (M+1)⁺.

Step 4: Preparation of 5-chloro-2-morpholinooxazolo[4,5-b]pyridine

Using the same reaction conditions as described in step 3 of example 1, 5-chloro-2-(methylthio)oxazolo[4,5-b]pyridine was substituted using morpholine (2 mL) and THF (10 mL) to afford the title compound (750 mg, 88%).
¹HNMR (DMSO-d₆, 400 MHz): δ 7.82-7.80 (d, 1H), 7.08-7.06 (d, 1H), 3.74-3.64 (m, 8H).
LCMS: m/z: 240.2 (M+1)⁺.

Step 5: Preparation of 5-chloro-2-morpholino-6-nitrooxazolo[4,5-b]pyridine

Using the same reaction conditions as described in step 4 of example 1 5-chloro-2-morpholinooxazolo[4,5-b]pyridine (50 mg) was nitrated using acetic acid (0.2 mL) and fuming nitric acid (0.1 mL) at 100° C. for 2 h to afford the title compound (25 mg, 43%).
¹HNMR (DMSO-d₆, 300 MHz): δ 8.60 (s, 1H), 3.72 (s, 8H)⁺.

Step 6: Preparation of 5-cyclopropyl-2-morpholino-6-nitrooxazolo[4,5-b]pyridine

Using the same reaction conditions as described in step 7 of example 1 5-chloro-2-morpholino-6-nitrooxazolo[4,5-b]pyridine (25 mg, 0.088 mmol) was coupled with cyclopropyl boronic acid (9 mg, 0.105 mmol) using potassium carbonate (24 mg, 0.176 mmol) and Pd(PPh₃)₄ (5 mg, 0.004 mmol) in xylene (2 mL) to get the crude product (50 mg). LCMS: m/z: 291.1 (M+1)⁺.

Step 7: Preparation of 5-cyclopropyl-2-morpholinooxazolo[4,5-b]pyridin-6-amine

Using the same reaction conditions as described in step 5 of example 1, 5-cyclopropyl-2-morpholino-6-nitrooxazolo[4,5-b]pyridine (220 mg, 0.758 mmol) was reduced with zinc dust (394 mg, 6.068 mmol) and ammonium chloride (327 mg, 6.068 mmol) in THF/methanol/H₂O (5 mL/1 ml/0.5 mL) to get the title compound (160 mg, 84%). LCMS: m/z: 261.0 (M+1)⁺.

Step 8: Preparation of 6-bromo-N-(5-cyclopropyl-2-morpholinooxazolo[4,5-b]pyridin-6-yl)picolinamide Using the same reaction conditions as described in step 6 of example 1, 5-cyclopropyl-2-morpholinooxazolo[4,5-b]pyridin-6-amine (100 mg, 0.384 mmol), was coupled with 6-bromopicolinic acid (85 mg, 0.423 mmol) using EDCI·HCl (110 mg, 0.576 mmol), HOBt (77 mg, 0.576 mmol), TEA (0.22 mL, 1.538 mmol) in DMF (2 mL) to afford the title compound (75 mg, 44%). LCMS: m/z: 444.2 (M+1)⁺.

Step 9: Preparation of tert-butyl (6-((5-cyclopropyl-2-morpholinooxazolo[4,5-b]pyridin-6-yl)carbamoyl)-[2,3'-bipyridin]-6'-yl)carbamate Using the same reaction conditions as described in step 7 of example 1, 6-bromo-N-(5-cyclopropyl-2-morpholinooxazolo[4,5-b]pyridin-6-yl)picolinamide (75 mg, 0.169 mmol) was coupled with tert-butyl (5-(4,4,5,5-tetramethyl-1,3,2-dioxaborolan-2-yl)pyridin-2-yl)carbamate (65 mg, 0.203 mmol) (intermediate 1) using sodium carbonate (53 mg, 0.507 mmol) and Pd(PPh₃)₂Cl₂ (7 mg, 0.0084 mmol) in 1,2-dimethoxyethane (5 mL) to get the crude product. The resultant crude was purified by 60-120 silica gel column chromatography using 50% ethyl acetate in hexane as eluent to obtain the title compound (50 mg, 54%). LCMS: m/z: 558.2 (M+1)⁺.

Step 10: Preparation of 6'-amino-N-(5-cyclopropyl-2-morpholinooxazolo[4,5-b]pyridin-6-yl)-[2,3'-bipyridine]-6-carboxamide Using the same reaction conditions as described in step 8 of example 1 tert-butyl (6-((5-cyclopropyl-2-morpholinooxazolo[4,5-b]pyridin-6-yl)carbamoyl)-[2,3'-bipyridin]-6'-yl)carbamate (50 mg, 0.089 mmol) was deprotected using methanolic HCl (5 mL) to get the crude product. This was then purified by prep HPLC to get the title compound (40 mg, 90%).

$^1$HNMR (DMSO-d$_6$, 400 MHz): δ 10.78 (s, 1H), 9.059-9.055 (d, 1H), 8.93-8.90 (dd, 1H), 8.40-8.25 (bs, 2H), 8.21-8.20 (d, 1H), 8.15-8.11 (t, 1H), 8.07-8.05 (d, 1H), 7.83 (s, 1H), 7.12-7.09 (d, 1H), 3.71-3.60 (m, 8H), 2.20-2.16 (m, 1H), 0.91-0.87 (m, 4H).

LCMS: 96.48%, m/z=458.2 (M+1)$^+$. HPLC: 98.7%.

Example 3

N-(5-cyclopropyl-2-morpholinooxazolo[4,5-b]pyridin-6-yl)-2-(2-methylpyridin-4-yl)oxazole-4-carboxamide Hydrochloride

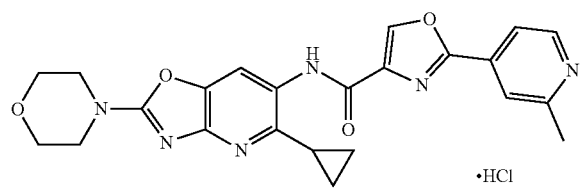 [SMILES: Cc1cc(-c2nc(C(=O)Nc3cc4oc(N5CCOCC5)nc4nc3C3CC3)co2)ccn1 ; Cl]

Using the same reaction conditions as described in step 6 of example 1, 5-cyclopropyl-2-morpholinooxazolo[4,5-b]pyridin-6-amine (product of step 7 of example 2) (60 mg, 0.23 mmol), was coupled with 2-(2-methyl-pyridin-4-yl)oxazole-4-carboxylic acid (71 mg, 0.396 mmol) using EDCI·HCl (66 mg, 0.396 mmol), HOBt (46 mg, 0.396 mmol), TEA (0.13 mL, 0.923 mmol) in DMF (2 mL) to afford the crude product. This was then purified by prep HPLC and treated with methanolic HCl to get the title compound (20 mg, 20%).

$^1$HNMR (DMSO-d$_6$, 400 MHz): δ 10.22 (s, 1H), 9.27 (s, 1H), 8.85-8.83 (d, 1H), 8.25 (s, 1H), 8.14-8.13 (d, 1H), 7.72 (s, 1H), 3.71-3.59 (m, 8H), 2.63 (s, 3H), 2.17-2.14 (m, 1H), 0.89-0.86 (m, 4H). LCMS: 93.91%, m/z=447.1 (M+1)$^+$. HPLC: 99.0%.

Example 4: N-(2,5-di(piperidin-1-yl)oxazolo[4,5-b]pyridin-6-yl)-6-(1H-pyrazol-4-yl)picolinamide Hydrochloride

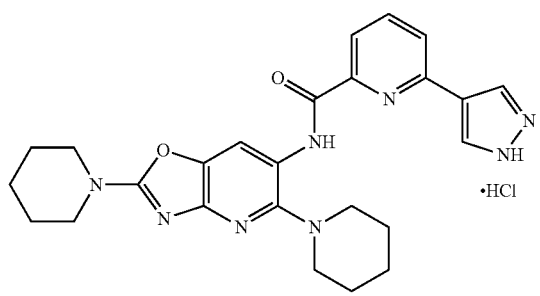 [SMILES: O=C(Nc1cc2oc(N3CCCCC3)nc2nc1N1CCCCC1)c1cccc(-c2cn[nH]c2)n1 ; Cl]

Step 1: Preparation of 5-chloro-2-(piperidin-1-yl)oxazolo[4,5-b]pyridine

Using the same reaction conditions as described in step 3 of example 1, 5-chloro-2-(methylthio)oxazolo[4,5-b]pyridine (product of step 3 of example 2) (3 g, 14.95 mmol) was substituted using piperidine (8 mL) and THF (30 mL) to afford the title compound (3 g, 90%).

LCMS: m/z=238.1 (M+1)$^+$.

Step 2: Preparation of 5-chloro-6-nitro-2-(piperidin-1-yl)oxazolo[4,5-b]pyridine Using the same reaction conditions as described in step 4 of example 20, 5-chloro-2-(piperidin-1-yl)oxazolo[4,5-b]pyridine (4 g, 168 mmol) was nitrated using potassium nitrate (3.4 g, 337 mmol) and conc. sulphuric acid (20 mL) at RT for 3 h to afford the crude title compound (4 g). LCMS: m/z=283.0 (M+1)$^+$.

Step 3: Preparation of 6-nitro-2,5-di(piperidin-1-yl)oxazolo[4,5-b]pyridine

A mixture of 5-chloro-6-nitro-2-(piperidin-1-yl)oxazolo[4,5-b]pyridine (product of step 5 of example 2) (300 mg, 1.056 mmol) was heated with piperidine (3 mL) at 100° C. for 2 h. Reaction was quenched with ice water and filtered the solid to get the title compound (300 mg, 86%).

LCMS: m/z: 332.1 (M+1)$^+$.

Step 4: Preparation of 2,5-di(piperidin-1-yl)oxazolo[4,5-b]pyridin-6-amine

Using the same reaction conditions as described in step 5 of example 1, 6-nitro-2,5-di(piperidin-1-yl)oxazolo[4,5-b]pyridine (300 mg, 0.90 mmol) was reduced with zinc dust (468 mg, 7.207 mmol) and ammonium chloride (389 mg, 7.207 mmol) in THF/methanol/H$_2$O (5 mL/1 mL/0.5 mL) to get the title compound (250 mg, 92%). LCMS: m/z: 302.4 (M+1)$^+$.

Step 5: Preparation of N-(2,5-di(piperidin-1-yl)oxazolo[4,5-b]pyridin-6-yl)-6-(1-(tetrahydro-2H-pyran-2-yl)-1H-pyrazol-4-yl)picolinamide Using the same reaction conditions as described in step 6 of example 1, 2,5-di(piperidin-1-yl)oxazolo[4,5-b]pyridin-6-amine (100 mg, 0.33 mmol), was coupled with 6-(1-(tetrahydro-2H-pyran-2-yl)-1H-pyrazol-4-yl)picolinic acid (intermediate 3) (108 mg, 0.396 mmol) using EDCI·HCl (94 mg, 0.495 mmol), HOBt (66 mg, 0.495 mmol), TEA (0.2 mL, 1.324 mmol) in DMF (2 mL) to afford the crude product. The resultant crude was purified by 60-120 silica gel column chromatography using 1% methanol in DCM as eluent to obtain the title compound (100 mg, 55%). LCMS: m/z: 557.4 (M+1)$^+$.

Step 6: Preparation of N-(2,5-di(piperidin-1-yl)oxazolo[4,5-b]pyridin-6-yl)-6-(1H-pyrazol-4-yl)picolinamide Hydrochloride Using the same reaction conditions as described in step 8 of example 1, N-(2,5-di(piperidin-1-yl)oxazolo[4,5-b]pyridin-6-yl)-6-(1-(tetrahydro-2H-pyran-2-yl)-1H-pyrazol-4-yl)picolinamide (100 mg, 0.179 mmol) was deprotected using methanolic HCl to get the crude product. This was then purified by prep HPLC to get the title compound (40 mg, 50%).

¹HNMR (DMSO-d₆, 300 MHz): δ 10.8 (s, 1H), 8.66 (s, 1H), 8.39 (s, 1H), 8.04-7.94 (m, 3H), 3.62 (s, 4H), 2.94 (s, 4H), 1.75 (s, 4H), 1.62-1.55 (m, 8H).
LCMS: 97.91%, m/z=473.5 (M+1)⁺. HPLC: 96.5%.

Example 5

N-(2,5-di(piperidin-1-yl)oxazolo[4,5-b]pyridin-6-yl)-2-(2-methylpyridin-4-yl)oxazole-4-carboxamide

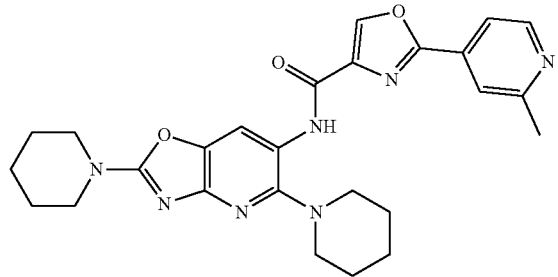 [SMILES: Cc1cc(-c2nc(C(=O)Nc3cc4oc(N5CCCCC5)nc4nc3N3CCCCC3)co2)ccn1]

Using the same reaction conditions as described in step 6 of example 1, 2,5-di(piperidin-1-yl)oxazolo[4,5-b]pyridin-6-amine (product of step 4 of example 4) (100 mg, 0.33 mmol), was coupled with 2-(2-methylpyridin-4-yl)oxazole-4-carboxylic acid (74 mg, 0.363 mmol) using EDCI·HCl (94 mg, 0.495 mmol), HOBt (66 mg, 0.495 mmol), TEA (0.2 mL, 1.324 mmol) in DMF (2 mL) to afford the crude product. This was then purified by prep HPLC to get the title compound (30 mg, 20%).

¹HNMR (DMSO-d₆, 300 MHz): δ 9.98 (s, 1H), 9.21 (s, 1H), 8.91-8.89 (d, 1H), 8.51 (s, 1H), 8.21 (s, 1H), 8.09-8.08 (d, 1H), 3.61 (m, 7H), 2.98 (s, 3H), 2.71 (s, 3H), 1.81 (s, 3H), 1.61 (s, 7H). LCMS: 100%, m/z=488.2 (M+1)⁺. HPLC: 92.1%.

Example 6

N-(2-morpholino-5-(piperidin-1-yl)oxazolo[4,5-b]pyridin-6-yl)-6-(1H-pyrazol-4-yl)picolinamide

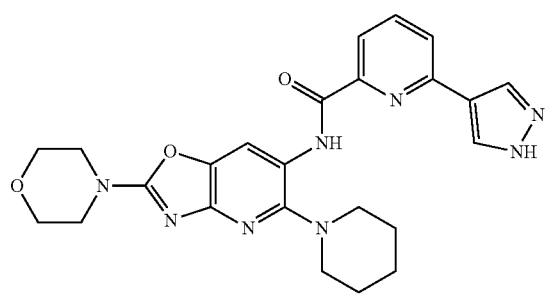 [SMILES: O=C(Nc1cc2oc(N3CCOCC3)nc2nc1N1CCCCC1)c1cccc(-c2cn[nH]c2)n1]

Step 1: Preparation of 2-morpholino-6-nitro-5-(piperidin-1-yl)oxazolo[4,5-b]pyridine To a solution of 5-chloro-2-morpholino-6-nitrooxazolo[4,5-b]pyridine (product of step-5 of example 2) (30 mg, 0.1056 mmol) in THF (2 mL) was added piperidine (11 mg, 0.126 mmol) and stirred at RT overnight. The reaction mixture was quenched with ice water and extracted with ethyl acetate (2×10 mL), dried over sodium sulphate and distilled out the solvent to obtain the title compound (30 mg, 89%). LCMS: m/z: 334.5 (M+1)⁺.

Step 2: Preparation of 2-morpholino-5-(piperidin-1-yl)oxazolo[4,5-b]pyridin-6-amine Using the same reaction conditions as described in step 5 of example 1, 2-morpholino-6-nitro-5-(piperidin-1-yl)oxazolo[4,5-b]pyridine (300 mg, 0.900 mmol) was reduced with zinc dust (468 mg, 7.207 mmol) and ammonium chloride (389 mg, 7.207 mmol) in THF/methanol/H₂O (5 mL/1 mL/0.5 mL) to get the title compound (260 mg, 96%). LCMS: m/z: 304.1 (M+1)⁺.

Step 3: Preparation of N-(2-morpholino-5-(piperidin-1-yl)oxazolo[4,5-b]pyridin-6-yl)-6-(1-(tetrahydro-2H-pyran-2-yl)-1H-pyrazol-4-yl)picolinamide Using the same reaction conditions as described in step 6 of example 1, 2-morpholino-5-(piperidin-1-yl)oxazolo[4,5-b]pyridin-6-amine (90 mg, 0.297 mmol), was coupled with 6-(1-(tetrahydro-2H-pyran-2-yl)-1H-pyrazol-4-yl)picolinic acid (intermediate 3) (97 mg, 0.356 mmol) using EDCI·HCl (85 mg, 0.445 mmol), HOBt (60 mg, 0.445 mmol), TEA (0.2 mL, 1.188 mmol) in DMF (4 mL) to afford the crude product. The resultant crude was purified by 60-120 silica gel column chromatography using 1% methanol in DCM as eluent to obtain the title compound (60 mg, 38%). LCMS: m/z: 559.6 (M+1)⁺.

Step 4: Preparation of N-(2-morpholino-5-(piperidin-1-yl)oxazolo[4,5-b]pyridin-6-yl)-6-(1H-pyrazol-4-yl)picolinamide Using the same reaction conditions as described in step 8 of example 1, N-(2-morpholino-5-(piperidin-1-yl)oxazolo[4,5-b]pyridin-6-yl)-6-(1-(tetrahydro-2H-pyran-2-yl)-1H-pyrazol-4-yl)picolinamide (60 mg, 0.107 mmol) was deprotected using methanolic HCl (2 mL) to get the title compound (50 mg, 90%).

¹HNMR (DMSO-d₆, 300 MHz): δ 10.80 (s, 1H), 8.65 (s, 1H), 8.43 (s, 2H), 8.05-7.93 (m, 3H), 3.76-3.62 (m, 8H), 2.98 (s, 4H), 1.76 (s, 4H), 1.54 (s, 2H). LCMS: 92.69%, m/z=475.5 (M+1)⁺.
HPLC: 90.31%.

Example 7

2-(2-methylpyridin-4-yl)-N-(2-morpholino-5-(piperidin-1-yl)oxazolo[4,5-b]pyridin-6-yl)oxazole-4-carboxamide

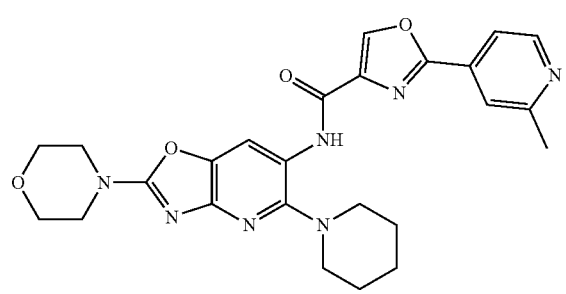 [SMILES: Cc1cc(-c2nc(C(=O)Nc3cc4oc(N5CCOCC5)nc4nc3N3CCCCC3)co2)ccn1]

Using the same reaction conditions as described in step 6 of example 1, 2-morpholino-5-(piperidin-1-yl)oxazolo[4,5-b]pyridin-6-amine (product of step 2 of example 6) (100 mg, 0.331 mmol), was coupled with 2-(2-methylpyridin-4-yl)oxazole-4-carboxylic acid (81 mg, 0.397 mmol) using EDCI·HCl (94 mg, 0.496 mmol), HOBt (66 mg, 0.496 mmol), TEA (0.2 mL, 1.302 mmol) in DMF (2 mL) to afford the crude product. The resultant crude was purified by 60-120 silica gel column chromatography using 1% methanol in DCM as eluent to obtain the title compound (35 mg, 22%).

¹HNMR (DMSO-d₆, 300 MHz): δ 9.80 (s, 1H), 9.20 (s, 1H), 8.90-8.88 (d, 1H), 8.57 (s, 1H), 8.18 (s, 1H), 8.06-8.04 (d, 1H), 3.72-3.61 (m, 8H), 2.96 (s, 4H), 2.73 (s, 3H), 1.81 (s, 4H), 1.63 (s, 2H). LCMS: 81.6%, m/z=490.2 (M+1)⁺. HPLC: 94.3%.

Example 8

6-chloro-N-(2-morpholino-5-(piperidin-1-yl)oxazolo[4,5-b]pyridin-6-yl)picolinamide

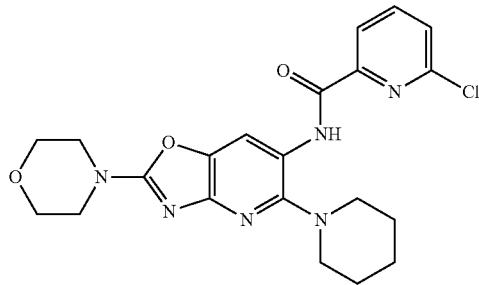 [SMILES: O=C(Nc1cc2oc(N3CCOCC3)nc2nc1N1CCCCC1)c1cccc(Cl)n1]

Using the same reaction conditions as described in step 6 of example 1, 2-morpholino-5-(piperidin-1-yl)oxazolo[4,5-b]pyridin-6-amine (product of step 2 of example 6) (70 mg, 0.2317 mmol), was coupled with 6-chloropicolinic acid (44 mg, 0.278 mmol) using EDCI·HCl (66 mg, 0.347 mmol), HOBt (46 mg, 0.347 mmol), TEA (0.2 mL, 0.926 mmol) in DMF (4 mL) to afford the crude product. The resultant crude was purified by 60-120 silica gel column chromatography using 1% methanol in DCM as eluent to obtain the title compound (35 mg, 35%).

¹HNMR (DMSO-d₆, 300 MHz): δ 10.60 (s, 1H), 8.70 (s, 1H), 8.15-8.14 (t, 2H), 7.84-7.81 (m, 1H), 3.77-3.60 (m, 8H), 2.93-2.10 (t, 4H), 1.81 (s, 4H), 1.58 (s, 2H). LCMS: 99.3%, m/z=443.2 (M+1)⁺. HPLC: 93.0%.

Example 9

N-(2,5-di(piperidin-1-yl)oxazolo[4,5-b]pyridin-6-yl)-6-(1-methyl-1H-pyrazol-4-yl)picolinamide

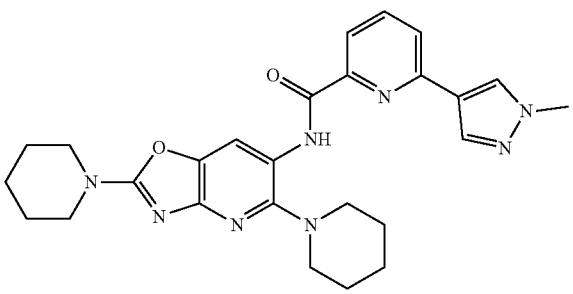 [SMILES: Cn1cc(-c2cccc(C(=O)Nc3cc4oc(N5CCCCC5)nc4nc3N3CCCCC3)n2)cn1]

Using the same reaction conditions as described in step 6 of example 1, 2,5-di(piperidin-1-yl)oxazolo[4,5-b]pyridin-6-amine (product of step 2 of example 4) (75 mg, 0.2483 mmol), was coupled with 6-(1-methyl-1H-pyrazol-4-yl)picolinic acid (intermediate 4)(61 mg, 0.298 mmol) using EDCI·HCl (72 mg, 0.372 mmol), HOBt (51 mg, 0.372 mmol), DIPEA (0.17 mL, 0.9933 mmol) in DMF (2 mL) to afford the crude product. This was then purified by prep HPLC to get the title compound (41 mg, 33.0%).

¹HNMR (DMSO-d₆, 400 MHz): δ 10.80 (s, 1H), 8.67 (s, 1H), 8.44 (s, 1H), 8.21 (s, 1H), 8.06-8.02 (t, 1H), 7.98-7.96 (d, 1H), 7.92-7.91 (d, 1H), 3.92 (s, 3H), 3.63 (s, 4H), 2.94 (s, 4H), 1.76 (s, 4H), 1.63 (s, 6H), 1.55 (s, 2H). LCMS: 98.9%, m/z=487.2 (M+1)⁺. HPLC: 94.0%.

Example 10

2-(2-chloropyridin-4-yl)-N-(2,5-di(piperidin-1-yl)oxazolo[4,5-b]pyridin-6-yl)oxazole-4-carboxamide

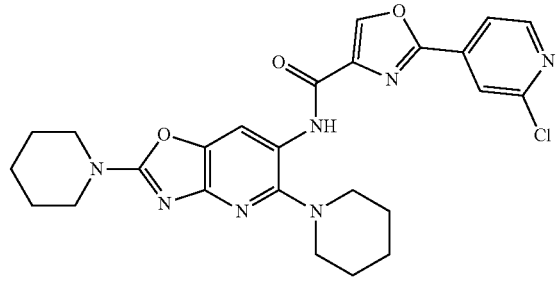 [SMILES: O=C(Nc1cc2oc(N3CCCCC3)nc2nc1N1CCCCC1)c1coc(-c2ccnc(Cl)c2)n1]

Using the same reaction conditions as described in step 6 of example 1, 2,5-di(piperidin-1-yl)oxazolo[4,5-b]pyridin-6-amine (product of step 2 of example 4) (75 mg, 0.2483 mmol), was coupled with 2-(2-chloropyridin-4-yl)oxazole-4-carboxylic acid (71 mg, 0.298 mmol) using EDCI·HCl (72 mg, 0.372 mmol), HOBt (51 mg, 0.372 mmol), DIPEA (0.17 mL, 0.9933 mmol) in DMF (2 mL) to afford the crude product. This was then purified by prep HPLC to get the title compound (62 mg, 45.9%).

¹HNMR (CD₃OD, 400 MHz): δ 8.82 (s, 1H), 8.64-8.62 (d, 1H), 8.14 (s, 1H), 8.04-8.03 (d, 1H), 3.81 (s, 8H), 2.06-1.96 (m, 4H), 1.79 (s, 8H). LCMS: 84.1%, m/z=508.2 (M+1)⁺. HPLC: 97.6%.

Example 11

(S)-2-(2-methylpyridin-4-yl)-N-(2-morpholino-5-(pyrrolidin-3-ylamino)oxazolo[4,5-b]pyridin-6-yl)oxazole-4-carboxamide

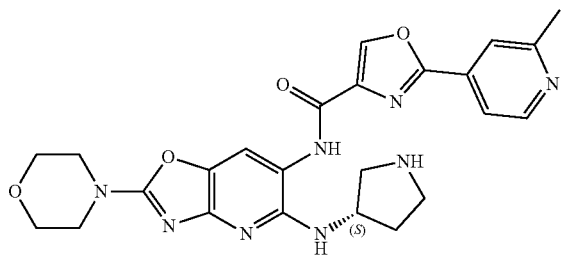

Step 1: Preparation of (S)-tert-butyl 3-((2-morpholino-6-nitrooxazolo[4,5-b]pyridin-5-yl)amino)pyrrolidine-1-carboxylate A solution of 5-chloro-2-morpholino-6-nitrooxazolo[4,5-b]pyridine (300 mg, 1.0563 mmol) (S)-tert-butyl 3-aminopyrrolidine-1-carboxylate (237 mg, 1.267 mmol) and potassium carbonate (292 mg, 2.112 mmol) in DMF (2 mL) was heated at 100° C. for 2 h. Reaction was quenched with ice water and filtered the solid. The resultant crude was purified by 60-120 silica gel column chromatography using 1% methanol in DCM as eluent to obtain the title compound (350 mg, 76.25%). LCMS: m/z: 435.4 (M+1)$^+$.

Step 2: Preparation of (S)-tert-butyl 3-((6-amino-2-morpholinooxazolo[4,5-b]pyridin-5-yl)amino)pyrrolidine-1-carboxylate Using the same reaction conditions as described in step 5 of example 1, (S)-tert-butyl 3-((2-morpholino-6-nitrooxazolo[4,5-b]pyridin-5-yl)amino)pyrrolidine-1-carboxylate (350 mg, 0.806 mmol) was reduced with zinc dust (422 mg, 6.451 mmol) and ammonium chloride (691 mg, 12.903 mmol) in THF/methanol/H$_2$O (10 mL/2 mL/1 mL) to get the title compound (240 mg, 71.8%). LCMS: m/z: 405.2 (M+1)$^+$.

Step 3: Preparation of (S)-tert-butyl 3-((6-(2-(2-methylpyridin-4-yl)oxazole-4-carboxamido)-2-morpholinooxazolo[4,5-b]pyridin-5-yl)amino)pyrrolidine-1-carboxylate Using the same reaction conditions as described in step 6 of example 1, (S)-tert-butyl 3-((6-amino-2-morpholinooxazolo[4,5-b]pyridin-5-yl)amino)pyrrolidine-1-carboxylate (115 mg, 0.284 mmol), was coupled with 2-(2-methylpyridin-4-yl)oxazole-4-carboxylic acid (70 mg, 0.341 mmol) using EDCI·HCl (82 mg, 0.426 mmol), HOBt (58 mg, 0.426 mmol), DIPEA (0.199 mL, 1.138 mmol) in DMF (2 mL) to afford the title compound (100 mg, 59.52%). LCMS: m/z: 591.4 (M+1)$^+$.

Step 4: Preparation of (S)-2-(2-methylpyridin-4-yl)-N-(2-morpholino-5-(pyrrolidin-3-ylamino)oxazolo[4,5-b]pyridin-6-yl)oxazole-4-carboxamide Using the same reaction conditions as described in step 8 of example 1, (S)-tert-butyl 3-((6-(2-(2-methylpyridin-4-yl)oxazole-4-carboxamido)-2-morpholinooxazolo[4,5-b]pyridin-5-yl)amino)pyrrolidine-1-carboxylate (100 mg, 0.169 mmol) was deprotected using methanolic HCl (5 mL) to get the crude product. This was then purified by prep HPLC to get the title compound (9 mg, 10.84%).

$^1$HNMR (CDCl$_3$, 400 MHz): δ 9.91 (s, 1H), 8.78 (s, 1H), 8.74-8.73 (d, 1H), 8.45 (s, 1H), 7.82 (s, 1H), 7.76-7.74 (d, 1H), 4.50 (s, 1H), 4.04-4.03 (d, 4H), 3.30-3.00 (m, 7H), 2.70 (s, 3H), 2.40-1.80 (m, 4H), 1.00-0.08 (m, 1H). LCMS: 100%, m/z=491.3 (M+1)$^+$.

Example 12

6'-amino-N-(2-morpholinooxazolo[5,4-b]pyridin-5-yl)-[2,3'-bipyridine]-6-carboxamide

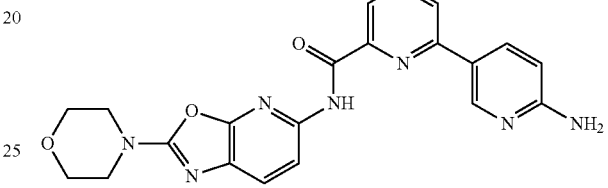

Step 1: Preparation of 3-amino-6-chloropyridin-2-ol

Using the same reaction conditions as described in step 5 of example 1 6-chloro-3-nitropyridin-2-ol (1.0 g, 5.747 mmol was reduced with zinc dust (3.0 g, 45.977 mmol) and ammonium chloride (4.92 g, 91.952 mmol) in THF/methanol/H$_2$O (20 m/4 mL/2 mL) to get the crude product. The resultant crude was purified by 60-120 silica gel column chromatography using 10% methanol in DCM as eluent to obtain the title compound (500 mg, 60.97%).

$^1$HNMR (DMSO-d$_6$, 300 MHz): δ 6.84-6.81 (d, 1H), 6.55-6.52 (d, 1H). LCMS: m/z: 145.0 (M+1)$^+$.

Step 2: Preparation of 5-chlorooxazolo[5,4-b]pyridine-2-thiol

Using the same reaction conditions as described in step 1 of example 1, 3-amino-6-chloropyridin-2-ol (900 mg, 6.25 mmol) was cyclised using potassium ethyl xanthate (1.1 g, 6.875 mmol) in pyridine (8 mL) to afford the title compound (1.0 g, 86.2%). LCMS: m/z: 185.0 (M−1)$^+$.

Step 3: Preparation of 5-chloro-2-morpholinooxazolo[5,4-b]pyridine

The mixture of 5-chlorooxazolo[5,4-b]pyridine-2-thiol (550 mg, 2.956 mmol), morpholine (5 mL) and heated at 110° C. overnight. Solvent was distilled off. The resultant crude was purified by 60-120 silica gel column chromatography using 40% ethyl acetate in hexane as eluent to obtain the title compound (200 mg, 28.5%). LCMS: m/z: 240.0 (M+1)$^+$.

Step 4: Preparation of 6'-amino-N-(2-morpholinooxazolo[5,4-b]pyridin-5-yl)-[2,3'-bipyridine]-6-carboxamide In a sealed tube, taken 5-chloro-2-morpholinooxazolo[5,4-b]pyridine (76 mg, 0.316 mmol), tert-butyl (6-carbamoyl-

[2,3'-bipyridin]-6'-yl)carbamate (100 mg, 0.316 mmol) (intermediate 2) and caesium carbonate (257 mg, 0.79 mmol) in toluene (5 mL) and purged argon for 10 min. Added X-Phos (15 mg, 0.32 mmol) and heated at 110° C. overnight. The solvent was distilled out. The resultant crude was purified by 60-120 silica gel column chromatography using 5% methanol in DCM as eluent. Further The resultant crude was purified by prep HPLC to obtain the title compound (11 mg, 10.0%).

$^1$HNMR (CDCl$_3$, 300 MHz): δ 8.81 (s, 1H), 8.25-8.24 (d, 1H), 8.10 (s, 1H), 7.80-7.75 (m, 3H), 7.50-7.44 (m, 1H), 7.25 (s, 1H), 3.77-3.62 (m, 8H). LCMS: 72.3%, m/z=418.2 (M+1)$^+$. HPLC: 96.1%.

Example 13

6'-amino-N-(2-morpholinothiazolo[4,5-c]pyridin-6-yl)-[2,3'-bipyridine]-6-carboxamide

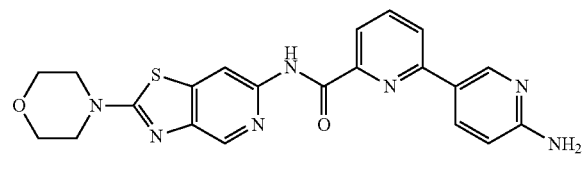 [SMILES: Nc1ccc(-c2cccc(C(=O)Nc3cc4sc(N5CCOCC5)nc4cn3)n2)cn1]

Step-1: Synthesis of 6-chloro thiazolo[4,5-c]pyridine-2(3H)-thione

Using the same reaction conditions as described in step 1 of example 1, 4,6-dichloropyridin-3-amine (1.3 g, 7 mmol) was cyclised using potassium ethyl xanthate (2.55 g, 15 mmol) in DMF (25 mL) at 150° C. for 8 h to afford the title compound (1.3 g, 86.6%) as a light brown solid.

$^1$HNMR (400 MHz, DMSO-d$_6$): δ 14.2-14.0 (b, 1H), 8.274 (s, 1H), 7.931 (s, 1H); LCMS: 100%, m/z=201.3 (M+1)$^+$.

Step-2: Synthesis of 4-(6-chloro thiazolo[4,5-c]pyridin-2-yl) morpholine

To a suspension of 6-chlorothiazolo[4,5-c]pyridine-2(3H)-thione (0.3 g, 1.16 mmol) in DCM (4 mL), oxalyl chloride (0.2 mL, 2.38 mmol) and DMF (1.5 mL) were added at 0° C. The resulting mixture was slowly allowed to warm to room temperature and stirred there for 1 h. The reaction mixture was again cooled to 0° C. and triethyl amine (0.66 mL, 4.76 mmol) and morpholine (0.13 mL, 1.75 mmol) were added. The reaction mixture was stirred at RT for 1 h and quenched with water and extracted with ethyl acetate. The combined organic layers were washed with water, brine, dried over sodium sulphate and concentrated under reduced pressure. The crude material was purified by column chromatography (EtOAc/n-hexanes 3:7) to afford the title compound (0.14 g, 39.6%) as a light brown solid.

$^1$H NMR (400 MHz, DMSO-d$_6$): δ 8.47 (s, 1H), 8.04 (s, 1H), 3.74-3.72 (m, 4H), 3.61-3.59 (m, 4H); LCMS: m/z=256.1 (M+1)$^+$.

Step-3: Synthesis of 6'-amino-N-(2-morpholino thiazolo [4,5-c]pyridin-6-yl)-[2,3'-bipyridine]-6-carboxamide Using the same reaction conditions as described in step 4 of example 12, 4-(6-chlorothiazolo[4,5-c] pyridin-2-yl) morpholine (0.081 g, 0.32 mmol), was coupled with tert-butyl (6-carbamoyl-[2,3'-bipyridin]-6'-yl)carbamate (intermediate 2) (0.1 g, 0.32 mmol) using cesium carbonate (0.21 g, 0.64 mmol), XantPhos (0.028 g, 0.047 mmol) and Pd$_2$(dba)$_3$ (0.015 mg, 0.015 mmol) in toluene:dioxane (2:2 mL) to get the crude product. The resultant crude was purified by 60-120 silica gel column chromatography using 2% methanol in DCM as eluent. Further the resultant crude was purified by prep HPLC to afford title compound (0.01 g, 6%) as an off-white solid.

$^1$H NMR (400 MHz, DMSO-d$_6$): δ 10.65 (s, 1H), 8.88 (d, 1H), 8.85 (dd, 1H), 8.71 (s, 1H), 8.55 (s, 1H), 8.22-8.13 (m, 4H), 7.09 (d, 1H), 3.73 (t, 4H), 3.58 (t, 4H). LCMS: 100%, m/z=434.2 (M+1)$^+$.

Example 14

6'-amino-N-(2-morpholinothiazolo[5,4-b]pyridin-5-yl)-[2,3'-bipyridine]-6-carboxamide

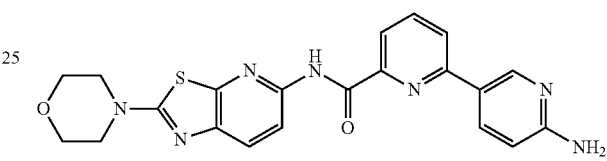

Step 1: Preparation of 5-chlorothiazolo[5,4-b]pyridine-2-thiol

Using the same reaction conditions as described in step 1 of example 1, 2,6-dichloropyridin-3-amine (5 g, 30 mmol) was cyclised using potassium ethyl xanthate (9.81 g, 61 mmol) in NMP (40 mL) at 150° C. for overnight to afford the title compound (5.5 gr, 92%).

$^1$HNMR (DMSO-d$_6$, 300 MHz): δ 14.10 (bs, 1H), 7.66-7.62 (d, 1H), 7.53-7.48 (d, 1H). LCMS: m/z: 202.9 (M+1)$^+$.

Step 2: Preparation of 4-(5-chlorothiazolo[5,4-b]pyridin-2-yl)morpholine

Using the same reaction conditions as described in step 1 of example 4, 5-chlorothiazolo[5,4-b]pyridine-2-thiol (5.5 g, 27.22 mmol) was substituted using morpholine (40 mL) to afford the title compound (4 gr, 58%).

$^1$HNMR (DMSO-d$_6$, 300 MHz): δ 7.83-7.80 (d, 1H), 7.42-7.39 (d, 1H), 3.75-3.71 (m, 4H), 3.61-3.58 (m, 4H). LCMS: m/z: 256.0 (M+1)$^+$.

Step 3: Preparation of 6'-amino-N-(2-morpholinothiazolo[5,4-b]pyridin-5-yl)-[2,3'-bipyridine]-6-carboxamide Using the same reaction conditions as described in step 4 of example 12, 6'-amino-N-(2-morpholinothiazolo[5,4-b]pyridin-5-yl)-[2,3'-bipyridine]-6-carboxamide (200 mg, 0.632 mmol), was coupled with tert-butyl (6-carbamoyl-[2,3'-bipyridin]-6'-yl)carbamate (intermediate 2) (177 mg, 0.692 mmol) using cesium carbonate (514 mg, 1.582 mmol), X-Phos (30 mg, 0.063 mmol) and Pd$_2$(dba)$_3$ (28 mg, 0.031 mmol) in toluene (5 mL) to get the crude product. The resultant crude was purified by 60-120 silica gel column chromatography using 2% methanol in DCM as eluent.

Further The resultant crude was purified by prep HPLC to obtain the title compound (13 mg, 5%).

¹HNMR (DMSO-d₆, 300 MHz): δ 10.06 (s, 1H), 9.17-9.16 (d, 1H), 8.64-8.60 (m, 1H), 8.39 (s, 1H), 8.15-8.13 (d, 1H), 8.04-7.99 (t, 1H), 7.93-7.91 (d, 1H), 7.80-7.69 (m, 4H), 3.75-3.72 (t, 4H), 3.55-3.52 (t, 4H). LCMS: 96.5%, m/z=434.4 (M+1)⁺. HPLC: 95.1%.

Example 15

2-(2-methylpyridin-4-yl)-N-(2-morpholinothiazolo[4,5-b]pyridin-6-yl)oxazole-4-carboxamide

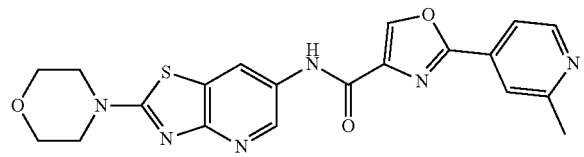 [SMILES: Cc1cc(-c2nc(C(=O)Nc3cnc4nc(N5CCOCC5)sc4c3)co2)ccn1]

Step 1: Preparation of thiazolo[4,5-b]pyridine-2-thiol

Using the same reaction conditions as described in step 1 of example 1, 3-bromopyridin-2-amine (5 gr, 28 mmol) was cyclised using potassium ethyl xanthate (9.24 gr, 57 mmol) in NMP (40 mL) at 150° C. for overnight to afford the title compound (4.2 gr, 88%).

¹HNMR (DMSO-d₆, 300 MHz): δ 8.37-8.35 (m, 1H), 8.15-8.12 (m, 1H), 7.32-7.28 (q, 1H) LCMS: m/z: 169.1 (M+1)⁺.

Step 2: Preparation of 4-(thiazolo[4,5-b]pyridin-2-yl)morpholine

Using the same reaction conditions as described in step 1 of example 4, thiazolo[4,5-b]pyridine-2-thiol (4.2 gr, 25 mmol) was substituted using morpholine (20 mL) at 110° C. to afford the title compound (3 g, 55%).

¹HNMR (DMSO-d₆, 300 MHz): δ 8.32-8.30 (dd, 1H), 8.22-8.18 (dd, 1H), 7.07-7.03 (q, 1H), 3.76-3.72 (m, 4H), 3.62-3.59 (m, 4H). LCMS: m/z: 222.3 (M+1)⁺.

Step 3: Preparation of 4-(6-nitrothiazolo[4,5-b]pyridin-2-yl)morpholine

Using the same reaction conditions as described in step 4 of example 1 4-(thiazolo[4,5-b]pyridin-2-yl)morpholine (2.5 g, 11.3 mmol) was nitrated using acetic acid (5 mL) and fuming nitric acid (10 mL) at 100° C. for overnight to afford the title compound (1.5 g, 50%). ¹HNMR (DMSO-d₆, 300 MHz): δ 9.15-9.09 (m, 2H), 3.70-3.60 (bs, 8H).

Step 4: Preparation of 2-morpholinothiazolo[4,5-b]pyridin-6-amine

Using the same reaction conditions as described in step 5 of example 1 4-(6-nitrothiazolo[4,5-b]pyridin-2-yl)morpholine (500 mg, 1.879 mmol) was reduced with zinc dust (977 mg, 15.03 mmol) and ammonium chloride (812 mg, 15.03 mmol) in THF/methanol/H₂O (10 mL/2 mL/1 mL) to get the title compound (430 mg, 97%).

¹HNMR (DMSO-d₆, 300 MHz): δ 7.75-7.74 (d, 1H), 7.36-7.35 (d, 1H), 5.10-5.05 (bs, 2H), 3.73-3.70 (m, 4H), 3.48-3.34 (m, 4H). LCMS: m/z: 237.4 (M+1)⁺.

Step 5: Preparation of 2-(2-methylpyridin-4-yl)-N-(2-morpholinothiazolo[4,5-b]pyridin-6-yl)oxazole-4-carboxamide Using the same reaction conditions as described in step 6 of example 1, 2-morpholinothiazolo[4,5-b]pyridin-6-amine (110 mg, 0.466 mmol), was coupled with 2-(2-methylpyridin-4-yl)oxazole-4-carboxylic acid (95 mg, 0.466 mmol) using EDCI·HCl (133 mg, 0.699 mmol), HOBt (94 mg, 0.69 mmol), DIPEA (0.2 mL, 1.165 mmol) in DMF (2 mL) to afford the crude product. The resultant crude was purified by 60-120 silica gel column chromatography using 2% methanol in DCM as eluent. The crude was further purified by prep HPLC to obtain the title compound (28 mg, 15%).

¹HNMR (DMSO-d₆, 300 MHz): δ 10.45 (s, 1H), 9.01 (s, 1H), 8.70-8.63 (d, 1H), 8.65-8.62 (dd, 2H), 7.89 (s, 1H), 7.80-7.75 (d, 1H), 3.77-3.72 (t, 4H), 3.62-3.60 (t, 4H), 2.60 (s, 3H).
LCMS: 100%, m/z=423.2 (M+1)⁺. HPLC: 96.9%.

Example 16

6'-amino-N-(2-morpholinothiazolo[4,5-b]pyridin-6-yl)-[2,3'-bipyridine]-6-carboxamide

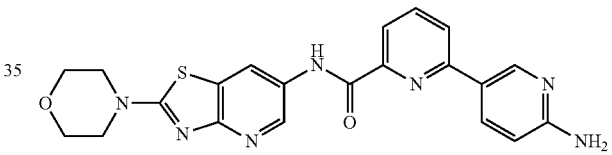

Step 1: Preparation of 6-bromo-N-(2-morpholinothiazolo[4,5-b]pyridin-6-yl)picolinamide Using the same reaction conditions as described in step 6 of example 1, 2-morpholinothiazolo[4,5-b]pyridin-6-amine (product of step 4 of example 15) (320 mg, 1.35 mmol), was coupled with 6-bromopicolinic acid (356 mg, 1.76 mmol) using EDCI·HCl (698 mg, 5.4 mmol), HOBt (239 mg, 1.76 mmol), DIPEA (338 mL, 1.76 mmol) in DMF (5 mL) to afford the title compound (250 mg, 43.9%). LCMS: m/z: 421.6 (M+1)⁺.

Step 2: Preparation of tert-butyl (6-((2-morpholinothiazolo[4,5-b]pyridin-6-yl)carbamoyl)-[2,3'-bipyridin]-6'-yl)carbamate Using the same reaction conditions as described in step 7 of example 1 6-bromo-N-(2-morpholinothiazolo[4,5-b]pyridin-6-yl)picolinamide (250 mg, 0.59 mmol) was coupled with tert-butyl (5-(4,4,5,5-tetramethyl-1,3,2-dioxaborolan-2-yl)pyridin-2-yl)carbamate (151 mg, 0.71 mmol) (intermediate 1) using sodium carbonate (188 mg, 1.77 mmol) and Pd(PPh₃)₂Cl₂ (22 mg, 0.029 mmol) in 1,2-dimethoxyethane (8 mL) to get the crude product. The resultant crude was purified by Combiflash using 0.2-2.0% methanol in chloroform as eluent to obtain the title compound (120 mg, 37.8%). LCMS: m/z: 534.2 (M+1)⁺.

Step 3: Preparation of 6'-amino-N-(2-morpholinothiazolo[4,5-b]pyridin-6-yl)-[2,3'-bipyridine]-6-carboxamide Using the same reaction conditions as described in step 8 of example 1, tert-butyl (6-((2-morpholinothiazolo[4,5-b]pyridin-6-yl)carbamoyl)-[2,3'-bipyridin]-6'-yl)carbamate (120 mg, 0.22 mmol) was deprotected using TFA (12 mL) to get the title compound (80 mg, 82%).

¹HNMR (DMSO-d₆, 300 MHz): δ 10.65 (s, 1H), 8.96 (s, 1H), 8.71 (s, 1H), 8.45-8.42 (d, 1H), 8.08-7.95 (m, 3H), 6.59-6.56 (d, 1H), 6.38 (s, 2H), 3.76-3.74 (t, 4H), 3.63-3.62 (t, 4H). LCMS: 98.9%, m/z=434.1 (M+1)⁺. HPLC: 95.9%.

Example 17

N-(2-morpholinothiazolo[4,5-b]pyridin-6-yl)-6-(1H-pyrazol-4-yl)picolinamide

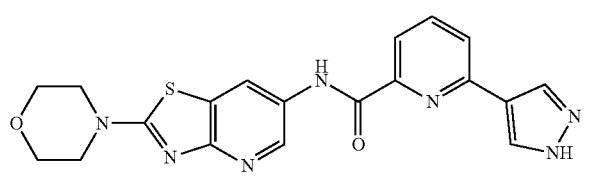 [SMILES: O=C(Nc1cnc2nc(N3CCOCC3)sc2c1)c1cccc(-c2cn[nH]c2)n1]

Using the same reaction conditions as described in step 7 of example 1, 6-bromo-N-(2-morpholinothiazolo[4,5-b]pyridin-6-yl)picolinamide (product of step 1 of example 16) (200 mg, 0.477 mmol) was coupled with 4-(4,4,5,5-tetramethyl-1,3,2-dioxaborolan-2-yl)-1H-pyrazole (111 mg, 0.572 mmol) using sodium carbonate (151 mg, 1.431 mmol) and Pd(PPh₃)₂Cl₂ (35 mg, 0.0477 mmol) in 1,2-dimethoxyethane (5 mL) to get the crude product. The resultant crude was purified by 60-120 silica gel column chromatography using 2% methanol in DCM as eluent. Further it was purified by prep HPLC to obtain the title compound (14 mg, 8%).

¹HNMR (DMSO-d₆, 400 MHz): δ 13.2 (s, 1H), 10.60 (s, 1H), 8.70-8.60 (m, 3H), 8.40 (s, 1H), 8.02-7.91 (m, 3H), 3.76-3.74 (t, 4H), 3.62-3.60 (t, 4H). LCMS: 100%, m/z=408.1 (M+1)⁺.
HPLC: 97.9%.

Example 18

3-(4-(aminomethyl)piperidin-1-yl)-5-fluoro-N-(2-morpholinothiazolo[4,5-b]pyridin-6-yl)benzamide

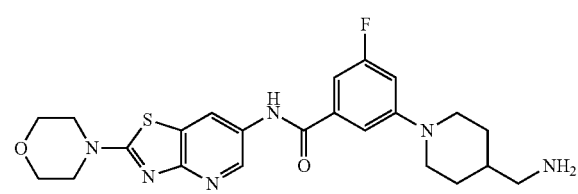 [SMILES: NCC1CCN(c2cc(F)cc(C(=O)Nc3cnc4nc(N5CCOCC5)sc4c3)c2)CC1]

Step 1: tert-butyl ((1-(3-fluoro-5-((2-morpholinothiazolo[4,5-b]pyridin-6-yl)carbamoyl)phenyl)piperidin-4-yl)methyl)carbamate Using the same reaction conditions as described in step 6 of example 1, 2-morpholinothiazolo[4,5-b]pyridin-6-amine (product of step 4 of example 15) (60 mg, 0.254 mmol), was coupled with 3-(4-(((tert-butoxycarbonyl)amino)methyl)piperidin-1-yl)-5-fluorobenzoic acid (intermediate 5) (98 mg, 0.279 mmol) using EDCI·HCl (72 mg, 0.381 mmol), HOBt (52 mg, 0.381 mmol), DIPEA (98 mg, 0.762 mmol) in DMF (5 mL) to afford the title compound (130 mg, 90.2%). LCMS: m/z: 571.2 (M+1)⁺.

Step 2: 3-(4-(aminomethyl)piperidin-1-yl)-5-fluoro-N-(2-morpholinothiazolo[4,5-b]pyridin-6-yl)benzamide Using the same reaction conditions as described in step 8 of example 1, tert-butyl ((1-(3-fluoro-5-((2-morpholinothiazolo[4,5-b]pyridin-6-yl)carbamoyl)phenyl)piperidin-4-yl)methyl)carbamate (130 mg, 0.228 mmol) was deprotected using methanolic HCl (4.7 mL) to get the crude compound. The resultant crude was purified by prep HPLC to obtain the title compound (55 mg, 47.8%).

¹HNMR (DMSO-d₆, 3⁰0 MHz): δ 10.74 (s, 1H), 8.87 (s, 1H), 8.69 (s, 1H), 7.96 (s, 3H), 7.41 (s, 1H), 7.14-7.01 (m, 2H), 3.69-3.68 (m, 6H), 2.83-2.73 (m, 5H), 2.27 (s, 1H), 1.85-1.81 (m, 4H), 1.30-1.23 (m, 3H). LCMS: 100%, m/z=471.5 (M+1)⁺. HPLC: 97.9%.

Example 19

2-(4-(aminomethyl)piperidin-1-yl)-5-fluoro-N-(2-morpholinothiazolo[4,5-b]pyridin-6-yl)benzamide

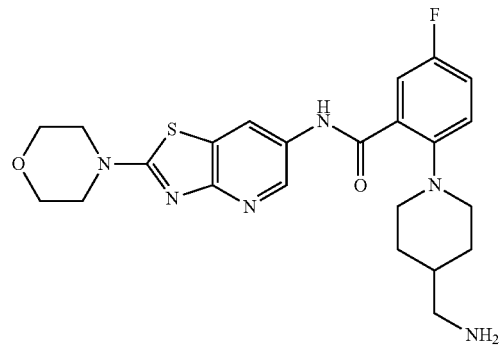 [SMILES: NCC1CCN(c2ccc(F)cc2C(=O)Nc2cnc3nc(N4CCOCC4)sc3c2)CC1]

Step 1: Preparation of tert-butyl ((1-(4-fluoro-2-((2-morpholinothiazolo[4,5-b]pyridin-6-yl)carbamoyl)phenyl)piperidin-4-yl)methyl)carbamate Using the same reaction conditions as described in step 6 of example 1, 2-morpholinothiazolo[4,5-b]pyridin-6-amine (product of step 4 of example 15) (100 mg, 0.423 mmol), was coupled with 2-(4-(((tert-butoxycarbonyl)amino)methyl)piperidin-1-yl)-5-fluorobenzoic acid (intermediate 6) (164 mg, 0.466 mmol) using EDCI·HCl (121 mg, 0.65 mmol), HOBt (85 mg, 0.635 mmol), TEA (0.3 mL, 1.694 mmol) in DMF (4 mL) to afford the title compound (50 mg, 21%). LCMS: m/z: 571.3 (M+1)⁺.

Step 2: Preparation of 2-(4-(aminomethyl)piperidin-1-yl)-5-fluoro-N-(2-morpholinothiazolo[4,5-b]pyridin-6-yl)benzamide Hydrochloride Using the same reaction conditions as described in step 8 of example 1, tert-butyl ((1-(4-fluoro-2-((2-morpholinothiazolo[4,5-b]pyridin-6-yl)carbamoyl)phenyl)piperidin-4-yl)methyl)carbamate (50 mg, 0.087 mmol) was deprotected using methanolic HCl (4.7 mL) to get the title compound (40 mg, 90%).

¹HNMR (DMSO-$d_6$, 300 MHz): δ 11.93 (s, 1H), 8.87-8.86 (d, 1H), 8.70-8.69 (d, 1H), 8.20-7.98 (m, 3H), 7.65-7.61 (m, 1H), 7.49-7.43 (m, 2H), 3.77-3.75 (t, 4H), 3.75-3.67 (t, 4H), 3.22-3.19 (m, 2H), 2.82-2.72 (m, 4H), 1.89-1.85 (m, 3H), 1.40-1.36 (m, 2H). LCMS: 100%, m/z=471.3 (M+1)⁺. HPLC: 96.8%.

Example 20

2-(2-methylpyridin-4-yl)-N-(2-morpholino-5-(piperidin-1-yl)thiazolo[4,5-b]pyridin-6-yl)oxazole-4-carboxamide

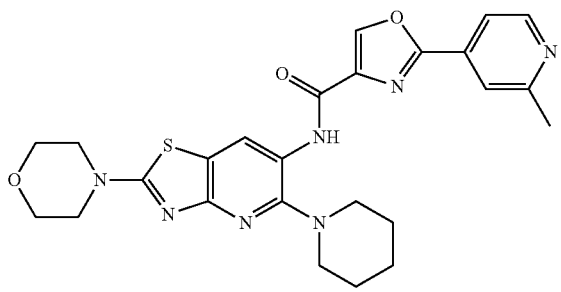 [SMILES: Cc1cc(-c2nc(C(=O)Nc3cc4sc(N5CCOCC5)nc4nc3N3CCCCC3)co2)ccn1]

Step 1: Preparation of 5-chlorothiazolo[4,5-b]pyridine-2-thiol

Using the same reaction conditions as described in step 1 of example 1, 3-bromo-6-chloropyridin-2-amine (1.8 g, 8.653 mmol) was cyclised using potassium ethyl xanthate (2.35 g, 14.71 mmol) in NMP (5 mL) at 165° C. for overnight to afford the crude product (2.0 g).

LCMS: m/z: 202.9 (M+1)⁺.

Step 2: Preparation of 5-chloro-2-(methylthio)thiazolo[4,5-b]pyridine

Using the same reaction conditions as described in step 2 of example 1, 5-chlorothiazolo[4,5-b]pyridine-2-thiol (2 g, 9.850 mmol) was methylated using potassium carbonate (2.71 g, 19.7 mmol) and methyl iodide (2.1 g, 14.775 mmol) in ethyl acetate (10 mL) to afford the crude product. The resultant crude was purified by 60-120 silica gel column chromatography using 20% ethyl acetate in hexane as eluent to obtain the title compound (500 mg, 23.8%).

¹HNMR (CDCl₃, 300 MHz): δ 8.02-8.00 (d, 1H), 7.37-7.24 (m, 2H), 2.85 (s, 3H).

Step 3: Preparation of 4-(5-chlorothiazolo[4,5-b]pyridin-2-yl)morpholine

Using the same reaction conditions as described in step 3 of example 1 5-chloro-2-(methylthio)thiazolo[4,5-b]pyridine (500 mg, 2.314 mmol) was substituted using morpholine (1 mL) and THF (1 mL) to afford the title compound (450 mg, 76.2%).

¹HNMR (CDCl₃, 400 MHz): δ 7.82-7.80 (d, 1H), 7.04-7.01 (d, 1H), 3.84-3.83 (m, 4H), 3.75-3.71 (m, 4H). LCMS: m/z: 256.0 (M+1)⁺.

Step 4: Preparation of 4-(5-chloro-6-nitrothiazolo[4,5-b]pyridin-2-yl)morpholine Potassium nitrate (266 mg, 2.64 mmol) was added to a solution of 4-(5-chlorothiazolo[4,5-b]pyridin-2-yl)morpholine (450 mg, 1.764 mmol) in conc. sulphuric acid (5 mL) and stirred at RT overnight. Ice water was added to the RM and filtered the solid to afford the title compound (450 mg, 86.0%).

¹HNMR (DMSO-$d_6$, 400 MHz): δ 9.06 (s, 1H), 3.75 (s, 8H). LCMS: m/z: 301.0 (M+1)⁺.

Step 5: Preparation of 4-(6-nitro-5-(piperidin-1-yl)thiazolo[4,5-b]pyridin-2-yl)morpholine Using the same reaction conditions as described in step 1 of example 6 4-(5-chloro-6-nitrothiazolo[4,5-b]pyridin-2-yl)morpholine (450 mg, 1.50 mmol) was substituted using piperidine (0.5 mL) in THF (5 mL) 75° C. for 2 h to obtain the title compound (450 mg, 85.7%).

LCMS: m/z: 350.1 (M+1)⁺.

Step 6: Preparation of 2-morpholino-5-(piperidin-1-yl)thiazolo[4,5-b]pyridin-6-amine Using the same reaction conditions as described in step 5 of example 1, 4-(6-nitro-5-(piperidin-1-yl)thiazolo[4,5-b]pyridin-2-yl)morpholine (400 mg, 1.142 mmol) was reduced with zinc dust (600 mg, 9.136 mmol) and ammonium chloride (1.0 g, 18.272 mmol) in THF/methanol/H₂O (10/2 mL/1 mL) to get the crude product (400 mg). LCMS: m/z: 320.25 (M+1)⁺.

Step 7: Preparation of 2-(2-methylpyridin-4-yl)-N-(2-morpholino-5-(piperidin-1-yl)thiazolo[4,5-b]pyridin-6-yl)oxazole-4-carboxamide Using the same reaction conditions as described in step 6 of example 1, 2-morpholino-5-(piperidin-1-yl)thiazolo[4,5-b]pyridin-6-amine (100 mg, 0.313 mmol) was coupled with 2-(2-methylpyridin-4-yl)oxazole-4-carboxylic acid (64 mg, 0.313 mmol) using EDCI·HCl (90 mg, 0.47 mmol), HOBt (64 mg, 0.47 mmol), DIPEA (101 mg, 0.782 mmol) in DMF (5 mL) to afford the crude product. The resultant crude was purified by prep HPLC to obtain the title compound (40 mg, 47.5%).

¹HNMR (DMSO-$d_6$, 400 MHz): δ 9.80 (s, 1H), 9.21 (s, 1H), 8.90-8.88 (m, 2H), 8.19 (s, 1H), 8.07-8.06 (m, 1H), 3.73-3.72 (t, 4H), 3.60-3.58 (t, 4H), 3.03-2.90 (t, 4H), 2.66 (s, 3H), 1.88-1.79 (t, 4H), 1.65-1.58 (m, 2H). LCMS: 90.4%, m/z=506.3 (M+1)⁺. HPLC: 92.6%.

Example 21

N-(2-morpholino-5-(piperidin-1-yl)thiazolo[4,5-b]pyridin-6-yl)-6-(1H-pyrazol-4-yl)picolinamide

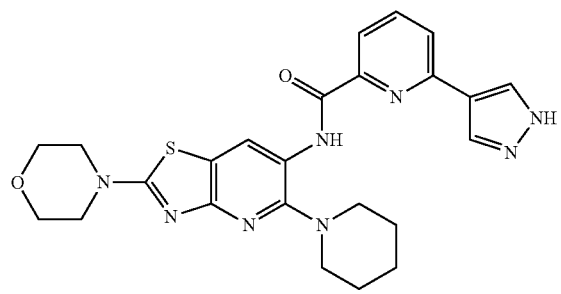 [SMILES: O=C(Nc1cc2sc(N3CCOCC3)nc2nc1N1CCCCC1)c1cccc(-c2cn[nH]c2)n1]

Using the same reaction conditions as described in step 6 of example 1, 2-morpholino-5-(piperidin-1-yl)thiazolo[4,5-b]pyridin-6-amine (product of step 6 of example 20) (100 mg, 0.313 mmol) was coupled with 6-(1-(tetrahydro-2H-pyran-2-yl)-1H-pyrazol-4-yl)picolinic acid (intermediate 3) (90 mg, 0.313 mmol) using EDCI·HCl (90 mg, 0.47 mmol), HOBt (64 mg, 0.47 mmol), DIPEA (101 mg, 0.782 mmol) in DMF (5 mL) to afford the crude coupled product. Using the same reaction conditions as described in step 8 of example 1, the above crude product was deprotected using methanolic HCl (5 mL) to get the crude compound. The resultant crude was purified by prep HPLC to obtain the title compound (30 mg, 43.5%).

$^1$HNMR (DMSO-$d_6$, 400 MHz): δ 10.80 (s, 1H), 9.05 (s, 1H), 8.39 (s, 2H), 8.05-7.98 (m, 3H), 3.73-3.58 (m, 8H), 2.99-2.90 (m, 4H), 1.75-1.68 (m, 4H), 1.54-1.48 (m, 2H). LCMS: 85.0%, m/z=491.3 (M+1)$^+$. HPLC: 95.7%.

Example 22

N-(2,5-di(piperidin-1-yl)thiazolo[4,5-b]pyridin-6-yl)-6-(1H-pyrazol-4-yl)picolinamide

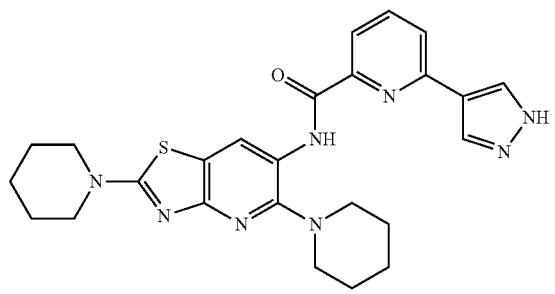 [SMILES: O=C(Nc1cc2sc(N3CCCCC3)nc2nc1N1CCCCC1)c1cccc(-c2cn[nH]c2)n1]

Step 1: Preparation of 5-chloro-2-(piperidin-1-yl)thiazolo[4,5-b]pyridine

Using the same reaction conditions as described in step 3 of example 1 5-chloro-2-(methylthio)thiazolo[4,5-b]pyridine (450 mg, 2.314 mmol) was substituted using piperidine (1 mL) and THF (mL) at 75° C. for 2 h to afford the crude product (500 mg). LCMS: m/z: 254.0 (M+1)$^+$.

Step 2: Preparation of 5-chloro-6-nitro-2-(piperidin-1-yl)thiazolo[4,5-b]pyridine Potassium nitrate (71 mg, 2.657 mmol) was added to the solution of 5-chloro-2-(piperidin-1-yl)thiazolo[4,5-b]pyridine (450 mg, 1.771 mmol) in conc. sulphuric acid (5 mL) and stirred at RT overnight. The ice water was added to the RM and filtered the solid to afford the title compound (400 mg, 75.5%). LCMS: m/z: 299.0 (M+1)$^+$.

Step 3: Preparation of 6-nitro-2,5-di(piperidin-1-yl)thiazolo[4,5-b]pyridine

Using the same reaction conditions as described in step 1 of example 6, 5-chloro-6-nitro-2-(piperidin-1-yl)thiazolo[4,5-b]pyridine (400 mg, 1.337 mmol) was substituted using piperidine (2.0 mL) in THF (5 mL) 75° C. for 30 min to obtain the crude product (400 mg). LCMS: m/z: 348.1 (M+1)$^+$.

Step 4: Preparation of 2,5-di(piperidin-1-yl)thiazolo[4,5-b]pyridin-6-amine

Using the same reaction conditions as described in step 5 of example 1, 6-nitro-2,5-di(piperidin-1-yl)thiazolo[4,5-b]pyridine (400 mg, 1.149 mmol) was reduced with zinc dust (597 mg, 9.192 mmol) and ammonium chloride (974 mg, 18.384 mmol) in THF (10 mL) to get the crude product (320 mg). LCMS: m/z: 318.1 (M+1)$^+$.

Step 5: Preparation of N-(2,5-di(piperidin-1-yl)thiazolo[4,5-b]pyridin-6-yl)-6-(1-(tetrahydro-2H-pyran-2-yl)-1H-pyrazol-4-yl)picolinamide Using the same reaction conditions as described in step 6 of example 1, 2,5-di(piperidin-1-yl)thiazolo[4,5-b]pyridin-6-amine (100 mg, 0.315 mmol) was coupled with 6-(1-(tetrahydro-2H-pyran-2-yl)-1H-pyrazol-4-yl)picolinic acid (intermediate 3) (77 mg, 0.378 mmol) using EDCI·HCl (90 mg, 0.472 mmol), HOBt (63 mg, 0.472 mmol), DIPEA (101 mg, 0.787 mmol) in DMF (5 mL) to afford the crude product (140 mg). LCMS: m/z: 573.3 (M+1)$^+$.

Step 6: Preparation of N-(2,5-di(piperidin-1-yl)thiazolo[4,5-b]pyridin-6-yl)-6-(1H-pyrazol-4-yl)picolinamide Using the same reaction conditions as described in step 8 of example 1, N-(2,5-di(piperidin-1-yl)thiazolo[4,5-b]pyridin-6-yl)-6-(1-(tetrahydro-2H-pyran-2-yl)-1H-pyrazol-4-yl)picolinamide (140 mg, 0.244) was deprotected using methanolic HCl (5 mL) to get the crude compound. The resultant crude was purified by prep HPLC to obtain the title compound (40 mg, 32.3%).

$^1$HNMR (CD$_3$OD, 400 MHz): δ 8.94 (s, 1H), 8.74 (s, 2H), 8.17-8.03 (m, 3H), 3.90-3.82 (m, 4H), 3.33-3.32 (m, 4H), 1.90-1.83 (m, 10H), 1.69-1.68 (m, 2H). LCMS: 99.0%, m/z=489.5 (M+1)$^+$.
HPLC: 96.2%.

Example 23

N-(2,5-di(piperidin-1-yl)thiazolo[4,5-b]pyridin-6-yl)-2-(2-methylpyridin-4-yl)oxazole-4-carboxamide

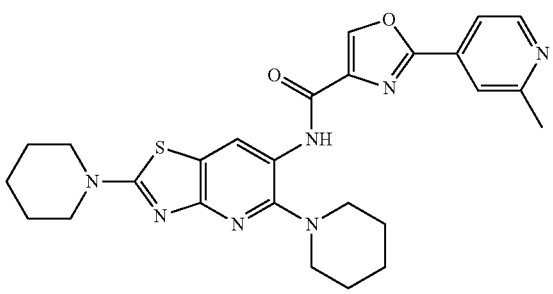 [SMILES: Cc1cc(-c2nc(C(=O)Nc3cc4sc(N5CCCCC5)nc4nc3N3CCCCC3)co2)ccn1]

Using the same reaction conditions as described in step 6 of example 1, 2,5-di(piperidin-1-yl)thiazolo[4,5-b]pyridin-6-amine (product of step 4 of example 22) (100 mg, 0.315 mmol) was coupled with 2-(2-methylpyridin-4-yl)oxazole-4-carboxylic acid (77 mg, 0.378 mmol) using EDCI·HCl (90 mg, 0.472 mmol), HOBt (63 mg, 0.472 mmol), DIPEA (101 mg, 0.787 mmol) in DMF (5 mL) to afford the crude product. The resultant crude was purified by prep HPLC to obtain the title compound (45 mg, 26.5%).

¹HNMR (CD₃OD, 400 MHz): δ 9.00 (s, 1H), 8.96-8.94 (d, 1H), 8.77 (s, 1H), 8.59 (s, 1H), 8.52-8.50 (d, 1H), 3.90-3.81 (m, 4H), 3.50-3.41 (m, 4H), 2.94 (s, 3H), 1.89-1.75 (m, 12H).

LCMS: 80.0%, m/z=504.2 (M+1)⁺. HPLC: 98.4%.

Example 24

N-(2,5-dimorpholinooxazolo[4,5-b]pyridin-6-yl)-2-(2-methylpyridin-4-yl)oxazole-4-carboxamide

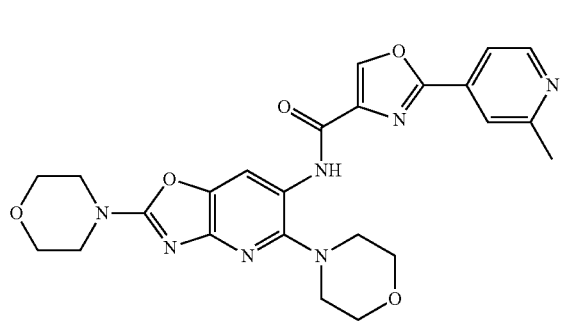 [SMILES: Cc1cc(-c2nc(C(=O)Nc3cc4oc(N5CCOCC5)nc4nc3N3CCOCC3)co2)ccn1]

Step 1: Preparation of 2,5-dimorpholino-6-nitrooxazolo[4,5-b]pyridine

Using the same reaction conditions as described in step 1 of example 4, 5-chloro-2-morpholino-6-nitrooxazolo[4,5-b]pyridine (product of step 5 of example 2) (175 mg, 0.6147 mmol) was heated with morpholine (2 mL) at 110° C. for 3 h. The solvent was distilled to afford the crude product. The resultant crude was purified by 60-120 silica gel column chromatography using 1% methanol in DCM as eluent to obtain the title compound (190 mg, 92.23%).

¹HNMR (CDCl₃, 300 MHz): δ 8.14 (s, 1H), 3.84-3.81 (m, 12H), 3.49-3.45 (m, 4H). LCMS: m/z=336.0 (M+1)⁺.

Step 2: Preparation of 2,5-dimorpholinooxazolo[4,5-b]pyridin-6-amine

Using the same reaction conditions as described in step 5 of example 1, 2,5-dimorpholino-6-nitrooxazolo[4,5-b]pyridine (190 mg, 0.5666 mmol) was reduced with zinc dust (297 mg, 4.5329 mmol) and ammonium chloride (485 mg, 9.0659 mmol) in THF/methanol/H₂O (10 mL/2 mL/1 mL) to get the title compound (150 mg, 86.70%).

¹HNMR (CDCl₃, 400 MHz): δ 6.97 (s, 1H), 3.87-3.66 (m, 14H), 3.12-3.10 (t, 4H). LCMS: m/z=306.1 (M+1)⁺.

Step 3: Preparation of N-(2,5-dimorpholinooxazolo[4,5-b]pyridin-6-yl)-2-(2-methylpyridin-4-yl)oxazole-4-carboxamide Hydrochloride Using the same reaction conditions as described in step 6 of example 1, 2,5-dimorpholinooxazolo[4,5-b]pyridin-6-amine (70 mg, 0.229 mmol), was coupled with 2-(pyridin-4-yl)oxazole-4-carboxylic acid (56 mg, 0.275 mmol) using EDCI·HCl (66 mg, 0.343 mmol), HOBt (47 mg, 0.343 mmol), DIPEA (0.16 mL, 0.917 mmol) in DMF (2 mL) to get the crude product. This was then treated with methanolic HCl to afford the title compound (61 mg, 50.41%).

¹HNMR (CD₃OD, 400 MHz): δ 8.90-8.88 (m, 2H), 8.7 (s, 1H), 8.6 (s, 1H), 8.5 (d, 1H), 3.99-3.95 (t, 4H), 3.84-3.83 (t, 4H), 3.78-3.76 (t, 4H), 3.20-3.18 (t, 4H), 2.92 (s, 3H). LCMS: m/z=492.0 (M+1)⁺. HPLC: 95.10%.

Example 25

N-(5-(4-methylpiperazin-1-yl)-2-morpholinooxazolo[4,5-b]pyridin-6-yl)-2-(2-methylpyridin-4-yl)oxazole-4-carboxamide

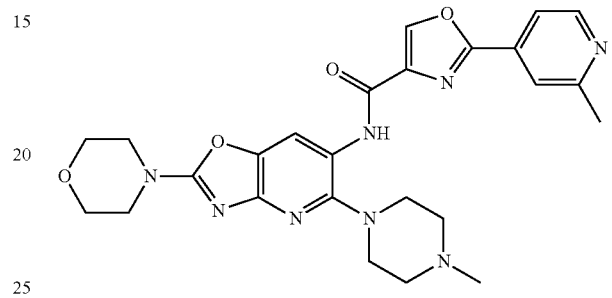

Step 1: Preparation of 5-(4-methylpiperazin-1-yl)-2-morpholino-6-nitrooxazolo[4,5-b]pyridine Using the same reaction conditions as described in step 1 of example 4, 5-chloro-2-morpholino-6-nitrooxazolo[4,5-b]pyridine (product of step 5 of example 2) (175 mg, 0.6147 mmol) was heated with N-methylpiperazine (185 mg, 1.844 mmol) at 75° C. for 3 h. The solvent was distilled to afford the crude product. The resultant crude was purified by 60-120 silica gel column chromatography using 5% methanol in DCM as eluent to obtain the title compound (200 mg, 93.45%). m/z=349.3 (M+1)⁺.

Step 2: Preparation of 5-(4-methylpiperazin-1-yl)-2-morpholinooxazolo[4,5-b]pyridin-6-amine Using the same reaction conditions as described in step 5 of example 1, 5-(4-methylpiperazin-1-yl)-2-morpholino-6-nitrooxazolo[4,5-b]pyridine (200 mg, 0.5747 mmol) was reduced with zinc dust (301 mg, 4.5977 mmol) and ammonium chloride (492 mg, 9.1954 mmol) in THF/methanol/H₂O (10 mL/2 mL/1 mL) to get the title compound (150 mg, 81.96%). LCMS: m/z=319.4 (M+1)⁺.

Step 3: Preparation of N-(5-(4-methylpiperazin-1-yl)-2-morpholinooxazolo[4,5-b]pyridin-6-yl)-2-(2-methylpyridin-4-yl)oxazole-4-carboxamide Hydrochloride Using the same reaction conditions as described in step 6 of example 1, 5-(4-methylpiperazin-1-yl)-2-morpholinooxazolo[4,5-b]pyridin-6-amine (70 mg, 0.2198 mmol), was coupled with 2-(2-methylpyridin-4-yl)oxazole-4-carboxylic acid (54 mg, 0.2638 mmol) using EDCI·HCl (64 mg, 0.3298 mmol), HOBt (45 mg, 0.3298 mmol), DIPEA (0.145 mL, 0.8794 mmol) in DMF (2 mL) to get the crude product. This was then purified by prep HPLC and treated with methanolic HCl to afford the title compound (50 mg, 42.01%).

¹HNMR (CD₃OD, 400 MHz): δ 8.91 (m, 2H), 8.70 (s, 1H), 8.60-8.55 (m, 2H), 3.85-3.82 (t, 4H), 3.76-3.74 (t, 4H), 3.67-3.30 (m, 8H), 3.04 (s, 3H), 2.93 (s, 3H). m/z=505.3 (M+1)⁺. HPLC: 97.92%.

Example 26

N-(2,5-di(piperidin-1-yl)oxazolo[4,5-b]pyridin-6-yl)-2-(6-methoxypyridin-3-yl)oxazole-4-carboxamide

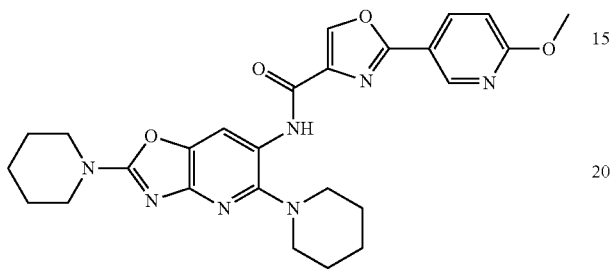

Using the same reaction conditions as described in step 6 of example 1, 2,5-di(piperidin-1-yl)oxazolo[4,5-b]pyridin-6-amine (product of step 4 of example 4) (70 mg, 0.2317 mmol), was coupled with 2-(6-methoxypyridin-3-yl)oxazole-4-carboxylic acid (intermediate 7) (62 mg, 0.2781 mmol) using EDCI·HCl (67 mg, 0.3476 mmol), HOBt (47 mg, 0.3476 mmol), DIPEA (0.162 mL, 0.9271 mmol) in DMF (2 mL) to afford the crude product. This was then purified by prep HPLC to get the title compound (10 mg, 8.54%).

¹HNMR (DMSO-d₆, 400 MHz): δ 9.77 (s, 1H), 8.84 (s, 1H), 8.85-8.84 (d, 1H), 8.60 (s, 1H), 8.27-8.24 (dd, 1H), 7.10-7.07 (d, 1H), 3.95 (s, 3H), 3.62-3.60 (t, 4H), 2.94-2.91 (t, 4H), 1.90 (s, 4H), 1.77-1.50 (s, 8H). LCMS: m/z=504.2 (M+1)⁺. HPLC: 97.23%.

Example 27

N-(2,5-di(piperidin-1-yl)oxazolo[4,5-b]pyridin-6-yl)-2-(2-methylpyridin-3-yl)oxazole-4-carboxamide

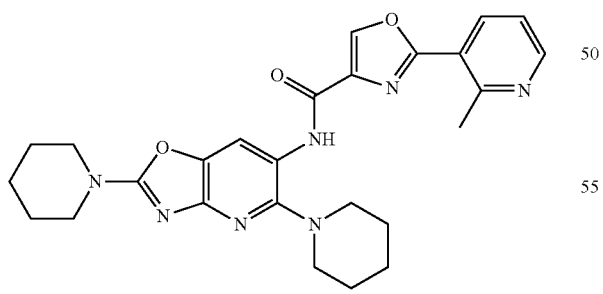

Using the same reaction conditions as described in step 6 of example 1, 2,5-di(piperidin-1-yl)oxazolo[4,5-b]pyridin-6-amine (product of step 4 of example 4) (70 mg, 0.2317 mmol), was coupled with 2-(2-methylpyridin-3-yl)oxazole-4-carboxylic acid (intermediate 8) (57 mg, 0.2781 mmol) using EDCI·HCl (67 mg, 0.3476 mmol), HOBt (47 mg, 0.3476 mmol), DIPEA (0.162 mL, 0.9271 mmol) in DMF (2 mL) to afford the crude product. This was then purified by prep HPLC to get the title compound (50 mg, 44.24%).

¹HNMR (DMSO-d₆, 400 MHz): δ 9.79 (s, 1H), 9.02 (s, 1H), 8.639-8.631 (d, 2H), 8.33-8.30 (d, 1H), 7.50-7.45 (m, 1H), 3.61-3.60 (m, 4H), 2.97 (s, 3H), 2.90-2.88 (t, 4H), 1.80-1.70 (m, 4H), 1.61-1.50 (m, 8H). LCMS: m/z=488.2 (M+1)⁺. HPLC: 97.55%.

Example 28

N-(2,5-di(piperidin-1-yl)oxazolo[4,5-b]pyridin-6-yl)-2-(2-hydroxypyridin-3-yl)oxazole-4-carboxamide

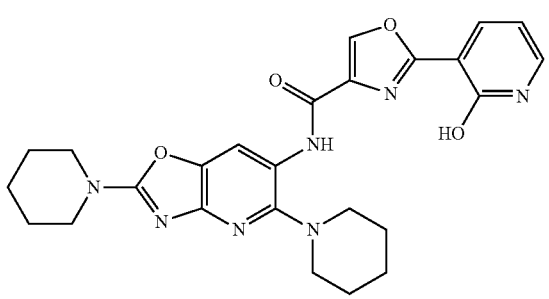 [SMILES: O=C(Nc1cc2oc(N3CCCCC3)nc2nc1N1CCCCC1)c1coc(-c2cccnc2O)n1]

Using the same reaction conditions as described in step 6 of example 1, 2,5-di(piperidin-1-yl)oxazolo[4,5-b]pyridin-6-amine (product of step 4 of example 4) (70 mg, 0.232 mmol), was coupled with 2-(2-hydroxypyridin-3-yl)oxazole-4-carboxylic acid (intermediate 9) (48 mg, 0.232 mmol) using EDCI·HCl (67 mg, 0.348 mmol), HOBt (47 mg, 0.348 mmol), DIPEA (75 mg, 0.581 mmol) in DMF (2 mL) to afford the title compound (75 mg, 66.3%).

¹HNMR (DMSO-d₆, 400 MHz): δ 12.4 (s, 1H), 9.80 (s, 1H), 8.87 (s, 1H), 8.61 (s, 1H), 8.22-8.20 (d, 1H), 7.70-7.69 (d, 1H), 6.45-6.42 (t, 1H), 3.62 (s, 4H), 2.90-2.89 (m, 4H), 1.90-1.77 (m, 4H), 1.69-1.55 (m, 8H). LCMS: m/z=490.1 (M+1)⁺. HPLC: 90.22%.

Example 29

2-(2-hydroxypyridin-3-yl)-N-(2-morpholino-5-(piperidin-1-yl)oxazolo[4,5-b]pyridin-6-yl)oxazole-4-carboxamide

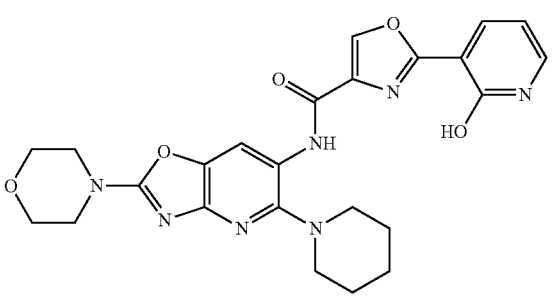 [SMILES: O=C(Nc1cc2oc(N3CCOCC3)nc2nc1N1CCCCC1)c1coc(-c2cccnc2O)n1]

Using the same reaction conditions as described in step 6 of example 1, 2-morpholino-5-(piperidin-1-yl)oxazolo[4,5-b]pyridin-6-amine (product of step 2 of example 6) (70 mg, 0.232 mmol), was coupled with 2-(2-hydroxypyridin-3-yl)oxazole-4-carboxylic acid (intermediate 9) (48 mg, 0.232 mmol) using EDCI·HCl (67 mg, 0.348 mmol), HOBt (47 mg, 0.348 mmol), DIPEA (75 mg, 0.581 mmol) in DMF (2 mL) to afford the title compound (65 mg, 57.5%).

$^1$HNMR (DMSO-$d_6$, 400 MHz): δ 12.30 (s, 1H), 9.80 (s, 1H), 8.88 (s, 1H), 8.65 (s, 1H), 8.24-8.13 (d, 1H), 7.70-7.64 (d, 1H), 6.50-6.30 (t, 1H), 3.73-3.72 (m, 4H), 3.63-3.62 (m, 4H), 2.90-2.89 (m, 4H), 1.90-1.76 (m, 4H), 1.64-1.54 (m, 2H). LCMS: m/z=492.0 (M+1)$^+$. HPLC: 90.53%.

Example 30

N-(2,5-di(piperidin-1-yl)oxazolo[4,5-b]pyridin-6-yl)-2-(6-hydroxypyridin-3-yl)oxazole-4-carboxamide

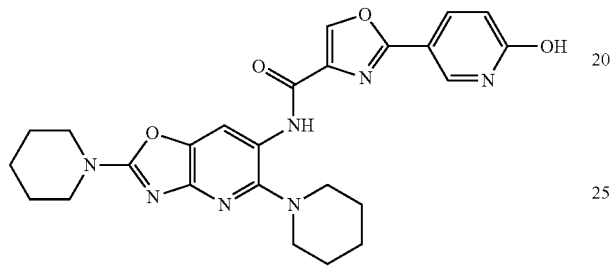

Using the same reaction conditions as described in step 6 of example 1, 2,5-di(piperidin-1-yl)oxazolo[4,5-b]pyridin-6-amine (product of step 4 of example 4) (75 mg, 0.247 mmol), was coupled with 2-(2-hydroxypyridin-5-yl)oxazole-4-carboxylic acid (intermediate 10) (61 mg, 0.297 mmol) using EDCI·HCl (70 mg, 0.371 mmol), HOBt (50 mg, 0.371 mmol), DIPEA (0.2 mL, 0.99 mmol) in DMF (4 mL) to afford the crude product. This was then purified by prep HPLC to get the title compound (25 mg, 21%).

$^1$HNMR (DMSO-$d_6$, 400 MHz): δ 12.30 (s, 1H), 9.90 (s, 1H), 8.84 (s, 1H), 8.59 (s, 1H), 8.14-8.02 (d, 1H), 7.98-7.88 (d, 1H), 6.68-6.53 (d, 1H), 3.64-3.52 (m, 4H), 2.94-2.92 (t, 4H), 1.84-1.73 (m, 4H), 1.70-1.54 (m, 8H). LCMS: m/z=490.2 (M+1)$^+$. HPLC: 93.74%.

Example 31

2-(2-methoxypyridin-4-yl)-N-(2-morpholino-5-(piperidin-1-yl)oxazolo[4,5-b]pyridin-6-yl)oxazole-4-carboxamide

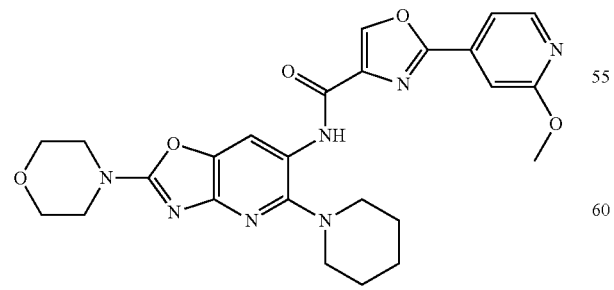

Using the same reaction conditions as described in step 6 of example 1, 2-morpholino-5-(piperidin-1-yl)oxazolo[4,5-b]pyridin-6-amine (product of step 2 of example 6) (70 mg, 0.230 mmol), was coupled with 2-(2-methoxypyridin-4-yl)oxazole-4-carboxylic acid (intermediate 11) (57 mg, 0.276 mmol) using EDCI·HCl (67 mg, 0.346 mmol), HOBt (47 mg, 0.346 mmol), DIPEA (0.161 mL, 0.929 mmol) in DMF (2 mL) to afford the crude product. This was then purified by prep HPLC to get the title compound (7 mg, 6.03%).

$^1$HNMR (CDCl$_3$, 400 MHz): δ 10.0 (s, 1H), 8.76 (s, 1H), 8.38-8.33 (d, 2H), 7.51 (s, 1H), 7.38 (s, 1H), 5.34 (s, 1H), 4.10 (s, 3H), 3.80-3.70 (d, 8H), 3.05 (s, 4H), 1.89-1.82 (m, 4H), 1.65-1.63 (bs, 2H). LCMS: m/z=506.2 (M+1)$^+$. HPLC: 95.81%.

Example 32

2-(2-methylpyridin-3-yl)-N-(2-morpholino-5-(piperidin-1-yl)oxazolo[4,5-b]pyridin-6-yl)oxazole-4-carboxamide

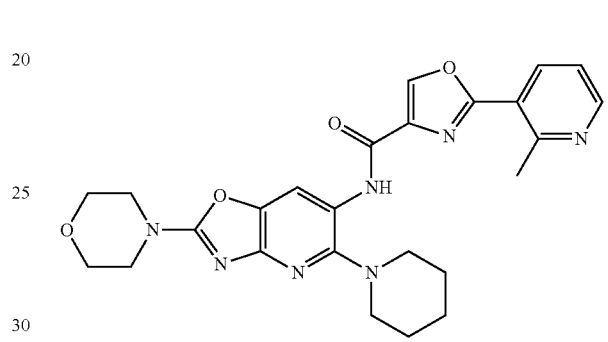

Using the same reaction conditions as described in step 6 of example 1, 2-morpholino-5-(piperidin-1-yl)oxazolo[4,5-b]pyridin-6-amine (product of step 2 of example 6) (70 mg, 0.230 mmol), was coupled with 2-(2-methoxypyridin-3-yl)oxazole-4-carboxylic acid (intermediate 8) (57 mg, 0.276 mmol) using EDCI·HCl (67 mg, 0.346 mmol), HOBt (47 mg, 0.346 mmol), DIPEA (0.161 mL, 0.929 mmol) in DMF (2 mL) to afford the crude product. This was then purified by prep HPLC to get the title compound (7 mg, 6.03%).

$^1$HNMR (DMSO-$d_6$, 400 MHz): δ 9.91 (s, 1H), 9.11 (s, 1H), 8.78-8.77 (d, 1H), 8.65-8.62 (m, 2H), 7.76-7.75 (t, 1H), 3.73-3.61 (m, 8H), 3.08 (s, 3H), 2.94-2.75 (m, 4H), 1.76-1.65 (m, 4H), 1.60-1.55 (m, 2H). LCMS: m/z=490.2 (M+1)$^+$. HPLC: 96.28%.

Example 33

2-(3-methylpyridin-4-yl)-N-(2-morpholino-5-(piperidin-1-yl)oxazolo[4,5-b]pyridin-6-yl)oxazole-4-carboxamide

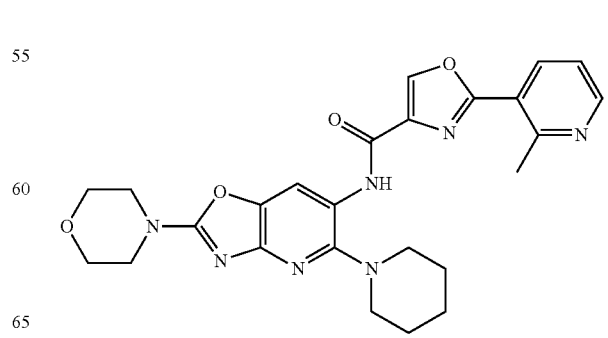

Using the same reaction conditions as described in step 6 of example 1, 2-morpholino-5-(piperidin-1-yl)oxazolo[4,5-b]pyridin-6-amine (product of step 2 of example 6) (54 mg, 0.265 mmol), was coupled with 2-(3-methylpyridin-4-yl)oxazole-4-carboxylic acid (intermediate 12) (80 mg, 0.265 mmol) using EDCI·HCl (77 mg, 0.397 mmol), HOBt (38 mg, 0.278 mmol), DIPEA (0.12 mL, 0.927 mmol) in DMF (5 mL) to afford the title compound (121 mg, 93%).

$^1$HNMR (DMSO-d$_6$, 300 MHz): δ 9.90 (s, 1H), 9.10 (s, 1H), 8.75-8.60 (m, 3H), 7.95-7.86 (d, 1H), 3.80-3.52 (m, 8H), 2.95-2.85 (m, 4H), 2.80 (s, 3H), 1.80-1.68 (m, 4H), 1.66-1.50 (m, 2H).
LCMS: m/z=490.4 (M+1)$^+$. HPLC: 95.93%.

Example 34

N-(2,5-di(piperidin-1-yl)oxazolo[4,5-b]pyridin-6-yl)-2-(3-methylpyridin-4-yl)oxazole-4-carboxamide

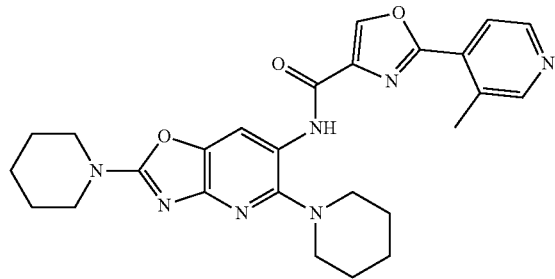 [SMILES: Cc1cnccc1-c1nc(C(=O)Nc2cc3oc(N4CCCCC4)nc3nc2N2CCCCC2)co1]

Using the same reaction conditions as described in step 6 of example 1, 2,5-di(piperidin-1-yl)oxazolo[4,5-b]pyridin-6-amine (product of step 4 of example 4) (54 mg, 0.265 mmol), was coupled with 2-(3-methylpyridin-4-yl)oxazole-4-carboxylic acid (intermediate 12) (80 mg, 0.265 mmol) using EDCI·HCl (77 mg, 0.397 mmol), HOBt (38 mg, 0.278 mmol), DIPEA (0.12 mL, 0.927 mmol) in DMF (5 mL) to afford the title compound (117 mg, 91%).

$^1$HNMR (DMSO-d$_6$, 300 MHz): δ 9.90 (s, 1H), 9.05 (s, 1H), 8.77 (s, 1H), 8.68-8.60 (m, 2H), 7.90-7.85 (d, 1H), 3.70-3.60 (m, 4H), 2.95-2.85 (m, 4H), 2.80 (s, 3H), 1.80-1.70 (m, 4H), 1.68-1.50 (m, 8H). LCMS: 98.99%, m/z=488.4 (M+1)$^+$. HPLC: 97.00%.

Example 35

2-(6-methylpyridin-3-yl)-N-(2-morpholino-5-(piperidin-1-yl)oxazolo[4,5-b]pyridin-6-yl)oxazole-4-carboxamide

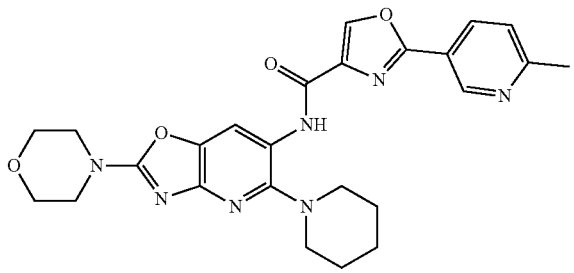

Using the same reaction conditions as described in step 6 of example 1, 2-morpholino-5-(piperidin-1-yl)oxazolo[4,5-b]pyridin-6-amine (product of step 2 of example 6) (70 mg, 0.230 mmol), was coupled with 2-(6-methylpyridin-3-yl)oxazole-4-carboxylic acid (intermediate 13) (57 mg, 0.276 mmol) using EDCI·HCl (67 mg, 0.346 mmol), HOBt (47 mg, 0.346 mmol), DIPEA (0.201 mL, 1.153 mmol) in DMF (2 mL) to afford crude product. This was then purified by prep HPLC to get the title compound (30 mg, 24.79%).

$^1$HNMR (DMSO-d$_6$, 400 MHz): δ 9.85 (s, 1H), 9.147-9.142 (d, 1H), 9.04 (s, 1H), 8.64 (s, 1H), 8.37-8.35 (dd, 1H), 7.64-7.62 (d, 1H), 3.74-3.72 (m, 4H), 3.64-3.62 (m, 4H), 3.15-2.90 (m, 4H), 2.62 (s, 3H), 1.90-1.75 (m, 4H), 1.70-1.55 (m, 2H). LCMS: 98.39%, m/z=490.0 (M+1)$^+$. HPLC: 95.97%.

Example 36

6-(1-methyl-1H-pyrazol-4-yl)-N-(2-morpholino-5-(piperidin-1-yl)oxazolo[4,5-b]pyridin-6-yl)picolinamide

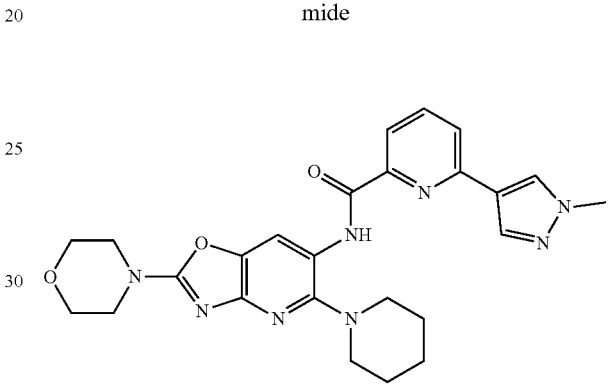

Using the same reaction conditions as described in step 6 of example 1, 2-morpholino-5-(piperidin-1-yl)oxazolo[4,5-b]pyridin-6-amine (product of step 2 of example 6) (80 mg, 0.2640 mmol), was coupled with 6-(1-methyl-1H-pyrazol-4-yl)picolinic acid (intermediate 4) (65 mg, 0.3168 mmol) using EDCI·HCl (76 mg, 0.3960 mmol), HOBt (38 mg, 0.2772 mmol), DIPEA (0.103 mg, 0.7920 mmol) in DMF (4 mL) to afford title compound (75 mg, 58.59%).

$^1$HNMR (DMSO-d$_6$, 400 MHz): δ 10.9 (s, 1H), 8.70 (s, 1H), 8.43 (s, 1H), 8.22 (s, 1H), 8.10-7.90 (m, 3H), 4.00 (s, 3H), 3.80-3.70 (m, 4H), 3.69-3.60 (m, 4H), 3.0 (s, 4H), 1.80 (s, 4H), 1.55 (s, 2H). LCMS: 100%, m/z=489.3 (M+1)$^+$. HPLC: 96.26%.

Example 37

N-(2,5-di(piperidin-1-yl)oxazolo[4,5-b]pyridin-6-yl)-2-(6-methylpyridin-3-yl)oxazole-4-carboxamide

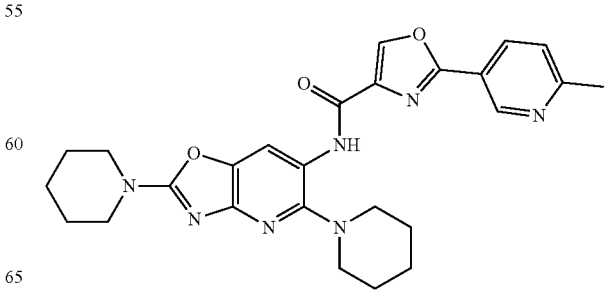

Using the same reaction conditions as described in step 6 of example 1, 2,5-di(piperidin-1-yl)oxazolo[4,5-b]pyridin-6-amine (product of step 4 of example 4) (80 mg, 0.265 mmol), was coupled with 2-(2-methylpyridin-5-yl)oxazole-5-carboxylic acid (intermediate 13) (60 mg, 0.292 mmol) using EDCI·HCl (77 mg, 0.398 mmol), HOBt (38 mg, 0.279 mmol), DIPEA (0.102 mg, 0.797 mmol) in DMF (4 mL) to afford the title compound (90 mg, 69.7%).

$^1$HNMR (DMSO-d$_6$, 400 MHz): δ 9.83 (s, 1H), 9.11 (s, 1H), 9.00 (s, 1H), 8.61 (s, 1H), 8.27-8.25 (dd, 1H), 7.54-7.52 (d, 1H), 3.63 (s, 4H), 2.94-2.93 (t, 4H), 2.58 (s, 3H), 1.82 (s, 4H), 1.63 (s, 8H). LCMS: 98.89%, m/z=488.2 (M+1)$^+$. HPLC: 98.54%.

Example 38

(S)—N-(5-(3-aminopyrrolidin-1-yl)-2-morpholinooxazolo[4,5-b]pyridin-6-yl)-2-(2-methylpyridin-4-yl)oxazole-4-carboxamide

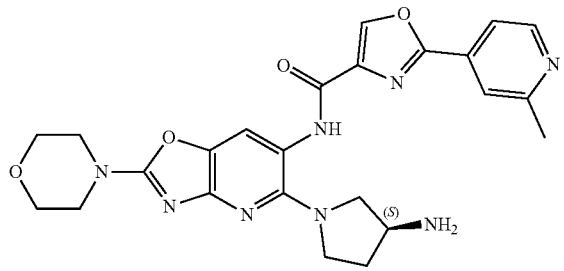

Step 1: Preparation of tert-butyl (S)-(1-(2-morpholino-6-nitrooxazolo[4,5-b]pyridin-5-yl)pyrrolidin-3-yl)carbamate In a round bottom flask, taken 5-chloro-2-morpholino-6-nitrooxazolo[4,5-b]pyridine (product of step 5 of example 2) (157 mg, 0.555 mmol), tert-butyl (S)-pyrrolidin-3-ylcarbamate (125 mg, 0.555 mmol) potassium carbonate (238 mg, 1.722 mmol) and DMF (5 mL) and stirred at RT overnight. The ice water was added and filtered the solid and dried under vacuum to afford the crude product which was used as such for next step.
LCMS: m/z=435.2 (M+1)$^+$. HPLC: 80.36%.

Step 2: Preparation of tert-butyl (S)-(1-(6-amino-2-morpholinooxazolo[4,5-b]pyridin-5-yl)pyrrolidin-3-yl)carbamate The crude tert-butyl (S)-(1-(2-morpholino-6-nitrooxazolo[4,5-b]pyridin-5-yl)pyrrolidin-3-yl)carbamate obtained above was dissolved in methanol (30 mL) and added 10% Pd/C (25 mg) and stirred under hydrogen balloon for two hours. The reaction mass was filtered through Celite® and concentrated to get the title compound (71 mg, 32%).
LCMS: m/z=405.2 (M+1)$^+$. HPLC: 79.86%.

Step 3: Preparation of tert-butyl (S)-(1-(6-(2-(2-methylpyridin-4-yl)oxazole-4-carboxamido)-2-morpholinooxazolo[4,5-b]pyridin-5-yl)pyrrolidin-3-yl)carbamate Using the same reaction conditions as described in step 6 of example 1, tert-butyl (S)-(1-(6-amino-2-morpholinooxazolo[4,5-b]pyridin-5-yl)pyrrolidin-3-yl)carbamate (70 mg, 0.341 mmol), was coupled with 2-(2-methylpyridin-4-yl)oxazole-4-carboxylic acid (115 mg, 0.284 mmol) using EDCI·HCl (98 mg, 0.512 mmol), HOBt (46 mg, 0.341 mmol), DIPEA (0.148 mg, 1.1384 mmol) in DMF (4 mL) to get the title compound (152 mg, 91%).
LCMS: m/z=591.6 (M+1)$^+$. HPLC: 86.43%.

Step 4: Preparation of (S)—N-(5-(3-aminopyrrolidin-1-yl)-2-morpholinooxazolo[4,5-b]pyridin-6-yl)-2-(2-methylpyridin-4-yl)oxazole-4-carboxamide Hydrochloride Using the same reaction conditions as described in step 8 of example 1, tert-butyl (S)-(1-(6-(2-(2-methylpyridin-4-yl)oxazole-4-carboxamido)-2-morpholinooxazolo[4,5-b]pyridin-5-yl)pyrrolidin-3-yl)carbamate (150 mg, 0.2542 mmol) was deprotected using methanolic HCl (5 mL) to get the crude product. This was then purified by prep HPLC to get the title compound (58 mg, 97%).

$^1$HNMR (CD$_3$OD, 400 MHz): δ 8.97 (s, 1H), 8.93-8.91 (d, 1H), 8.64 (s, 1H), 8.56-8.55 (d, 1H), 8.02 (s, 1H), 4.02-3.67 (m, 13H), 2.90 (s, 3H), 2.50-2.40 (m, 1H), 2.25-2.05 (m, 1H).
LCMS: 96.74%, m/z=491.4 (M+1)$^+$. HPLC: 95.27%.

Example 39

(S)—N-(5-(3-hydroxypyrrolidin-1-yl)-2-morpholinooxazolo[4,5-b]pyridin-6-yl)-2-(2-methylpyridin-4-yl)oxazole-4-carboxamide

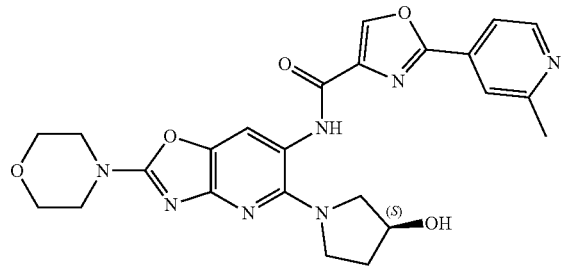

Step 1: Preparation of (S)-1-(2-morpholino-6-nitrooxazolo[4,5-b]pyridin-5-yl)pyrrolidin-3-ol Using the same reaction conditions as described in step 1 of example 38, 5-chloro-2-morpholino-6-nitrooxazolo[4,5-b]pyridine (product of step 5 of example 2) (200 mg, 0.704 mmol) was substituted with(S)-pyrrolidin-3-ol (61 mg, 0.704 mmol) using potassium carbonate (291 mg, 2.112 mmol) and DMF (5 mL) to afford the title product (195 mg, 82%) LCMS: m/z=335.9 (M+1)$^+$.

Step 2: Preparation of (S)-1-(6-amino-2-morpholinooxazolo[4,5-b]pyridin-5-yl)pyrrolidin-3-ol Using the same reaction conditions as described in step 2 of example 38, (S)-1-(2-morpholino-6-nitrooxazolo[4,5-b]pyridin-5-yl)pyrrolidin-3-ol (194 mg, 0.579 mmol) was reduced using 10% Pd/C (50 mg) in methanol (40 mL) to get the title compound (162 mg, 92%). LCMS: m/z=306.1 (M+1)$^+$.

Step 3: Preparation of (S)—N-(5-(3-hydroxypyrrolidin-1-yl)-2-morpholinooxazolo[4,5-b]pyridin-6-yl)-2-(2-methylpyridin-4-yl)oxazole-4-carboxamide Using the same reaction conditions as described in step 6 of example 1, (S)-1-(6-amino-2-morpholinooxazolo[4,5-b]pyridin-5-yl)pyrrolidin-3-ol (160 mg, 0.526 mmol), was coupled with 2-(2-methylpyridin-4-yl)oxazole-4-carboxylic acid (108 mg, 0.526 mmol) using EDCI·HCl (151 mg, 0.789 mmol), HOBt (75 mg, 0.5523 mmol), DIPEA (0.272 mg, 2.104 mmol) in DMF (5 mL) to get the title compound (45 mg, 17%).
$^1$HNMR (CD$_3$OD, 400 MHz): δ 8.70 (s, 1H), 8.64-8.63 (d, 1H), 8.02 (s, 1H), 7.94-7.93 (d, 1H), 7.87 (s, 1H), 4.49-4.45 (m, 1H), 3.84-3.71 (m, 10H), 3.70-3.47 (m, 2H), 2.67 (s, 3H), 2.13-2.10 (m, 1H), 2.00-1.80 (m, 1H). LCMS: 100%, m/z=492.2 (M+1)$^+$. HPLC: 97.90%.

Example 40

(R)—N-(5-(3-aminopyrrolidin-1-yl)-2-morpholinooxazolo[4,5-b]pyridin-6-yl)-2-(2-methylpyridin-4-yl)oxazole-4-carboxamide

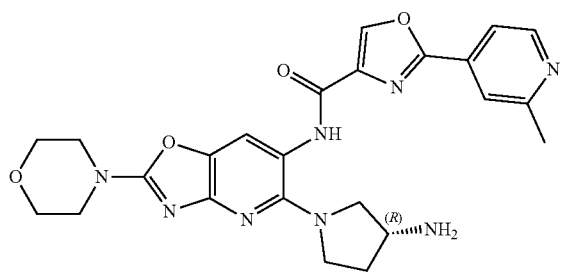

Step 1: Preparation of tert-butyl (R)-(1-(2-morpholino-6-nitrooxazolo[4,5-b]pyridin-5-yl)pyrrolidin-3-yl)carbamate Using the same reaction conditions as described in step 1 of example 38, 5-chloro-2-morpholino-6-nitrooxazolo[4,5-b]pyridine (product of step 5 of example 2) (126 mg, 0.444 mmol) was substituted with tert-butyl (R)-pyrrolidin-3-ylcarbamate (100 mg, 0.444 mmol) using potassium carbonate (183 mg, 1.33 mmol) and DMF (5 mL) to afford the crude product. The resultant crude was purified by 60-120 silica gel column chromatography using 1% methanol in DCM as eluent to obtain the title compound (127 mg, 66%). LCMS: m/z=435.2 (M+1)$^+$.

Step 2: Preparation of tert-butyl (R)-(1-(6-amino-2-morpholinooxazolo[4,5-b]pyridin-5-yl)pyrrolidin-3-yl)carbamate Using the same reaction conditions as described in step 2 of example 38, (R)-(1-(2-morpholino-6-nitrooxazolo[4,5-b]pyridin-5-yl)pyrrolidin-3-yl)carbamate (126 mg, 0.290 mmol) was reduced using 10% Pd/C (25 mg) in methanol (20 mL) to get the title compound (102 mg, 87%). LCMS: m/z=405.3 (M+1)$^+$.

Step 3: Preparation of tert-butyl (R)-(1-(6-(2-(2-methylpyridin-4-yl)oxazole-4-carboxamido)-2-morpholinooxazolo[4,5-b]pyridin-5-yl)pyrrolidin-3-yl)carbamate Using the same reaction conditions as described in step 6 of example 1, tert-butyl (R)-(1-(6-amino-2-morpholinooxazolo[4,5-b]pyridin-5-yl)pyrrolidin-3-yl)carbamate (100 mg, 0.2475 mmol), was coupled with 2-(2-methylpyridin-4-yl)oxazole-4-carboxylic acid (51 mg, 0.2475 mmol) using EDCI·HCl (72 mg, 0.3712 mmol), HOBt (35 mg, 0.2599 mmol), DIPEA (0.128 mg, 0.990 mmol) in DMF (5 mL) to get the title compound (73 mg, 51%). LCMS: m/z=591.1 (M+1)$^+$.

Step 4: Preparation of (R)—N-(5-(3-aminopyrrolidin-1-yl)-2-morpholinooxazolo[4,5-b]pyridin-6-yl)-2-(2-methylpyridin-4-yl)oxazole-4-carboxamide Hydrochloride Using the same reaction conditions as described in step 8 of example 1, tert-butyl (R)-(1-(6-(2-(2-methylpyridin-4-yl)oxazole-4-carboxamido)-2-morpholinooxazolo[4,5-b]pyridin-5-yl)pyrrolidin-3-yl)carbamate (73 mg, 0.123 mmol) was deprotected using methanolic HCl (5 mL) to get the title compound (32 mg, 53%).
$^1$HNMR (CD$_3$OD, 400 MHz): δ 9.72 (s, 1H), 8.65-8.63 (d, 1H), 8.01 (s, 1H), 7.93-7.90 (t, 2H), 3.84-3.81 (t, 4H), 3.70-3.64 (m, 7H), 3.60-3.50 (m, 2H), 2.67 (s, 3H), 2.30-2.20 (m, 1H), 1.90-1.80 (m, 1H). LCMS: 96.75%, m/z=491.2 (M+1)$^+$. HPLC: 95.80%.

Example 41

(R)—N-(5-(3-hydroxypyrrolidin-1-yl)-2-morpholinooxazolo[4,5-b]pyridin-6-yl)-2-(2-methylpyridin-4-yl)oxazole-4-carboxamide

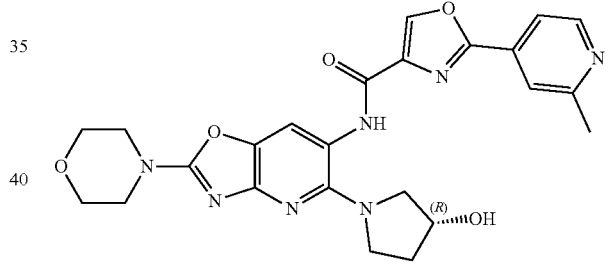

Step 1: Preparation of (R)-1-(2-morpholino-6-nitrooxazolo[4,5-b]pyridin-5-yl)pyrrolidin-3-ol Using the same reaction conditions as described in step 1 of example 38, 5-chloro-2-morpholino-6-nitrooxazolo[4,5-b]pyridine (product of step 5 of example 2) (200 mg, 0.704 mmol) was substituted with (R)-pyrrolidin-3-ol (61 mg, 0.704 mmol) using potassium carbonate (291 mg, 2.112 mmol) and DMF (5 mL) to afford the title product (231 mg, 98.7%). LCMS: m/z=336.1 (M+1)$^+$.

Step 2: Preparation of (R)-5-(3-((tert-butyldimethylsilyl)oxy)pyrrolidin-1-yl)-2-morpholino-6-nitrooxazolo[4,5-b]pyridine To the solution of (R)-1-(2-morpholino-6-nitrooxazolo[4,5-b]pyridin-5-yl)pyrrolidin-3-ol (230 mg, 0.698 mmol) in DMF (5 mL) was added TBDMS chloride (124 mg, 0.822 mmol) and imidazole (116 mg, 1.70 mmol) and stirred at RT overnight. Reaction mass was quenched with water and extracted with ethyl acetate to get the crude product. The resultant crude was purified by 60-120 silica gel column chromatography using 1% methanol in DCM as eluent to obtain the title compound (310 mg, 99%). LCMS: m/z=450.3 (M+1)⁺.

Step 3: Preparation of (R)-5-(3-((tert-butyldimethylsilyl)oxy)pyrrolidin-1-yl)-2-morpholinooxazolo[4,5-b]pyridin-6-amine Using the same reaction conditions as described in step 2 of example 38, (R)-5-(3-((tert-butyldimethylsilyl)oxy)pyrrolidin-1-yl)-2-morpholino-6-nitrooxazolo[4,5-b]pyridine (308 mg, 0.685 mmol) was reduced using 10% Pd/C (30 mg) in methanol (20 mL) to get the title compound (235 mg, 81%). LCMS: m/z=420.2 (M+1)⁺.

Step 4: Preparation of (R)—N-(5-(3-((tert-butyldimethylsilyl)oxy)pyrrolidin-1-yl)-2-morpholinooxazolo[4,5-b]pyridin-6-yl)-2-(2-methylpyridin-4-yl)oxazole-4-carboxamide Using the same reaction conditions as described in step 6 of example 1, (R)-5-(3-((tert-butyldimethylsilyl)oxy)pyrrolidin-1-yl)-2-morpholinooxazolo[4,5-b]pyridin-6-amine (234 mg, 0.5587 mmol), was coupled with 2-(2-methylpyridin-4-yl)oxazole-4-carboxylic acid (114 mg, 0.5584 mmol) using EDCI·HCl (180 mg, 0.840 mmol), HOBt (81 mg, 0.5863 mmol), DIPEA (0.290 mg, 2.237 mmol) in DMF (5 mL) to get the title compound (167 mg, 50%). LCMS: m/z=606.2 (M+1)⁺.

Step 5: Preparation of (R)—N-(5-(3-hydroxypyrrolidin-1-yl)-2-morpholinooxazolo[4,5-b]pyridin-6-yl)-2-(2-methylpyridin-4-yl)oxazole-4-carboxamide Using the same reaction conditions as described in step 8 of example 1, (R)—N-(5-(3-((tert-butyldimethylsilyl)oxy)pyrrolidin-1-yl)-2-morpholinooxazolo[4,5-b]pyridin-6-yl)-2-(2-methylpyridin-4-yl)oxazole-4-carboxamide (167 mg, 0.276 mmol) was deprotected using methanolic HCl (5 mL) to get the title compound (106 mg, 78%).

¹HNMR (DMSO-d₆, 300 MHz): δ 9.82 (s, 1H), 8.96 (s, 1H), 8.68-8.67 (d, 1H), 7.86 (s, 1H), 7.80-7.77 (d, 1H), 7.66 (s, 1H), 4.86 (s, 1H), 4.27 (s, 1H), 3.72-3.6.0 (m, 11H), 3.25-3.21 (m, 1H), 2.58 (s, 3H), 1.89-1.78 (m, 2H). LCMS: 98.95%, m/z=492.2 (M+1)⁺. HPLC: 95.08%.

Example 42

(S)-2-(3-aminopyrrolidin-1-yl)-N-(2-morpholino-5-(piperidin-1-yl)oxazolo[4,5-b]pyridin-6-yl)oxazole-4-carboxamide

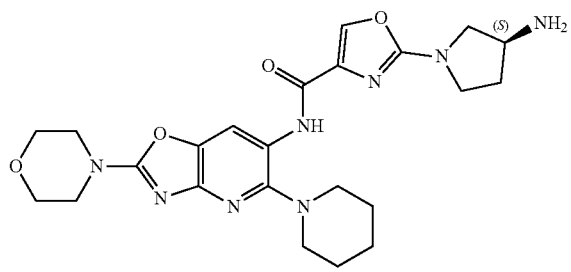

Step 1: Preparation of tert-butyl (S)-(1-(4-((2-morpholino-5-(piperidin-1-yl)oxazolo[4,5-b]pyridin-6-yl)carbamoyl)oxazol-2-yl)pyrrolidin-3-yl)carbamate Using the same reaction conditions as described in step 6 of example 1, 2-morpholino-5-(piperidin-1-yl)oxazolo[4,5-b]pyridin-6-amine (product of step 2 of example 6) (100 mg, 0.3296 mmol), was coupled with (S)-2-(3-((tert-butoxycarbonyl)amino)pyrrolidin-1-yl)oxazole-4-carboxylic acid (intermediate 14) (147 mg, 0.4944 mmol) using EDCI·HCl (95 mg, 0.4944 mmol), HOBt (67 mg, 0.4944 mmol), DIPEA (0.23 mL, 1.3185 mmol) in DMF (2 mL) to afford crude product. The resultant crude was purified by 60-120 silica gel column chromatography using 1% methanol in DCM as eluent to obtain the title compound (130 mg, 67.7%). LCMS: m/z=583.5 (M+1)⁺.

Step 2: Preparation of (S)-2-(3-aminopyrrolidin-1-yl)-N-(2-morpholino-5-(piperidin-1-yl)oxazolo[4,5-b]pyridin-6-yl)oxazole-4-carboxamide Using the same reaction conditions as described in step 8 of example 1, tert-butyl (S)-(1-(4-((2-morpholino-5-(piperidin-1-yl)oxazolo[4,5-b]pyridin-6-yl)carbamoyl)oxazol-2-yl)pyrrolidin-3-yl)carbamate (130 mg, 4.482 mmol) was deprotected using TFA (5 mL) and DCM (5 mL) to get the title compound (73 mg, 68.22%).

¹HNMR (CDCl₃, 400 MHz): δ 9.90 (s, 1H), 8.77 (s, 1H), 7.82 (s, 1H), 3.81-3.73 (m, 10H), 3.69-3.59 (m, 1H), 3.38-3.28 (m, 1H), 3.02 (s, 4H), 2.30-2.15 (m, 1H), 1.82 (m, 5H), 1.70-1.60 (m, 3H). LCMS: 99.52%, m/z=483.2 (M+1)⁺. HPLC: 98.70%.

Example 43

(S)-6-(3-hydroxypyrrolidin-1-yl)-N-(2-morpholino-5-(piperidin-1-yl)oxazolo[4,5-b]pyridin-6-yl)picolinamide

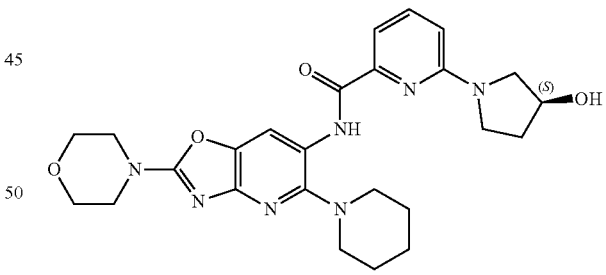

Step 1: Preparation of 6-bromo-N-(2-morpholino-5-(piperidin-1-yl)oxazolo[4,5-b]pyridin-6-yl)picolinamide Using the same reaction conditions as described in step 6 of example 1, 2-morpholino-5-(piperidin-1-yl)oxazolo[4,5-b]pyridin-6-amine (product of step 2 of example 6) (400 mg, 1.3245 mmol), was coupled with 6-bromopicolinic acid (321 mg, 1.5894 mmol) using EDCI·HCl (321 mg, 1.9867 mmol), HOBt (268 mg, 1.9867 mmol), DIPEA (683 mg, 5.2980 mmol) in DMF (20 mL) to afford the title compound (487 mg, 75%).

¹HNMR (CDCl₃, 400 MHz): δ 10.86 (s, 1H), 8.82 (s, 1H), 8.24-8.22 (d, 1H), 7.80-7.86 (t, 1H), 7.67-7.65 (d, 1H), 3.83-3.73 (m, 8H), 3.06-3.03 (t, 4H), 1.90-1.88 (m, 4H), 1.70-1.60 (m, 2H).
LCMS: m/z=489.1 (M+2)⁺. HPLC: 97.69%.

Step 2: Preparation of (S)-6-(3-hydroxypyrrolidin-1-yl)-N-(2-morpholino-5-(piperidin-1-yl)oxazolo[4,5-b]pyridin-6-yl)picolinamide The mixture of 6-bromo-N-(2-morpholino-5-(piperidin-1-yl)oxazolo[4,5-b]pyridin-6-yl)picolinamide (130 mg, 0.2269 mmol), (S)-pyrrolidin-3-ol (35 mg, 0.4 mmol) and sodium carbonate (85 mg, 0.8 mmol) in DMF (2 mL) was heated at 140° C. for 12 h. The reaction was quenched with ice water, filtered and purified by 60-120 silica gel column chromatography using 1% methanol in DCM as eluent to obtain the title compound (80 mg, 60.79%).
¹HNMR (CDCl₃, 400 MHz): δ 10.66 (s, 1H), 8.83 (s, 1H), 7.64-7.62 (t, 1H), 7.58-7.56 (d, 1H), 6.58-6.56 (d, 1H), 3.83-3.79 (m, 4H), 3.76-3.72 (m, 7H), 3.04-3.03 (m, 4H), 2.30-2.10 (m, 2H), 1.77-1.72 (m, 4H), 1.61-1.57 (m, 3H).
LCMS: 96.72%, m/z=494.2 (M+1)⁺. HPLC: 98.60%.

Example 44

(S)-6-(3-aminopyrrolidin-1-yl)-N-(2-morpholino-5-(piperidin-1-yl)oxazolo[4,5-b]pyridin-6-yl)picolinamide

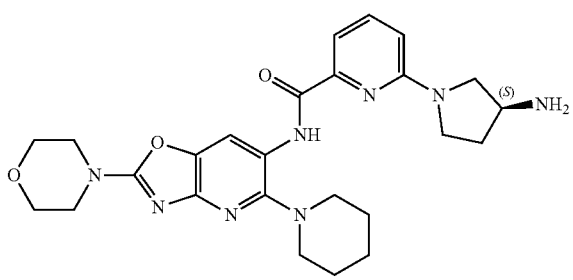

Step 1: Preparation of tert-butyl (S)-(1-(6-((2-morpholino-5-(piperidin-1-yl)oxazolo[4,5-b]pyridin-6-yl)carbamoyl)pyridin-2-yl)pyrrolidin-3-yl)carbamate Using the same reaction conditions as described in step 2 of example 43, 6-bromo-N-(2-morpholino-5-(piperidin-1-yl)oxazolo[4,5-b]pyridin-6-yl)picolinamide (product of step 2 of example 6) (100 mg, 0.2053 mmol) was substituted with tert-butyl (S)-pyrrolidin-3-ylcarbamate (57 mg, 0.3080 mmol) using sodium carbonate (65 mg, 0.6160 mmol) in DMF (2 mL) at 140° C. for 12 h to obtain the title compound (60 mg, 49.34%).

Step 2: Preparation of (S)-6-(3-aminopyrrolidin-1-yl)-N-(2-morpholino-5-(piperidin-1-yl)oxazolo[4,5-b]pyridin-6-yl)picolinamide Using the same reaction conditions as described in step 8 of example 1, tert-butyl (S)-(1-(6-((2-morpholino-5-(piperidin-1-yl)oxazolo[4,5-b]pyridin-6-yl)carbamoyl)pyridin-2-yl)pyrrolidin-3-yl)carbamate (60 mg, 0.1013 mmol) was deprotected using TFA (2 mL) and DCM (2 mL) to get the title compound (30 mg, 60.16%).
¹HNMR (CDCl₃, 400 MHz): δ 10.70 (s, 1H), 8.84 (s, 1H), 7.65-7.61 (t, 1H), 7.57-7.55 (d, 1H), 6.56-6.54 (d, 1H), 3.87-3.63 (m, 9H), 3.39-3.37 (m, 1H), 3.04-3.01 (t, 4H), 2.28-2.25 (m, 2H), 1.90-1.87 (m, 1H), 1.771-1.76 (m, 5H), 1.60-1.56 (m, 3H).
LCMS: 98.72%, m/z=493.3 (M+1)⁺. HPLC: 97.84%.

Example 45

(S)-2-(3-hydroxypyrrolidin-1-yl)-N-(2-morpholino-5-(piperidin-1-yl)oxazolo[4,5-b]pyridin-6-yl)oxazole-4-carboxamide

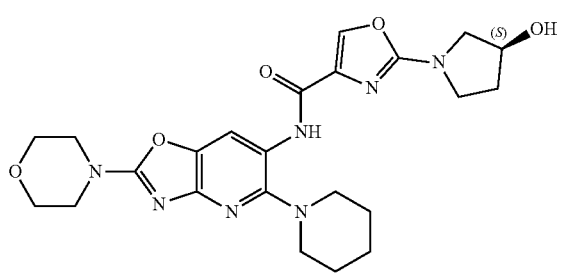

Using the same reaction conditions as described in step 6 of example 1, 2-morpholino-5-(piperidin-1-yl)oxazolo[4,5-b]pyridin-6-amine (product of step 2 of example 6) (100 mg, 0.3296 mmol), was coupled with (S)-2-(3-((tert-butyldimethylsilyl)oxy)pyrrolidin-1-yl)oxazole-4-carboxylic acid (intermediate 15) (124 mg, 0.3955 mmol) using EDCI·HCl (95 mg, 0.4944 mmol), HOBt (67 mg, 0.4944 mmol), DIPEA (0.23 mL, 1.3185 mmol) in DMF (2 mL) to afford crude product. Using the same reaction conditions as described in step 8 of example 1, this crude product was deprotected using methanolic HCl (5 mL) to get the title compound (128 mg, 80.5%).
¹HNMR (CDCl₃, 300 MHz): δ 9.78 (s, 1H), 8.76 (s, 1H), 7.82 (s, 1H), 4.70-4.60 (m, 1H), 3.82-3.56 (m, 12H), 3.03-3.00 (t, 4H), 2.19-2.11 (m, 2H), 1.81-1.78 (m, 6H). LCMS: 95.04%, m/z=484.2 (M+1)⁺. HPLC: 95.55%.

Example 46

(S)—N-(5-cyclopropyl-2-morpholinooxazolo[4,5-b]pyridin-6-yl)-2-(3-hydroxypyrrolidin-1-yl)oxazole-4-carboxamide

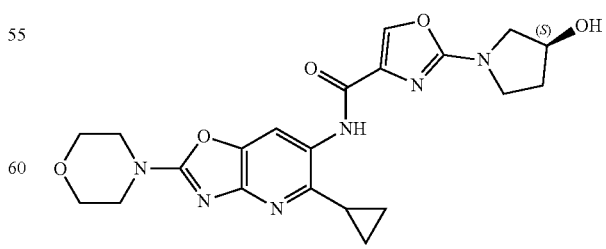

Using the same reaction conditions as described in example 45, 5-cyclopropyl-2-morpholinooxazolo[4,5-b]pyridin-6-amine (product of step 7 of example 2) (100 mg, 0.384 mmol), was coupled with (S)-2-(3-((tert-butyldimethylsilyl)oxy)pyrrolidin-1-yl)oxazole-4-carboxylic acid (intermediate 15) (145 mg, 0.4615 mmol) using EDCI·HCl (110 mg, 0.5769 mmol), HOBt (78 mg, 0.5769 mmol), DIPEA (0.268 mL, 1.5384 mmol) in DMF (2 mL) followed by deprotection using methanolic HCl (5 mL) to get the title compound (56 mg, 50.4%).

$^1$HNMR (CDCl$_3$, 300 MHz): δ 9.17 (s, 1H), 8.33 (s, 1H), 7.84 (s, 1H), 4.70-4.60 (m, 1H), 3.82-3.56 (m, 12H), 2.13-2.03 (m, 3H), 1.86-1.84 (d, 1H), 1.16-1.13 (m, 2H), 1.04-1.00 (m, 2H).

LCMS: 93.32%, m/z=440.8 (M+1)$^+$. HPLC: 95.51%.

Example 47

(S)-2-(3-aminopyrrolidin-1-yl)-N-(5-cyclopropyl-2-morpholinooxazolo[4,5-b]pyridin-6-yl)oxazole-4-carboxamide

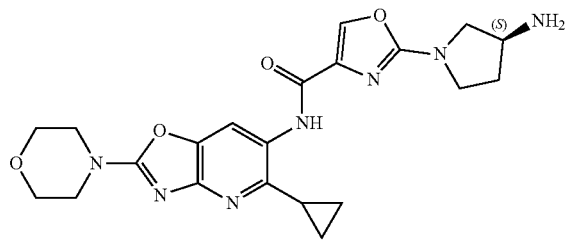

Using the same reaction conditions as described in example 45, 5-cyclopropyl-2-morpholinooxazolo[4,5-b]pyridin-6-amine (product of step 7 of example 2) (100 mg, 0.384 mmol), was coupled with (S)-2-(3-((tert-butoxycarbonyl)amino)pyrrolidin-1-yl)oxazole-4-carboxylic acid (intermediate 14) (137 mg, 0.4615 mmol) using EDCI·HCl (110 mg, 0.5769 mmol), HOBt (78 mg, 0.5769 mmol), DIPEA (0.268 mL, 1.5384 mmol) in DMF (2 mL) followed by deprotection using TFA (5 mL) and DCM (5 mL) to get the title compound (27 mg, 18.49%).

$^1$HNMR (CDCl$_3$, 400 MHz): δ 9.17 (s, 1H), 8.34 (s, 1H), 7.83 (s, 1H), 3.82-3.72 (m, 10H), 3.61-3.59 (m, 1H), 3.29-3.26 (m, 1H), 2.30-2.18 (m, 2H), 2.10-2.00 (m, 1H), 1.90-1.78 (m, 1H), 1.16-1.15 (m, 2H), 1.04-1.00 (m, 2H). LCMS: 100%, m/z=440.2 (M+1)$^+$. HPLC: 98.06%.

Example 48

2-(2-methylpyridin-4-yl)-N-(5-(piperidin-1-yl)-2-(pyrrolidin-1-yl)oxazolo[4,5-b]pyridin-6-yl)oxazole-4-carboxamide Hydrochloride

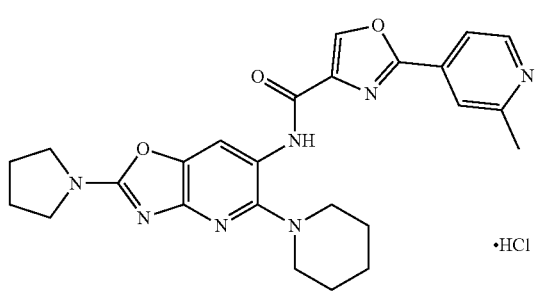 [SMILES: Cc1cc(-c2nc(C(=O)Nc3cc4oc(N5CCCC5)nc4nc3N3CCCCC3)co2)ccn1 ; Cl]

Step 1: Preparation of 5-chloro-2-(pyrrolidin-1-yl)oxazolo[4,5-b]pyridine

Using the same reaction conditions as described in step 3 of example 1, 5-chloro-2-(methylthio)oxazolo[4,5-b]pyridine (250 mg) was substituted using pyrrolidine (2 mL) and THF (5 mL) at 75° C. for 2 h to afford the title compound (250 mg).

$^1$HNMR (CDCl$_3$, 400 MHz): δ 7.35-7.33 (d, 1H), 6.89-6.87 (d, 1H), 3.70-3.60 (m, 4H), 2.10-2.00 (m, 4H). LCMS: m/z=224.1 (M+1)$^+$.

Step 2: Preparation of 5-chloro-6-nitro-2-(pyrrolidin-1-yl)oxazolo[4,5-b]pyridine Using the same reaction conditions as described in step 4 of example 20, 5-chloro-6-nitro-2-(pyrrolidin-1-yl)oxazolo[4,5-b]pyridine (250 mg, 1.121 mmol) was nitrated using potassium nitrate (226 mg, 2.242 mmol) and conc. sulphuric acid (3 mL) at RT for 24 h to afford the crude title compound (180 mg, 60%).

Step 3: Preparation of 6-nitro-5-(piperidin-1-yl)-2-(pyrrolidin-1-yl)oxazolo[4,5-b]pyridine Using the same reaction conditions as described in step 1 of example 6, 5-chloro-6-nitro-2-(pyrrolidin-1-yl)oxazolo[4,5-b]pyridine (180 mg, 0.6716 mmol) was substituted using piperidine (57 mg) in THF (3 mL) at RT for 12 h to obtain the title compound (150 mg, 70.7%).

LCMS: m/z=318.45 (M+1)$^+$.

Step 4: Preparation of 5-(piperidin-1-yl)-2-(pyrrolidin-1-yl)oxazolo[4,5-b]pyridin-6-amine Using the same reaction conditions as described in step 5 of example 1, 6-nitro-5-(piperidin-1-yl)-2-(pyrrolidin-1-yl)oxazolo[4,5-b]pyridine (150 mg, 0.4731 mmol) was reduced with zinc dust (247 mg, 3.7854 mmol) and ammonium chloride (404 mg, 7.5696 mmol) in THF/methanol/H$_2$O (5 m/1 mL/0.5 mL) to get the crude title product (152 mg). LCMS: m/z=288.2 (M+1)$^+$.

Step 5: Preparation of 2-(2-methylpyridin-4-yl)-N-(5-(piperidin-1-yl)-2-(pyrrolidin-1-yl)oxazolo[4,5-b]pyridin-6-yl)oxazole-4-carboxamide Hydrochloride Using the same reaction conditions as described in step 6 of example 1, 5-(piperidin-1-yl)-2-(pyrrolidin-1-yl)oxazolo[4,5-b]pyridin-6-amine (150 mg, 0.5226 mmol) was coupled with 2-(2-methylpyridin-4-yl)oxazole-4-carboxylic acid (127 mg, 0.6271 mmol) using EDCI·HCl (149 mg, 0.7839 mmol), HOBt (108 mg, 0.7839 mmol), DIPEA (0.18 mL, 1.0452 mmol) in DMF (2 mL) to afford the crude product. The resultant crude was purified by prep HPLC and treated with methanolic HCl to obtain the title compound (38 mg, 14.28%).

$^1$HNMR (CDCl$_3$, 400 MHz): δ 13.4-12.8 (bs, 1H), 11.80 (s, 1H), 9.19 (s, 1H), 8.74 (s, 1H), 8.47-8.42 (m, 2H), 7.93 (s, 1H), 3.74 (s, 4H), 3.65 (s, 4H), 3.08 (s, 3H), 2.48 (s, 2H), 2.12 (s, 4H), 1.99 (s, 2H), 1.90-1.70 (m, 2H). LCMS: 100%, m/z=474.2 (M+1)⁺. HPLC: 97.93%.

Example 49

N-(2-(2,6-dimethylmorpholino)-5-(piperidin-1-yl) oxazolo[4,5-b]pyridin-6-yl)-2-(2-methylpyridin-4-yl)oxazole-4-carboxamide Hydrochloride

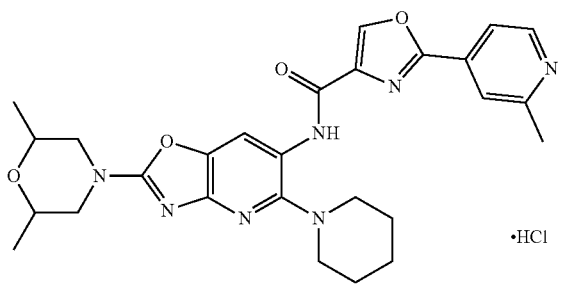 [SMILES: Cc1cc(-c2nc(C(=O)Nc3cc4oc(N5CC(C)OC(C)C5)nc4nc3N3CCCCC3)co2)ccn1 ; Cl]

Step 1: Preparation of 5-chloro-2-(2,6-dimethylmorpholino)oxazolo[4,5-b]pyridine Using the same reaction conditions as described in step 3 of example 1, 5-chloro-2-(methylthio)oxazolo[4,5-b]pyridine (product of step 3 example 2) (250 mg, 1.25 mmol) was substituted using 2,6-dimethylmorpholine (2 mL) and THF (5 mL) at 75° C. for 2 h to afford the title compound (251 mg).
$^1$HNMR (CDCl$_3$, 400 MHz): δ 7.38-7.36 (d, 1H), 6.94-6.92 (d, 1H), 4.17-4.14 (d, 2H), 3.75-3.68 (m, 2H), 2.90-2.84 (t, 2H), 1.27-1.26 (d, 6H). LCMS: m/z=268.0 (M+1)⁺.

Step 2: Preparation of 5-chloro-2-(2,6-dimethylmorpholino)-6-nitrooxazolo[4,5-b]pyridine Using the same reaction conditions as described in step 4 of example 20, 5-chloro-2-(2,6-dimethylmorpholino)oxazolo[4,5-b]pyridine (250 mg, 0.9363 mmol) was nitrated using potassium nitrate (189 mg, 1.8726 mmol) and conc. sulphuric acid (3 mL) at RT for 24 h to afford the title compound (150 mg, 51.3%). LCMS: m/z=313.0 (M+1)⁺.

Step 3: Preparation of 2-(2,6-dimethylmorpholino)-6-nitro-5-(piperidin-1-yl)oxazolo[4,5-b]pyridine Using the same reaction conditions as described in step 1 of example 6, 5-chloro-2-(2,6-dimethylmorpholino)-6-nitrooxazolo[4,5-b]pyridine (150 mg, 0.1602 mmol) was substituted using piperidine (45 mg) in THF (3 mL) at RT for 12 h to obtain the title compound (152 mg, 86.2%).
LCMS: m/z=362.4 (M+1)⁺.

Step 4: Preparation of 2-(2,6-dimethylmorpholino)-5-(piperidin-1-yl)oxazolo[4,5-b]pyridin-6-amine Using the same reaction conditions as described in step 5 of example 1, 2-(2,6-dimethylmorpholino)-6-nitro-5-(piperidin-1-yl)oxazolo[4,5-b]pyridine (152 mg, 0.4143 mmol) was reduced with zinc dust (216 mg, 3.3147 mmol) and ammonium chloride (353 mg, 6.6288 mmol) in THF/methanol/H$_2$O (5 mL/1 mL/0.5 mL) to get the crude title compound (160 mg).

$^1$HNMR (CDCl$_3$, 400 MHz): δ 6.96 (s, 1H), 4.11-4.07 (dd, 2H), 3.74-3.70 (m, 2H), 3.02-3.01 (m, 4H), 2.83-2.77 (t, 2H), 1.76-1.68 (m, 4H), 1.64-1.56 (m, 2H), 1.26-1.24 (d, 6H). LCMS: m/z=332.2 (M+1)⁺.

Step 5: Preparation of N-(2-(2,6-dimethylmorpholino)-5-(piperidin-1-yl)oxazolo[4,5-b]pyridin-6-yl)-2-(2-methylpyridin-4-yl)oxazole-4-carboxamide Hydrochloride Using the same reaction conditions as described in step 6 of example 1, 2-(2,6-dimethylmorpholino)-5-(piperidin-1-yl)oxazolo[4,5-b]pyridin-6-amine (152 mg, 0.6024 mmol) was coupled with 2-(2-methylpyridin-4-yl)oxazole-4-carboxylic acid (147 mg, 0.7228 mmol) using EDCI·HCl (172 mg, 0.9036 mmol), HOBt (125 mg, 0.9036 mmol), DIPEA (0.2 mL, 1.2048 mmol) in DMF (2 mL) to afford the crude product. The resultant crude was purified by prep HPLC and treated with methanolic HCl to obtain the title compound (80 mg).
$^1$HNMR (CDCl$_3$, 400 MHz): δ 13.15-12.90 (bs, 1H), 11.90 (s, 1H), 9.18 (s, 1H), 8.74 (s, 1H), 8.46-8.42 (d, 1H), 7.96 (s, 1H), 4.21-4.18 (m, 2H), 3.76-3.60 (m, 6H), 3.08 (s, 3H), 2.99-2.92 (t, 2H), 2.60-2.41 (m, 2H), 2.08-1.90 (m, 2H), 1.60-1.80 (m, 2H), 1.29-1.27 (d, 6H).
LCMS: 100%, m/z=518.5 (M+1)⁺. HPLC: 98.81%.

Example 50

N-(2,5-di(piperidin-1-yl)thiazolo[4,5-b]pyridin-6-yl)-6-(1-methyl-1H-pyrazol-4-yl)picolinamide Hydrochloride

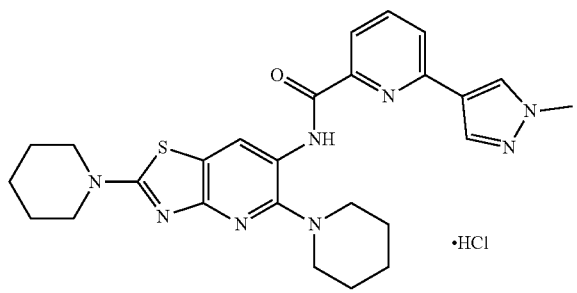 [SMILES: Cn1cc(-c2cccc(C(=O)Nc3cc4sc(N5CCCCC5)nc4nc3N3CCCCC3)n2)cn1 ; Cl]

Using the same reaction conditions as described in step 6 of example 1, 2,5-di(piperidin-1-yl)thiazolo[4,5-b]pyridin-6-amine (product of step 4 of example 22) (70 mg, 0.220 mmol) was coupled 6-(1-methyl-1H-pyrazol-4-yl)picolinic acid (intermediate 4) (53 mg, 0.264 mmol) using EDCI·HCl (63 mg, 0.33 mmol), HOBt (45 mg, 0.33 mmol), DIPEA (78 mg, 0.66 mmol) in DMF (5 mL) to afford the crude product. The resultant crude was purified by prep HPLC and treated with methanolic HCl to obtain the title compound (25 mg, 21.2%).
$^1$HNMR (CD$_3$OD, 300 MHz): δ 9.01 (s, 1H), 8.42 (s, 1H), 8.30 (s, 1H), 8.10-8.01 (m, 2H), 7.92-7.89 (dd, 1H), 4.01 (s, 3H), 3.80 (s, 4H), 3.39-3.30 (m, 4H), 1.82 (s, 10H), 1.69-1.67 (d, 2H).
LCMS: 98.92%, m/z=503.3 (M+1)⁺. HPLC: 98.03%.

Example 51

6-(1-methyl-1H-pyrazol-4-yl)-N-(2-morpholino-5-(piperidin-1-yl)thiazolo[4,5-b]pyridin-6-yl)picolinamide

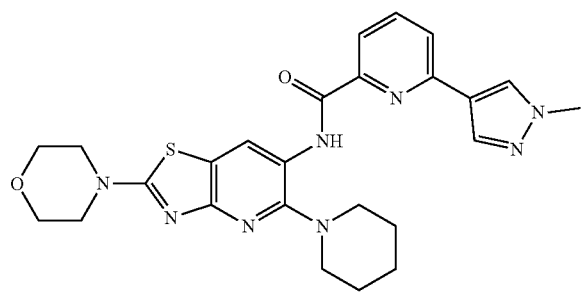

Using the same reaction conditions as described in step 6 of example 1, 2-morpholino-5-(piperidin-1-yl)thiazolo[4,5-b]pyridin-6-amine (product of step 6 of example 20) (70 mg, 0.313 mmol) was coupled with 6-(1-methyl-1H-pyrazol-4-yl)picolinic acid (intermediate 4) (53 mg, 0.262 mmol) using EDCI·HCl (62 mg, 0.327 mmol), HOBt (45 mg, 0.327 mmol), DIPEA (85 mg, 0.654 mmol) in DMF (5 mL) to afford the crude coupled product. The resultant crude was purified by prep HPLC to obtain the title compound (35 mg, 30%).

$^1$HNMR (CD$_3$OD, 300 MHz): δ 8.96 (bs, 1H), 8.46 (s, 1H), 8.34 (s, 1H), 8.11-8.01 (m, 2H), 7.94-7.91 (d, 1H), 4.02 (s, 3H), 3.88-3.82 (m, 8H), 3.55-3.21 (m, 4H), 1.87 (s, 4H), 1.80-1.60 (m, 2H). LCMS: 82.87%, m/z=505.2 (M+1)$^+$. HPLC: 97.63%.

Example 52

N-(2,5-di(piperidin-1-yl)thiazolo[4,5-b]pyridin-6-yl)-2-(2-methylpyridin-3-yl)oxazole-4-carboxamide Hydrochloride

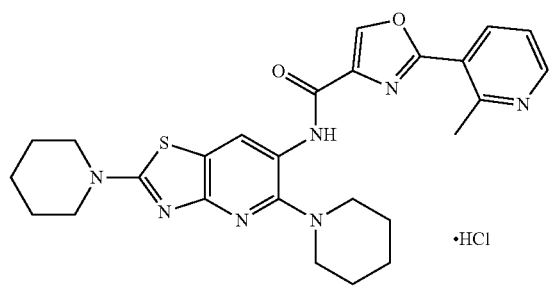 [SMILES: Cc1ncccc1-c1nc(C(=O)Nc2cc3sc(N4CCCCC4)nc3nc2N2CCCCC2)co1 ; Cl]

Using the same reaction conditions as described in step 6 of example 1, 2,5-di(piperidin-1-yl)thiazolo[4,5-b]pyridin-6-amine (product of step 4 of example 22) (70 mg, 0.220 mmol) was coupled with 2-(2-methylpyridin-3-yl)oxazole-4-carboxylic acid (intermediate 8) (50 mg, 0.242 mmol) using EDCI·HCl (63 mg, 0.33 mmol), HOBt (45 mg, 0.33 mmol), DIPEA (85 mg, 0.66 mmol) in DMF (5 mL) to afford the crude product. The resultant crude was purified by prep HPLC and treated with methanolic HCl to obtain the title compound (30 mg, 27.2%).

$^1$HNMR (CD$_3$OD, 400 MHz): δ 9.21-9.19 (d, 2H), 8.91-8.88 (m, 3H), 8.80 (bs, 1H), 8.15-8.11 (t, 2H), 3.78 (s, 8H), 3.18 (s, 3H), 1.80 (s, 8H), 1.71-1.70 (m, 4H). LCMS: 85.44%, m/z=504.2 (M+1)$^+$. HPLC: 98.54%.

Example 53

N-(2-((2S,6R)-2,6-dimethylmorpholino)-5-(piperidin-1-yl)thiazolo[4,5-b]pyridin-6-yl)-2-(2-methylpyridin-4-yl)oxazole-4-carboxamide

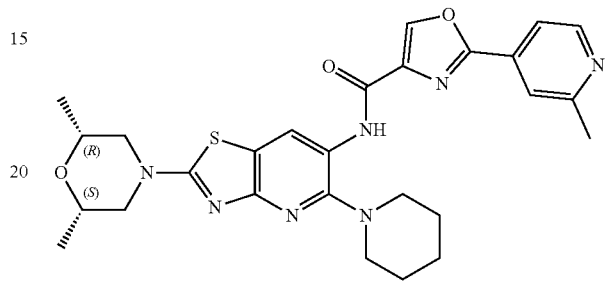

Step 1: Preparation of (2R, 6S)-4-(5-chlorothiazolo[4,5-b]pyridin-2-yl)-2,6-dimethylmorpholine Using the same reaction conditions as described in step 3 of example 1, 5-chloro-2-(methylthio)thiazolo[4,5-b]pyridine (product of step 2 of example 20) (170 mg, 0.784 mmol) was substituted using (2R,6S)-2,6-dimethylmorpholine (1 mL) and THF (2 mL) at 75° C. for 16 h to afford the crude title compound (260 mg). LCMS: m/z=284.1 (M+1)$^+$.

Step 2: Preparation of (2R,6S)-4-(5-chloro-6-nitrothiazolo[4,5-b]pyridin-2-yl)-2,6-dimethylmorpholine Using the same reaction conditions as described in step 4 of example 20, (2R,6S)-4-(5-chlorothiazolo[4,5-b]pyridin-2-yl)-2,6-dimethylmorpholine (260 mg, 0.916 mmol) was nitrated using potassium nitrate (277 mg, 2.74 mmol) and conc. sulphuric acid (5 mL) at RT for 2 days to afford the crude title compound (120 mg). LCMS: m/z=328.9 (M+1)$^+$.

Step 3: Preparation of (2R,6S)-2,6-dimethyl-4-(6-nitro-5-(piperidin-1-yl)thiazolo[4,5-b]pyridin-2-yl)morpholine Using the same reaction conditions as described in step 1 of example 6, (2R,6S)-4-(5-chloro-6-nitrothiazolo[4,5-b]pyridin-2-yl)-2,6-dimethylmorpholine (120 mg, 0.365 mmol) was substituted using piperidine (0.5 mL) in THF (2 mL) at RT for 30 min to obtain the title compound (190 mg). m/z=378.0 (M+1)$^+$.

Step 4: Preparation of 2-((2R,6S)-2,6-dimethylmorpholino)-5-(piperidin-1-yl)thiazolo[4,5-b]pyridin-6-amine Using the same reaction conditions as described in step 5 of example 1, (2R,6S)-2,6-dimethyl-4-(6-nitro-5-(piperidin-1-yl)thiazolo[4,5-b]pyridin-2-yl)morpholine (190 mg, 0.503 mmol) was reduced with zinc dust (260 mg, 4.026 mmol) and ammonium chloride (430 mg, 8.04 mmol) in THF/ methanol/H₂O (3 mL/0.8 mL/0.3 mL) to get the crude product (170 mg). LCMS: m/z=348.2 (M+1)⁺.

Step 5: Preparation of N-(2-((2S,6R)-2,6-dimethyl-morpholino)-5-(piperidin-1-yl)thiazolo[4,5-b]pyridin-6-yl)-2-(2-methylpyridin-4-yl)oxazole-4-carboxamide Hydrochloride Using the same reaction conditions as described in step 6 of example 1, 2-((2R,6S)-2,6-dimethylmorpholino)-5-(piperidin-1-yl)thiazolo[4,5-b]pyridin-6-amine (85 mg, 0.244 mmol) was coupled with 2-(2-methylpyridin-4-yl)oxazole-4-carboxylic acid (60 mg, 0.293 mmol) using EDCI·HCl (70 mg, 0.366 mmol), HOBt (50 mg, 0.366 mmol), DIPEA (0.94 mg, 0.732 mmol) in DMF (2 mL) to afford the crude product. The resultant crude was purified by prep HPLC and treated with methanolic HCl to obtain the title compound (25 mg, 19.20%).

¹HNMR (CD₃OD, 300 MHz): δ 9.05 (s, 1H), 8.90-8.85 (d, 1H), 8.70 (s, 1H), 8.60 (s, 1H), 8.58-8.45 (d, 1H), 4.06-3.97 (m, 2H), 3.85-3.79 (m, 2H), 3.49 (s, 4H), 3.21-3.05 (t, 2H), 2.93 (s, 3H), 1.89 (s, 4H), 1.76 (s, 2H), 1.29-1.21 (d, 6H). LCMS: 98.99%, m/z=534.3 (M+1)⁺. HPLC: 96.10%.

Example 54

2-(2-methylpyridin-3-yl)-N-(2-morpholino-5-(piperidin-1-yl)thiazolo[4,5-b]pyridin-6-yl)oxazole-4-carboxamide

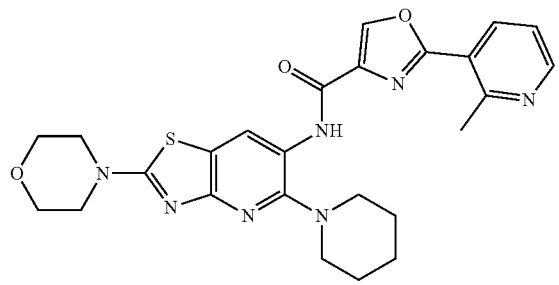 [SMILES: Cc1ncccc1-c1nc(C(=O)Nc2cc3sc(N4CCOCC4)nc3nc2N2CCCCC2)co1]

Using the same reaction conditions as described in step 6 of example 1,2-morpholino-5-(piperidin-1-yl)thiazolo[4,5-b]pyridin-6-anine (product of step 6 of example 20) (70 mg, 0.219 mmol) was coupled with 2-(2-methylpyridin-3-yl)oxazole-4-carboxylic acid (intermediate 8) (45 mg, 0.219 mmol) using EDCI·HCl (63 mg, 0.329 mmol), HOBt (45 mg, 0.329 mmol), DIPEA (71 mg, 0.548 mmol) in DMF (5 mL) to afford the crude title compound. The resultant crude was purified by prep HPLC to obtain the title compound (35 mg, 30%).

¹HNMR (DMSO-d₆, 400 MHz): δ 9.70 (s, 1H), 9.12 (s, 1H), 8.95 (s, 1H), 8.82-8.74 (d, 1H), 8.68-8.62 (d, 1H), 7.83-7.72 (t, 1H), 3.74-3.72 (m, 4H), 3.59-3.57 (m, 4H), 3.08 (s, 3H), 2.99 (s, 4H), 1.74 (s, 4H), 1.65-1.52 (m, 2H). LCMS: 88.8%, m/z=506.2 (M+1)⁺. HPLC: 97.66%.

Example 55

2-(2-hydroxypyridin-3-yl)-N-(2-morpholino-5-(piperidin-1-yl)thiazolo[4,5-b]pyridin-6-yl)oxazole-4-carboxamide

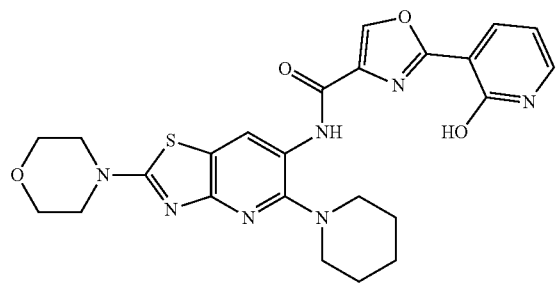 [SMILES: O=C(Nc1cc2sc(N3CCOCC3)nc2nc1N1CCCCC1)c1coc(-c2cccnc2O)n1]

Using the same reaction conditions as described in step 6 of example 1, 2-morpholino-5-(piperidin-1-yl)thiazolo[4,5-b]pyridin-6-anine (product of step 6 of example 20) (70 mg, 0.219 mmol) was coupled with 2-(2-hydroxypyridin-3-yl)oxazole-4-carboxylic acid (intermediate 9) (45 mg, 0.219 mmol) using EDCI·HCl (63 mg, 0.329 mmol), HOBt (45 mg, 0.329 mmol), DIPEA (71 mg, 0.548 mmol) in DMF (5 mL) to afford the crude title compound. The resultant crude was purified by prep HPLC to obtain the title compound (35 mg, 31.5%).

¹HNMR (DMSO-d₆, 400 MHz): δ 12.40 (s, 1H), 9.62 (s, 1H), 8.97 (s, 1H), 8.89 (s, 1H), 8.23-8.21 (dd, 1H), 7.73-7.62 (m, 1H), 3.75-3.73 (m, 4H), 3.58-3.56 (m, 4H), 2.99-2.96 (, 4H), 1.80 (s, 4H), 1.68-1.53 (m, 2H). LCMS: 100%, m/z=508.0 (M+1)⁺. HPLC: 96.21%.

Example 56

N-(2,5-di(piperidin-1-yl)thiazolo[4,5-b]pyridin-6-yl)-2-(2-methoxypyridin-4-yl)oxazole-4-carboxamide

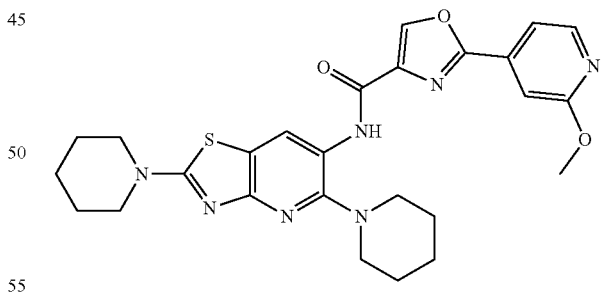

Using the same reaction conditions as described in step 6 of example 1, 2,5-di(piperidin-1-yl)thiazolo[4,5-b]pyridin-6-amine (product of step 4 of example 22) (70 mg, 0.220 mmol) was coupled with 2-(2-methoxypyridin-4-yl)oxazole-4-carboxylic acid (intermediate 11) (53 mg, 0.242 mmol) using EDCI·HCl (57 mg, 0.30 mmol), HOBt (41 mg, 0.30 mmol), DIPEA (85 mg, 0.66 mmol) in DMF (5 mL) to afford the crude product. The resultant crude was purified by prep HPLC to obtain the title compound (13 mg, 11%).

¹HNMR (CDCl₃, 300 MHz): δ 9.84 (s, 1H), 9.00 (s, 1H), 8.37 (s, 1H), 8.34-8.33 (d, 1H), 7.52-7.50 (dd, 1H), 7.38 (s,

1H), 4.01 (s, 3H), 3.66 (s, 4H), 3.12-3.09 (t, 4H), 1.88 (s, 4H), 1.69 (s, 8H). LCMS: 100%, m/z=520.0 (M+1)⁺. HPLC: 94.16%.

Example 57

2-(6-methoxypyridin-3-yl)-N-(2-morpholino-5-(piperidin-1-yl)thiazolo[4,5-b]pyridin-6-yl)oxazole-4-carboxamide

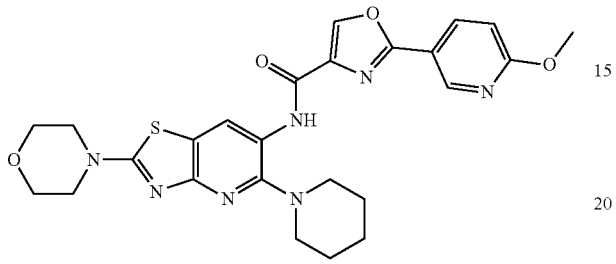

Using the same reaction conditions as described in step 6 of example 1, 2-morpholino-5-(piperidin-1-yl)thiazolo[4,5-b]pyridin-6-amine (product of step 6 of example 20) (540 mg, 1.692 mmol) was coupled with 2-(2-methoxypyridin-5-yl)oxazole-4-carboxylic acid (intermediate 7) (442 mg, 2.031 mmol) using EDCI·HCl (484 mg, 25.39 mmol), HOBt (228 mg, 1.692 mmol), DIPEA (1.3 g, 6.771 mmol) in DMF (5 mL) to afford the title compound (400 mg, 45%).

¹HNMR (DMSO-d₆, 400 MHz): δ 9.65 (s, 1H), 8.98-8.97 (d, 2H), 8.87 (s, 1H), 8.35-8.30 (dd, 1H), 7.11-7.09 (d, 1H), 3.96 (s, 3H), 3.75-3.73 (m, 4H), 3.59-3.58 (m, 4H), 3.10-3.00 (t, 4H), 1.82 (s, 4H), 1.20-1.10 (m, 2H). LCMS: 95.26%, m/z=522.2 (M+1)⁺. HPLC: 95.37%.

Example 58

2-(2-methoxypyridin-4-yl)-N-(2-morpholino-5-(piperidin-1-yl)thiazolo[4,5-b]pyridin-6-yl)oxazole-4-carboxamide

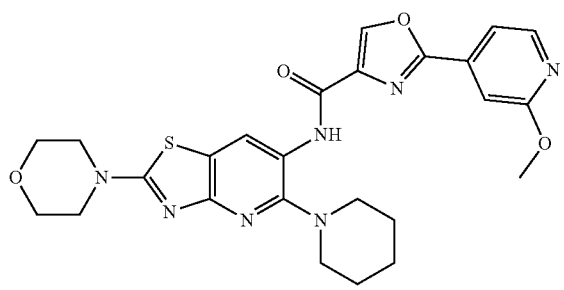 [SMILES: COc1cc(-c2nc(C(=O)Nc3cc4sc(N5CCOCC5)nc4nc3N3CCCCC3)co2)ccn1]

Using the same reaction conditions as described in step 6 of example 1, 2-morpholino-5-(piperidin-1-yl)thiazolo[4,5-b]pyridin-6-amine (product of step 6 of example 20) (70 mg, 0.22 mmol) was coupled with 2-(2-methoxypyridin-4-yl)oxazole-4-carboxylic acid (intermediate 11) (53 mg, 0.242 mmol) using EDCI·HCl (63 mg, 0.33 mmol), HOBt (45 mg, 0.33 mmol), DIPEA (85 mg, 0.66 mmol) in DMF (5 mL) to afford the title compound (25 mg, 21%).

¹HNMR (CD₃OD, 300 MHz): δ 8.99 (s, 1H), 8.59 (s, 1H), 8.35-8.30 (d, 1H), 7.60-7.52 (d, 1H), 7.42 (s, 1H), 3.99 (s, 3H), 3.84-3.81 (t, 4H), 3.67-3.64 (t, 4H), 3.11-3.08 (t, 4H), 1.90-1.85 (m, 4H), 1.80-1.70 (m, 2H). LCMS: 88.28%, m/z=522.2 (M+1)⁺. HPLC: 91.56%.

Example 59

(S)—N-(5-(3-fluoropiperidin-1-yl)-2-morpholinothiazolo[4,5-b]pyridin-6-yl)-2-(2-methylpyridin-4-yl)oxazole-4-carboxamide Step 1: Preparation of (S)-1-(2-morpholino-6-nitrothiazolo[4,5-b]pyridin-5-yl)piperidin-3-ol Using the same reaction conditions as described in step 2 of example 43, 4-(5-chloro-6-nitrothiazolo[4,5-b]pyridin-2-yl)morpholine (product of step 4 of example 20) (250 mg, 1.50 mmol) was substituted using (S)-piperidin-3-ol hydrochloride (137 mg, 0.9976 mmol) using sodium carbonate (265 mg, 2.4940 mmol) in DMF (2 mL) at 140° C. for 4 h to obtain the title compound (190 mg, 62.70%). LCMS: m/z=366.1 (M+1)⁺.

Step 2: Preparation of (S)-4-(5-(3-fluoropiperidin-1-yl)-6-nitrothiazolo[4,5-b]pyridin-2-yl)morpholine DAST (0.17 mL, 1.3013 mmol) was added to the cooled (−78° C.) solution of (S)-1-(2-morpholino-6-nitrothiazolo[4,5-b]pyridin-5-yl)piperidin-3-ol (190 mg, 0.5205 mmol) in DCM (5 mL). The reaction was quenched with ice water after stirring at −78° C. for 30 min. The compound was extracted with DCM and purified by 60-120 silica gel column chromatography using 2% methanol in DCM as eluent to obtain the title compound (100 mg, 52.35%). LCMS: m/z=368.1 (M+1)⁺.

Step 3: Preparation of (S)-5-(3-fluoropiperidin-1-yl)-2-morpholinothiazolo[4,5-b]pyridin-6-amine Using the same reaction conditions as described in step 5 of example 1, (S)-4-(5-(3-fluoropiperidin-1-yl)-6-nitrothiazolo[4,5-b]pyridin-2-yl)morpholine (100 mg, 0.2724 mmol) was reduced with zinc dust (143 mg, 2.1798 mmol) and ammonium chloride (233 mg, 4.3596 mmol) in THF/methanol/H₂O (10 mL/2 mL/1 mL) to get the crude product (100 mg). LCMS: m/z=338.1 (M+1)⁺.

Step 4: Preparation of (S)—N-(5-(3-fluoropiperidin-1-yl)-2-morpholinothiazolo[4,5-b]pyridin-6-yl)-2-(2-methylpyridin-4-yl)oxazole-4-carboxamide Using the same reaction conditions as described in step 6 of example 1, (S)-5-(3-fluoropiperidin-1-yl)-2-morpholinothiazolo[4,5-b]pyridin-6-amine (100 mg, 0.2724 mmol) was coupled with 2-(2-methylpyridin-4-yl)oxazole-4-carboxylic acid (84 mg, 0.4087 mmol) using EDCI·HCl (79 mg, 0.4087 mmol), HOBt (56 mg, 0.4087 mmol), DIPEA (0.19 mL, 1.0899 mmol) in DMF (2 mL) to afford the crude product. The resultant crude was purified by prep HPLC to obtain the title compound (26 mg, 18.30%).

¹HNMR (CDCl₃, 400 MHz): δ 9.94 (s, 1H), 9.09 (s, 1H), 8.69-8.68 (d, 1H), 8.39 (s, 1H), 7.87 (s, 1H), 7.76-7.75 (d, 1H), 5.04-4.92 (m, 1H), 3.84-3.82 (t, 4H), 3.71-3.68 (t, 4H), 3.45-3.36 (m, 2H), 3.15-3.02 (m, 2H), 2.67 (s, 3H), 2.26-1.83 (m, 4H). LCMS: 97.00%, m/z=524.1 (M+1)⁺. HPLC: 95.24%.

Example 60

2-(6-methylpyridin-3-yl)-N-(2-morpholino-5-(piperidin-1-yl)thiazolo[4,5-b]pyridin-6-yl)oxazole-4-carboxamide

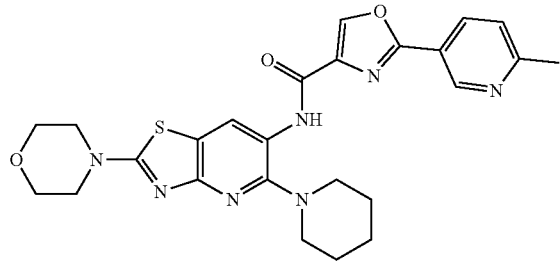 [SMILES: Cc1ccc(-c2nc(C(=O)Nc3cc4sc(N5CCOCC5)nc4nc3N3CCCCC3)co2)cn1]

Using the same reaction conditions as described in step 6 of example 1, 2-morpholino-5-(piperidin-1-yl)thiazolo[4,5-b]pyridin-6-amine (product of step 6 of example 20) (70 mg, 0.22 mmol) was coupled with 2-(2-methylpyridin-5-yl)oxazole-4-carboxylic acid (intermediate 13) (54 mg, 0.264 mmol) using EDCI·HCl (63 mg, 0.33 mmol), HOBt (40 mg, 0.33 mmol), DIPEA (85 mg, 0.66 mmol) in DMF (5 mL) to afford the title compound (30 mg, 26%).

¹HNMR (CD₃OD, 400 MHz): δ 9.36 (s, 1H), 9.08-9.05 (dd, 1H), 8.85 (s, 1H), 8.70 (s, 1H), 8.15-8.13 (d, 1H), 3.85-3.83 (t, 8H), 3.50-3.48 (m, 4H), 2.88 (s, 3H), 1.85 (s, 4H), 1.80-1.70 (m, 2H).
LCMS: 98.51%, m/z=506.2 (M+1)⁺. HPLC: 94.43%.

Example 61

2-(3-methylpyridin-4-yl)-N-(2-morpholino-5-(piperidin-1-yl)thiazolo[4,5-b]pyridin-6-yl)oxazole-4-carboxamide

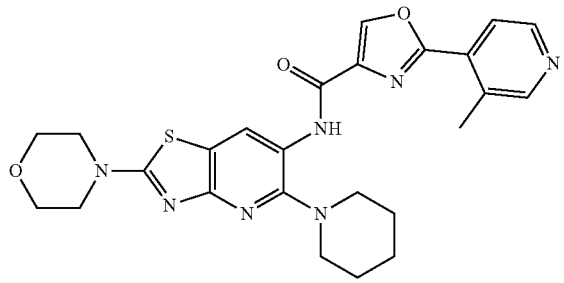 [SMILES: Cc1cnccc1-c1nc(C(=O)Nc2cc3sc(N4CCOCC4)nc3nc2N2CCCCC2)co1]

Using the same reaction conditions as described in step 6 of example 1, 2-morpholino-5-(piperidin-1-yl)thiazolo[4,5-b]pyridin-6-amine (product of step 6 of example 20) (80 mg, 0.25 mmol) was coupled with 2-(3-methylpyridin-4-yl)oxazole-4-carboxylic acid (intermediate 12) (61 mg, 0.3 mmol) using EDCI·HCl (72 mg, 0.376 mmol), HOBt (36 mg, 0.263 mmol), DIPEA (97 mg, 0.75 mmol) in DMF (3.4 mL) to afford the title compound (29 mg, 23%).

¹HNMR (DMSO-d₆, 400 MHz): δ 9.70 (s, 1H), 9.09 (s, 1H), 8.99 (s, 1H), 8.71 (s, 1H), 8.65-8.64 (d, 1H), 7.92-7.91 (d, 1H), 3.73-3.72 (m, 4H), 3.65-3.55 (m, 4H), 2.96-2.95 (m, 4H), 2.78 (s, 3H), 1.76 (s, 4H), 1.59 (s, 2H). LCMS: 99.47%, m/z=506.2 (M+1)⁺. HPLC: 98.79%.

Example 62

(S)-6-(3-aminopyrrolidin-1-yl)-N-(2-morpholino-5-(piperidin-1-yl)thiazolo[4,5-b]pyridin-6-yl)picolinamide

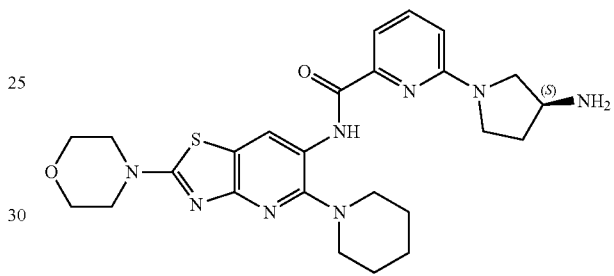

Step 1: Preparation of 6-bromo-N-(2-morpholino-5-(piperidin-1-yl)thiazolo[4,5-b]pyridin-6-yl)picolinamide Using the same reaction conditions as described in step 6 of example 1, 2-morpholino-5-(piperidin-1-yl)thiazolo[4,5-b]pyridin-6-amine (product of step 6 of example 20) (35 mg, 0.994 mmol) was coupled with 6-bromopicolinic acid (301 mg, 1.49 mmol) using EDCI·HCl (285 mg, 1.49 mmol), HOBt (141 mg, 1.04 mmol), DIPEA (384 mg, 2.98 mmol) in DMF (10 mL) to afford the crude product. The resultant crude was purified by 60-120 silica gel column chromatography using 1% methanol in DCM as eluent to obtain the title compound (220 mg, 40%). LCMS: m/z=503.0 (M)⁺.

Step 2: Preparation of tert-butyl (S)-(1-(6-((2-morpholino-5-(piperidin-1-yl)thiazolo[4,5-b]pyridin-6-yl)carbamoyl)pyridin-2-yl)pyrrolidin-3-yl)carbamate Using the same reaction conditions as described in step 2 of example 43, 6-bromo-N-(2-morpholino-5-(piperidin-1-yl)thiazolo[4,5-b]pyridin-6-yl)picolinamide (70 mg, 0.139 mmol) was substituted with tert-butyl (S)-pyrrolidin-3-ylcarbamate (39 mg, 0.209 mmol) using sodium carbonate (59 mg, 0.556 mmol) in DMF (3 mL) at 140° C. for 4 h to obtain the title compound (40 mg, 46.5%).

Step 3: Preparation of (S)-6-(3-aminopyrrolidin-1-yl)-N-(2-morpholino-5-(piperidin-1-yl)thiazolo[4,5-b]pyridin-6-yl)picolinamide Using the same reaction conditions as described in step 8 of example 1, tert-butyl (S)-(1-(6-((2-morpholino-5-(piperidin-1-yl)thiazolo[4,5-b]pyridin-6-yl)carbamoyl)pyridin-2-yl)pyrrolidin-3-yl)carbamate (65 mg, 9.3655) was deprotected using TFA (2 mL) and DCM (8 mL) to get the title compound (45 mg, 83.3%).

$^1$HNMR (CDCl$_3$, 400 MHz): δ 10.58 (s, 1H), 9.11 (s, 1H), 7.65-7.55 (m, 2H), 6.57-6.55 (d, 1H), 3.87-3.77 (m, 6H), 3.68-3.3.63 (m, 5H), 3.38-3.37 (m, 1H), 3.10-3.07 (t, 4H), 2.28-2.25 (m, 1H), 1.90-1.87 (m, 1H), 1.77 (s, 4H), 1.57-1.55 (m, 3H). LCMS: 100%, m/z=509.1 (M+1)$^+$. HPLC: 95.95%.

Example 63

(S)-6-(3-hydroxypyrrolidin-1-yl)-N-(2-morpholino-5-(piperidin-1-yl)thiazolo[4,5-b]pyridin-6-yl)picolinamide

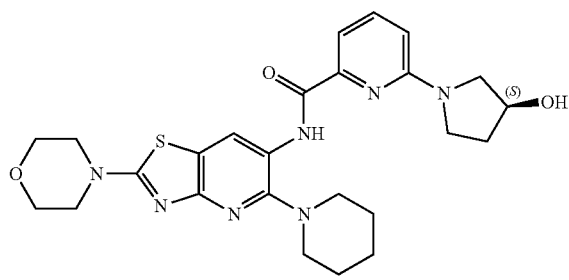

Using the same reaction conditions as described in step 2 of example 43, 6-bromo-N-(2-morpholino-5-(piperidin-1-yl)thiazolo[4,5-b]pyridin-6-yl)picolinamide (product of step 1 of example 63) (70 mg, 0.139 mmol) was substituted with (S)-pyrrolidin-3-ol (19 mg, 0.208 mmol) using sodium carbonate (59 mg, 0.556 mmol) in DMF (3 mL) at 140° C. for 12 h to obtain the title compound (50 mg, 71.4%).

$^1$HNMR (DMSO-d$_6$, 400 MHz): δ 10.45 (s, 1H), 9.05 (s, 1H), 7.74-7.70 (t, 1H), 7.38-7.37 (d, 1H), 6.75-6.74 (d, 1H), 5.06-5.05 (d, 1H), 4.44 (s, 1H), 3.75-3.72 (m, 4H), 3.64-3.56 (m, 7H), 2.94-2.93 (d, 4H), 2.09-2.07 (m, 1H), 1.98-1.95 (m, 1H), 1.72 (s, 4H), 1.57 (s, 2H).

LCMS: 94.83%, m/z=510.2 (M+1)$^+$. HPLC: 95.34%.

Example 64

(S)-6-(3-aminopyrrolidin-1-yl)-N-(2,5-di(piperidin-1-yl)thiazolo[4,5-b]pyridin-6-yl)picolinamide

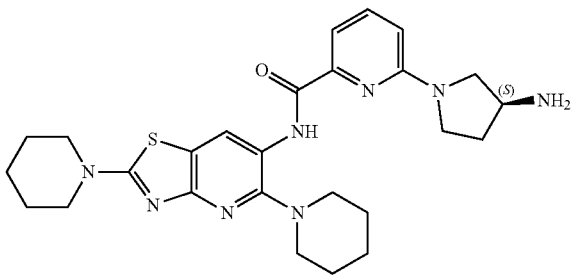

Step 1: Preparation of 6-bromo-N-(2,5-di(piperidin-1-yl)thiazolo[4,5-b]pyridin-6-yl)picolinamide Using the same reaction conditions as described in step 6 of example 1, 2,5-di(piperidin-1-yl)thiazolo[4,5-b]pyridin-6-amine (product of step 4 of example 22) (300 mg, 0.946 mmol) was coupled with 6-bromopicolinic acid (286 mg, 1.419 mmol) using EDCI·HCl (270 mg, 1.419 mmol), HOBt (191 mg, 1.419 mmol), DIPEA (370 mg, 2.838 mmol) in DMF (5 mL) to afford the title compound (350 mg, 73.83%).

$^1$HNMR (CDCl$_3$, 300 MHz): δ 10.7 (s, 1H), 9.06 (s, 1H), 8.24-8.21 (d, 1H), 7.80-7.75 (t, 1H), 7.67-7.64 (d, 1H), 3.65 (s, 4H), 3.12-3.08 (t, 4H), 1.95-1.85 (m, 4H), 1.69 (s, 8H). LCMS: m/z=503.1 (M+2)$^+$.

Step 2: Preparation of tert-butyl (S)-(1-(6-((2,5-di(piperidin-1-yl)thiazolo[4,5-b]pyridin-6-yl)carbamoyl)pyridin-2-yl)pyrrolidin-3-yl)carbamate Using the same reaction conditions as described in step 2 of example 43, 6-bromo-N-(2,5-di(piperidin-1-yl)thiazolo[4,5-b]pyridin-6-yl)picolinamide (100 mg, 0.2 mmol) was substituted with tert-butyl (S)-pyrrolidin-3-ylcarbamate (56 mg, 0.3 mmol) using sodium carbonate (64 mg, 0.6 mmol) in DMF (2 mL) at 100° C. for 4 h to obtain the title compound (120 mg, 100%). LCMS: m/z=607.3 (M+1)$^+$.

Step 3: Preparation of (S)-6-(3-aminopyrrolidin-1-yl)-N-(2,5-di(piperidin-1-yl)thiazolo[4,5-b]pyridin-6-yl)picolinamide Using the same reaction conditions as described in step 8 of example 1, tert-butyl (S)-(1-(6-((2,5-di(piperidin-1-yl)thiazolo[4,5-b]pyridin-6-yl)carbamoyl)pyridin-2-yl)pyrrolidin-3-yl)carbamate (120 mg, 0.197 mmol) was deprotected using TFA (1 mL) and DCM (1 mL) to afford the crude product. The resultant crude was purified by prep HPLC to obtain the title compound (65 mg, 65%).

$^1$HNMR (CDCl$_3$, 300 MHz): δ 10.53 (s, 1H), 9.05 (s, 1H), 7.65-7.54 (m, 2H), 6.55-6.53 (d, 1H), 3.84-3.73 (m, 3H), 3.64 (s, 6H), 3.50-3.35 (m, 1H), 3.08-3.04 (t, 4H), 2.31-2.25 (m, 1H), 2.10-1.85 (m, 1H), 1.80-1.60 (m, 11H). LCMS: 92.92%, m/z=507.2 (M+1)$^+$. HPLC: 96.92%.

Example 65

(S)—N-(2,5-di(piperidin-1-yl)thiazolo[4,5-b]pyridin-6-yl)-6-(3-hydroxypyrrolidin-1-yl)picolinamide

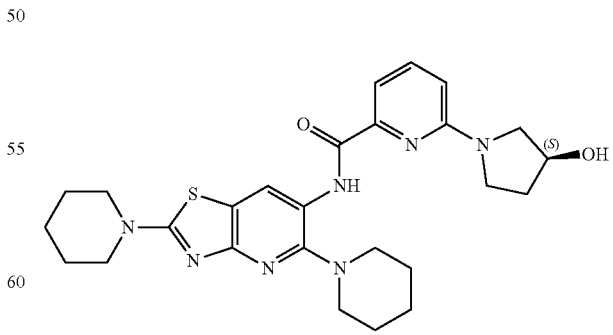

Using the same reaction conditions as described in step 2 of example 43, 6-bromo-N-(2,5-di(piperidin-1-yl)thiazolo[4,5-b]pyridin-6-yl)picolinamide (product of step 1 of example 65) (70 mg, 0.14 mmol) was substituted with (S)-pyrrolidin-3-ol (20 mg, 0.209 mmol) using sodium carbonate (45 mg, 0.42 mmol) in DMF (2 mL) at 100° C. for 4 h to obtain the title compound (60 mg, 84.5%).

¹HNMR (CDCl₃, 400 MHz): δ 10.57 (s, 1H), 9.06 (s, 1H), 7.66-7.62 (t, 1H), 7.59-7.57 (d, 1H), 6.58-6.56 (d, 1H), 4.68 (s, 1H), 3.79-3.74 (m, 4H), 3.65 (s, 4H), 3.09-3.07 (m, 4H), 2.24-2.12 (m, 2H), 1.77-1.76 (m, 4H), 1.69 (s, 6H), 1.61-1.56 (m, 3H). LCMS: 99.49%, m/z=508.2 (M+1)⁺.

HPLC: 99.62%.

Example 66

(S)-2-(3-aminopyrrolidin-1-yl)-N-(2-morpholino-5-(piperidin-1-yl)thiazolo[4,5-b]pyridin-6-yl)oxazole-4-carboxamide

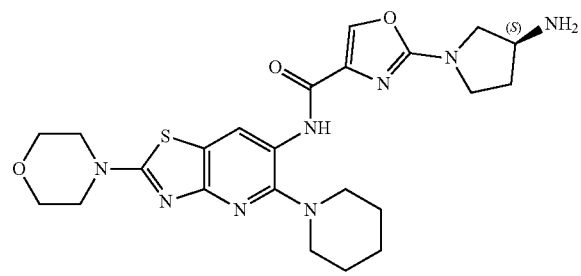

Step 1: Preparation of tert-butyl (S)-(1-(4-((2-morpholino-5-(piperidin-1-yl)thiazolo[4,5-b]pyridin-6-yl)carbamoyl)oxazol-2-yl)pyrrolidin-3-yl)carbamate Using the same reaction conditions as described in step 6 of example 1, 2-morpholino-5-(piperidin-1-yl)thiazolo[4,5-b]pyridin-6-amine (product of step 6 of example 20) (100 mg, 0.3134 mmol), was coupled with (S)-2-(3-((tert-butoxycarbonyl)amino)pyrrolidin-1-yl)oxazole-4-carboxylic acid (intermediate 14) (140 mg, 0.4702 mmol) using EDCI·HCl (91 mg, 0.4702 mmol), HOBt (64 mg, 0.4702 mmol), DIPEA (0.218 mL, 1.2539 mmol) in DMF (2 mL) to afford crude product. The resultant crude was purified by 60-120 silica gel column chromatography using 1% methanol in DCM as eluent to obtain the title compound (170 mg, 90.9%). LCMS: m/z=599.3 (M+1)⁺. HPLC: 88.43%.

Step 2: Preparation of (S)-2-(3-aminopyrrolidin-1-yl)-N-(2-morpholino-5-(piperidin-1-yl)thiazolo[4,5-b]pyridin-6-yl)oxazole-4-carboxamide Using the same reaction conditions as described in step 8 of example 1, tert-butyl (S)-(1-(4-((2-morpholino-5-(piperidin-1-yl)thiazolo[4,5-b]pyridin-6-yl)carbamoyl)oxazol-2-yl)pyrrolidin-3-yl)carbamate (170 mg, 0.2839 mmol) was deprotected using TFA (5 mL) and DCM (5 mL) to get the title compound (69 mg, 48.93%).

¹HNMR (CDCl₃, 400 MHz): δ 9.07 (s, 1H), 9.06 (s, 1H), 7.82 (s, 1H), 3.82-3.68 (m, 11H), 3.30-3.28 (m, 1H), 3.15-3.03 (m, 4H), 2.30-2.20 (m, 1H), 1.90-1.80 (m, 5H), 1.62-1.55 (m, 3H).

LCMS: 98.35%, m/z=499.2 (M+1)⁺. HPLC: 97.34%.

Example 67

(S)—N-(5-(3-aminopyrrolidin-1-yl)-2-morpholinothiazolo[4,5-b]pyridin-6-yl)-2-(2-methylpyridin-4-yl)oxazole-4-carboxamide

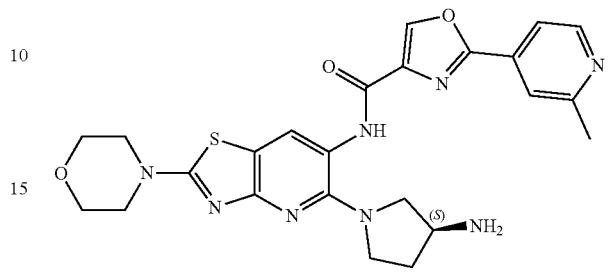

Step 1: Preparation of tert-butyl (S)-(1-(2-morpholino-6-nitrothiazolo[4,5-b]pyridin-5-yl)pyrrolidin-3-yl)carbamate Using the same reaction conditions as described in step 1 of example 38, 4-(5-chloro-6-nitrothiazolo[4,5-b]pyridin-2-yl)morpholine (product of step 4 of example 20) (150 mg, 0.5 mmol) was substituted with tert-butyl (S)-pyrrolidin-3-ylcarbamate (93 mg, 0.5 mmol) using potassium carbonate (207 mg, 1.5 mmol) and DMF (5 mL) to afford the crude product. The resultant crude was purified by 60-120 silica gel column chromatography using 1% methanol in DCM as eluent to obtain the title compound (195 mg, 87%). LCMS: m/z=451.3 (M+1)⁺.

Step 2: Preparation of tert-butyl tert-butyl (S)-(1-(6-amino-2-morpholinothiazolo[4,5-b]pyridin-5-yl)pyrrolidin-3-yl)carbamate Using the same reaction conditions as described in step 2 of example 38, tert-butyl (S)-(1-(2-morpholino-6-nitrothiazolo[4,5-b]pyridin-5-yl)pyrrolidin-3-yl)carbamate (194 mg, 0.431 mmol) was reduced with zinc dust (224 mg, 3.448 mmol) and ammonium chloride (366 mg, 6.8977 mmol) in THF/methanol/H₂O (10 mL/2 mL/1 mL) to get the title compound (171 mg, 94%). LCMS: m/z=421.2 (M+1)⁺.

Step 3: Preparation of tert-butyl (S)-(1-(6-(2-(2-methylpyridin-4-yl)oxazole-4-carboxamido)-2-morpholinothiazolo[4,5-b]pyridin-5-yl)pyrrolidin-3-yl)carbamate Using the same reaction conditions as described in step 6 of example 1, tert-butyl (S)-(1-(6-amino-2-morpholinothiazolo[4,5-b]pyridin-5-yl)pyrrolidin-3-yl)carbamate (83 mg, 0.4047 mmol), was coupled with 2-(2-methylpyridin-4-yl)oxazole-4-carboxylic acid (170 mg, 0.4047 mmol) using EDCI·HCl (117 mg, 0.6155 mmol), HOBt (58 mg, 0.4293 mmol), DIPEA (209 mg, 1.624 mmol) in DMF (5 mL) to get the title compound (162 mg, 66%). LCMS: m/z=607.2 (M+1)⁺. HPLC: 95.47%.

Step 4: Preparation of (S)—N-(5-(3-aminopyrrolidin-1-yl)-2-morpholinothiazolo[4,5-b]pyridin-6-yl)-2-(2-methylpyridin-4-yl)oxazole-4-carboxamide Using the same reaction conditions as described in step 8 of example 1, tert-butyl (S)-(1-(6-(2-(2-methylpyridin-4-yl)

oxazole-4-carboxamido)-2-morpholinothiazolo[4,5-b]pyridin-5-yl)pyrrolidin-3-yl)carbamate (161 mg, 0.2656 mmol) was deprotected using methanolic HCl (5 mL) to get the title compound (83 mg, 62%).

¹HNMR (CDCl₃, 300 MHz): δ 8.97 (s, 1H), 8.69-8.68 (d, 1H), 8.53 (s, 1H), 8.40 (s, 1H), 7.79 (s, 1H), 7.73-7.71 (d, 1H), 3.84-3.80 (t, 4H), 3.72-3.68 (m, 8H), 3.63-3.54 (m, 2H), 3.33-3.26 (m, 1H), 2.67 (s, 3H), 2.28-2.24 (m, 1H), 1.82-1.78 (m, 1H). LCMS: 100%, m/z=507.1 (M+1)⁺. HPLC: 97.85%.

Example 68

(S)-2-(3-aminopyrrolidin-1-yl)-N-(5-cyclopropyl-2-morpholinothiazolo[4,5-b]pyridin-6-yl)oxazole-4-carboxamide

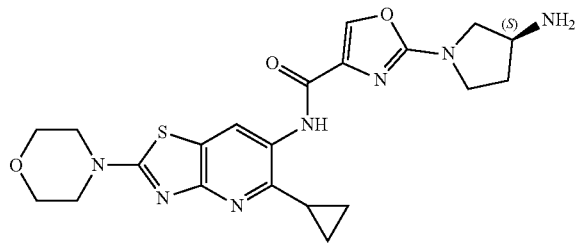

Step 1: Preparation of 4-(5-cyclopropyl-6-nitrothiazolo[4,5-b]pyridin-2-yl)morpholine Using the same reaction conditions as described in step 7 of example 1,4-(5-chloro-6-nitrothiazolo[4,5-b]pyridin-2-yl)morpholine (product of step 4 of example 20) (500 mg, 1.666 mmol) was coupled with cyclopropyl boronic acid (286 mg, 3.333 mmol) using potassium phosphate (882 mg, 4.165 mmol) and Pd(OAc)₂ (57 mg, 0.254 mmol) and tricyclohexyl phosphine (70 mg, 0.254 mmol) in toluene:water (10/1 mL) to get the crude product. The resultant crude was purified by 60-120 silica gel column chromatography using 30% ethyl acetate in hexane as eluent to obtain the title compound (400 mg, 80%). LCMS: m/z=306.9 (M+1)⁺.

Step 2: Preparation of 5-cyclopropyl-2-morpholinothiazolo[4,5-b]pyridin-6-amine

Using the same reaction conditions as described in step 5 of example 1,4-(5-cyclopropyl-6-nitrothiazolo[4,5-b]pyridin-2-yl)morpholine (400 mg, 1.307 mmol) was reduced with zinc dust (680 mg, 10.457 mmol) and ammonium chloride (1.13 g, 20.916 mmol) in THF (10 mL) to get the title compound (350 mg, 100%). LCMS: m/z=277.1 (M+1)⁺.

Step 3: Preparation of tert-butyl (S)-(1-(4-((5-cyclopropyl-2-morpholinothiazolo[4,5-b]pyridin-6-yl)carbamoyl)oxazol-2-yl)pyrrolidin-3-yl)carbamate Using the same reaction conditions as described in step 6 of example 1, 5-cyclopropyl-2-morpholinothiazolo[4,5-b]pyridin-6-amine (100 mg, 0.362 mmol), was coupled with (S)-2-(3-((tert-butoxycarbonyl)amino)pyrrolidin-1-yl)oxazole-4-carboxylic acid (intermediate 14) (129 mg, 0.434 mmol) using EDCI·HCl (102 mg, 0.54 mmol), HOBt (73 mg, 0.54 mmol), DIPEA (0.280 mL, 2.16 mmol) in DMF (5 mL) to afford the title compound (180 mg, 85.1%). LCMS: m/z=556.2 (M+1)⁺.

Step 4: Preparation of (S)-2-(3-aminopyrrolidin-1-yl)-N-(5-cyclopropyl-2-morpholinothiazolo[4,5-b]pyridin-6-yl)oxazole-4-carboxamide Using the same reaction conditions as described in step 8 of example 1, tert-butyl (S)-(1-(4-((5-cyclopropyl-2-morpholinothiazolo[4,5-b]pyridin-6-yl)carbamoyl)oxazol-2-yl)pyrrolidin-3-yl)carbamate (180 mg, 0.324 mmol) was deprotected using TFA (1 mL) and DCM (0.5 mL) to get the crude product. The resultant crude was purified by prep HPLC to obtain the title compound (60 mg, 40.8%).

¹HNMR (CDCl₃, 300 MHz): δ 9.20 (s, 1H), 8.72 (s, 1H), 7.83 (s, 1H), 3.83-3.56 (m, 12H), 3.28-3.25 (m, 1H), 2.22-2.18 (m, 1H), 2.10-2.03 (m, 1H), 1.88-1.77 (m, 1H), 1.33-1.21 (m, 2H), 1.07-1.00 (m, 2H). LCMS: 98.66%, m/z=456.2 (M+1)⁺. HPLC: 95.53%.

Example 69

N-(5-cyclopropyl-2-morpholinothiazolo[4,5-b]pyridin-6-yl)-2-(2-methylpyridin-4-yl)oxazole-4-carboxamide

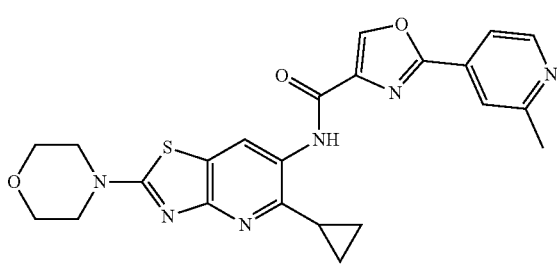 [SMILES: Cc1cc(-c2nc(C(=O)Nc3cc4sc(N5CCOCC5)nc4nc3C3CC3)co2)ccn1]

Using the same reaction conditions as described in step 6 of example 1, 5-cyclopropyl-2-morpholinothiazolo[4,5-b]pyridin-6-amine (product of step 2 of example 69) (100 mg, 0.362 mmol) was coupled with 2-(2-methylpyridin-4-yl)oxazole-4-carboxylic acid (110 mg, 0.54 mmol) using EDCI·HCl (102 mg, 0.54 mmol), HOBt (73 mg, 0.54 mmol), DIPEA (280 mg, 2.16 mmol) in DMF (5 mL) to afford the title compound (45 mg, 26.94%).

¹HNMR (CDCl₃, 400 MHz): δ 9.30 (s, 1H), 8.75-8.57 (m, 2H), 8.48 (s, 1H), 7.85 (s, 1H), 7.75-7.72 (d, 1H), 3.90-3.80 (t, 4H), 3.78-3.70 (t, 4H), 2.75 (s, 3H), 2.25-2.15 (m, 1H), 1.35-1.25 (m, 2H), 1.15-1.05 (m, 2H). LCMS: 98.37%, m/z=463.1 (M+1)⁺. HPLC: 97.74%.

Example 70

(S)-2-(3-hydroxypyrrolidin-1-yl)-N-(2-morpholino-5-(piperidin-1-yl)thiazolo[4,5-b]pyridin-6-yl)oxazole-4-carboxamide

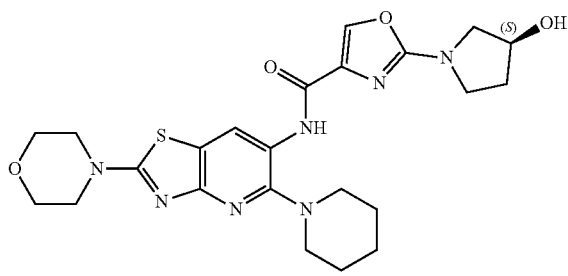

Using the same reaction conditions as described in example 45, 2-morpholino-5-(piperidin-1-yl)thiazolo[4,5-b]pyridin-6-amine (product of step 6 of example 20) (90 mg, 0.281 mmol), was coupled with (S)-2-(3-((tert-butyldimethylsilyl)oxy)pyrrolidin-1-yl)oxazole-4-carboxylic acid (intermediate 15) (105 mg, 0.3375 mmol) using EDCI·HCl (81 mg, 0.4218 mmol), HOBt (57 mg, 0.4218 mmol), DIPEA (145 mg, 1.125 mmol) in DMF (2 mL) followed by deprotection using methanolic HCl (2 mL) to get the title compound (63 mg, 84%).

$^1$HNMR (CDCl$_3$, 400 MHz): δ 9.75 (s, 1H), 9.07 (s, 1H), 7.85 (s, 1H), 4.67 (bs, 1H), 3.843.59 (m, 12H), 3.12-3.09 (t, 4H), 2.30-2.10 (m, 2H), 1.85 (s, 4H), 1.63-1.59 (m, 3H).

LCMS: 100%, m/z=500.3 (M+1)$^+$. HPLC: 97.36%.

Example 71

(S)—N-(5-(3-hydroxypyrrolidin-1-yl)-2-morpholinothiazolo[4,5-b]pyridin-6-yl)-2-(2-methylpyridin-4-yl)oxazole-4-carboxamide

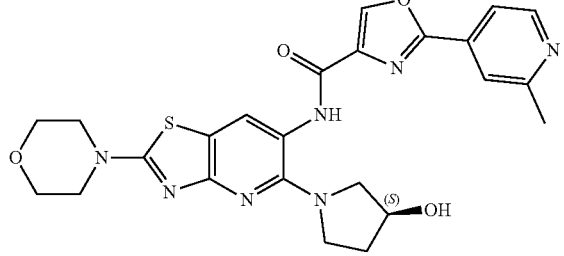

Step 1: Preparation of (S)-1-(2-morpholino-6-nitrothiazolo[4,5-b]pyridin-5-yl)pyrrolidin-3-ol Using the same reaction conditions as described in step 1 of example 38, 4-(5-chloro-6-nitrothiazolo[4,5-b]pyridin-2-yl)morpholine (product of step 4 of example 20) (150 mg, 0.5 mmol) was substituted with (S)-pyrrolidin-3-ol (43 mg, 0.5 mmol) using potassium carbonate (207 mg, 1.5 mmol) and DMF (2 mL) to afford the title product (171 mg, 97%). LCMS: m/z=352.1 (M+1)$^+$.

Step 2: Preparation of (S)-1-(6-amino-2-morpholinothiazolo[4,5-b]pyridin-5-yl)pyrrolidin-3-ol Using the same reaction conditions as described in step 2 of example 38, (S)-1-(6-amino-2-morpholinothiazolo[4,5-b]pyridin-5-yl)pyrrolidin-3-ol (167 mg, 0.475 mmol) was reduced with zinc dust (247 mg, 3.806 mmol) and ammonium chloride (403 mg, 7.6 mmol) in THF (10 mL) to get the title compound (147 mg, 96.7%). LCMS: m/z=322.1 (M+1)$^+$.

Step 3: Preparation of (S)—N-(5-(3-hydroxypyrrolidin-1-yl)-2-morpholinothiazolo[4,5-b]pyridin-6-yl)-2-(2-methylpyridin-4-yl)oxazole-4-carboxamide Using the same reaction conditions as described in step 6 of example 1, (S)-1-(6-amino-2-morpholinothiazolo[4,5-b]pyridin-5-yl)pyrrolidin-3-ol (146 mg, 0.6074 mmol), was coupled with 2-(2-methylpyridin-4-yl)oxazole-4-carboxylic acid (124 mg, 0.6074 mmol) using EDCI·HCl (175 mg, 0.911 mmol), HOBt (82 mg, 0.6074 mmol), DIPEA (354 mg, 2.429 mmol) in DMF (5 mL) to get the crude product. The resultant crude was purified by prep HPLC to obtain the title compound (30 mg, 10%).

$^1$HNMR (CDCl$_3$, 400 MHz): δ 9.17 (s, 1H), 8.71-8.70 (d, 1H), 8.67 (s, 1H), 8.43 (s, 1H), 7.83 (s, 1H), 7.76-7.75 (d, 1H), 4.60 (bs, 1H), 3.86-3.83 (t, 4H), 3.76-3.68 (m, 6H), 3.60-3.54 (m, 3H), 2.69 (s, 3H), 2.26-2.24 (m, 1H), 2.10-2.01 (m, 1H). LCMS: 100%, m/z=508.4 (M+1)$^+$.

HPLC: 98.23%.

Example 72

(S)—N-(5-cyclopropyl-2-morpholinothiazolo[4,5-b]pyridin-6-yl)-6-(3-hydroxypyrrolidin-1-yl)picolinamide

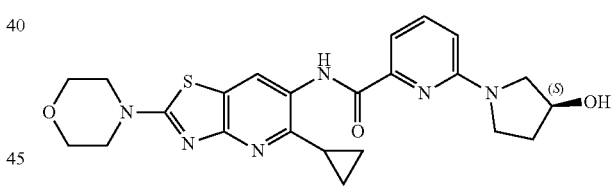

Step 1: Preparation of 6-bromo-N-(5-cyclopropyl-2-morpholinothiazolo[4,5-b]pyridin-6-yl)picolinamide Using the same reaction conditions as described in example 45, 5-cyclopropyl-2-morpholinothiazolo[4,5-b]pyridin-6-amine (product of step 2 of example 69) (220 mg, 0.797 mmol), was coupled with 6-bromopicolinic acid (193 mg, 0.956 mmol) using EDCI·HCl (228 mg, 1.19 mmol), HOBt (112 mg, 0.836 mmol), DIPEA (308 mg, 2.39 mmol) in DMF (10 mL) to get the title compound (200 mg, 54.64%).

LCMS: m/z=460.0 (M+1)$^+$.

Step 2: Preparation of (S)—N-(5-cyclopropyl-2-morpholinothiazolo[4,5-b]pyridin-6-yl)-6-(3-hydroxypyrrolidin-1-yl)picolinamide Using the same reaction conditions as described in step 2 of example 43, 6-bromo-N-(5-cyclopropyl-2-morpholinothiazolo[4,5-b]pyridin-6-yl)picolinamide (100 mg, 0.217 mmol) was substituted with (S)-pyrrolidin-3-ol (40 mg, 0.325 mmol) using sodium carbonate (92 mg, 0.868 mmol) in DMF (2 mL) at 100° C. for 4 h to obtain the title compound (55 mg, 54.45%).

$^1$HNMR (DMSO-d$_6$, 400 MHz): δ 10.41 (s, 1H), 8.60 (s, 1H), 7.71-7.67 (t, 1H), 7.32-7.30 (d, 1H), 6.72-6.70 (d, 1H), 5.00-4.99 (d, 1H), 4.40 (s, 1H), 3.73-3.70 (t, 4H), 3.58-3.51 (m, 7H), 2.19-2.16 (m, 1H), 2.18-2.00 (m, 2H), 0.98-0.96 (m, 4H). LCMS: 100%, m/z=467.2 (M+1)$^+$.

HPLC: 95.50%.

Example 73

(S)—N-(5-cyclopropyl-2-morpholinothiazolo[4,5-b]pyridin-6-yl)-2-(3-hydroxypyrrolidin-1-yl)oxazole-4-carboxamide

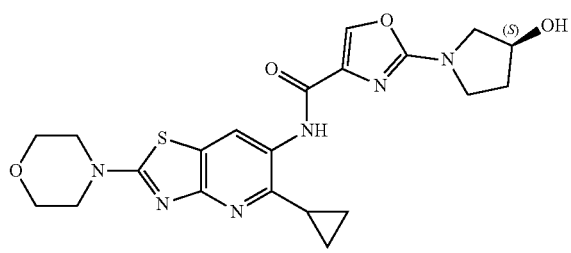

Using the same reaction conditions as described in example 45, 5-cyclopropyl-2-morpholinothiazolo[4,5-b]pyridin-6-amine (product of step 2 of example 69) (80 mg, 0.289 mmol), was coupled with (S)-2-(3-((tert-butyldimethylsilyl)oxy)pyrrolidin-1-yl)oxazole-4-carboxylic acid (intermediate 15) (90 mg, 0.289 mmol) using EDCI·HCl (83 mg, 0.433 mmol), HOBt (59 mg, 0.433 mmol), DIPEA (149 mg, 1.156 mmol) in DMF (5 mL) followed by deprotection using methanolic HCl (5 mL) to get the title compound (40 mg, 44.4%).

$^1$HNMR (CDCl$_3$, 300 MHz): δ 9.19 (s, 1H), 8.71 (s, 1H), 7.84 (s, 1H), 4.65 (s, 1H), 3.83-3.74 (t, 4H), 3.71-3.60 (m, 9H), 2.10-2.08 (m, 3H), 1.21-1.19 (m, 2H), 1.06-1.02 (m, 2H). LCMS: 97.34%, m/z=457.4 (M+1). HPLC: 95.05%.

Example 74

(S)—N-(5-cyclopropyl-2-morpholinothiazolo[4,5-b]pyridin-6-yl)-6-(1-(2-hydroxypropyl)-1H-pyrazol-4-yl)picolinamide

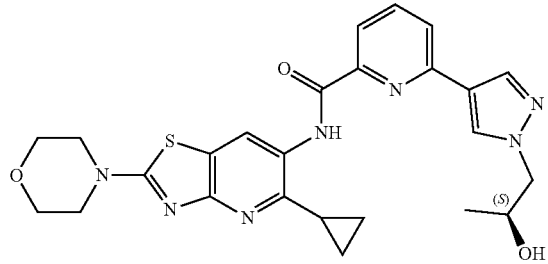

Step 1: Preparation of N-(5-cyclopropyl-2-morpholinothiazolo[4,5-b]pyridin-6-yl)-6-(1-(tetrahydro-2H-pyran-2-yl)-1H-pyrazol-4-yl)picolinamide Using the same reaction conditions as described in step 7 of example 1, 6-bromo-N-(5-cyclopropyl-2-morpholinothiazolo[4,5-b]pyridin-6-yl)picolinamide (product of step 1 of example 73) (100 mg, 0.217 mmol) was coupled with 1-(tetrahydro-2H-pyran-2-yl)-4-(4,4,5,5-tetramethyl-1,3,2-dioxaborolan-2-yl)-1H-pyrazole (79 mg, 0.282 mmol) using sodium carbonate (69 mg, 0.651 mmol) and Pd(PPh$_3$)$_2$Cl$_2$ (8 mg, 0.108 mmol) in 1,2-dimethoxyethane/water (5/1 mL) to get the crude product. The resultant crude was purified by 60-120 silica gel column chromatography using 30% ethyl acetate in hexane as eluent to obtain the title compound (100 mg, 86.9%). LCMS: m/z=531.7 (M+1)$^+$.

Step 2: Preparation of N-(5-cyclopropyl-2-morpholinothiazolo[4,5-b]pyridin-6-yl)-6-(1H-pyrazol-4-yl)picolinamide Hydrochloride Using the same reaction conditions as described in step 8 of example 1, N-(5-cyclopropyl-2-morpholinothiazolo[4,5-b]pyridin-6-yl)-6-(1-(tetrahydro-2H-pyran-2-yl)-1H-pyrazol-4-yl)picolinamide (100 mg, 0.188 mmol) was deprotected using methanolic HCl (8 mL) to get the title compound (90 mg, 94.7%). LCMS: m/z=447.7 (M+1)$^+$.

Step 3: Preparation of (S)—N-(5-cyclopropyl-2-morpholinothiazolo[4,5-b]pyridin-6-yl)-6-(1-(2-hydroxypropyl)-1H-pyrazol-4-yl)picolinamide Using the same reaction conditions as described in step 2 of example 43, N-(5-cyclopropyl-2-morpholinothiazolo[4,5-b]pyridin-6-yl)-6-(1H-pyrazol-4-yl)picolinamide hydrochloride (90 mg, 0.201 mmol) was substituted with (S)-2-methyloxirane (24 mg, 0.402 mmol) using sodium carbonate (107 mg, 1.00 mmol) in DMF (2 mL) at 140° C. for 4 h to obtain the crude product. The resultant crude was purified by prep HPLC to obtain the title compound (35 mg, 34.6%).

$^1$HNMR (DMSO-d$_6$, 400 MHz): δ 10.8 (s, 1H), 8.61 (s, 1H), 8.31-8.30 (d, 2H), 8.00-7.98 (m, 1H), 7.93-7.89 (m, 2H), 5.02-5.01 (d, 1H), 4.05-4.02 (m, 3H), 3.75 (s, 4H), 3.61 (s, 4H) 2.33-2.23 (m, 1H), 1.08-1.07 (d, 3H), 0.99-0.95 (m, 4H). LCMS: m/z=505.7 (M+1)$^+$. HPLC: 98.67%.

Example 75

(S)—N-(5-cyclopropyl-2-morpholinothiazolo[4,5-b]pyridin-6-yl)-2-(1-(2-hydroxypropyl)-1H-pyrazol-4-yl)oxazole-4-carboxamide

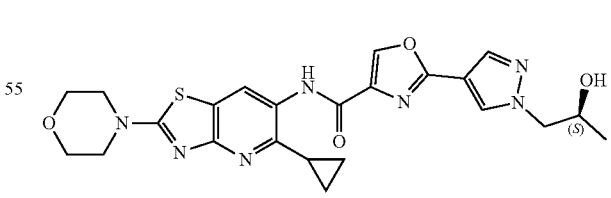

Step 1: Preparation of N-(5-cyclopropyl-2-morpholinothiazolo[4,5-b]pyridin-6-yl)-2-(1H-pyrazol-4-yl)oxazole-4-carboxamide Hydrochloride Using the same reaction conditions as described in example 45, 6-bromo-N-(5-cyclopropyl-2-morpholinothiazolo[4,5-b]pyridin-6-yl)picolinamide (product of step 1 of example 73) (100 mg, 0.362 mmol) was coupled with 2-(1-(tetrahydro-2H-pyran-2-yl)-1H-pyrazol-4-yl)oxazole-4-carboxylic acid (intermediate 16) (95 mg, 0.362 mmol) using EDCI·HCl (103 mg, 0.543 mmol), HOBt (73 mg, 0.543 mmol), DIPEA (187 mg, 1.448 mmol) in DMF (5 mL) followed by deprotection using methanol/methanolic HCl (1/5 mL) to get the title compound (145 mg, 85.1%). LCMS: m/z=437.7 (M+1)⁺.

Step 2: Preparation of (S)—N-(5-cyclopropyl-2-morpholinothiazolo[4,5-b]pyridin-6-yl)-2-(1-(2-hydroxypropyl)-1H-pyrazol-4-yl)oxazole-4-carboxamide Using the same reaction conditions as described in step 2 of example 43, N-(5-cyclopropyl-2-morpholinothiazolo[4,5-b]pyridin-6-yl)-2-(1H-pyrazol-4-yl)oxazole-4-carboxamide hydrochloride (145 mg, 0.306 mmol) was substituted with (S)-2-methyloxirane (35 mg, 0.613 mmol) using sodium carbonate (162 mg, 1.53 mmol) in DMF (2 mL) at 100° C. for 14 h to obtain the crude product. The resultant crude was purified by prep HPLC to obtain the title compound (50 mg, 21.2%).

¹HNMR (CDCl₃, 400 MHz): δ 9.18 (s, 1H), 8.70 (s, 1H), 8.25 (s, 1H), 8.05-8.03 (d, 2H), 4.28-4.25 (d, 3H), 3.83-3.81 (m, 4H), 3.70-3.69 (m, 4H), 2.22-2.15 (m, 2H), 1.28-1.27 (m, 4H) 1.11-1.09 (d, 2H). LCMS: 98.69%, m/z=496.2 (M+1)⁺. HPLC: 97.79%.

Example 76

N-(5-(3-hydroxypyrrolidin-1-yl)-2-morpholinothiazolo[4,5-b]pyridin-6-yl)-2-(6-methoxypyridin-3-yl)oxazole-4-carboxamide

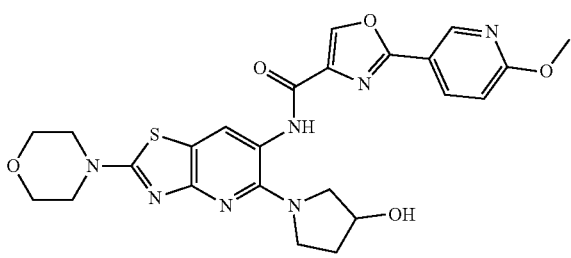

Step 1: Preparation of 1-(2-morpholino-6-nitrothiazolo[4,5-b]pyridin-5-yl)pyrrolidin-3-ol Using the same reaction conditions as described in step 1 of example 38, 4-(5-chloro-6-nitrothiazolo[4,5-b]pyridin-2-yl)morpholine (product of step 4 of example 20) (125 mg, 0.4166 mmol) was substituted with pyrrolidin-3-ol hydrochloride (54 mg, 0.437 mmol) using potassium carbonate (230 mg, 1.666 mmol) and DMF (5 mL) to afford the title product (102 mg, 70%).

LCMS: m/z=351.8 (M+1)⁺.

Step 2: Preparation of 4-(5-(3-((tert-butyldimethylsilyl)oxy)pyrrolidin-1-yl)-6-nitrothiazolo[4,5-b]pyridin-2-yl)morpholine Using the same reaction conditions as described in step 2 of example 41, 1-(2-morpholino-6-nitrothiazolo[4,5-b]pyridin-5-yl)pyrrolidin-3-ol (100 mg, 0.2857 mmol) was protected using TBDMS chloride (52 mg, 0.3428 mmol) and imidazole (43 mg, 0.712 mmol) in DMF (5 mL) at RT for 14 h to get the crude product. The resultant crude was purified by 60-120 silica gel column chromatography using 40% ethyl acetate in hexane as eluent to obtain the title compound (111 mg, 84%). LCMS: m/z=465.7 (M+1)⁺.

Step 3: Preparation of 5-(3-((tert-butyldimethylsilyl)oxy)pyrrolidin-1-yl)-2-morpholinothiazolo[4,5-b]pyridin-6-amine Using the same reaction conditions as described in step 2 of example 38, 4-(5-(3-((tert-butyldimethylsilyl)oxy)pyrrolidin-1-yl)-6-nitrothiazolo[4,5-b]pyridin-2-yl)morpholine (110 mg, 0.2365 mmol) was reduced with zinc dust (123 mg, 1.8923 mmol) and ammonium chloride (200 mg, 3.7816 mmol) in THF/methanol/H₂O (10 mL/2 mL/1 mL) to get the title compound (101 mg, 99%). LCMS: m/z=436.2 (M+1)⁺.

Step 4: Preparation of N-(5-(3-((tert-butyldimethylsilyl)oxy)pyrrolidin-1-yl)-2-morpholinothiazolo[4,5-b]pyridin-6-yl)-2-(6-methoxypyridin-3-yl)oxazole-4-carboxamide Using the same reaction conditions as described in step 6 of example 1, 5-(3-((tert-butyldimethylsilyl)oxy)pyrrolidin-1-yl)-2-morpholinothiazolo[4,5-b]pyridin-6-amine (60 mg, 0.2727 mmol), was coupled with 2-(6-methoxypyridin-3-yl)oxazole-4-carboxylic acid (intermediate 7) (100 mg, 0.2298 mmol) using EDCI·HCl (80 mg, 0.4108 mmol), HOBt (39 mg, 0.2865 mmol), DIPEA (142 mg, 1.095 mmol) in DMF (5 mL) to get the title compound (103 mg, 70%). LCMS: m/z=637.6 (M+1)⁺.

Step 5: Preparation of N-(5-(3-hydroxypyrrolidin-1-yl)-2-morpholinothiazolo[4,5-b]pyridin-6-yl)-2-(6-methoxypyridin-3-yl)oxazole-4-carboxamide TBAF (0.3 mL) was added to the stirred solution of N-(5-(3-((tert-butyldimethylsilyl)oxy)pyrrolidin-1-yl)-2-morpholinothiazolo[4,5-b]pyridin-6-yl)-2-(6-methoxypyridin-3-yl)oxazole-4-carboxamide (100 mg, 0.1569 mmol) in THF (5 mL) and stirred at RT for 1 hr. The reaction mass was diluted with saturated ammonium chloride solution and the solid was filtered and suck dried to get the crude product. The resultant crude was purified by 60-120 silica gel column chromatography using 2% methanol in DCM as eluent to obtain the title compound (35 mg, 43%).

¹HNMR (CDCl₃, 400 MHz): δ 9.17 (s, 1H), 8.88 (s, 1H), 8.69 (s, 1H), 8.33 (s, 1H), 8.22-8.20 (d, 1H), 6.88-6.86 (d, 1H), 4.57 (s, 1H), 4.02 (s, 3H), 3.84-3.53 (m, 9H) 2.50-2.49 (d, 1H), 2.31-2.21 (m, 2H), 2.09-2.01 (m, 2H). LCMS: 100%, m/z=524.3 (M+1)⁺. HPLC: 97.99%.

Example 77

(S)—N-(5-(3-hydroxypyrrolidin-1-yl)-2-morpholinothiazolo[4,5-b]pyridin-6-yl)-2-(6-methoxypyridin-3-yl)oxazole-4-carboxamide

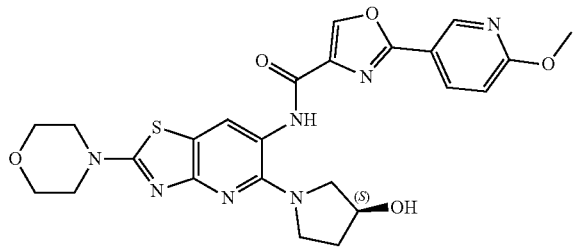

Step 1: Preparation of (S)-4-(5-(3-((tert-butyldimethylsilyl)oxy)pyrrolidin-1-yl)-6-nitrothiazolo[4,5-b]pyridin-2-yl)morpholine Using the same reaction conditions as described in step 2 of example 41, (S)-1-(2-morpholino-6-nitrothiazolo[4,5-b]pyridin-5-yl)pyrrolidin-3-ol (product of step 1 of example 72) (100 mg, 0.2857 mmol) was protected using TBDMS chloride (52 mg, 0.3428 mmol) and imidazole (43 mg, 0.712 mmol) in DMF (5 mL) at RT for 14 h to get the crude product. The resultant crude was purified by 60-120 silica gel column chromatography using 40% ethyl acetate in hexane as eluent to obtain the title compound (113 mg, 85%). LCMS: m/z=465.7 (M+1)$^+$.

Step 2: Preparation of (S)-5-(3-((tert-butyldimethylsilyl)oxy)pyrrolidin-1-yl)-2-morpholinothiazolo[4,5-b]pyridin-6-amine Using the same reaction conditions as described in step 2 of example 38, (S)-4-(5-(3-((tert-butyldimethylsilyl)oxy)pyrrolidin-1-yl)-6-nitrothiazolo[4,5-b]pyridin-2-yl)morpholine (110 mg, 0.2365 mmol) was reduced with zinc dust (123 mg, 1.8923 mmol) and ammonium chloride (200 mg, 3.7816 mmol) in THF/methanol/H$_2$O (20 mL/2 mL/1 mL) to get the title compound (100 mg, 98%). LCMS: m/z=436.3 (M+1)$^+$.

Step 3: Preparation of (S)—N-(5-(3-((tert-butyldimethylsilyl)oxy)pyrrolidin-1-yl)-2-morpholinothiazolo[4,5-b]pyridin-6-yl)-2-(6-methoxypyridin-3-yl)oxazole-4-carboxamide Using the same reaction conditions as described in step 6 of example 1, (S)-5-(3-((tert-butyldimethylsilyl)oxy)pyrrolidin-1-yl)-2-morpholinothiazolo[4,5-b]pyridin-6-amine (60 mg, 0.2727 mmol), was coupled with 2-(6-methoxypyridin-3-yl)oxazole-4-carboxylic acid (intermediate 7) (100 mg, 0.2298 mmol) using EDCI·HCl (80 mg, 0.4108 mmol), HOBt (39 mg, 0.2865 mmol), DIPEA (142 mg, 1.095 mmol) in DMF (5 mL) to get the title compound (102 mg, 70%). LCMS: m/z=637.6 (M+1)$^+$.

Step 4: Preparation of (S)—N-(5-(3-hydroxypyrrolidin-1-yl)-2-morpholinothiazolo[4,5-b]pyridin-6-yl)-2-(6-methoxypyridin-3-yl)oxazole-4-carboxamide TBAF (0.3 mL) was added to the stirred solution of (S)—N-(5-(3-((tert-butyldimethylsilyl)oxy)pyrrolidin-1-yl)-2-morpholinothiazolo[4,5-b]pyridin-6-yl)-2-(6-methoxypyridin-3-yl)oxazole-4-carboxamide (100 mg, 0.1569 mmol) in THF (5 mL) and stirred at RT for 1 hr. The reaction mass was diluted with saturated ammonium chloride solution and the solid was filtered and suck dried to get the crude product. The resultant crude was purified by 60-120 silica gel column chromatography using 2% methanol in DCM as eluent to obtain the title compound (15 mg, 18%).

$^1$HNMR (CDCl$_3$, 400 MHz): δ 9.17 (s, 1H), 8.88 (s, 1H), 8.69 (s, 1H), 8.33 (s, 1H), 8.22-8.20 (d, 1H), 6.88-6.86 (d, 1H), 4.57 (s, 1H), 4.02 (s, 3H), 3.83-3.81 (m, 4H), 3.76-3.69 (m, 4H), 3.68-3.51 (m, 4H), 2.47-2.46 (d, 1H), 2.27-2.21 (m, 1H), 2.04-2.02 (m, 1H). LCMS: 100%, m/z=524.1 (M+1)$^+$. HPLC: 99.55%.

Example 78

(R)—N-(5-(3-hydroxypyrrolidin-1-yl)-2-morpholinothiazolo[4,5-b]pyridin-6-yl)-2-(6-methoxypyridin-3-yl)oxazole-4-carboxamide

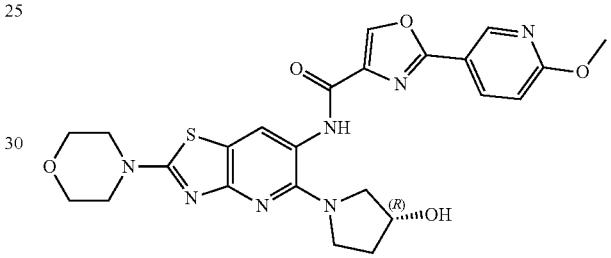

Step 1: Preparation of (R)-1-(2-morpholino-6-nitrothiazolo[4,5-b]pyridin-5-yl)pyrrolidin-3-ol Using the same reaction conditions as described in step 1 of example 38, 4-(5-chloro-6-nitrothiazolo[4,5-b]pyridin-2-yl)morpholine (product of step 4 of example 20) (125 mg, 0.4166 mmol) was substituted with (R)-pyrrolidin-3-ol (38 mg, 0.437 mmol) using potassium carbonate (230 mg, 1.666 mmol) and DMF (5 mL) to afford the title product (101 mg, 70%). LCMS: m/z=351.8 (M+1)$^+$.

Step 2: Preparation of (R)-4-(5-(3-((tert-butyldimethylsilyl)oxy)pyrrolidin-1-yl)-6-nitrothiazolo[4,5-b]pyridin-2-yl)morpholine Using the same reaction conditions as described in step 2 of example 41, (R)-1-(2-morpholino-6-nitrothiazolo[4,5-b]pyridin-5-yl)pyrrolidin-3-ol (100 mg, 0.2857 mmol) was protected using TBDMS chloride (52 mg, 0.3428 mmol) and imidazole (43 mg, 0.712 mmol) in DMF (5 mL) at RT for 14 h to get the crude product. The resultant crude was purified by 60-120 silica gel column chromatography using 40% ethyl acetate in hexane as eluent to obtain the title compound (115 mg, 85.5%). LCMS: m/z=465.7 (M+1)$^+$.

Step 3: Preparation of (R)-5-(3-((tert-butyldimethylsilyl)oxy)pyrrolidin-1-yl)-2-morpholinothiazolo[4,5-b]pyridin-6-amine Using the same reaction conditions as described in step 2 of example 38, (R)-4-(5-(3-((tert-butyldimethylsilyl)oxy)

pyrrolidin-1-yl)-6-nitrothiazolo[4,5-b]pyridin-2-yl)morpholine (110 mg, 0.2365 mmol) was reduced with zinc dust (123 mg, 1.8923 mmol) and ammonium chloride (200 mg, 3.7816 mmol) in THF/methanol/H₂O (20 mL/2 mL/1 mL) to get the title compound (100 mg, 98%). LCMS: m/z=436.5 (M+1)⁺.

Step 4: Preparation of (R)—N-(5-(3-((tert-butyldimethylsilyl)oxy)pyrrolidin-1-yl)-2-morpholinothiazolo[4,5-b]pyridin-6-yl)-2-(6-methoxypyridin-3-yl)oxazole-4-carboxamide Using the same reaction conditions as described in step 6 of example 1, (R)-5-(3-((tert-butyldimethylsilyl)oxy)pyrrolidin-1-yl)-2-morpholinothiazolo[4,5-b]pyridin-6-amine (60 mg, 0.2727 mmol), was coupled with 2-(6-methoxypyridin-3-yl)oxazole-4-carboxylic acid (intermediate 7) (100 mg, 0.2298 mmol) using EDCI·HCl (79 mg, 0.4108 mmol), HOBt (39 mg, 0.2865 mmol), DIPEA (141 mg, 1.095 mmol) in DMF (5 mL) to get the title compound (110 mg, 75%). LCMS: m/z=637.6 (M+1)⁺.

Step 5: Preparation of (R)—N-(5-(3-hydroxypyrrolidin-1-yl)-2-morpholinothiazolo[4,5-b]pyridin-6-yl)-2-(6-methoxypyridin-3-yl)oxazole-4-carboxamide TBAF (0.3 mL) was added to the stirred solution of (R)—N-(5-(3-((tert-butyldimethylsilyl)oxy)pyrrolidin-1-yl)-2-morpholinothiazolo[4,5-b]pyridin-6-yl)-2-(6-methoxypyridin-3-yl)oxazole-4-carboxamide (100 mg, 0.1569 mmol) in THF (5 mL) and stirred at RT for 1 hr. The reaction mass was diluted with saturated ammonium chloride solution and the solid was filtered and suck dried to get the crude product. The resultant crude was purified by 60-120 silica gel column chromatography using 2% methanol in DCM as eluent to obtain the title compound (45 mg, 55%).
¹HNMR (CDCl₃, 400 MHz): δ 9.17 (s, 1H), 8.88 (s, 1H), 8.69 (s, 1H), 8.33 (s, 1H), 8.22-8.20 (dd, 1H), 6.88-6.86 (d, 1H), 4.57 (s, 1H), 4.02 (s, 3H), 3.84-3.81 (m, 4H), 3.76-3.63 (m, 4H), 3.61-3.48 (m, 4H), 2.50-2.49 (d, 1H), 2.44-2.22 (m, 1H), 2.04-2.03 (m, 1H). LCMS: 100%, m/z=524.1 (M+1)⁺. HPLC: 98.62%.

Example 79

(S)—N-(5-(azetidin-1-yl)-2-morpholinothiazolo[4,5-b]pyridin-6-yl)-6-(3-hydroxypyrrolidin-1-yl)picolinamide

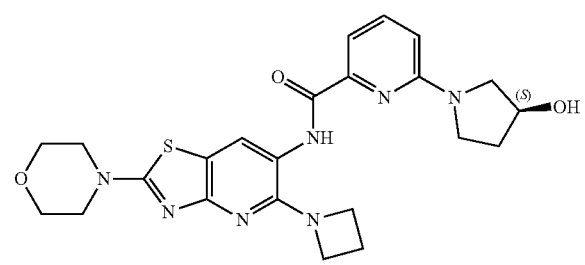

Step 1: Preparation of 4-(5-(azetidin-1-yl)-6-nitrothiazolo[4,5-b]pyridin-2-yl)morpholine Using the same reaction conditions as described in step 1 of example 38, 4-(5-chloro-6-nitrothiazolo[4,5-b]pyridin-2-yl)morpholine (product of step 4 of example 20) (200 mg, 0.666 mmol) was substituted with azetidine (76 mg, 1.333 mmol) using sodium carbonate (283 mg, 2.664 mmol) and DMF (5 mL) to afford the title product (150 mg, 71.4%). LCMS: m/z=322.1 (M+1)⁺.

Step 2: Preparation of 5-(azetidin-1-yl)-2-morpholinothiazolo[4,5-b]pyridin-6-amine Using the same reaction conditions as described in step 2 of example 38, 4-(5-(azetidin-1-yl)-6-nitrothiazolo[4,5-b]pyridin-2-yl)morpholine (150 mg, 0.465 mmol) was reduced with zinc dust (243 mg, 3.726 mmol) and ammonium chloride (402 mg, 7.440 mmol) in THF/methanol/H₂O (10 mL/2 mL/1 mL) to get the title compound (150 mg, crude). LCMS: m/z=292.1 (M+1)⁺.

Step 3: Preparation of N-(5-(azetidin-1-yl)-2-morpholinothiazolo[4,5-b]pyridin-6-yl)-6-bromopicolinamide Using the same reaction conditions as described in example 45, 5-(azetidin-1-yl)-2-morpholinothiazolo[4,5-b]pyridin-6-amine (80 mg, 0.2373 mmol), was coupled with 6-bromopicolinic acid (83 mg, 0.410 mmol) using EDCI·HCl (80 mg, 0.41 mmol), HOBt (55 mg, 0.410 mmol), DIPEA (141 mg, 1.092 mmol) in DMF (5 mL) to get the title compound (130 mg, 100%). LCMS: m/z=477.1 (M+2)⁺.

Step 4: Preparation of (S)—N-(5-(azetidin-1-yl)-2-morpholinothiazolo[4,5-b]pyridin-6-yl)-6-(3-hydroxypyrrolidin-1-yl)picolinamide Using the same reaction conditions as described in step 2 of example 43, N-(5-(azetidin-1-yl)-2-morpholinothiazolo[4,5-b]pyridin-6-yl)-6-bromopicolinamide (100 mg, 0.210 mmol) was substituted with (S)-pyrrolidin-3-ol hydrochloride (40 mg, 0.315 mmol) using sodium carbonate (90 mg, 0.840 mmol) in DMF (2 mL) at 100° C. for 14 h to obtain the title compound (35 mg, 35%).
¹HNMR (CDCl₃, 300 MHz): δ 9.79 (s, 1H), 8.59 (s, 1H), 7.66-7.60 (m, 1H), 7.55-7.53 (d, 1H), 6.59-6.56 (d, 1H), 4.71 (s, 1H), 4.26-4.12 (m, 4H), 3.83-3.76 (m, 4H), 3.74-3.65 (m, 8H), 2.32-2.19 (m, 4H). LCMS: 97.98%, m/z=482.2 (M+1)⁺. HPLC: 97.38%.

Example 80

N-(5-(3-hydroxyazetidin-1-yl)-2-morpholinothiazolo[4,5-b]pyridin-6-yl)-2-(2-methylpyridin-4-yl)oxazole-4-carboxamide

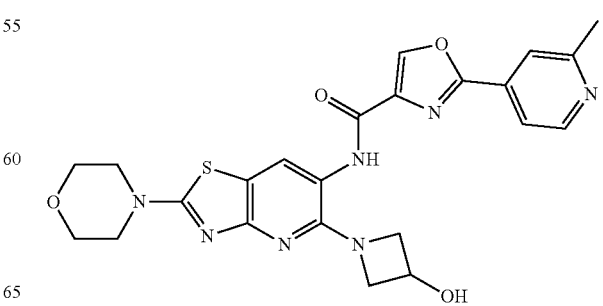

Step 1: Preparation of 1-(2-morpholino-6-nitrothiazolo[4,5-b]pyridin-5-yl)azetidin-3-ol Using the same reaction conditions as described in step 1 of example 38, 4-(5-chloro-6-nitrothiazolo[4,5-b]pyridin-2-yl)morpholine (product of step 4 of example 20) (200 mg, 0.6666 mmol) was substituted with azetidin-3-ol hydrochloride (109 mg, 1.0 mmol) using sodium carbonate (212 mg, 3.0 mmol) and DMF (2 mL) at 80° C. for 1 h to afford the title product (160 mg, 71.11%). LCMS: m/z=338.1 (M+1)$^+$.

Step 2: Preparation of 4-(5-(3-((tert-butyldimethylsilyl)oxy)azetidin-1-yl)-6-nitrothiazolo[4,5-b]pyridin-2-yl)morpholine Using the same reaction conditions as described in step 2 of example 41, t-(2-morpholino-6-nitrothiazolo[4,5-b]pyridin-5-yl)azetidin-3-ol (160 mg, 0.4742 mmol) was protected using TBDMS chloride (86 mg, 0.5691 mmol) and imidazole (113 mg, 1.658 mmol) and DAMP (64 mg, 0.5217 mmol) in DMF (5 mL) at RT for 1 h to get the crude product. The resultant crude was purified by 60-120 silica gel column chromatography using 1% methanol in DCM as eluent to obtain the title compound (210 mg, 98.59%). LCMS: m/z=452.2 (M+1)$^+$.

Step 3: Preparation of 5-(3-((tert-butyldimethylsilyl)oxy)azetidin-1-yl)-2-morpholinothiazolo[4,5-b]pyridin-6-amine Using the same reaction conditions as described in step 2 of example 38, 4-(5-(3-((tert-butyldimethylsilyl)oxy)azetidin-1-yl)-6-nitrothiazolo[4,5-b]pyridin-2-yl)morpholine (210 mg, 0.4656 mmol) was reduced with zinc dust (244 mg, 3.725 mmol) and ammonium chloride (399 mg, 7.4501 mmol) in THF/methanol/H$_2$O (10 mL/2 mL/1 mL) to get the title compound (180 mg, 91.83%). LCMS: m/z=422.2 (M+1)$^+$.

Step 4: Preparation of N-(5-(3-((tert-butyldimethylsilyl)oxy)azetidin-1-yl)-2-morpholinothiazolo[4,5-b]pyridin-6-yl)-2-(2-methylpyridin-4-yl)oxazole-4-carboxamide Using the same reaction conditions as described in step 6 of example 1, 5-(3-((tert-butyldimethylsilyl)oxy)azetidin-1-yl)-2-morpholinothiazolo[4,5-b]pyridin-6-amine (180 mg, 0.4275 mmol), was coupled with 2-(2-methylpyridin-4-yl)oxazole-4-carboxylic acid (131 mg, 0.6413 mmol) using EDCI·HCl (123 mg, 0.6413 mmol), HOBt (87 mg, 0.6413 mmol), DIPEA (0.297 mL, 1.7102 mmol) in DMF (2 mL) to get the title compound (150 mg, 57.91%).

Step 5: Preparation of N-(5-(3-hydroxyazetidin-1-yl)-2-morpholinothiazolo[4,5-b]pyridin-6-yl)-2-(2-methylpyridin-4-yl)oxazole-4-carboxamide TBAF (1M in THF) (0.5 mL) was added to the stirred solution of N-(5-(3-((tert-butyldimethylsilyl)oxy)azetidin-1-yl)-2-morpholinothiazolo[4,5-b]pyridin-6-yl)-2-(2-methylpyridin-4-yl)oxazole-4-carboxamide (150 mg, 0.2467 mmol) in THF (20 mL) and stirred at RT for 1 hr. The reaction mass was diluted with saturated ammonium chloride solution and the solid was filtered and dried to get the crude product. The resultant crude was purified by 60-120 silica gel column chromatography using 2% methanol in DCM as eluent to obtain the title compound (35 mg, 28.92%).

$^1$HNMR (DMSO-d$_6$, 300 MHz): δ 9.71 (s, 1H), 8.96 (s, 1H), 8.68-8.66 (d, 1H), 7.90 (s, 1H), 7.85 (s, 1H), 7.77-7.75 (d, 1H), 5.51-5.49 (d, 1H), 4.48-4.42 (m, 1H), 4.19-4.14 (t, 2H), 3.76-3.70 (m, 6H), 3.56-3.54 (m, 4H), 2.57 (s, 3H). LCMS: 100%, m/z=494.1 (M+1)$^+$. HPLC: 98.83%.

Example 81

(S)—N-(5-(3-hydroxypyrrolidin-1-yl)-2-morpholinothiazolo[4,5-b]pyridin-6-yl)-5-(2-methylpyridin-4-yl)thiophene-2-carboxamide

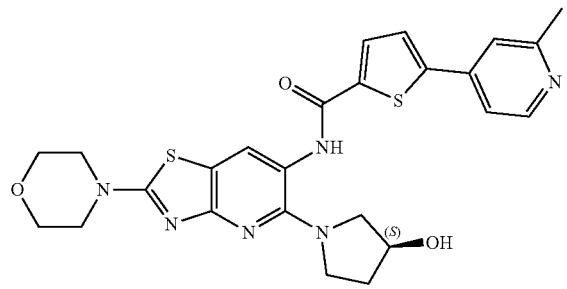

Step 1: Preparation of (S)—N-(5-(3-((tert-butyldimethylsilyl)oxy)pyrrolidin-1-yl)-2-morpholinothiazolo[4,5-b]pyridin-6-yl)-5-(2-methylpyridin-4-yl)thiophene-2-carboxamide Using the same reaction conditions as described in step 6 of example 1, (S)-5-(3-((tert-butyldimethylsilyl)oxy)pyrrolidin-1-yl)-2-morpholinothiazolo[4,5-b]pyridin-6-amine (product of step 2 of compound 78) (90 mg, 0.206 mmol), was coupled with 5-(2-methylpyridin-4-yl)thiophene-2-carboxylic acid (intermediate 17) (54 mg, 0.248 mmol) using EDCI·HCl (59 mg, 0.309 mmol), HOBt (42 mg, 0.309 mmol), DIPEA (106 mg, 0.824 mmol) in DMF (5 mL) to get the title compound (120 mg, crude). LCMS: m/z=637.2 (M+1)$^+$.

Step 2: Preparation of (S)—N-(5-(3-hydroxypyrrolidin-1-yl)-2-morpholinothiazolo[4,5-b]pyridin-6-yl)-5-(2-methylpyridin-4-yl)thiophene-2-carboxamide Using the same reaction conditions as described in step 8 of example 1 (S)—N-(5-(3-((tert-butyldimethylsilyl)oxy)pyrrolidin-1-yl)-2-morpholinothiazolo[4,5-b]pyridin-6-yl)-5-(2-methylpyridin-4-yl)thiophene-2-carboxamide (120 mg, 0.188 mmol) was deprotected using methanolic HCl/methanol (5/1 mL) to get the crude product. This was then purified by prep HPLC to get the title compound (45 mg, 45.4%).

$^1$HNMR (CDCl$_3$, 400 MHz): δ 8.66 (s, 1H), 8.54-8.53 (d, 1H), 8.38 (s, 1H), 7.70-7.69 (d, 1H), 7.489-7.480 (d, 1H), 7.38 (s, 1H), 7.34-7.32 (s, 1H), 4.59 (s, 1H), 3.83-3.81 (m, 4H), 3.69-3.67 (m, 4H), 3.64-3.61 (m, 1H), 3.53-3.50 (m, 3H), 2.62 (s, 3H), 229-2.19 (m, 1H), 2.18-4.90 (m, 1H). LCMS: 99.27%, m/z=523.1 (M+1)$^+$. HPLC: 96.58%.

Example 82

(S)—N-(5-(3-hydroxypyrrolidin-1-yl)-2-morpholinothiazolo[4,5-b]pyridin-6-yl)-5-(2-methylpyridin-4-yl)furan-2-carboxamide

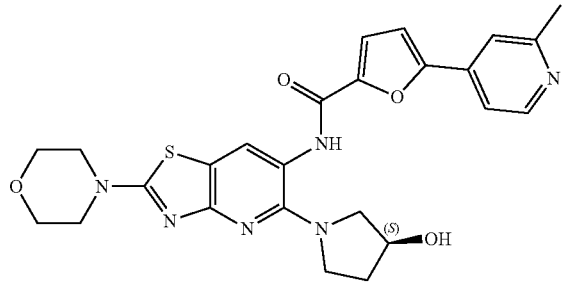

Step 1: Preparation of (S)—N-(5-(3-((tert-butyldimethylsilyl)oxy)pyrrolidin-1-yl)-2-morpholinothiazolo[4,5-b]pyridin-6-yl)-5-(2-methylpyridin-4-yl)furan-2-carboxamide Using the same reaction conditions as described in step 6 of example 1, (S)-5-(3-((tert-butyldimethylsilyl)oxy)pyrrolidin-1-yl)-2-morpholinothiazolo[4,5-b]pyridin-6-amine (product of step 2 of compound 78) (90 mg, 0.206 mmol), was coupled with 5-(2-methylpyridin-4-yl)furan-2-carboxylic acid (intermediate 18) (50 mg, 0.248 mmol) using EDCI·HCl (59 mg, 0.309 mmol), HOBt (42 mg, 0.309 mmol), DIPEA (106 mg, 0.824 mmol) in DMF (5 mL) to get the title compound (130 mg, crude).

Step 2: Preparation of (S)—N-(5-(3-hydroxypyrrolidin-1-yl)-2-morpholinothiazolo[4,5-b]pyridin-6-yl)-5-(2-methylpyridin-4-yl)furan-2-carboxamide Using the same reaction conditions as described in step 8 of example 1 (S)—N-(5-(3-((tert-butyldimethylsilyl)oxy)pyrrolidin-1-yl)-2-morpholinothiazolo[4,5-b]pyridin-6-yl)-5-(2-methylpyridin-4-yl)furan-2-carboxamide (130 mg, 0.209 mmol) was deprotected using methanolic HCl/methanol (5/1 mL) to get the crude product. This was then purified by prep HPLC to get the title compound (50 mg, 47.16%).

$^1$HNMR (CDCl$_3$, 300 MHz): δ 8.72 (s, 2H), 8.57-8.55 (d, 1H), 7.51 (s, 1H), 7.44-7.42 (d, 1H), 7.36-7.34 (d, 1H), 7.00-6.99 (d, 1H), 4.62 (s, 1H), 3.84-3.75 (m, 4H), 3.75-3.65 (m, 6H), 3.55-3.43 (m, 2H), 2.63 (s, 3H), 2.42-2.39 (m, 1H), 2.26-2.21 (m, 1H), 2.06-1.99 (m, 1H). LCMS: 97.85%, m/z=507.2 (M+1)$^+$. HPLC: 99.02%.

Example 83

(S)—N-(5-(3-hydroxypiperidin-1-yl)-2-morpholinothiazolo[4,5-b]pyridin-6-yl)-2-(2-methylpyridin-4-yl)oxazole-4-carboxamide

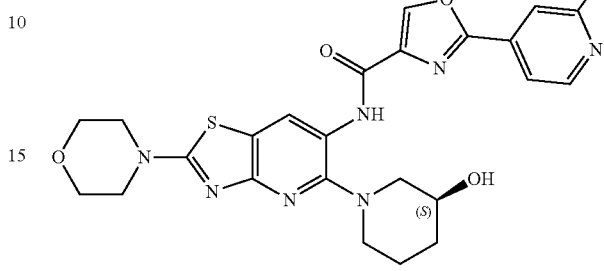

Step 1: Preparation of (S)-4-(5-(3-((tert-butyldimethylsilyl)oxy)piperidin-1-yl)-6-nitrothiazolo[4,5-b]pyridin-2-yl)morpholine Using the same reaction conditions as described in step 2 of example 41, (S)-1-(2-morpholino-6-nitrothiazolo[4,5-b]pyridin-5-yl)piperidin-3-ol (product of step 1 of example 59) (210 mg, 0.575 mmol) was protected using TBDMS chloride (108 mg, 0.719 mmol) and imidazole (98 mg, 1.438 mmol) and DMAP (88 mg, 0.719 mmol) in DMF (5 mL) at RT for 14 h to get the crude product. The resultant crude was purified by 60-120 silica gel column chromatography using 1% methanol in DCM as eluent to obtain the title compound (177 mg, 64%). LCMS: m/z=480.3 (M+1)$^+$.

Step 2: Preparation of (S)-5-(3-((tert-butyldimethylsilyl)oxy)piperidin-1-yl)-2-morpholinothiazolo[4,5-b]pyridin-6-amine Using the same reaction conditions as described in step 2 of example 38, (S)-4-(5-(3-((tert-butyldimethylsilyl)oxy)piperidin-1-yl)-6-nitrothiazolo[4,5-b]pyridin-2-yl)morpholine (175 mg, 0.3645 mmol) was reduced with zinc dust (190 mg, 2.916 mmol) and ammonium chloride (312 mg, 5.833 mmol) in THF/methanol/water (20/10/5 mL) to get the title compound (162 mg, 98.7%). LCMS: m/z=450.2 (M+1)$^+$.

Step 3: Preparation of (S)—N-(5-(3-((tert-butyldimethylsilyl)oxy)piperidin-1-yl)-2-morpholinothiazolo[4,5-b]pyridin-6-yl)-2-(2-methylpyridin-4-yl)oxazole-4-carboxamide Using the same reaction conditions as described in step 6 of example 1, (S)-5-(3-((tert-butyldimethylsilyl)oxy)piperidin-1-yl)-2-morpholinothiazolo[4,5-b]pyridin-6-amine (160 mg, 0.355 mmol), was coupled with 2-(2-methylpyridin-4-yl)oxazole-4-carboxylic acid (91 mg, 0.444 mmol) using HATU (202 mg, 0.532 mmol) and DIPEA (183 mg, 1.42 mmol) in DMF (5 mL) to get the title compound (198 mg, 88%). LCMS: m/z=634.3 (M−1)$^+$.

Step 4: Preparation of (S)—N-(5-(3-hydroxypiperidin-1-yl)-2-morpholinothiazolo[4,5-b]pyridin-6-yl)-2-(2-methylpyridin-4-yl)oxazole-4-carboxamide Using the same reaction conditions as described in step 8 of example 1 (S)—N-(5-(3-((tert-butyldimethylsilyl)oxy)piperidin-1-yl)-2-morpholinothiazolo[4,5-b]pyridin-6-yl)-2-(2-methylpyridin-4-yl)oxazole-4-carboxamide (197 mg, 0.3102 mmol) was deprotected using methanolic HCl/methanol (5/5 mL) to get the title compound (138 mg, 85.7%).

¹HNMR (CDCl₃, 300 MHz): δ 9.78 (s, 1H), 9.05 (s, 1H), 8.71-8.69 (d, 1H), 8.41 (s, 1H), 7.86 (s, 1H), 7.77-7.75 (d, 1H), 4.19-4.12 (m, 1H), 3.84-3.81 (m, 4H), 3.71-3.67 (m, 4H), 3.33-3.32 (m, 1H), 3.24-3.13 (m, 4H), 2.68 (s, 3H), 2.21-2.00 (m, 1H), 1.86-1.83 (m, 3H). LCMS: 98.40%, m/z=522.2 (M+1)⁺. HPLC: 98.37%.

Example 84

N-(5-(4-hydroxypiperidin-1-yl)-2-morpholinothiazolo[4,5-b]pyridin-6-yl)-2-(2-methylpyridin-4-yl)oxazole-4-carboxamide

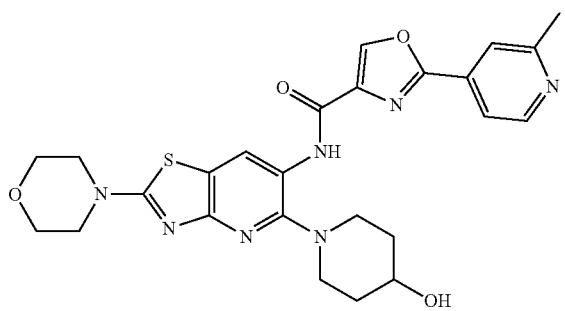 [SMILES: Cc1cc(-c2nc(C(=O)Nc3cc4sc(N5CCOCC5)nc4nc3N3CCC(O)CC3)co2)ccn1]

Step 1: Preparation of 1-(2-morpholino-6-nitrothiazolo[4,5-b]pyridin-5-yl)piperidin-4-ol Using the same reaction conditions as described in step 1 of example 38, 4-(5-chloro-6-nitrothiazolo[4,5-b]pyridin-2-yl)morpholine (product of step 4 of example 20) (200 mg, 0.6666 mmol) was substituted with piperidine-4-ol (68 mg, 0.666 mmol) using potassium carbonate (311 mg, 2.66 mmol) and DMF (5 mL) at RT for 14 h to afford the title product (211 mg, 87%).
LCMS: m/z=366.1 (M+1)⁺.

Step 2: Preparation of 4-(5-(4-((tert-butyldimethylsilyl)oxy)piperidin-1-yl)-6-nitrothiazolo[4,5-b]pyridin-2-yl)morpholine Using the same reaction conditions as described in step 2 of example 41, 1-(2-morpholino-6-nitrothiazolo[4,5-b]pyridin-5-yl)piperidin-4-ol (210 mg, 0.575 mmol) was protected using TBDMS chloride (108 mg, 0.7191 mmol) and imidazole (98 mg, 1.438 mmol) and DMAP (88 mg, 0.719 mmol) in DMF (5 mL) at RT for 1 h to get the crude product. The resultant crude was purified by 60-120 silica gel column chromatography using 1% methanol in DCM as eluent to obtain the title compound (216 mg, 78.2%). LCMS: m/z=480.2 (M+1)⁺.

Step 3: Preparation of 5-(4-((tert-butyldimethylsilyl)oxy)piperidin-1-yl)-2-morpholinothiazolo[4,5-b]pyridin-6-amine Using the same reaction conditions as described in step 2 of example 38, 4-(5-(4-((tert-butyldimethylsilyl)oxy)piperidin-1-yl)-6-nitrothiazolo[4,5-b]pyridin-2-yl)morpholine (215 mg, 0.448 mmol) was reduced with zinc dust (233 mg, 3.583 mmol) and ammonium chloride (387 mg, 7.16 mmol) in THF/methanol/H₂O (20 mL/5 mL/2 mL) to get the title compound (161 mg, 80%).
LCMS: m/z=450.2 (M+1)⁺.

Step 4: Preparation of N-(5-(4-((tert-butyldimethylsilyl)oxy)piperidin-1-yl)-2-morpholinothiazolo[4,5-b]pyridin-6-yl)-2-(2-methylpyridin-4-yl)oxazole-4-carboxamide Using the same reaction conditions as described in step 6 of example 1, 5-(4-((tert-butyldimethylsilyl)oxy)piperidin-1-yl)-2-morpholinothiazolo[4,5-b]pyridin-6-amine (160 mg, 0.355 mmol), was coupled with 2-(2-methylpyridin-4-yl)oxazole-4-carboxylic acid (91 mg, 0.444 mmol) using HATU (202 mg, 0.532 mmol) and DIPEA (0.183 mg, 1.42 mmol) in DMF (5 mL) to get the title compound (192 mg, 68%). LCMS: m/z=634.3 (M−1)⁺.

Step 5: Preparation of N-(5-(4-hydroxypiperidin-1-yl)-2-morpholinothiazolo[4,5-b]pyridin-6-yl)-2-(2-methylpyridin-4-yl)oxazole-4-carboxamide Using the same reaction conditions as described in step 8 of example 1 N-(5-(4-((tert-butyldimethylsilyl)oxy)piperidin-1-yl)-2-morpholinothiazolo[4,5-b]pyridin-6-yl)-2-(2-methylpyridin-4-yl)oxazole-4-carboxamide (191 mg, 0.3 mmol) was deprotected using methanolic HCl/methanol (5/5 mL) to get the title compound (130 mg, 83.3%).

¹HNMR (CDCl₃, 300 MHz): δ 9.87 (s, 1H), 9.05 (s, 1H), 8.70-8.68 (d, 1H), 8.40 (s, 1H), 7.85 (s, 1H), 7.75-7.73 (d, 1H), 3.99-3.93 (m, 1H), 3.84-3.81 (m, 4H), 3.70-3.67 (m, 4H), 3.35-3.30 (m, 2H), 3.11-3.08 (m, 2H), 2.68 (s, 3H), 2.22-2.15 (m, 2H), 2.13-1.97 (m, 2H), 1.69-1.68 (m, 1H). LCMS: 94.22%, m/z=522.2 (M+1)⁺. HPLC: 97.51%.

Example 85

(R)—N-(5-(3-hydroxypyrrolidin-1-yl)-2-morpholinothiazolo[4,5-b]pyridin-6-yl)-2-(2-methylpyridin-4-yl)oxazole-4-carboxamide

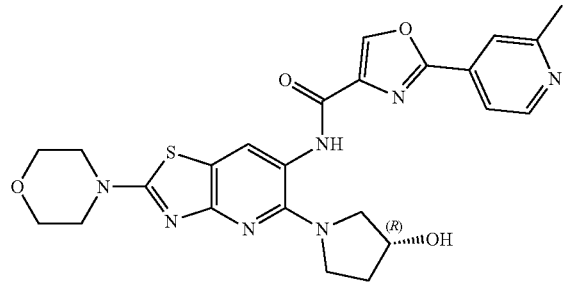

Step 1: Preparation of (R)—N-(5-(3-((tert-butyldimethylsilyl)oxy)pyrrolidin-1-yl)-2-morpholinothiazolo[4,5-b]pyridin-6-yl)-2-(2-methylpyridin-4-yl)oxazole-4-carboxamide Using the same reaction conditions as described in step 6 of example 1, (R)-5-(3-((tert-butyldimethylsilyl)oxy)pyrrolidin-1-yl)-2-morpholinothiazolo[4,5-b]pyridin-6-amine (product of step 3 of example 79) (150 mg, 0.34 mmol), was coupled with 2-(2-methylpyridin-4-yl)oxazole-4-carboxylic acid (85 mg, 0.413 mmol) using HATU (196 mg, 0.517 mmol) and DIPEA (177 mg, 1.37 mmol) in DMF (8 mL) to get the title compound (120 mg, 52.1%). LCMS: m/z=622.3 (M+1)$^+$.

Step 2: Preparation of (R)—N-(5-(3-hydroxypyrrolidin-1-yl)-2-morpholinothiazolo[4,5-b]pyridin-6-yl)-2-(2-methylpyridin-4-yl)oxazole-4-carboxamide Using the same reaction conditions as described in step 8 of example 1, (R)—N-(5-(3-((tert-butyldimethylsilyl)oxy) pyrrolidin-1-yl)-2-morpholinothiazolo[4,5-b]pyridin-6-yl)-2-(2-methylpyridin-4-yl)oxazole-4-carboxamide (120 mg, 0.1759 mmol) was deprotected using methanolic HCl/methanol (5/5 mL) to get the title compound (77 mg, 65%).
$^1$HNMR (DMSO-d$_6$, 400 MHz): δ 9.99 (s, 1H), 8.96 (s, 1H), 8.69-8.68 (d, 1H), 7.86 (s, 2H), 7.78-7.76 (d, 1H), 4.48 (s, 1H), 4.27 (s, 1H), 3.74-3.72 (m, 4H), 3.64-3.52 (m, 6H), 2.59 (s, 3H), 2.09 (s, 1H), 1.89-1.87 (m, 1H), 1.84-1.77 (m, 1H). LCMS: 97.25%, m/z=508.2 (M+1)$^+$.
HPLC: 95.18%.

Example 86

N-(5-(4-hydroxypiperidin-1-yl)-2-morpholinothiazolo[4,5-b]pyridin-6-yl)-5-(2-methylpyridin-4-yl)furan-2-carboxamide

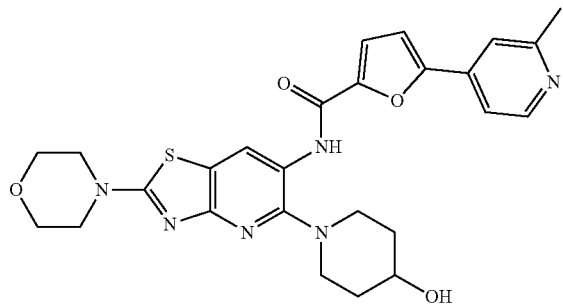

Step 1: Preparation of N-(5-(4-((tert-butyldimethylsilyl)oxy)piperidin-1-yl)-2-morpholinothiazolo[4,5-b]pyridin-6-yl)-5-(2-methylpyridin-4-yl)furan-2-carboxamide Using the same reaction conditions as described in step 6 of example 1, 5-(4-((tert-butyldimethylsilyl)oxy)piperidin-1-yl)-2-morpholinothiazolo[4,5-b]pyridin-6-amine (product of step 3 of example 85) (150 mg, 0.334 mmol), was coupled with 5-(2-methylpyridin-4-yl)furan-2-carboxylic acid (intermediate 18) (68 mg, 0.334 mmol) using HATU (190 mg, 0.501 mmol) and DIPEA (172 mg, 1.336 mmol) in DMF (5 mL) to get the title compound (165 mg, 77.8%). LCMS: m/z=633.3 (M−1)$^+$.

Step 2: Preparation of N-(5-(4-hydroxypiperidin-1-yl)-2-morpholinothiazolo[4,5-b]pyridin-6-yl)-5-(2-methylpyridin-4-yl)furan-2-carboxamide Using the same reaction conditions as described in step 8 of example 1 N-(5-(4-(((tert-butyldimethylsilyl)oxy)piperidin-1-yl)-2-morpholinothiazolo[4,5-b]pyridin-6-yl)-5-(2-methylpyridin-4-yl)furan-2-carboxamide (160 mg, 0.252 mmol) was deprotected using methanolic HCl/methanol (5/5 mL) to get the title compound (107 mg, 81.6%).
$^1$HNMR (DMSO-d$_6$, 300 MHz): δ 9.61 (s, 1H), 8.58 (s, 1H), 8.55-8.53 (d, 1H), 7.74 (s, 1H), 7.68-7.67 (d, 1H), 7.45-7.44 (d, 2H), 4.74 (s, 1H), 3.74-3.73 (m, 4H), 3.66-3.58 (m, 5H), 2.90-2.83 (m, 2H), 2.56 (s, 3H), 2.71-1.88 (m, 2H), 1.64-1.61 (m, 2H). LCMS: 99.09%, m/z=521.2 (M+1)$^+$.
HPLC: 95.12%.

Example 87

N-(5-(azetidin-1-yl)-2-(piperidin-1-yl)thiazolo[4,5-b]pyridin-6-yl)-2-(2-methylpyridin-4-yl)oxazole-4-carboxamide

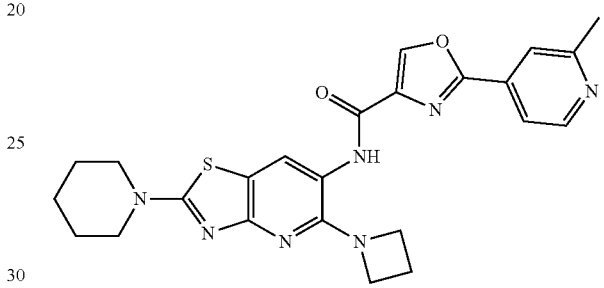

Step 1: Preparation of 5-(azetidin-1-yl)-6-nitro-2-(piperidin-1-yl)thiazolo[4,5-b]pyridine Using the same reaction conditions as described in step 1 of example 38, 5-chloro-6-nitro-2-(piperidin-1-yl)thiazolo[4,5-b]pyridine (product of step 2 of example 22) (250 mg, 0.8389 mmol) was substituted with azetidine hydrochloride (117 mg, 1.2583 mmol) using sodium carbonate (267 mg, 2.5167 mmol) and DMF (5 mL) at RT overnight to afford the title product (170 mg, 63.43%). LCMS: m/z=320.1 (M+1)$^+$.

Step 2: Preparation of 5-(azetidin-1-yl)-2-(piperidin-1-yl)thiazolo[4,5-b]pyridin-6-amine Using the same reaction conditions as described in step 2 of example 38, 5-(azetidin-1-yl)-6-nitro-2-(piperidin-1-yl) thiazolo[4,5-b]pyridine (170 mg, 0.5329 mmol) was reduced with zinc dust (228 mg, 4.2633 mmol) and ammonium chloride (558 mg, 8.5266 mmol) in THF/methanol/H$_2$O (10 mL/2 mL/1 mL) to get the title compound (140 mg, 90.9%). LCMS: m/z=290.1 (M+1)$^+$.

Step 3: Preparation of N-(5-(azetidin-1-yl)-2-(piperidin-1-yl)thiazolo[4,5-b]pyridin-6-yl)-2-(2-methylpyridin-4-yl)oxazole-4-carboxamide Using the same reaction conditions as described in step 6 of example 1, 5-(azetidin-1-yl)-2-(piperidin-1-yl)thiazolo[4,5-b]pyridin-6-amine (140 mg, 0.4844 mmol), was coupled with 2-(2-methylpyridin-4-yl)oxazole-4-carboxylic acid (119 mg, 0.5813 mmol) using HATU (294 mg, 0.6297 mmol) and DIPEA (0.338 mL, 1.9377 mmol) in DMF (3 mL) to get the title compound (96 mg, 41.73%).

¹HNMR (CDCl₃, 400 MHz): δ 8.70-8.69 (d, 1H), 8.55 (s, 1H), 8.38-8.36 (d, 2H), 7.81 (s, 1H), 7.78-7.76 (d, 1H), 4.24-4.20 (t, 4H), 3.65 (s, 4H), 2.69 (s, 3H), 2.40-2.33 (m, 2H), 1.69 (s, 6H).
LCMS: 100%, m/z=476.1 (M+1)⁺. HPLC: 97.70%.

Example 88

2-(2-methylpyridin-4-yl)-N-(2-(piperidin-1-yl)-5-(pyrrolidin-1-yl)thiazolo[4,5-b]pyridin-6-yl)oxazole-4-carboxamide

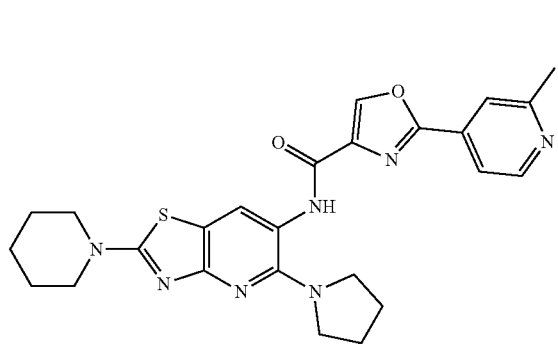 [SMILES: Cc1cc(-c2nc(C(=O)Nc3cc4sc(N5CCCCC5)nc4nc3N3CCCC3)co2)ccn1]

Step 1: Preparation of 6-nitro-2-(piperidin-1-yl)-5-(pyrrolidin-1-yl)thiazolo[4,5-b]pyridine Using the same reaction conditions as described in step 1 of example 38, 5-chloro-6-nitro-2-(piperidin-1-yl)thiazolo[4,5-b]pyridine (product of step 2 of example 22) (250 mg, 0.8389 mmol) was substituted with pyrrolidine (90 mg, 1.2583 mmol) using sodium carbonate (178 mg, 1.6778 mmol) and DMF (5 mL) at RT overnight to afford the title product (200 mg, 71.42%).
LCMS: m/z=334.1 (M+1)⁺.

Step 2: Preparation of 2-(piperidin-1-yl)-5-(pyrrolidin-1-yl)thiazolo[4,5-b]pyridin-6-amine Using the same reaction conditions as described in step 2 of example 38, 6-nitro-2-(piperidin-1-yl)-5-(pyrrolidin-1-yl)thiazolo[4,5-b]pyridine (200 mg, 0.5998 mmol) was reduced with zinc dust (257 mg, 4.7988 mmol) and ammonium chloride (628 mg, 9.5977 mmol) in THF/methanol/H₂O (10 mL/2 mL/1 mL) to get the title compound (140 mg, 76.92%). LCMS: m/z=304.1 (M+1)⁺.

Step 3: Preparation of 2-(2-methylpyridin-4-yl)-N-(2-(piperidin-1-yl)-5-(pyrrolidin-1-yl)thiazolo[4,5-b]pyridin-6-yl)oxazole-4-carboxamide Using the same reaction conditions as described in step 6 of example 1, 2-(piperidin-1-yl)-5-(pyrrolidin-1-yl)thiazolo[4,5-b]pyridin-6-amine (100 mg, 0.3300 mmol), was coupled with 2-(2-methylpyridin-4-yl)oxazole-4-carboxylic acid (81 mg, 0.3960 mmol) using HATU (163 mg, 0.4290 mmol) and DIPEA (0.23 mL, 1.3201 mmol) in DMF (3 mL) to get the title compound (59 mg, 36.64%).
¹HNMR (CDCl₃, 300 MHz): δ 8.95 (s, 1H), 8.69-8.68 (d, 1H), 8.48 (s, 1H), 8.39 (s, 1H), 7.79 (s, 1H), 7.73-7.71 (d, 1H), 3.75-3.65 (m, 4H), 3.55-3.49 (m, 4H), 2.67 (s, 3H), 1.99-1.94 (m, 4H), 1.69 (s, 6H). LCMS: 98.26%, m/z=490.1 (M+1)⁺. HPLC: 97.87%.

Example 89

2-(2-methylpyridin-4-yl)-N-(2-morpholino-5-(pyrrolidin-1-yl)thiazolo[4,5-b]pyridin-6-yl)oxazole-4-carboxamide

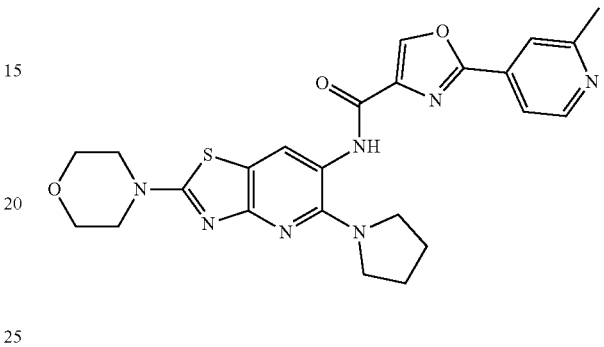

Step 1: Preparation of 4-(6-nitro-5-(pyrrolidin-1-yl)thiazolo[4,5-b]pyridin-2-yl)morpholine Using the same reaction conditions as described in step 1 of example 38, 4-(5-chloro-6-nitrothiazolo[4,5-b]pyridin-2-yl)morpholine (product of step 4 of example 20) (200 mg, 0.666 mmol) was substituted with pyrrolidine (71 mg, 0.999 mmol) using potassium carbonate (275 mg, 1.998 mmol) and DMF (5 mL) at RT overnight to afford the title product (200 mg, 89.68%).
LCMS: m/z=336.0 (M+1)⁺.

Step 2: Preparation of 2-morpholino-5-(pyrrolidin-1-yl)thiazolo[4,5-b]pyridin-6-amine Using the same reaction conditions as described in step 2 of example 38, 4-(6-nitro-5-(pyrrolidin-1-yl)thiazolo[4,5-b]pyridin-2-yl)morpholine (200 mg, 0.597 mmol) was reduced with zinc dust (310 mg, 4.776 mmol) and ammonium chloride (515 mg, 9.552 mmol) in THF/methanol/H₂O (10 mL/2 mL/1 mL) to get the title compound (200 mg, crude).
LCMS: m/z=306.1 (M+1)⁺.

Step 3: 2-(2-methylpyridin-4-yl)-N-(2-morpholino-5-(pyrrolidin-1-yl)thiazolo[4,5-b]pyridin-6-yl)oxazole-4-carboxamide Using the same reaction conditions as described in step 6 of example 1, 2-morpholino-5-(pyrrolidin-1-yl)thiazolo[4,5-b]pyridin-6-amine (100 mg, 0.327 mmol), was coupled with 2-(2-methylpyridin-4-yl)oxazole-4-carboxylic acid (80 mg, 0.393 mmol) using HATU (186 mg, 0.490 mmol) and DIPEA (169 mg, 1.3081 mmol) in DMF (5 mL) to get the title compound (90 mg, 56.2%).
¹HNMR (CDCl₃, 300 MHz): δ 8.94 (s, 1H), 8.70-8.68 (d, 1H), 8.52 (s, 1H), 8.40 (s, 1H), 7.79 (s, 1H), 7.73-7.71 (d, 1H), 3.83-3.80 (m, 4H), 3.70-3.65 (m, 4H), 3.56-3.52 (m, 4H), 2.68 (s, 3H), 2.00-1.95 (m, 4H). LCMS: 100%, m/z=492.1 (M+1)⁺. HPLC: 97.29%.

Example 90

5-(2-methylpyridin-4-yl)-N-(2-morpholino-5-(piperidin-1-yl)thiazolo[4,5-b]pyridin-6-yl)furan-2-carboxamide

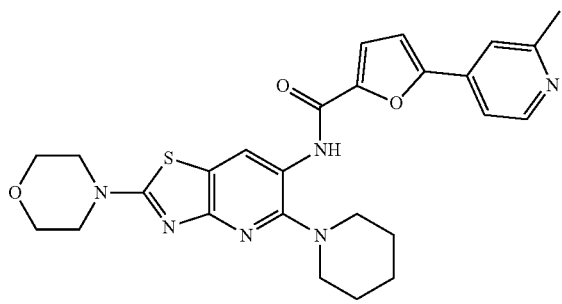 [SMILES: Cc1cc(-c2ccc(C(=O)Nc3cc4sc(N5CCOCC5)nc4nc3N3CCCCC3)o2)ccn1]

Using the same reaction conditions as described in step 6 of example 1, 2-morpholino-5-(piperidin-1-yl)thiazolo[4,5-b]pyridin-6-amine (product of step 6 of example 20) (150 mg, 0.468 mmol) was coupled with 5-(2-methylpyridin-4-yl)furan-2-carboxylic acid (intermediate 18) (114 mg, 0.562 mmol) using HATU (267 mg, 0.702 mmol) and DIPEA (241 mg, 1.872 mmol) in DMF (5 mL) to afford the title compound (60 mg, 25.4%).

$^1$HNMR (CDCl$_3$, 400 MHz): δ 9.08 (s, 1H), 8.58-8.57 (d, 1H), 7.58 (s, 1H), 7.44-7.42 (d, 1H), 7.35-7.34 (d, 1H), 7.02-7.01 (d, 1H), 3.84-3.82 (m, 4H), 3.71-3.68 (m, 4H), 3.13-3.10 (m, 4H), 2.64 (s, 3H), 1.99-1.86 (m, 4H), 1.69 (s, 2H). LCMS: 100%, m/z=505.3 (M+1)$^+$. HPLC: 95.52%.

Example 91

N-(5-(azepan-1-yl)-2-morpholinothiazolo[4,5-b]pyridin-6-yl)-2-(2-methylpyridin-4-yl)oxazole-4-carboxamide

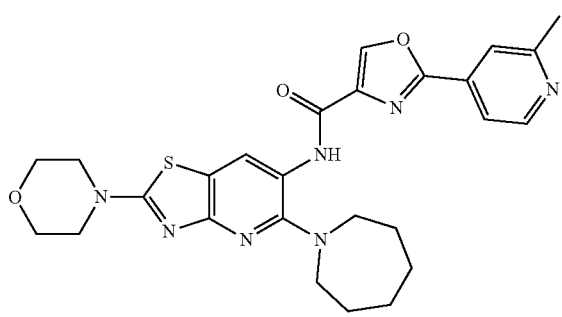 [SMILES: Cc1cc(-c2nc(C(=O)Nc3cc4sc(N5CCOCC5)nc4nc3N3CCCCCC3)co2)ccn1]

Step 1: Preparation of 4-(5-(azepan-1-yl)-6-nitrothiazolo[4,5-b]pyridin-2-yl)morpholine Using the same reaction conditions as described in step 1 of example 38, 4-(5-chloro-6-nitrothiazolo[4,5-b]pyridin-2-yl)morpholine (product of step 4 of example 20) (250 mg, 0.8333 mmol) was substituted with azepane (165 mg, 1.6666 mmol) using sodium carbonate (221 mg, 2.0833 mmol) and DMF (4 mL) at 80° C. for 2 h to afford the title product (200 mg, 66.22%).

LCMS: m/z=364.0 (M+1)$^+$.

Step 2: Preparation of 5-(azepan-1-yl)-2-morpholinothiazolo[4,5-b]pyridin-6-amine Using the same reaction conditions as described in step 2 of example 38, 4-(5-(azepan-1-yl)-6-nitrothiazolo[4,5-b]pyridin-2-yl)morpholine (200 mg, 0.550 mmol) was reduced with zinc dust (236 mg, 4.407 mmol) and ammonium chloride (577 mg, 8.8154 mmol) in THF/methanol/H$_2$O (10 mL/2 mL/2 mL) to get the title compound (100 mg, 52.93).

LCMS: m/z=334.3 (M+1)$^+$.

Step 3: Preparation of N-(5-(azepan-1-yl)-2-morpholinothiazolo[4,5-b]pyridin-6-yl)-2-(2-methylpyridin-4-yl)oxazole-4-carboxamide Using the same reaction conditions as described in step 6 of example 1, 5-(azepan-1-yl)-2-morpholinothiazolo[4,5-b]pyridin-6-amine (100 mg, 0.300 mmol), was coupled with 2-(2-methylpyridin-4-yl)oxazole-4-carboxylic acid (74 mg, 0.360 mmol) using HATU (149 mg, 0.390 mmol) and DIPEA (0.21 mL, 1.2012 mmol) in DMF (5 mL) to get the title compound (84 mg, 53.84%).

$^1$HNMR (CDCl$_3$, 300 MHz): δ 9.85 (s, 1H), 9.07 (s, 1H), 8.69-8.67 (d, 1H), 8.40 (s, 1H), 7.83 (s, 1H), 7.72-7.71 (d, 1H), 3.84-3.81 (m, 4H), 3.70-3.67 (m, 4H), 3.39-3.32 (m, 4H), 2.67 (s, 3H), 1.93 (s, 8H). LCMS: 89.19%, m/z=520.2 (M+1)$^+$. HPLC: 95.29%.

Example 92

2-(2-aminopyridin-4-yl)-N-(2-morpholino-5-(piperidin-1-yl)thiazolo[4,5-b]pyridin-6-yl)oxazole-4-carboxamide Hydrochloride

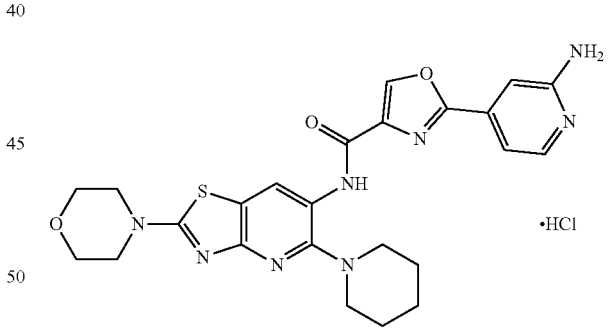

Using the same reaction conditions as described in example 45, 2-morpholino-5-(piperidin-1-yl)thiazolo[4,5-b]pyridin-6-amine (product of step 6 of example 20) (70 mg, 0.2191 mmol), was coupled with 2-(2-((tert-butoxycarbonyl)amino)pyridin-4-yl)oxazole-4-carboxylic acid (intermediate 19) (74 mg, 0.2410 mmol) using HATU (108 mg, 0.2848 mmol) and DIPEA (0.153 mL, 0.8765 mmol) in DMF (2 mL) followed by deprotection using methanolic HCl/DCM (2/5 mL) to get the crude product. This was then purified by prep HPLC and treated with methanolic HCl to get the title compound (47 mg, 52.80%).

$^1$HNMR (DMSO-d$_6$, 400 MHz): δ 9.61 (s, 1H), 9.19 (s, 1H), 8.91 (s, 1H), 8.49-8.41 (m, 2H), 8.21-8.19 (d, 1H), 7.53 (s, 1H), 7.30-7.28 (d, 1H), 3.74-3.73 (m, 4H), (3.52-3.60 (m,

4H), 3.06-3.01 (m, 4H), 1.82-1.78 (m, 4H), 1.64-1.61 (m, 2H). LCMS: 93.04%, m/z=507.2 (M+1)⁺.
HPLC: 98.15%.

Example 93

N-(5-(azetidin-1-yl)-2-morpholinothiazolo[4,5-b]pyridin-6-yl)-2-(2-methylpyridin-4-yl)oxazole-4-carboxamide

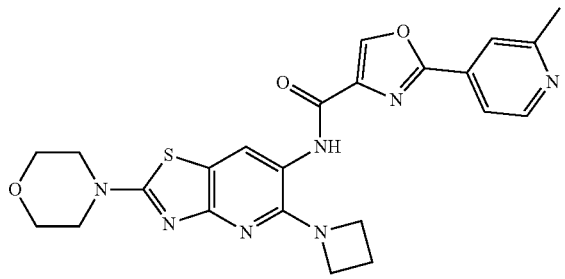

Using the same reaction conditions as described in step 6 of example 1, 5-(azetidin-1-yl)-2-morpholinothiazolo[4,5-b]pyridin-6-amine (product of step 2 of example 80) (100 mg, 0.344 mmol), was coupled with 2-(2-methylpyridin-4-yl)oxazole-4-carboxylic acid (105 mg, 0.517 mmol) using HATU (196 mg, 0.517 mmol) and DIPEA (177 mg, 1.376 mmol) in DMF (5 mL) to afford title compound (40 mg, 25.0%).
¹HNMR (CDCl₃, 300 MHz): δ 8.71-8.69 (d, 1H), 8.57 (s, 1H), 8.42-8.39 (d, 2H), 7.81 (s, 1H), 7.75-7.73 (d, 1H), 4.26-4.21 (t, 4H), 3.84-3.80 (m, 4H), 3.69-3.66 (m, 4H), 2.69 (s, 3H), 2.39-2.34 (m, 2H). LCMS: 94.95%, m/z=478.1 (M+1)⁺. HPLC: 98.37%.

Example 94

(R)—N-(5-(3-hydroxypiperidin-1-yl)-2-morpholinothiazolo[4,5-b]pyridin-6-yl)-2-(2-methylpyridin-4-yl)oxazole-4-carboxamide

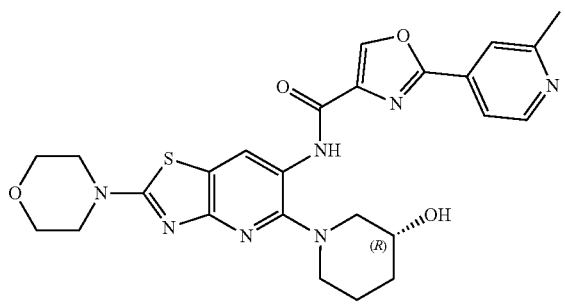

Step 1: Preparation of (R)-1-(2-morpholino-6-nitrothiazolo[4,5-b]pyridin-5-yl)piperidin-3-ol Using the same reaction conditions as described in step 2 of example 43, 4-(5-chloro-6-nitrothiazolo[4,5-b]pyridin-2-yl)morpholine (product of step 4 of example 20) (400 mg, 1.333 mmol) was substituted using (R)-piperidin-3-ol hydrochloride (218 mg, 1.6 mmol) using potassium carbonate (552 mg, 4 mmol) in DMF (5 mL) at RT for 14 h to obtain the title compound (420 mg, 86.4%). LCMS: m/z=365.3 (M+1)⁺.

Step 2: Preparation of (R)-4-(5-(3-((tert-butyldimethylsilyl)oxy)piperidin-1-yl)-6-nitrothiazolo[4,5-b]pyridin-2-yl)morpholine Using the same reaction conditions as described in step 2 of example 41, (R)-1-(2-morpholino-6-nitrothiazolo[4,5-b]pyridin-5-yl)piperidin-3-ol (420 mg, 0.903 mmol) was protected using TBDMS chloride (110 mg, 0.903 mmol) and imidazole (92 mg, 1.354 mmol) and DMAP (204 mg, 1.354 mmol) in DMF/DCM (10/2 mL) at RT for 0.5 h to get the crude product. The resultant crude was purified by 60-120 silica gel column chromatography using 2% methanol in DCM as eluent to obtain the title compound (520 mg, 94.5%). LCMS: m/z=480.2 (M+1)⁺.

Step 3: Preparation of (R)-5-(3-((tert-butyldimethylsilyl)oxy)piperidin-1-yl)-2-morpholinothiazolo[4,5-b]pyridin-6-amine Using the same reaction conditions as described in step 2 of example 38, (R)-4-(5-(3-((tert-butyldimethylsilyl)oxy)piperidin-1-yl)-6-nitrothiazolo[4,5-b]pyridin-2-yl)morpholine (520 mg, 0.898 mmol) was reduced with zinc dust (467 mg, 7.184 mmol) and ammonium chloride (776 mg, 14.368 mmol) in THF/water (20/5 mL) to get the title compound (500 mg crude).
LCMS: m/z=450.0 (M+1)⁺.

Step 4: Preparation of (R)—N-(5-(3-((tert-butyldimethylsilyl)oxy)piperidin-1-yl)-2-morpholinothiazolo[4,5-b]pyridin-6-yl)-2-(2-methylpyridin-4-yl)oxazole-4-carboxamide Using the same reaction conditions as described in step 6 of example 1, (R)-5-(3-((tert-butyldimethylsilyl)oxy)piperidin-1-yl)-2-morpholinothiazolo[4,5-b]pyridin-6-amine (120 mg, 0.266 mmol), was coupled with 2-(2-methylpyridin-4-yl)oxazole-4-carboxylic acid (81 mg, 0.399 mmol) using HATU (152 mg, 0.399 mmol) and DIPEA (137 mg, 1.064 mmol) in DMF (3 mL) to get the crude title compound (200 mg). LCMS: m/z=636.2 (M+1)⁺.

Step 5: Preparation of (R)—N-(5-(3-hydroxypiperidin-1-yl)-2-morpholinothiazolo[4,5-b]pyridin-6-yl)-2-(2-methylpyridin-4-yl)oxazole-4-carboxamide Using the same reaction conditions as described in step 5 of example 77, (R)—N-(5-(3-((tert-butyldimethylsilyl)oxy)piperidin-1-yl)-2-morpholinothiazolo[4,5-b]pyridin-6-yl)-2-(2-methylpyridin-4-yl)oxazole-4-carboxamide (200 mg, 0.314 mmol) was deprotected using TBAF/THF (2/5 mL) to get the crude product. The resultant crude was purified by prep plate using 5% methanol in DCM as eluent to obtain the title compound (50 mg, 30.4%).
¹HNMR (CDCl₃, 400 MHz): δ 9.92 (s, 1H), 9.05 (s, 1H), 8.75 (s, 1H), 8.40 (s, 1H), 7.87 (s, 1H), 7.69-7.67 (d, 1H), 4.15 (s, 1H), 3.84-3.82 (m, 4H), 3.71-3.69 (m, 4H), 3.39-3.36 (m, 1H), 3.34-3.31 (m, 3H), 3.12-3.05 (m, 1H), 2.68 (s, 3H), 2.20-2.10 (m, 1H), 1.90-1.60 (m, 3H). LCMS: 97.74%, m/z=522.2 (M+1)⁺. HPLC: 98.12%.

Example 95

(R)—N-(5-(3-hydroxypiperidin-1-yl)-2-morpholinothiazolo[4,5-b]pyridin-6-yl)-5-(2-methylpyridin-4-yl)furan-2-carboxamide

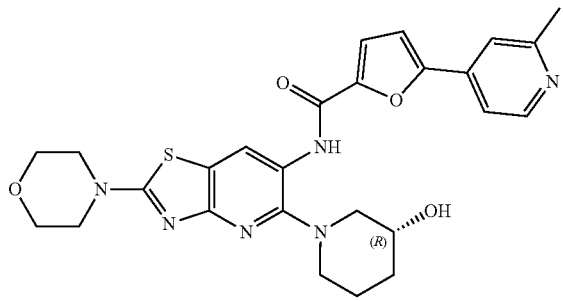

Using the same reaction conditions as described in example 45, (R)-5-(3-((tert-butyldimethylsilyl)oxy)piperidin-1-yl)-2-morpholinothiazolo[4,5-b]pyridin-6-amine (product of step 3 of example 95) (100 mg, 0.209 mmol), was coupled with 5-(2-methylpyridin-4-yl)furan-2-carboxylic acid (intermediate 18) (51 mg, 0.250 mmol) using HATU (120 mg, 0.315 mmol) and DIPEA (108 mg, 0.840 mmol) in DMF (5 mL) followed by deprotection using TBAF/THF (1/2 mL) to get the crude product. This was then purified by prep plate using 5% methanol in DCM as eluent to obtain the title compound (50 mg, 59.5%).

¹HNMR (CDCl₃, 300 MHz): δ 9.33 (s, 1H), 9.09 (s, 1H), 8.57-8.56 (d, 1H), 7.59 (s, 1H), 7.45-7.44 (d, 1H), 7.37-7.35 (d, 1H), 7.00-6.99 (d, 1H), 4.13 (s, 1H), 3.84-3.81 (m, 4H), 3.71-3.69 (m, 4H), 3.36-3.11 (m, 1H), 3.19-3.10 (m, 3H), 2.64 (s, 3H), 2.39 (s, 1H) 2.17-2.11 (m, 1H), 1.99-1.90 (m, 1H), 1.80-1.77 (m, 2H). LCMS: 93.43%, m/z=521.4 (M+1)⁺. HPLC: 95.34%.

Example 96

(S)-6-(1-(2-hydroxypropyl)-1H-pyrazol-4-yl)-N-(2-morpholino-5-(piperidin-1-yl)thiazolo[4,5-b]pyridin-6-yl)picolinamide

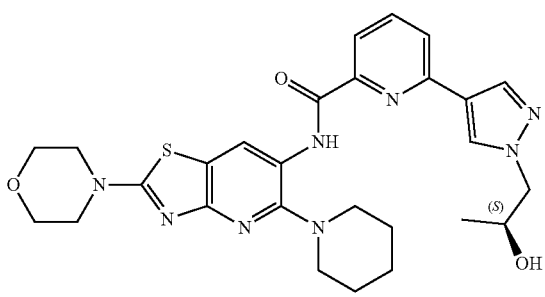

Using the same reaction conditions as described in step 2 of example 43, N-(2-morpholino-5-(piperidin-1-yl)thiazolo[4,5-b]pyridin-6-yl)-6-(1H-pyrazol-4-yl)picolinamide (example 21) (200 mg, 0.380 mmol) was substituted with (S)-2-methyloxirane (34 mg, 0.570 mmol) using sodium carbonate (201 mg, 1.900 mmol) in DMF (5 mL) at 100° C. for 14 h to obtain the crude product. The resultant crude was purified by prep plate using 5% methanol in DCM as eluent to obtain the title compound (50 mg, 24.5%).

¹HNMR (DMSO-d₆, 300 MHz): δ 10.59 (s, 1H), 9.03 (s, 1H), 8.42 (s, 1H), 8.22 (s, 1H), 8.04-8.01 (m, 1H), 7.97-7.96 (m, 2H), 5.02 (s, 1H), 4.06-4.04 (m, 3H), 3.72-3.70 (m, 4H), 3.58-3.55 (m, 4H), 3.02-2.89 (m, 4H), 1.78-1.73 (m, 4H), 1.61-1.55 (m, 2H), 1.11-1.04 (m, 3H). LCMS: 92.56%, m/z=549.3 (M+1)⁺. HPLC: 96.98%.

Example 97

N-(5-(4-fluoropiperidin-1-yl)-2-morpholinothiazolo[4,5-b]pyridin-6-yl)-5-(2-methylpyridin-4-yl)furan-2-carboxamide

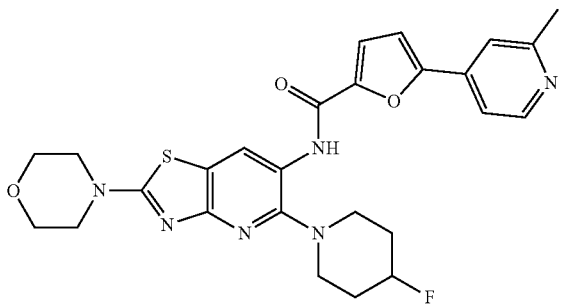 [SMILES: Cc1cc(-c2ccc(C(=O)Nc3cc4sc(N5CCOCC5)nc4nc3N3CCC(F)CC3)o2)ccn1]

Step 1: Preparation of 4-(5-(4-fluoropiperidin-1-yl)-6-nitrothiazolo[4,5-b]pyridin-2-yl)morpholine Using the same reaction conditions as described in step 2 of example 59, 1-(2-morpholino-6-nitrothiazolo[4,5-b]pyridin-5-yl)piperidin-4-ol (product of step 1 of example 85) (450 mg, 1.3846 mmol) was fluorinated using DAST (0.3 mL, 2.353 mmol) in DCM (10 mL) at −78° C. for 30 min. The resultant crude was purified by 60-120 silica gel column chromatography using 50% ethyl acetate in hexane as eluent to obtain the crude title compound (360 mg). LCMS: m/z=368.0 (M+1)⁺.

Step 2: Preparation of 5-(4-fluoropiperidin-1-yl)-2-morpholinothiazolo[4,5-b]pyridin-6-amine Using the same reaction conditions as described in step 5 of example 1, 4-(5-(4-fluoropiperidin-1-yl)-6-nitrothiazolo[4,5-b]pyridin-2-yl)morpholine (360 mg, 0.9809 mmol) was reduced with zinc dust (510 mg, 0.7847 mmol) and ammonium chloride (423 mg, 0.7847 mmol) in THF/methanol/H₂O (10 mL/2 mL/1 mL) to get the crude product (240 mg). LCMS: m/z=338.3 (M+1)⁺.

Step 3: Preparation of N-(5-(4-fluoropiperidin-1-yl)-2-morpholinothiazolo[4,5-b]pyridin-6-yl)-5-(2-methylpyridin-4-yl)furan-2-carboxamide Using the same reaction conditions as described in step 6 of example 1, 5-(4-fluoropiperidin-1-yl)-2-morpholinothiazolo[4,5-b]pyridin-6-amine (120 mg, 0.3560 mmol) was coupled with 5-(2-methylpyridin-4-yl)furan-2-carboxylic acid (intermediate 18) (86 mg, 0.4272 mmol) using HATU (202 mg, 0.5341 mmol) and DIPEA (0.3 mL, 1.424 mmol) in DMF (5 mL) to afford the crude product. The resultant crude was purified by prep HPLC to obtain the title compound (75 mg, 40%).

¹HNMR (DMSO-d₆, 400 MHz): δ 9.85 (s, 1H), 8.55-8.53 (d, 2H), 7.77 (s, 1H), 7.69-7.68 (d, 1H), 7.46 (s, 2H), 4.95-4.79 (m, 1H), 3.75-3.73 (m, 4H), 3.60-3.58 (m, 4H), 3.28-3.27 (m, 2H), 3.06-3.02 (m, 2H), 2.53 (s, 3H), 2.06-2.02 (m, 2H), 1.92-1.90 (m, 2H). LCMS: 100%, m/z=523.2 (M+1)⁺. HPLC: 97.39%.

Example 98

N-(5-(4-fluoropiperidin-1-yl)-2-morpholinothiazolo[4,5-b]pyridin-6-yl)-2-(2-methylpyridin-4-yl)oxazole-4-carboxamide

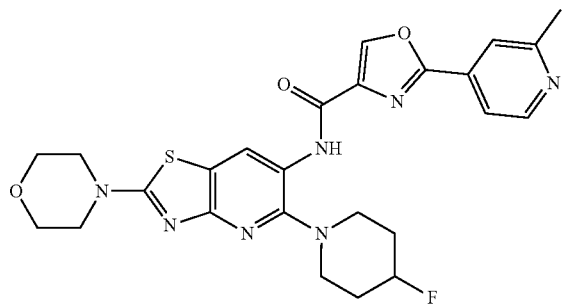 [SMILES: Cc1cc(-c2nc(C(=O)Nc3cc4sc(N5CCOCC5)nc4nc3N3CCC(F)CC3)co2)ccn1]

Using the same reaction conditions as described in step 6 of example 1, 5-(4-fluoropiperidin-1-yl)-2-morpholinothiazolo[4,5-b]pyridin-6-amine (product of step 2 of 98) (120 mg, 0.3560 mmol) was coupled with 2-(2-methylpyridin-4-yl)oxazole-4-carboxylic acid (87 mg, 0.4272 mmol) using HATU (202 mg, 0.5341 mmol) and DIPEA (183 mg, 1.024 mmol) in DMF (5 mL) to afford the crude product. The resultant crude was purified by prep HPLC to obtain the title compound (30 mg, 20%).

¹HNMR (DMSO-d₆, 400 MHz): δ 9.72 (s, 1H), 9.25 (s, 1H), 8.91-8.89 (m, 2H), 8.24 (s, 1H), 8.14-8.12 (d, 1H), 5.08-4.91 (m, 1H), 3.7-3.73 (m, 4H), 3.60-3.58 (m, 4H), 3.27-3.23 (m, 2H), 3.16 (s, 1H), 3.06-3.03 (m, 2H), 2.76 (s, 2H), 2.25-2.15 (m, 2H), 2.10-2.02 (m, 2H). LCMS: 99.32%, m/z=524.0 (M+1)⁺. HPLC: 98.71%.

Example 99

N-(5-(1-methyl-1H-pyrazol-4-yl)-2-morpholinothiazolo[4,5-b]pyridin-6-yl)-2-(2-methylpyridin-4-yl)oxazole-4-carboxamide

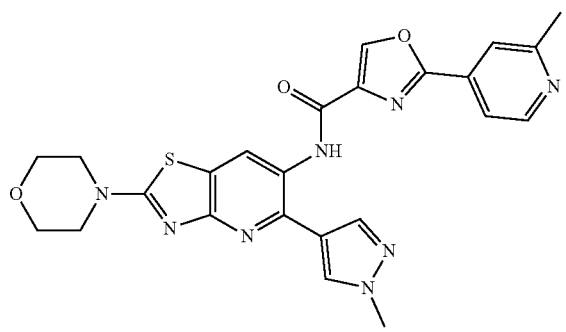 [SMILES: Cc1cc(-c2nc(C(=O)Nc3cc4sc(N5CCOCC5)nc4nc3-c3cnn(C)c3)co2)ccn1]

Step 1: Preparation of 4-(5-(1-methyl-1H-pyrazol-4-yl)-6-nitrothiazolo[4,5-b]pyridin-2-yl)morpholine Using the same reaction conditions as described in step 7 of example 1, 4-(5-chloro-6-nitrothiazolo[4,5-b]pyridin-2-yl)morpholine (product of step 4 of example 20) (200 mg, 0.66 mmol) was coupled with 1-methyl-4-(4,4,5,5-tetramethyl-1,3,2-dioxaborolan-2-yl)-1H-pyrazole (200 mg, 0.99 mmol) using sodium iodide (200 mg, 1.33 mmol), potassium carbonate (220 mg, 1.99 mmol) and Pd(dppf)Cl₂ (48 mg, 0.066 mmol) in 1,2-dimethoxyethane/water (0.5/0.2 mL) to get the title compound (150 mg, %). LCMS: m/z=346.9 (M+1)⁺.

Step 2: Preparation of 5-(1-methyl-1H-pyrazol-4-yl)-2-morpholinothiazolo[4,5-b]pyridin-6-amine Using the same reaction conditions as described in step 5 of example 1, 4-(5-(1-methyl-1H-pyrazol-4-yl)-6-nitrothiazolo[4,5-b]pyridin-2-yl)morpholine (150 mg, 0.43 mmol) was reduced with zinc dust (220 mg, 3.4 mmol) and ammonium chloride (360 mg, 6.9 mmol) in THF/methanol/H₂O (10 mL/2 mL/1 mL) (2 mL) to get the crude product (100 mg). LCMS: m/z=317.3 (M+1)⁺.

Step 3: Preparation of N-(5-(1-methyl-1H-pyrazol-4-yl)-2-morpholinothiazolo[4,5-b]pyridin-6-yl)-2-(2-methylpyridin-4-yl)oxazole-4-carboxamide Using the same reaction conditions as described in step 6 of example 1, 5-(1-methyl-1H-pyrazol-4-yl)-2-morpholinothiazolo[4,5-b]pyridin-6-amine (100 mg, 0.316 mmol) was coupled with 2-(2-methylpyridin-4-yl)oxazole-4-carboxylic acid (77 mg, 0.38 mmol) using HATU (156 mg, 0.41 mmol) and DIPEA (122 mg, 0.94 mmol) in DMF (5 mL) to afford the title compound (40 mg, %).

¹HNMR (DMSO-d₆, 400 MHz): δ 10.1 (s, 1H), 9.05 (s, 1H), 8.71-8.70 (d, 1H), 8.30 (s, 1H), 8.21 (s, 1H), 7.94 (s, 1H), 7.88 (s, 1H), 7.80-7.79 (d, 1H), 3.87 (s, 3H), 3.82-3.76 (m, 4H), 3.69-3.64 (m, 4H), 2.60 (s, 3H). LCMS: 97.70%, m/z=503.2 (M+1)⁺. HPLC: 96.20%.

Example 100

N-(5-(3-fluorophenyl)-2-morpholinothiazolo[4,5-b]pyridin-6-yl)-2-(2-methylpyridin-4-yl)oxazole-4-carboxamide

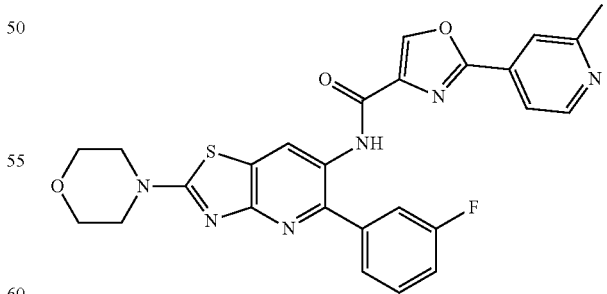

Step 1: Preparation of 4-(5-(3-fluorophenyl)-6-nitrothiazolo[4,5-b]pyridin-2-yl)morpholine Using the same reaction conditions as described in step 7 of example 1, 4-(5-chloro-6-nitrothiazolo[4,5-b]pyridin-2- yl)morpholine (product of step 4 of example 20) (250 mg, 0.83 mmol) was coupled with 3-fluoro phenyl boronic acid (173 mg, 1.25 mmol) using sodium iodide (375 mg, 2.5 mmol), potassium carbonate (517 mg, 3.7 mmol) and Pd(dppf)Cl$_2$ (61 mg, 0.1056 mmol) in 1,2-dimethoxyethane/water (0.5/0.2 mL) to get the title compound (200 mg, %). LCMS: m/z=361.2 (M+1)$^+$.

Step 2: Preparation of 5-(3-fluorophenyl)-2-morpholinothiazolo[4,5-b]pyridin-6-amine Using the same reaction conditions as described in step 5 of example 1, 4-(5-(3-fluorophenyl)-6-nitrothiazolo[4,5-b]pyridin-2-yl)morpholine (360 mg, 0.9809 mmol) was reduced with zinc dust (510 mg, 0.7847 mmol) and ammonium chloride (423 mg, 0.7847 mmol) in THF/methanol/H$_2$O (10 mL/2 mL/1 mL) to get the crude product (240 mg). LCMS: m/z=330.9 (M+1)$^+$.

Step 3: Preparation of N-(5-(3-fluorophenyl)-2-morpholinothiazolo[4,5-b]pyridin-6-yl)-2-(2-methylpyridin-4-yl)oxazole-4-carboxamide Using the same reaction conditions as described in step 6 of example 1, 5-(3-fluorophenyl)-2-morpholinothiazolo[4,5-b]pyridin-6-amine (120 mg, 0.36 mmol) was coupled with 2-(2-methylpyridin-4-yl)oxazole-4-carboxylic acid (89 mg, 0.43 mmol) using HATU (180 mg, 0.47 mmol) and DIPEA (190 mg, 1.45 mmol) in DMF (5 mL) to afford the title compound (50 mg).
$^1$HNMR (DMSO-d$_6$, 400 MHz): δ 10.10 (s, 1H), 8.94 (s, 1H), 8.68-8.67 (d, 1H), 8.51 (s, 1H), 7.79 (s, 1H), 7.71-7.70 (d, 1H), 7.53-7.48 (m, 2H), 7.27-7.24 (t, 1H), 3.77-3.75 (m, 4H), 3.70-3.66 (m, 4H), 2.54 (s, 3H). LCMS: 97.4%, m/z=517.0 (M+1)$^+$. HPLC: 98.80%.

Example 101

N-(5-(4-hydroxypiperidin-1-yl)-2-morpholinothiazolo[4,5-b]pyridin-6-yl)-5-(2-methylpyridin-4-yl)furan-2-carboxamide

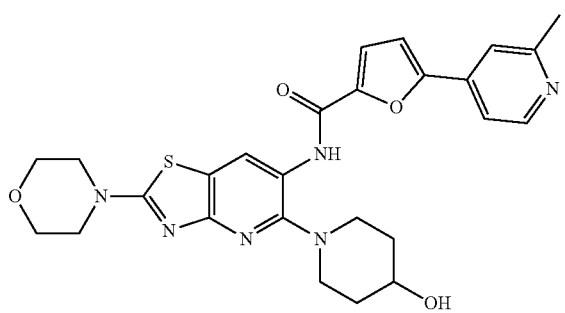 [SMILES: Cc1cc(-c2ccc(C(=O)Nc3cc4sc(N5CCOCC5)nc4nc3N3CCC(O)CC3)o2)ccn1]

Using the same reaction conditions as described in example 45, 5-(4-((tert-butyldimethylsilyl)oxy)piperidin-1-yl)-2-morpholinothiazolo[4,5-b]pyridin-6-amine (product of step 3 of example 85) (200 mg, 0.445 mmol), was coupled with 5-(2-methylpyridin-4-yl)furan-2-carboxylic acid (intermediate 18) (135 mg, 0.668 mmol) using HATU (253 mg, 0.668 mmol) and DIPEA (230 mg, 1.780 mmol) in DMF (5 mL) followed by deprotection using methanol/methanolic HCl (1/5 mL) to get the crude product. This was then purified by prep HPLC to obtain the title compound (50 mg, 30.4%).
$^1$HNMR (CDCl$_3$, 400 MHz): δ 9.33 (s, 1H), 9.10 (s, 1H), 8.58-8.57 (d, 1H), 7.60 (s, 1H), 7.46-7.45 (d, 1H), 7.37-7.36 (d, 1H), 7.01-7.00 (d, 1H), 4.13 (s, 1H), 3.85-3.82 (m, 4H), 3.71-3.69 (m, 4H), 3.35-3.33 (m, 1H), 3.20-3.10 (m, 3H), 2.65 (s, 3H), 2.35 (s, 1H), 2.14-2.12 (m, 1H), 1.97-1.91 m, 1H), 1.79-1.77 (m, 2H). LCMS: 99.89%, m/z=521.20 (M+1)$^+$. HPLC: 97.27%.

Example 102

N-(5-(3-fluoropiperidin-1-yl)-2-morpholinothiazolo[4,5-b]pyridin-6-yl)-5-(2-methylpyridin-4-yl)furan-2-carboxamide

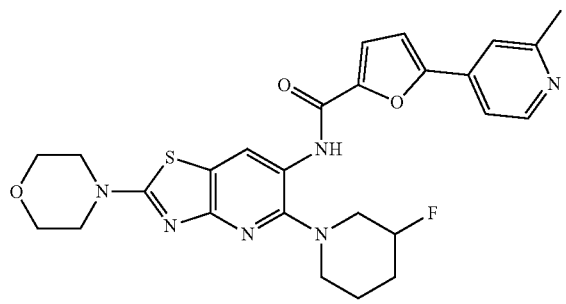 [SMILES: Cc1cc(-c2ccc(C(=O)Nc3cc4sc(N5CCOCC5)nc4nc3N3CCCC(F)C3)o2)ccn1]

Using the same reaction conditions as described in step 6 of example 1, (S)-5-(3-fluoropiperidin-1-yl)-2-morpholinothiazolo[4,5-b]pyridin-6-amine (product of step 4 of example 59) (200 mg, 0.593 mmol) was coupled with 5-(2-methylpyridin-4-yl)furan-2-carboxylic acid (intermediate 18) (180 mg, 0.890 mmol) using HATU (338 mg, 0.890 mmol) and DIPEA (305 mg, 2.372 mmol) in DMF (5 mL) to afford the crude product. The resultant crude was purified by prep HPLC to obtain the title compound (40 mg, 12.9%).
$^1$HNMR (CDCl$_3$, 300 MHz): δ 9.51 (s, 1H), 9.14 (s, 1H), 8.56-8.54 (d, 1H), 7.65 (s, 1H), 7.48-7.46 (d, 1H), 7.35-7.34 (d, 1H), 7.00-6.99 (d, 1H), 5.05-4.90 (m, 1H), 3.85-3.81 (m, 4H), 3.71-3.68 (m, 4H), 3.49-3.44 (m, 2H), 3.23-3.08 (m, 2H), 2.63 (s, 3H), 2.20-2.17 (m, 2H), 1.79-1.75 (m, 2H). LCMS: 98.09%, m/z=523.0 (M+1)$^+$. HPLC: 99.18%.

Example 103

(S)—N-(5-(3-hydroxypyrrolidin-1-yl)-2-morpholinooxazolo[4,5-b]pyridin-6-yl)-2-(6-methoxypyridin-3-yl)oxazole-4-carboxamide

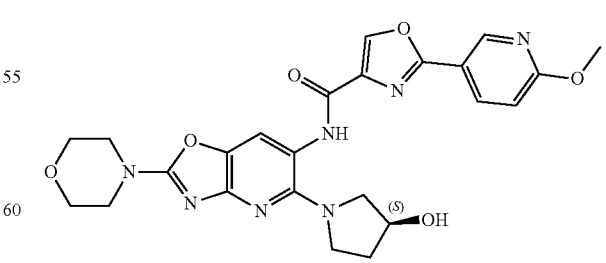

Using the same reaction conditions as described in example 45, (S)-5-(3-((tert-butyldimethylsilyl)oxy)pyrrolidin-1-yl)-2-morpholinooxazolo[4,5-b]pyridin-6-amine (product of step 2 of example 39) (130 mg, 0.3090 mmol), was coupled with 2-(2-methoxypyridin-5-yl)oxazole-4-carboxylic acid (intermediate 7) (80 mg, 0.3636 mmol) using EDCI·HCl (105 mg, 0.5454 mmol), HOBt (52 mg, 0.3817 mmol), DIPEA (188 mg, 1.454 mmol) in DMF (5 mL) to get the coupled product followed by deprotection using 1M TBAF in THF/THF (0.3/5 mL) to get the title compound (59 mg, 33%).

$^1$HNMR (CDCl$_3$, 300 MHz): δ 9.46 (s, 1H), 8.89-8.88 (d, 1H), 8.55 (s, 1H), 8.32 (s, 1H), 8.23-8.19 (dd, 1H), 6.88-6.85 (dd, 1H), 4.55 (m, 1H), 4.02 (s, 1H), 3.83-3.80 (m, 4H), 3.75-3.72 (m, 4H), 3.50-3.48 (m, 4H), 2.85 (s, 1H), 2.26-2.22 (m, 1H), 2.05-2.01 (m, 1H). LCMS: 100%, m/z=508.1 (M+1)$^+$. HPLC: 98.32%.

Example 104

N-(5-(3-hydroxypyrrolidin-1-yl)-2-morpholinooxazolo[4,5-b]pyridin-6-yl)-2-(2-methylpyridin-4-yl)oxazole-4-carboxamide

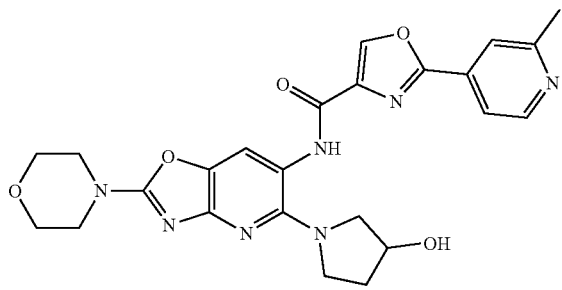 [SMILES: Cc1cc(-c2nc(C(=O)Nc3cc4oc(N5CCOCC5)nc4nc3N3CCC(O)C3)co2)ccn1]

Step 1: Preparation of 1-(2-morpholino-6-nitrooxazolo[4,5-b]pyridin-5-yl)pyrrolidin-3-ol Using the same reaction conditions as described in step 1 of example 38, 5-chloro-2-morpholino-6-nitrooxazolo[4,5-b]pyridine (product of step 5 of example 2) (250 mg, 0.880 mmol) was substituted with pyrrolidin-3-ol (108 mg, 0.880 mmol) using potassium carbonate (183 mg, 1.320 mmol) and DMF (5 mL) to afford the title product (210 mg, 72.41%). LCMS: m/z=335.8 (M+1)$^+$.

Step 2: Preparation 5-(3-((tert-butyldimethylsilyl)oxy)pyrrolidin-1-yl)-2-morpholino-6-nitrooxazolo[4,5-b]pyridine Using the same reaction conditions as described in step 2 of example 41, 1-(2-morpholino-6-nitrooxazolo[4,5-b]pyridin-5-yl)pyrrolidin-3-ol (150 mg, 0.447 mmol) was protected using TBDMS chloride (102 mg, 0.6716 mmol), imidazole (60 mg, 0.8955 mmol) and DMAP (10 mg, 0.089 mmol) in DMF (5 mL) at RT for 2 h to get the crude product. The resultant crude was purified by 60-120 silica gel column chromatography using ethyl acetate in hexane as eluent to obtain the title compound (160 mg, 80%). LCMS: m/z=449.8 (M+1)$^+$.

Step 3: Preparation of 5-(3-((tert-butyldimethylsilyl)oxy)pyrrolidin-1-yl)-2-morpholinooxazolo[4,5-b]pyridin-6-amine Using the same reaction conditions as described in step 5 of example 1, 5-(3-((tert-butyldimethylsilyl)oxy)pyrrolidin-1-yl)-2-morpholino-6-nitrooxazolo[4,5-b]pyridine (160 mg, 0.3555 mmol) was reduced with zinc dust (0.1859 mg, 2.8444 mmol) and ammonium chloride (304 mg, 5.688 mmol) in THF/methanol/H$_2$O (5 mL/2 mL/1 mL) to get the title product (90 mg, 60.44%). LCMS: m/z=420.5 (M+1)$^+$.

Step 4: Preparation of N-(5-(3-hydroxypyrrolidin-1-yl)-2-morpholinooxazolo[4,5-b]pyridin-6-yl)-2-(2-methylpyridin-4-yl)oxazole-4-carboxamide Using the same reaction conditions as described in example 45, 5-(3-((tert-butyldimethylsilyl)oxy)pyrrolidin-1-yl)-2-morpholinooxazolo[4,5-b]pyridin-6-amine (80 mg, 0.190 mmol), was coupled with 2-(2-methylpyridin-4-yl)oxazole-4-carboxylic acid (42 mg, 0.229 mmol) using EDCI·HCl (54 mg, 0.286 mmol), HOBt (38 mg, 0.2863 mmol), DIPEA (99 mg, 0.7637 mmol) in DMF (3 mL) to get the coupled product followed by deprotection using TBAF/THF (0.173/5 mL) to get the title compound (30 mg, 53.57%).

$^1$HNMR (CDCl$_3$, 400 MHz): δ 9.46 (s, 1H), 8.69-8.68 (d, 1H), 8.52 (s, 1H), 8.40 (s, 1H), 7.81 (s, 1H), 7.74-7.70 (d, 1H), 4.57 (s, 1H), 3.82-3.81 (m, 4H), 3.75-3.74 (m, 4H), 3.61-3.59 (m, 1H), 3.57-3.46 (m, 1H), 3.42-3.33 (m, 1H), 2.80-2.78 (d, 1H), 2.68 (s, 1H), 2.27-2.24 (m, 2H), 2.05-2.02 (m, 2H), 1.03-0.99 (m, 1H). LCMS: 100%, m/z=492.1 (M+1)$^+$. HPLC: 98.80%.

Example 105

(R)—N-(5-(3-hydroxypyrrolidin-1-yl)-2-morpholinooxazolo[4,5-b]pyridin-6-yl)-2-(6-methoxypyridin-3-yl)oxazole-4-carboxamide

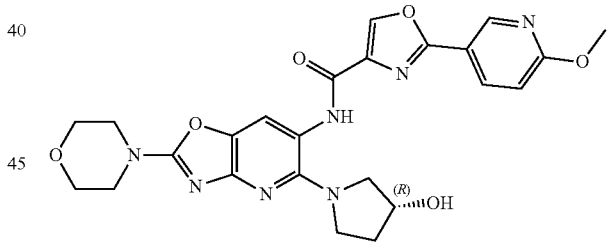

Using the same reaction conditions as described in step example 45, (R)-5-(3-((tert-butyldimethylsilyl)oxy)pyrrolidin-1-yl)-2-morpholinooxazolo[4,5-b]pyridin-6-amine (product of step 3 of example 41) (57 mg, 0.1357 mmol), was coupled with 2-(2-methoxypyridin-5-yl)oxazole-4-carboxylic acid (intermediate 7) (35 mg, 0.1628 mmol) using EDCI·HCl (38 mg, 0.2035 mmol), HOBt (27 mg, 0.2035 mmol), DIPEA (70 mg, 0.542 mmol) in DMF (5 mL) to get the coupled product followed by deprotection using TBAF/THF (0.144/5 mL) to get the title compound (10 mg, 20.44%).

$^1$HNMR (CDCl$_3$, 400 MHz): δ 9.47 (s, 1H), 8.89 (s, 1H), 8.55 (s, 1H), 8.33 (s, 1H), 8.22-8.20 (d, 1H), 6.88-6.86 (d, 1H), 4.56-4.45 (m, 1H), 4.02 (s, 3H), 3.82-3.81 (m, 4H), 3.75-3.74 (m, 4H), 3.65-3.47 (m, 3H), 2.35-2.26 (m, 2H), 2.20-2.01 (m, 2H). LCMS: 94.67%, m/z=507.7 (M+1)$^+$.

HPLC: 97.15%.

Example 106

N-(5-(3-hydroxypyrrolidin-1-yl)-2-morpholinooxazolo[4,5-b]pyridin-6-yl)-2-(6-methoxypyridin-3-yl)oxazole-4-carboxamide

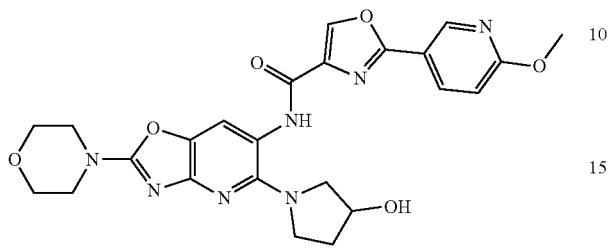

Using the same reaction conditions as described in step 6 of example 1, 5-(3-((tert-butyldimethylsilyl)oxy)pyrrolidin-1-yl)-2-morpholinooxazolo[4,5-b]pyridin-6-amine (product of step 3 of example 105) (90 mg, 0.2142 mmol), was coupled with 2-(2-methoxypyridin-5-yl)oxazole-4-carboxylic acid (intermediate 7) (56 mg, 0.2571 mmol) using EDCI·HCl (62 mg, 0.3214 mmol), HOBt (43 mg, 0.3214 mmol), DIPEA (110 mg, 0.8571 mmol) in DMF (3 mL) to get the coupled product followed by deprotection using TBAF/THF (0.144/5 mL) to get the title compound (15 mg, 31.25%).

$^1$HNMR (CDCl$_3$, 400 MHz): δ 9.47 (s, 1H), 8.89 (s, 1H), 8.55 (s, 1H), 8.33 (s, 1H), 8.22-8.20 (d, 1H), 6.88-6.86 (d, 1H), 4.56 (s, 1H), 4.02 (s, 3H), 3.83-3.81 (m, 4H), 3.75-3.73 (m, 4H), 3.55-3.45 (m, 4H), 2.94-2.93 (d, 1H), 2.30-2.25 (m, 1H), 2.09-2.01 (m, 1H). LCMS: 98.15%, m/z=507.7 (M+1)$^+$. HPLC: 98.95%.

Example 107

(S)—N-(5-(3-hydroxypyrrolidin-1-yl)-2-morpholinooxazolo[4,5-b]pyridin-6-yl)-5-(2-methylpyridin-4-yl)furan-2-carboxamide

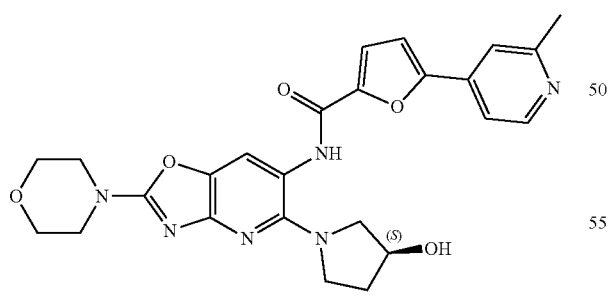

Using the same reaction conditions as described in example 45, (S)-5-(3-((tert-butyldimethylsilyl)oxy)pyrrolidin-1-yl)-2-morpholinooxazolo[4,5-b]pyridin-6-amine (product of step 2 of example 39) (109 mg, 0.261 mmol), was coupled with 5-(2-methylpyridin-4-yl)furan-2-carboxylic acid (intermediate 18) (53 mg, 0.261 mmol) using EDCI·HCl (75 mg, 0.3916 mmol), HOBt (37 mg, 0.2741 mmol), DIPEA (135 mg, 1.046 mmol) in DMF (5 mL) to get the coupled product followed by deprotection using TBAF/THF (1/5 mL) to get the title compound (26 mg, 41.2%).

$^1$HNMR (CD$_3$OD, 400 MHz): δ 8.49-8.47 (d, 1H), 7.85 (s, 1H), 7.74-7.72 (d, 1H), 7.70 (s, 1H), 7.40-7.39 (d, 1H), 7.33-7.32 (d, 1H), 4.45 (s, 1H), 3.83-3.77 (m, 4H), 3.74-3.69 (m, 4H), 3.49-3.47 (m, 1H), 3.42-3.40 (m, 1H), 3.21-3.16 (m, 1H), 2.61 (s, 3H), 2.09-2.07 (m, 1H), 1.89-1.86 (m, 1H), 1.88-1.72 (m, 1H), 1.43-1.37 (m, 1H). LCMS: 100%, m/z=491.2 (M+1)$^+$. HPLC: 97.91%.

Example 108

(S)—N-(5-(3-hydroxypyrrolidin-1-yl)-2-morpholinooxazolo[4,5-b]pyridin-6-yl)-5-(2-methylpyridin-4-yl)thiophene-2-carboxamide

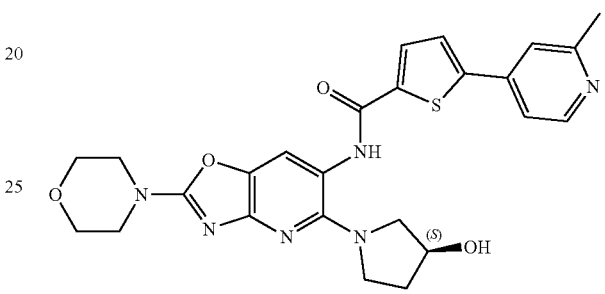

Using the same reaction conditions as described in example 45, (S)-5-(3-((tert-butyldimethylsilyl)oxy)pyrrolidin-1-yl)-2-morpholinooxazolo[4,5-b]pyridin-6-amine (product of step 2 of example 39) (109 mg, 0.261 mmol), was coupled with 5-(2-methylpyridin-4-yl)thiophene-2-carboxylic acid (intermediate 17) (57 mg, 0.261 mmol) using EDCI·HCl (75 mg, 0.3916 mmol), HOBt (37 mg, 0.2741 mmol), DIPEA (135 mg, 1.046 mmol) in DMF (5 mL) to get the coupled product followed by deprotection using TBAF/THF (1/5 mL) to get the title compound (55 mg, 66%).

$^1$HNMR (CD$_3$OD, 400 MHz): δ 8.46-8.45 (d, 1H), 7.93-7.92 (d, 1H), 7.76-7.75 (d, 1H), 7.65 (s, 1H), 7.61 (s, 1H), 7.57-7.56 (d, 1H), 4.43 (s, 1H), 3.83-3.75 (m, 4H), 3.72-3.68 (m, 6H), 3.51-3.50 (m, 1H), 3.42-3.36 (m, 1H), 2.60 (s, 3H), 2.07-2.05 (m, 1H), 1.93-1.92 (m, 1H). LCMS: 92.94%, m/z=507.2 (M+1)$^+$. HPLC: 96.09%.

Example 109

N-(5-(azetidin-1-yl)-2-(piperidin-1-yl)oxazolo[4,5-b]pyridin-6-yl)-2-(2-methylpyridin-4-yl)oxazole-4-carboxamide

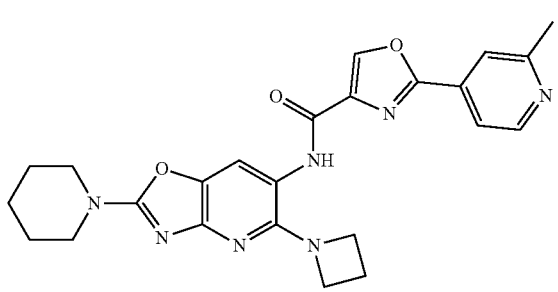 [SMILES: Cc1cc(-c2nc(C(=O)Nc3cc4oc(N5CCCCC5)nc4nc3N3CCC3)co2)ccn1]

121

Step 1: Preparation of 5-chloro-2-(piperidin-1-yl)oxazolo[4,5-b]pyridine

Using the same reaction conditions as described in step 3 of example 1, 5-chloro-2-(methylthio)oxazolo[4,5-b]pyridine (product of step 3 of example 2) (3 g) was substituted using piperidine (8 mL) and THF (30 mL) to afford the title compound (3 g, 90%).

LCMS: m/z=238.1 (M+1)$^+$.

Step 2: Preparation of 5-chloro-6-nitro-2-(piperidin-1-yl)oxazolo[4,5-b]pyridine Using the same reaction conditions as described in step 4 of example 20, 5-chloro-2-(piperidin-1-yl)oxazolo[4,5-b]pyridine (4 g, 168 mmol) was nitrated using potassium nitrate (3.4 g, 337 mmol) and conc. sulphuric acid (20 mL) at RT for 3 h to afford the crude title compound (4 g). LCMS: m/z=283.0 (M+1)$^+$.

Step 3: Preparation of 5-(azetidin-1-yl)-6-nitro-2-(piperidin-1-yl)oxazolo[4,5-b]pyridine Using the same reaction conditions as described in step t of example 38, 5-chloro-6-nitro-2-(piperidin-1-yl)oxazolo[4,5-b]pyridine (400 mg, 1.418 mmol) was substituted with azetidine hydrochloride (161 mg, 1.7021 mmol) using potassium carbonate (391 mg, 2.836 mmol) and THF (5 mL) to afford the crude product (300 mg). LCMS: m/z=304.3 (M+1)$^+$.

Step 4: Preparation of 5-(azetidin-1-yl)-2-(piperidin-1-yl)oxazolo[4,5-b]pyridin-6-amine Using the same reaction conditions as described in step 5 of example 1, 5-(azetidin-1-yl)-6-nitro-2-(piperidin-1-yl)oxazolo[4,5-b]pyridine (300 mg, 0.990 mmol) was reduced with zinc dust (514 mg, 7.92 mmol) and ammonium chloride (427 mg, 7.92 mmol) in THF/methanol/H$_2$O (10 mL/2 mL/1 mL) to get the crude product (200 mg). LCMS: m/z=274.1 (M+1)$^+$.

Step 5: Preparation of N-(5-(azetidin-1-yl)-2-(piperidin-1-yl)oxazolo[4,5-b]pyridin-6-yl)-2-(2-methylpyridin-4-yl)oxazole-4-carboxamide Using the same reaction conditions as described in step 6 of example 1, 5-(azetidin-1-yl)-2-(piperidin-1-yl)oxazolo[4,5-b]pyridin-6-amine (100 mg, 0.366 mmol) was coupled with 2-(2-methylpyridin-4-yl)oxazole-4-carboxylic acid (90 mg, 0.439 mmol) using HATU (208 mg, 0.549 mmol) and DIPEA (0.3 mL, 1.465 mmol) in DMF (5 mL) to afford the title compound (60 mg, 36%).

$^1$HNMR (DMSO-d$_6$, 400 MHz): δ 9.81 (s, 1H), 8.97 (s, 1H), 8.69-8.68 (d, 1H), 7.86 (s, 1H), 7.78-7.77 (d, 1H), 7.60 (s, 1H), 3.97-3.93 (t, 4H), 3.65-3.60 (m, 4H), 2.59 (s, 3H), 2.20-2.17 (t, 2H), 1.62 (s, 6H). LCMS: 97.60%, m/z=460.1 (M+1)$^+$. HPLC: 96.38%.

122

Example 110

N-(5-(azetidin-1-yl)-2-morpholinooxazolo[4,5-b]pyridin-6-yl)-2-(2-methylpyridin-4-yl)oxazole-4-carboxamide

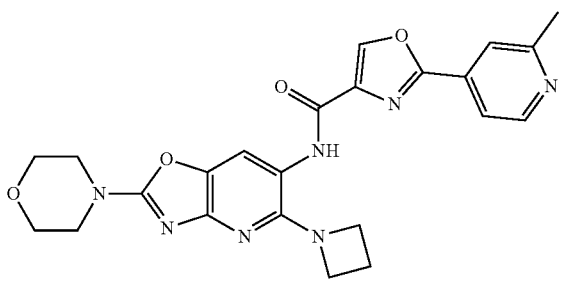

Step 1: Preparation of 5-(azetidin-1-yl)-2-morpholino-6-nitrooxazolo[4,5-b]pyridine Using the same reaction conditions as described in step 3 of example 1, 5-chloro-2-morpholino-6-nitrooxazolo[4,5-b]pyridine (product of step 5 of example 2) (200 mg, 0.701 mmol) was substituted with azetidine (81 mg, 0.140 mmol and THF (5 mL) at RT for 2 h to afford the title compound (160 mg, 73.39%). LCMS: m/z=306.1 (M+1)$^+$.

Step 2: Preparation of 5-(azetidin-1-yl)-2-morpholinooxazolo[4,5-b]pyridin-6-amine Using the same reaction conditions as described in step 5 of example 1, 5-(azetidin-1-yl)-2-morpholino-6-nitrooxazolo[4,5-b]pyridine (160 mg, 0.5245 mmol) was reduced with zinc dust (274 mg, 4.196 mmol) and ammonium chloride (448 mg, 8.393 mmol) in THF/methanol/H$_2$O (8 mL/2 mL/1 mL) to get the title product (138 mg, 95.83%). LCMS: m/z=274.1 (M−1)$^+$.

Step 3: Preparation of N-(5-(azetidin-1-yl)-2-morpholinooxazolo[4,5-b]pyridin-6-yl)-2-(2-methylpyridin-4-yl)oxazole-4-carboxamide Using the same reaction conditions as described in step 6 of example 1, 5-(azetidin-1-yl)-2-morpholinooxazolo[4,5-b]pyridin-6-amine (150 mg, 0.5454 mmol) was coupled with 2-(2-methylpyridin-4-yl)oxazole-4-carboxylic acid (166 mg, 0.818 mmol) using EDCI·HCl (156 mg, 0.818 mmol), HOBt (110 mg, 0.818 mmol) and DIPEA (282 mg, 2.1818 mmol) in DMF (5 mL) to afford the title compound (20 mg, 8.0%).

$^1$HNMR (CDCl$_3$, 400 MHz): δ 8.70-8.69 (d, 1H), 8.62 (s, 1H), 8.39 (s, 1H), 8.17 (s, 1H), 7.81 (s, 1H), 7.75-7.74 (d, 1H), 4.19-4.15 (t, 4H), 3.82-3.81 (m, 4H), 3.74-3.73 (m, 4H), 2.69 (s, 3H), 2.37-2.33 (t, 2H). LCMS: 83.88%, m/z=462.1 (M+1)$^+$. HPLC: 95.19%.

Example 111

2-(2-methylpyridin-4-yl)-N-(2-(piperidin-1-yl)-5-(pyrrolidin-1-yl)oxazolo[4,5-b]pyridin-6-yl)oxazole-4-carboxamide

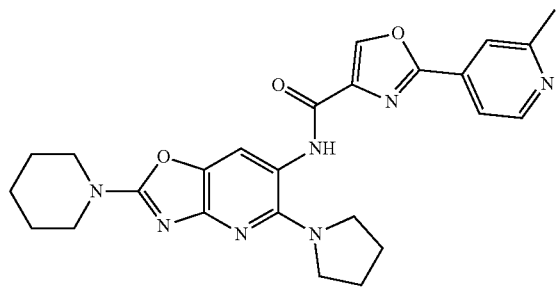

Step 1: Preparation of 6-nitro-2-(piperidin-1-yl)-5-(pyrrolidin-1-yl)oxazolo[4,5-b]pyridine Using the same reaction conditions as described in step 1 of example 38, 5-chloro-6-nitro-2-(piperidin-1-yl)oxazolo[4,5-b]pyridine (product of step 2 of example 110) (400 mg, 1.418 mmol) was substituted with pyrrolidine (120 mg, 1.7021 mmol) in THF (10 mL) to afford the crude product (300 mg). LCMS: m/z=318.2 (M+1)$^+$.

Step 2: Preparation of 2-(piperidin-1-yl)-5-(pyrrolidin-1-yl)oxazolo[4,5-b]pyridin-6-amine Using the same reaction conditions as described in step 5 of example 1, 6-nitro-2-(piperidin-1-yl)-5-(pyrrolidin-1-yl)oxazolo[4,5-b]pyridine (300 mg, 0.946 mmol) was reduced with zinc dust (492 mg, 7.57 mmol) and ammonium chloride (409 mg, 7.57 mmol) in THF/methanol/H$_2$O (5 mL/2 mL/1 mL) to get the crude product (200 mg). LCMS: m/z=288.1 (M+1)$^+$.

Step 3: Preparation of 2-(2-methylpyridin-4-yl)-N-(2-(piperidin-1-yl)-5-(pyrrolidin-1-yl)oxazolo[4,5-b]pyridin-6-yl)oxazole-4-carboxamide Using the same reaction conditions as described in step 6 of example 1, 2-(piperidin-1-yl)-5-(pyrrolidin-1-yl)oxazolo[4,5-b]pyridin-6-amine (100 mg, 0.348 mmol) was coupled with 2-(2-methylpyridin-4-yl)oxazole-4-carboxylic acid (80 mg, 0.418 mmol) using HATU (198 mg, 0.522 mmol) and DIPEA (0.3 mL, 1.393 mmol) in DMF (5 mL) to afford the title compound (140 mg, 86%).

$^1$HNMR (DMSO-d$_6$, 400 MHz): δ 9.80 (s, 1H), 8.97 (s, 1H), 8.69-8.68 (d, 1H), 7.85 (s, 1H), 7.77-7.76 (d, 1H), 7.66 (s, 1H), 3.61-3.60 (m, 4H), 3.39-3.34 (m, 4H), 2.59 (s, 3H), 1.83 (s, 4H), 1.62 (s, 6H). LCMS: 97.7%, m/z=474.2 (M+1)$^+$. HPLC: 95.05%.

Example 112

2-(2-methylpyridin-4-yl)-N-(2-morpholino-5-(pyrrolidin-1-yl)oxazolo[4,5-b]pyridin-6-yl)oxazole-4-carboxamide

Step 1: Preparation of 2-morpholino-6-nitro-5-(pyrrolidin-1-yl)oxazolo[4,5-b]pyridine Using the same reaction conditions as described in step 3 of example 1, 5-chloro-2-morpholino-6-nitrooxazolo[4,5-b]pyridine (product of step 5 of example 2) (200 mg, 0.701 mmol) was substituted with pyrrolidine (100 mg, 0.7403 mmol and THF (5 mL) at RT for 2 h to afford the title compound (160 mg, 71.11%). LCMS: m/z=320.1 (M+1)$^+$.

Step 2: Preparation of 2-morpholino-5-(pyrrolidin-1-yl)oxazolo[4,5-b]pyridin-6-amine Using the same reaction conditions as described in step 5 of example 1, 2-morpholino-6-nitro-5-(pyrrolidin-1-yl)oxazolo[4,5-b]pyridine (160 mg, 0.5015 mmol) was reduced with zinc dust (262 mg, 0.4012 mmol) and ammonium chloride (430 mg, 8.0250 mmol) in THF/methanol/H$_2$O (5 mL/2 mL/1 mL) to get the title product (130 mg, 92.85%).

Step 3: Preparation of 2-(2-methylpyridin-4-yl)-N-(2-morpholino-5-(pyrrolidin-1-yl)oxazolo[4,5-b]pyridin-6-yl)oxazole-4-carboxamide Using the same reaction conditions as described in step 6 of example 1, 2-morpholino-5-(pyrrolidin-1-yl)oxazolo[4,5-b]pyridin-6-amine (148 mg, 0.5172 mmol) was coupled with 2-(2-methylpyridin-4-yl)oxazole-4-carboxylic acid (158 mg, 0.7758 mmol) using EDCI·HCl (148 mg, 0.7758 mmol), HOBt (104 mg, 0.7758 mmol) and DIPEA (267 mg, 2.0689 mmol) in DMF (5 mL) to afford the title compound (80 mg, 33.05%).

$^1$HNMR (DMSO-d$_6$, 400 MHz): δ 9.82 (s, 1H), 8.96 (s, 1H), 8.69-8.68 (s, 1H), 7.85 (s, 1H), 7.77-7.76 (d, 1H), 7.69 (s, 1H), 3.73-3.72 (m, 4H), 3.69-3.68 (m, 4H), 3.62-3.59 (m, 4H), 2.59 (s, 3H), 1.84-1.81 (m, 4H). LCMS: 98.97%, m/z=476.2 (M+1)$^+$. HPLC: 99.34%.

Example 113

5-(2-methylpyridin-4-yl)-N-(2-morpholino-5-(piperidin-1-yl)oxazolo[4,5-b]pyridin-6-yl)furan-2-carboxamide

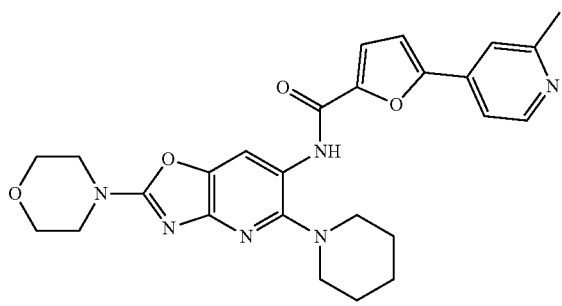

Using the same reaction conditions as described in step 6 of example 1, 2-morpholino-5-(piperidin-1-yl)oxazolo[4,5-b]pyridin-6-amine (product of step 2 of example 6) (70 mg, 0.3448 mmol), was coupled with 5-(2-methylpyridin-4-yl) furan-2-carboxylic acid (intermediate 18) using HATU (196 mg, 0.5172 mmol), DIPEA (134 mg, 1.034 mmol) in DMF (5 mL) to afford the crude product. The resultant crude was purified by 60-120 silica gel column chromatography using 2% methanol in DCM as eluent to obtain the title compound (46 mg, 29.8%).

$^1$HNMR (CDCl$_3$, 400 MHz): δ 9.85 (s, 1H), 8.79 (s, 1H), 8.58-8.56 (d, 1H), 7.59 (s, 1H), 7.44-7.43 (d, 1H), 7.34-7.33 (d, 1H), 7.02-7.01 (d, 1H), 3.84-3.81 (m, 4H), 3.76-3.74 (m, 4H), 3.07-3.04 (t, 4H), 2.64 (s, 3H), 1.88-1.85 (m, 4H), 1.69 (s, 2H). LCMS: 100%, m/z=489.2 (M+1)$^+$.
HPLC: 98.98%.

Example 114

N-(5-(4-hydroxypiperidin-1-yl)-2-morpholinooxazolo[4,5-b]pyridin-6-yl)-5-(2-methylpyridin-4-yl)furan-2-carboxamide

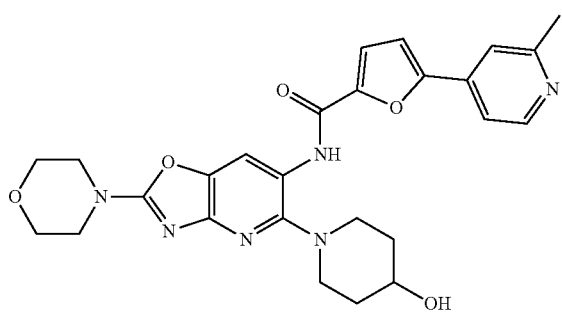

Step 1: Preparation of 1-(2-morpholino-6-nitrooxazolo[4,5-b]pyridin-5-yl)piperidin-4-ol Using the same reaction conditions as described in step 3 of example 1, 5-chloro-2-morpholino-6-nitrooxazolo[4,5-b]pyridine (product of step 5 of example 2) (250 mg, 0.8802 mmol) was substituted with piperidin-4-ol (178 mg, 1.760 mmol) and THF (10 mL) at RT for 2 h to afford the title compound (300 mg, 97.71%). LCMS: m/z=350.1 (M+1)$^+$.

Step 2: Preparation of 5-(4-((tert-butyldimethylsilyl)oxy)piperidin-1-yl)-2-morpholino-6-nitrooxazolo[4,5-b]pyridine Using the same reaction conditions as described in step 2 of example 41, 1-(2-morpholino-6-nitrooxazolo[4,5-b]pyridin-5-yl)piperidin-4-ol (300 mg, 0.859 mmol) was protected using TBDMS chloride (194 mg, 1.289 mmol) and imidazole (117 mg, 1.7191 mmol) and DMAP (21 mg, 1.719 mmol) in DMF (5 mL) at RT for 2 h to get the title compound (300 mg, 76%).
LCMS: m/z=464.2 (M+1)$^+$.

Step 3: Preparation of 5-(4-((tert-butyldimethylsilyl)oxy)piperidin-1-yl)-2-morpholinooxazolo[4,5-b]pyridin-6-amine Using the same reaction conditions as described in step 5 of example 1, 5-(3-((tert-butyldimethylsilyl)oxy)pyrrolidin-1-yl)-2-morpholino-6-nitrooxazolo[4,5-b]pyridine (300 mg, 0.6479 mmol) was reduced with zinc dust (330 mg, 5.183 mmol) and ammonium chloride (554 mg, 10.367 mmol) in THF/methanol/H$_2$O (10 mL/2 mL/1 mL) to get the title product (150 mg, 53.57%). LCMS: m/z=434.2 (M+1)$^+$.

Step 4: Preparation of N-(5-(4-hydroxypiperidin-1-yl)-2-morpholinooxazolo[4,5-b]pyridin-6-yl)-5-(2-methylpyridin-4-yl)furan-2-carboxamide Using the same reaction conditions as described in example 45, 5-(4-((tert-butyldimethylsilyl)oxy)piperidin-1-yl)-2-morpholinooxazolo[4,5-b]pyridin-6-amine (150 mg, 0.346 mmol), was coupled with 5-(2-methylpyridin-4-yl) furan-2-carboxylic acid (intermediate 18) (84 mg, 0.415 mmol) using HATU (171 mg, 0.4503 mmol) and DIPEA (178 mg, 1.385 mmol) in DMF (3 mL) to get the coupled product followed by deprotection using TBAF/THF (63 mg/5 mL) to get the title compound (40 mg, 50%).

$^1$HNMR (DMSO-d$_6$, 400 MHz): δ 9.62 (s, 1H), 8.55-8.54 (d, 1H), 8.37 (s, 1H), 7.74 (s, 1H), 7.68-7.67 (d, 1H), 7.48-7.45 (d, 2H), 4.80-4.79 (d, 1H), 3.73-3.63 (m, 8H), 3.20-3.17 (m, 3H), 2.86-2.81 (t, 2H), 2.56 (s, 3H), 1.91 (s, 2H), 1.67-1.65 (m, 2H). LCMS: 100%, m/z=505.2 (M+1)$^+$.
HPLC: 96.82%.

Example 115

(R)—N-(5-(3-hydroxypiperidin-1-yl)-2-morpholinooxazolo[4,5-b]pyridin-6-yl)-5-(2-methylpyridin-4-yl)furan-2-carboxamide

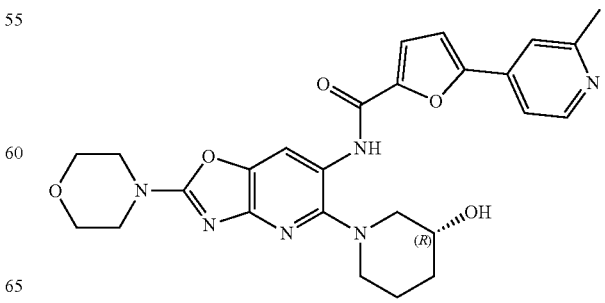

Step 1: Preparation of (R)-1-(2-morpholino-6-nitrooxazolo[4,5-b]pyridin-5-yl)piperidin-3-ol Using the same reaction conditions as described in step 3 of example 1, 5-chloro-2-morpholino-6-nitrooxazolo[4,5-b]pyridine (product of step 5 of example 2) (250 mg, 0.8802 mmol) was substituted with (R)-piperidin-3-ol (121 mg, 1.88 mmol) and THF (10 mL) at RT for 2 h to afford the title compound (230 mg, 74.91%). LCMS: m/z=350.1 (M+1)$^+$.

Step 2: Preparation of (R)-5-(3-((tert-butyldimethylsilyl)oxy)piperidin-1-yl)-2-morpholino-6-nitrooxazolo[4,5-b]pyridine Using the same reaction conditions as described in step 2 of example 41, (R)-1-(2-morpholino-6-nitrooxazolo[4,5-b]pyridin-5-yl)piperidin-3-ol (230 mg, 0.659 mmol) was protected using TBDMS chloride (149 mg, 0.9885 mmol) and imidazole (89 mg, 1.318 mmol) and DMAP (16 mg, 0.1318 mmol) in DMF (5 mL) at RT for 2 h to get the title compound (300 mg, 99.5%). LCMS: m/z=464.2 (M+1)$^+$.

Step 3: Preparation of (R)-5-(3-((tert-butyldimethylsilyl)oxy)piperidin-1-yl)-2-morpholinooxazolo[4,5-b]pyridin-6-amine Using the same reaction conditions as described in step 5 of example 1, (R)-5-(3-((tert-butyldimethylsilyl)oxy)piperidin-1-yl)-2-morpholino-6-nitrooxazolo[4,5-b]pyridine (300 mg, 0.6479 mmol) was reduced with zinc dust (330 mg, 5.183 mmol) and ammonium chloride (554 mg, 10.367 mmol) in THF/methanol/H$_2$O (10 mL/2 mL/1 mL) to get the title product (150 mg, 53.57%). LCMS: m/z=434.2 (M+1)$^+$.

Step 4: Preparation of (R)—N-(5-(3-hydroxypiperidin-1-yl)-2-morpholinooxazolo[4,5-b]pyridin-6-yl)-5-(2-methylpyridin-4-yl)furan-2-carboxamide Using the same reaction conditions as described in example 45, (R)-5-(3-((tert-butyldimethylsilyl)oxy)piperidin-1-yl)-2-morpholinooxazolo[4,5-b]pyridin-6-amine (150 mg, 0.346 mmol), was coupled with 5-(2-methylpyridin-4-yl)furan-2-carboxylic acid (intermediate 18) (84 mg, 0.415 mmol) using HATU (171 mg, 0.4503 mmol) and DIPEA (178 mg, 1.385 mmol) in DMF (3 mL) to get the coupled product followed by deprotection using TBAF/THF (63 mg/5 mL) to get the title compound (32 mg, 30.18%).

$^1$HNMR (DMSO-d$_6$, 400 MHz): δ +0.85 (s, 1H), 8.55-8.54 (d, 1H), 8.42 (s, 1H), 7.81 (s, 1H), 7.70-7.68 (d, 1H), 7.48-7.46 (m, 2H), 4.92-4.91 (d, 1H), 3.83 (s, 1H), 3.74-3.64 (m, 4H), 3.64-3.62 (m, 4H), 3.17-3.15 (m, 1H), 3.02-2.99 (m, 1H), 2.83-2.79 (m, 1H), 2.73-2.70 (m, 1H), 2.55 (s, 3H), 1.90-1.84 (m, 2H), 1.66-1.64 (m, 1H), 1.45-1.43 (m, 1H). LCMS: 98.47%, m/z=505.2 (M+1)$^+$. HPLC: 98.78%.

Example 116

N-(5-(furan-3-yl)-2-morpholinooxazolo[4,5-b]pyridin-6-yl)-2-(2-methylpyridin-4-yl)oxazole-4-carboxamide

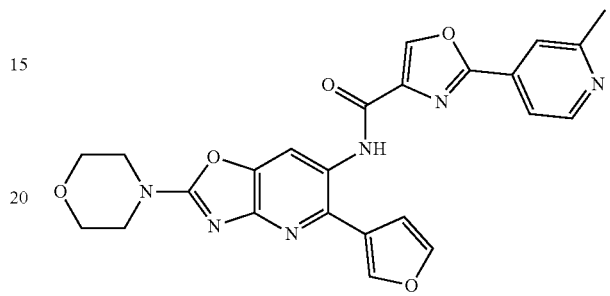

Step 1: Preparation of 5-(furan-3-yl)-2-morpholino-6-nitrooxazolo[4,5-b]pyridine Using the same reaction conditions as described in step 7 of example 1, 5-chloro-2-morpholino-6-nitrooxazolo[4,5-b]pyridine (product of step 5 of example 2) (300 mg, 1.0563 mmol) was coupled with furan-3-boronic acid (177 mg, 1.5845 mmol) using sodium iodide (237 mg, 1.5843 mmol) and Pd(dppf)Cl$_2$ (86 mg, 0.1056 mmol) in 1,2-dimethoxyethane/water (5/1 mL) to get the crude title compound (170 mg). LCMS: m/z=317.1 (M+1)$^+$.

Step 2: Preparation of 5-(furan-3-yl)-2-morpholinooxazolo[4,5-b]pyridin-6-amine Using the same reaction conditions as described in step 5 of example 1, 5-chloro-2-morpholino-6-nitrooxazolo[4,5-b]pyridine (170 mg, 0.5379 mmol) was reduced with zinc dust (281 mg, 4.303 mmol) and ammonium chloride (460 mg, 8.607 mmol) in THF/methanol/H$_2$O (10 mL/2 mL/1 mL) to get the title product (130 mg, 43.33%).

Step 3: Preparation of N-(5-(furan-3-yl)-2-morpholinooxazolo[4,5-b]pyridin-6-yl)-2-(2-methylpyridin-4-yl)oxazole-4-carboxamide Using the same reaction conditions as described in step 6 of example 1, 5-(furan-3-yl)-2-morpholinooxazolo[4,5-b]pyridin-6-amine (100 mg, 0.3496 mmol) was coupled with 2-(2-methylpyridin-4-yl)oxazole-4-carboxylic acid (106 mg, 0.5244 mmol) using HATU (172 mg, 0.4545 mmol) and DIPEA (180 mg) in DMF (5 mL) to afford the title compound (70 mg, 42.42%).

$^1$HNMR (DMSO-d$_6$, 400 MHz): δ 10.19 (s, 1H), 9.02 (s, 1H), 8.71-8.69 (d, 1H), 8.14 (s, 1H), 7.94-7.87 (d, 2H), 7.79-7.75 (m, 2H), 7.01 (s, 1H), 3.76-3.65 (m, 8H), 2.60 (s, 3H). LCMS: 100%, m/z=473.1 (M+1)$^+$. HPLC: 95.76%.

Example 117

N-(5-(3-fluoropiperidin-1-yl)-2-morpholinooxazolo[4,5-b]pyridin-6-yl)-2-(2-methylpyridin-4-yl)oxazole-4-carboxamide

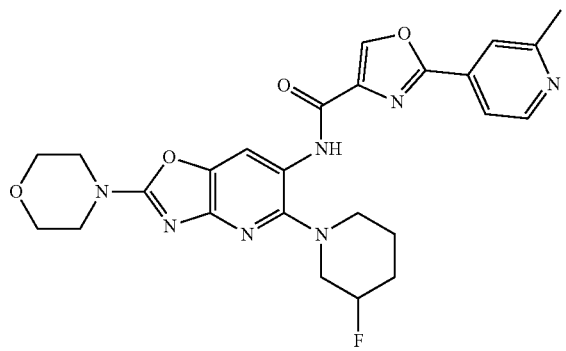 [SMILES: Cc1cc(-c2nc(C(=O)Nc3cc4oc(N5CCOCC5)nc4nc3N3CCCC(F)C3)co2)ccn1]

Step 1: Preparation of 1-(2-morpholino-6-nitrooxazolo[4,5-b]pyridin-5-yl)piperidin-3-ol Using the same reaction conditions as described in step 3 of example 1, 5-chloro-2-morpholino-6-nitrooxazolo[4,5-b]pyridine (product of step 5 of example 2) (300 mg, 1.056 mmol) was substituted with piperidin-3-ol (211 mg, 2.110 mmol) and THF (5 mL) at RT for 14 h to afford the title compound (298 mg, 81%). LCMS: m/z=350.3 (M+1)+.

Step 2: Preparation of 5-(3-fluoropiperidin-1-yl)-2-morpholino-6-nitrooxazolo[4,5-b]pyridine Using the same reaction conditions as described in step 2 of example 59, 1-(2-morpholino-6-nitrooxazolo[4,5-b]pyridin-5-yl)piperidin-3-ol (270 mg, 0.7736 mmol) was fluorinated using DAST (218 mg, 1.353 mmol) in DCM (20 mL) at −78° C. for 1 h to obtain the title compound (240 mg, 88.4%).

Step 3: Preparation of 5-(3-fluoropiperidin-1-yl)-2-morpholinooxazolo[4,5-b]pyridin-6-amine Using the same reaction conditions as described in step 5 of example 1, 5-(3-fluoropiperidin-1-yl)-2-morpholino-6-nitrooxazolo[4,5-b]pyridine (230 mg, 0.6552 mmol) was reduced with zinc dust (340 mg, 5.24 mmol) and ammonium chloride (555 mg, 10.48 mmol) in THF/water (20/5 mL) to get the title compound (145 mg, 69%).

Step 4: Preparation of N-(5-(3-fluoropiperidin-1-yl)-2-morpholinooxazolo[4,5-b]pyridin-6-yl)-2-(2-methylpyridin-4-yl)oxazole-4-carboxamide Using the same reaction conditions as described in step 6 of example 1, 5-(3-fluoropiperidin-1-yl)-2-morpholinooxazolo[4,5-b]pyridin-6-anine (120 mg, 0.3738 mmol) was coupled with 2-(2-methylpyridin-4-yl)oxazole-4-carboxylic acid (95 mg, 0.4672 mmol) using HATU (213 mg, 0.5605 mmol) and DIPEA (193 mg) in DMF (5 mL) to afford the crude compound. This was then purified by prep TLC using 3.5% methanol in chloroform to obtain the title compound (81 mg, 34%).

1HNMR (DMSO-d6, 300 MHz): δ 9.86 (s, 1H), 9.05 (s, 1H), 8.70-8.68 (d, 1H), 8.62 (s, 1H), 7.85 (s, 1H), 7.75-7.74 (d, 1H), 5.10-4.90 (d, 1H), 3.73-3.70 (t, 4H), 3.62-3.61 (t, 4H), 3.26-3.10 (m, 2H), 2.80-2.90 (m, 2H), 2.57 (s, 3H), 2.20-1.70 (m, 4H). LCMS: 100%, m/z=508.0 (M+1)+. HPLC: 99.27%.

Example 118

N-(5-(4-hydroxypiperidin-1-yl)-2-morpholinooxazolo[4,5-b]pyridin-6-yl)-2-(2-methylpyridin-4-yl)oxazole-4-carboxamide

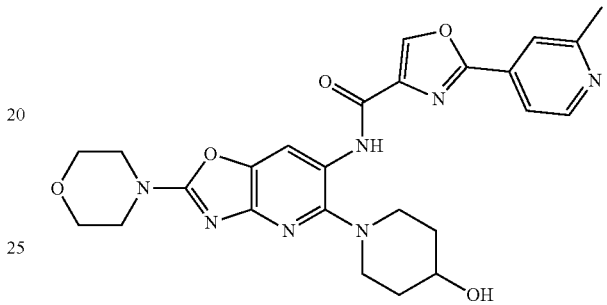

Using the same reaction conditions as described in example 45, 5-(4-((tert-butyldimethylsilyl)oxy)piperidin-1-yl)-2-morpholinooxazolo[4,5-b]pyridin-6-amine (product of step 3 of example 115) (140 mg, 0.3233 mmol), was coupled with 2-(2-methylpyridin-4-yl)oxazole-4-carboxylic acid (66 mg, 0.3233 mmol) using HATU (185 mg, 0.4868 mmol) and DIPEA (167 mg, 1.295 mmol) in DMF (5 mL) to get the coupled product followed by deprotection using methanol/MeOH. HCl (5/5 mL) to get the title compound (127 mg, 88%).

1HNMR (DMSO-d6, 300 MHz): δ 9.90 (s, 1H), 9.00 (s, 1H), 8.66-8.64 (d, 1H), 8.58 (s, 1H), 7.83 (s, 1H), 7.74-7.72 (d, 1H), 4.90 (s, 1H), 3.71-3.70 (m, 5H), 3.61-3.59 (d, 4H), 3.12-3.08 (m, 2H), 2.85-2.78 (t, 2H), 2.57 (s, 3H), 1.99-1.96 (m, 2H), 1.79-1.76 (m, 2H). LCMS: 100%, m/z=506.1 (M+1)+. HPLC: 98.00%.

Example 119

N-(5-(4-fluoropiperidin-1-yl)-2-morpholinooxazolo[4,5-b]pyridin-6-yl)-2-(2-methylpyridin-4-yl)oxazole-4-carboxamide

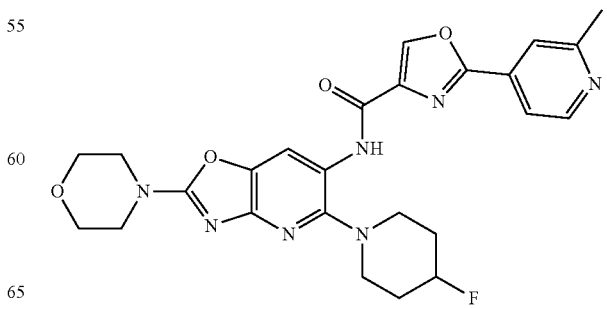

Step 1: Preparation of 5-(4-fluoropiperidin-1-yl)-2-morpholino-6-nitrooxazolo[4,5-b]pyridine Using the same reaction conditions as described in step 2 of example 59, 1-(2-morpholino-6-nitrooxazolo[4,5-b]pyridin-5-yl)piperidin-4-ol (product of step 1 of example 115) (200 mg, 0.5730 mmol) was fluorinated using DAST (161 mg, 1.002 mmol) in DCM (20 mL) at −78° C. for 1 h to obtain the title compound (191 mg, 95%). LCMS: m/z=352.1 (M+1)⁺.

Step 2: Preparation of 5-(4-fluoropiperidin-1-yl)-2-morpholinooxazolo[4,5-b]pyridin-6-amine Using the same reaction conditions as described in step 5 of example 1, 5-(4-fluoropiperidin-1-yl)-2-morpholino-6-nitrooxazolo[4,5-b]pyridine (190 mg, 0.5413 mmol) was reduced with zinc dust (281 mg, 4.33 mmol) and ammonium chloride (460 mg, 8.66 mmol) in THF/water (20/5 mL) to get the title product (90 mg, 52%).

Step 3: Preparation of N-(5-(4-fluoropiperidin-1-yl)-2-morpholinooxazolo[4,5-b]pyridin-6-yl)-2-(2-methylpyridin-4-yl)oxazole-4-carboxamide Using the same reaction conditions as described in step 6 of example 1, 5-(4-fluoropiperidin-1-yl)-2-morpholinooxazolo[4,5-b]pyridin-6-amine (85 mg, 0.2647 mmol) was coupled with 2-(2-methylpyridin-4-yl)oxazole-4-carboxylic acid (67 mg, 0.328 mmol) using HATU (149 mg, 0.394 mmol) and DIPEA (135 mg, 1.050 mmol) in DMF (5 mL) to afford the crude compound. This was then purified by prep TLC using 3.5% methanol in chloroform to obtain the title compound (81 mg, 34%).
¹HNMR (CDCl₃, 300 MHz): δ 10.00 (s, 1H), 8.76 (s, 1H), 8.70-8.69 (d, 1H), 8.39 (s, 1H), 7.82 (s, 1H), 7.71-7.69 (dd, 1H), 5.00-4.70 (m, 1H), 3.84-3.81 (t, 4H), 3.76-3.73 (t, 4H), 3.29-3.21 (m, 2H), 3.10-3.05 (m, 2H), 2.67 (s, 3H), 2.27-2.18 (m, 4H). LCMS: 100%, m/z=508.3 (M+1)⁺.
HPLC: 90.17%.

Example 120

(S)—N-(5-(3-aminopiperidin-1-yl)-2-morpholinothiazolo[4,5-b]pyridin-6-yl)-2-(2-methylpyridin-4-yl)oxazole-4-carboxamide Hydrochloride Step 1: Preparation of tert-butyl (S)-(1-(2-morpholino-6-nitrothiazolo[4,5-b]pyridin-5-yl)piperidin-3-yl)carbamate Using the same reaction conditions as described in step 1 of example 38, 4-(5-chloro-6-nitrothiazolo[4,5-b]pyridin-2-yl)morpholine (product of step 4 of example 20) (200 mg, 0.66 mol) was substituted with tert-butyl (S)-piperidin-3-ylcarbamate (199 mg, 0.99 mmol) using potassium carbonate (276 mg, 1.99 mmol) and THF (10 mL) to afford the crude product which was taken as such for next step.

Step 2: Preparation of tert-butyl (S)-(1-(6-amino-2-morpholinothiazolo[4,5-b]pyridin-5-yl)piperidin-3-yl)carbamate Using the same reaction conditions as described in step 5 of example 1, crude tert-butyl (S)-(1-(2-morpholino-6-nitrothiazolo[4,5-b]pyridin-5-yl)piperidin-3-yl)carbamate was reduced with zinc dust (338 mg, 5.1724 mmol) and ammonium chloride (553 mg, 10.344 mmol) in THF/methanol/H₂O (10 mL/2 mL/1 mL) to get the title compound (180 mg, 64.48%). LCMS: m/z=435.4 (M+1)⁺.

Step 3: Preparation of tert-butyl (S)-(1-(6-(2-(2-methylpyridin-4-yl)oxazole-4-carboxamido)-2-morpholinothiazolo[4,5-b]pyridin-5-yl)piperidin-3-yl)carbamate Using the similar reaction conditions as described in step 6 of example 1, tert-butyl (S)-(1-(6-amino-2-morpholinothiazolo[4,5-b]pyridin-5-yl)piperidin-3-yl)carbamate (450 mg, 0.464 mmol), was coupled with 2-(2-methylpyridin-4-yl)oxazole-4-carboxylic acid (296 mg, 1.4547 mmol) using HATU (479 mg, 1.2607 mmol) and DIPEA (501 mg, 3.8793 mmol) in DMF (5 mL) to get the title compound (400 mg, 66.66%). LCMS: m/z=621.4 (M+1)⁺.

Step 4: Preparation of (S)—N-(5-(3-aminopiperidin-1-yl)-2-morpholinothiazolo[4,5-b]pyridin-6-yl)-2-(2-methylpyridin-4-yl)oxazole-4-carboxamide Hydrochloride Using the same reaction conditions as described in step 8 of example 1, tert-butyl (S)-(1-(6-(2-(2-methylpyridin-4-yl)oxazole-4-carboxamido)-2-morpholinothiazolo[4,5-b]pyridin-5-yl)piperidin-3-yl)carbamate (400 mg, 0.6451 mmol) was deprotected using methanolic HCl/methanol (5/5 mL) to get the title compound (100 mg, 94.33%).
¹HNMR (DMSO-d₆, 400 MHz): δ 9.71 (s, 1H), 9.24 (s, 1H), 8.85-8.83 (d, 1H), 8.75 (s, 1H), 8.26 (s, 2H), 8.13 (s, 1H), 8.05-8.03 (d, 1H), 3.75-3.73 (m, 5H), 3.42-3.39 (m, 4H), 3.16-3.04 (m, 3H), 2.90-2.80 (m, 2H), 2.72 (s, 3H), 2.04-1.90 (m, 3H), 1.79-1.69 (m, 2H). LCMS: 86.06%, m/z=521.4 (M+1)⁺. HPLC: 98.61%.

Example 121

2-(2-methylpyridin-4-yl)-N-(2-morpholino-5-(1H-pyrazol-4-yl)thiazolo[4,5-b]pyridin-6-yl)oxazole-4-carboxamide

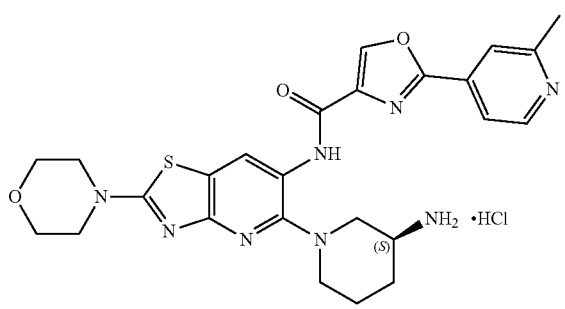

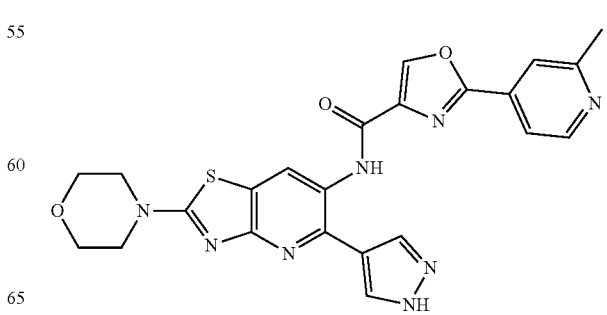

Step 1: Preparation of 4-(6-nitro-5-(1-(tetrahydro-2H-pyran-2-yl)-1H-pyrazol-4-yl)thiazolo[4,5-b]pyridin-2-yl)morpholine Using the same reaction conditions as described in step 7 of example 1, 4-(5-chloro-6-nitrothiazolo[4,5-b]pyridin-2-yl)morpholine (product of step 4 of example 20) (250 mg, 0.833 mmol) was coupled with 1-(tetrahydro-2H-pyran-2-yl)-4-(4,4,5,5-tetramethyl-1,3,2-dioxaborolan-2-yl)-1H-pyrazole (579 mg, 2.083 mmol) using sodium iodide (375 mg, 2.5 mmol), potassium carbonate (345 mg, 2.5 mmol) and Pd(dppf)Cl$_2$ (304 mg, 0.4166 mmol) in 1,2-dimethoxyethane/water (5/1 mL) to get the title compound (150 mg, 43.35%). LCMS: m/z=417.15 (M+1)$^+$.

Step 2: Preparation of 2-morpholino-5-(1-(tetrahydro-2H-pyran-2-yl)-1H-pyrazol-4-yl)thiazolo[4,5-b]pyridin-6-amine Using the same reaction conditions as described in step 5 of example 1, 4-(6-nitro-5-(1-(tetrahydro-2H-pyran-2-yl)-1H-pyrazol-4-yl)thiazolo[4,5-b]pyridin-2-yl)morpholine (150 mg, 0.360 mmol) was reduced with zinc dust (188 mg, 2.8846 mmol) and ammonium chloride (308 mg, 5.769 mmol) in THF/water (5/1 mL) to get the crude product (110 mg, 79.23%). LCMS: m/z=387.2 (M+1)$^+$.

Step 3: Preparation of 2-(2-methylpyridin-4-yl)-N-(2-morpholino-5-(1H-pyrazol-4-yl)thiazolo[4,5-b]pyridin-6-yl)oxazole-4-carboxamide Using the same reaction conditions as described in example 45, 2-morpholino-5-(1-(tetrahydro-2H-pyran-2-yl)-1H-pyrazol-4-yl)thiazolo[4,5-b]pyridin-6-amine (130 mg, 0.336 mmol), was coupled with 2-(2-methylpyridin-4-yl)oxazole-4-carboxylic acid (103 mg, 0.505 mmol) using HATU (166 mg, 0.4378 mmol) and DIPEA (174 mg, 1.347 mmol) in DMF (5 mL) to get the coupled product followed by deprotection using methanol/MeOH HCl (2/5 mL) to get the title compound (75 mg, 67.56%).

$^1$HNMR (DMSO-d$_6$, 400 MHz): δ 13.0 (s, 1H), 10.18 (s, 1H), 9.02 (s, 1H), 8.69-8.68 (d, 1H), 8.31 (s, 1H), 8.20-8.00 (bs, 2H), 7.87 (s, 1H), 7.79-7.78 (d, 1H), 3.76-3.64 (m, 8H), 2.60 (s, 3H).

LCMS: 100%, m/z=489.3 (M+1)$^+$. HPLC: 95.64%.

Example 122

N-(5-(6-fluoropyridin-3-yl)-2-morpholinothiazolo[4,5-b]pyridin-6-yl)-2-(2-methylpyridin-4-yl)oxazole-4-carboxamide

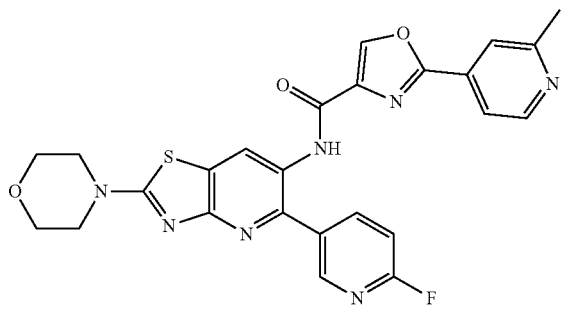 [SMILES: Cc1cc(-c2nc(C(=O)Nc3cc4sc(N5CCOCC5)nc4nc3-c3ccc(F)nc3)co2)ccn1]

Step 1: Preparation of 4-(5-(6-fluoropyridin-3-yl)-6-nitrothiazolo[4,5-b]pyridin-2-yl)morpholine Using the same reaction conditions as described in step 7 of example 1, 4-(5-chloro-6-nitrothiazolo[4,5-b]pyridin-2-yl)morpholine (product of step 4 of example 20) (200 mg, 0.666 mmol) was coupled with (6-fluoropyridin-3-yl)boronic acid (234 mg, 1.66 mmol) using sodium iodide (299 mg, 1.99 mmol), potassium carbonate (276 mg, 1.99 mmol) and Pd(dppf)Cl$_2$ (243 mg, 0.333 mmol) in 1,2-dimethoxyethane/water (5/1 mL) to get the title compound (152 mg, 63.33%).

Step 2: Preparation of 5-(6-fluoropyridin-3-yl)-2-morpholinothiazolo[4,5-b]pyridin-6-amine Using the same reaction conditions as described in step 5 of example 1, 4-(5-(6-fluoropyridin-3-yl)-6-nitrothiazolo[4,5-b]pyridin-2-yl)morpholine (152 mg, 0.4210 mmol) was reduced with zinc dust (220 mg, 3.368 mmol) and ammonium chloride (360 mg, 6.736 mmol) in THF/water (5/1 mL) to get the crude product (150 mg). LCMS: m/z=331.9 (M+1)$^+$.

Step 3: Preparation of N-(5-(6-fluoropyridin-3-yl)-2-morpholinothiazolo[4,5-b]pyridin-6-yl)-2-(2-methylpyridin-4-yl)oxazole-4-carboxamide Using the similar reaction conditions as described in step 6 of example 1, crude 5-(6-fluoropyridin-3-yl)-2-morpholinothiazolo[4,5-b]pyridin-6-amine (150 mg, 0.4531 mmol), was coupled with 2-(2-methylpyridin-4-yl)oxazole-4-carboxylic acid (138 mg, 6.797 mmol) using HATU (223 mg, 0.589 mmol) and DIPEA (234 mg, 1.812 mmol) in DMF (5 mL) to get the title compound (110 mg, 47%).

$^1$HNMR (DMSO-d$_6$, 400 MHz): δ 10.4 (s, 1H), 8.91 (s, 1H), 8.74 (s, 1H), 8.68-8.66 (d, 1H), 8.589-8.582 (d, 1H), 8.427 (s, 1H), 8.00-7.98 (d, 1H), 7.82 (s, 1H), 7.74-7.73 (d, 1H), 3.76-3.75 (t, 4H), 3.67-3.66 (t, 4H), 2.58 (s, 3H). LCMS: 79.07%, m/z=518.3 (M+1)$^+$. HPLC: 95.64%.

Example 123

N-(5-(3-hydroxy-8-azabicyclo[3.2.1]octan-8-yl)-2-morpholinothiazolo[4,5-b]pyridin-6-yl)-2-(2-methylpyridin-4-yl)oxazole-4-carboxamide

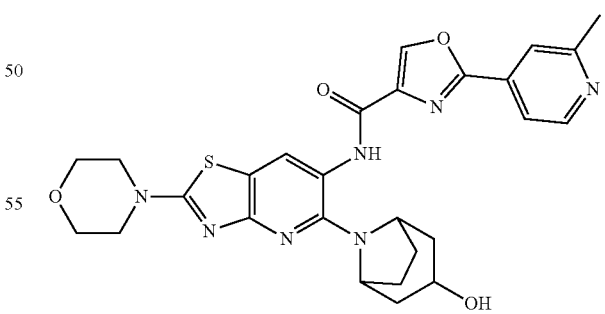

Step 1: Preparation of 8-(2-morpholino-6-nitrothiazolo[4,5-b]pyridin-5-yl)-8-azabicyclo[3.2.1]octan-3-ol Using the same reaction conditions as described in step 1 of example 38, 4-(5-chloro-6-nitrothiazolo[4,5-b]pyridin-2- yl)morpholine (product of step 4 of example 20) (300 mg, 1 mmol) was substituted with 8-azabicyclo[3.2.1]octan-3-ol hydrochloride (195 mg, 1.2 mmol) using potassium carbonate (552 mg, 4 mmol) and DMF (5 mL) to afford the title product (360 mg, 92.3%). LCMS: m/z=392.1 (M+1)⁺.

Step 2: Preparation of 8-(6-amino-2-morpholinothiazolo[4,5-b]pyridin-5-yl)-8-azabicyclo[3.2.1]octan-3-ol Using the same reaction conditions as described in step 2 of example 38, 8-(2-morpholino-6-nitrothiazolo[4,5-b]pyridin-5-yl)-8-azabicyclo[3.2.1]octan-3-ol (350 mg, 0.8951 mmol) was reduced with zinc dust (468 mg, 7.161 mmol) and ammonium chloride (766 mg, 14.321 mmol) in THF/water (10/2 mL) to get the title compound (280 mg, 86.68%). LCMS: m/z=362.1 (M+1)⁺.

Step 3: Preparation of N-(5-(3-hydroxy-8-azabicyclo[3.2.1]octan-8-yl)-2-morpholinothiazolo[4,5-b]pyridin-6-yl)-2-(2-methylpyridin-4-yl)oxazole-4-carboxamide Using the same reaction conditions as described in step 6 of example 1, 8-(6-amino-2-morpholinothiazolo[4,5-b]pyridin-5-yl)-8-azabicyclo[3.2.1]octan-3-ol (100 mg, 0.2770 mmol), was coupled with 2-(2-methylpyridin-4-yl)oxazole-4-carboxylic acid (85 mg, 0.4155 mmol) using HATU (136 mg, 0.3601 mmol) and DIPEA (143 mg, 1.108 mmol) in DMF (5 mL) to get the title compound (120 mg, 79.47%).
¹HNMR (DMSO-d₆, 400 MHz): δ 9.52 (s, 1H), 9.08 (s, 1H), 8.78 (s, 1H), 8.71-8.70 (d, 1H), 7.81 (s, 1H), 7.73-7.72 (s, 1H), 4.568-4.563 (d, 1H), 4.10 (s, 1H), 4.03 (s, 2H), 3.74-3.72 (t, 4H), 3.58-3.55 (m, 4H), 2.59 (s, 3H), 2.42-2.39 (m, 2H), 2.20-2.18 (m, 2H), 1.94-1.93 (m, 2H), 1.83-1.80 (m, 2H). LCMS: 100%, m/z=548.5 (M+1)⁺. HPLC: 95.67%.

Example 124

N-(2-(3-hydroxypiperidin-1-yl)-5-(piperidin-1-yl)thiazolo[4,5-b]pyridin-6-yl)-2-(2-methylpyridin-4-yl)oxazole-4-carboxamide

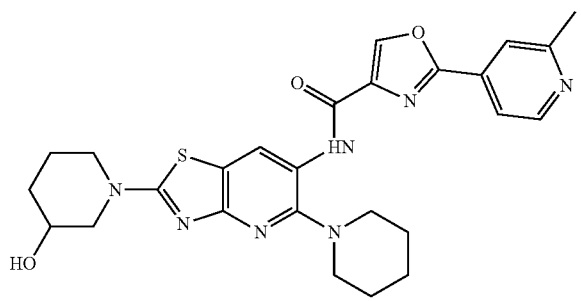 [SMILES: Cc1cc(-c2nc(C(=O)Nc3cc4sc(N5CCCC(O)C5)nc4nc3N3CCCCC3)co2)ccn1]

Step 1: Preparation of 6-bromo-5-chlorothiazolo[4,5-b]pyridine-2-thiol

Using the same reaction conditions as described in step 1 of example 1, 3,5-dibromo-6-chloropyridin-2-amine (3 g, 10.489 mmol) was cyclised using potassium ethyl xanthate (3 g, 18.881 mmol) in DMF (50 mL) at 155° C. for 3 h to afford the title product (2.95 g, 100%). LCMS: m/z=280.8 (M-1)⁺.

Step 2: Preparation of 6-bromo-5-chloro-2-(methylthio)thiazolo[4,5-b]pyridine

Using the same reaction conditions as described in step 2 of example 1, 6-bromo-5-chlorothiazolo[4,5-b]pyridine-2-thiol (3 g, 10.676 mmol) was methylated using potassium carbonate (2.94 g, 21.352 mmol) and methyl iodide (2.29 g, 16.014 mmol) in ethyl acetate (100 mL) to afford the title compound (3.16 g, 100%). LCMS: m/z=296.7 (M+1)⁺.

Step 3: Preparation of 2-(3-(benzyloxy)piperidin-1-yl)-6-bromo-5-chlorothiazolo[4,5-b]pyridine Using the same reaction conditions as described in step 1 of example 38, 6-bromo-5-chloro-2-(methylthio)thiazolo[4,5-b]pyridine (500 mg, 1.689 mmol) was substituted with 3-(benzyloxy)piperidine hydrochloride (322 mg, 1.689 mmol) using potassium carbonate (932 mg, 6.756 mmol) and THF (5 mL) at 85° C. for 14 h to afford the crude product. The crude product was purified by using 60-120 silica-gel column chromatography and compound was eluted using 30% ethyl acetate in hexane as eluent to afford the title compound (280 mg, 37.8%). LCMS: m/z=438.2 (M)⁺.

Step 4: Preparation of 2-(3-(benzyloxy)piperidin-1-yl)-6-bromo-5-(piperidin-1-yl)thiazolo[4,5-b]pyridine Using the same reaction conditions as described in step 1 of example 6,2-(3-(benzyloxy)piperidin-1-yl)-6-bromo-5-chlorothiazolo[4,5-b]pyridine (280 mg, 0.639 mmol) was substituted using piperidine (1 mL) in THF (1 mL) 125° C. for 14 h to obtain the crude product (280 mg). LCMS: m/z=489.1 (M+2)⁺.

Step 5: Preparation of N-(2-(3-(benzyloxy)piperidin-1-yl)-5-(piperidin-1-yl)thiazolo[4,5-b]pyridin-6-yl)-2-(2-methylpyridin-4-yl)oxazole-4-carboxamide To the solution of 2-(3-(benzyloxy)piperidin-1-yl)-6-bromo-5-(piperidin-1-yl)thiazolo[4,5-b]pyridine (50 mg, 0.102 mmol), 2-(2-methylpyridin-4-yl)oxazole-4-carboxamide (31 mg, 0.154 mmol) (intermediate 23) and potassium phosphate (65 mg, 0.306 mmol) in 1,4-dioxane (4 mL) was added copper iodide (2 mg, 0.01 mmol) and trans-N1,N2-dimethylcyclohexane-1,2-diamine (5 mg, 0.030 mmol) and heated at 110° C. for 14 h. The solvent was distilled out and purified by 60-120 silica gel column chromatography using 5% methanol in DCM as eluent to obtain the title compound (40 mg, 64.5%). LCMS: m/z=610.3 (M+1)⁺.

Step 6: Preparation of N-(2-(3-hydroxypiperidin-1-yl)-5-(piperidin-1-yl)thiazolo[4,5-b]pyridin-6-yl)-2-(2-methylpyridin-4-yl)oxazole-4-carboxamide Using the similar reaction conditions as described in step 8 of example 1, N-(2-(3-(benzyloxy)piperidin-1-yl)-5-(piperidin-1-yl)thiazolo[4,5-b]pyridin-6-yl)-2-(2-methylpyridin-4-yl)oxazole-4-carboxamide (200 mg, 0.328 mmol) was deprotected using TFA (5 mL) and toluene (1 mL) at 110° C. for 14 h to afford the crude product. The resultant crude was purified by prep HPLC to obtain the title compound (50 mg, 29.4%).
¹HNMR (CDCl₃, 300 MHz): δ 9.90 (s, 1H), 9.00 (s, 1H), 8.70-8.69 (d, 1H), 8.39 (s, 1H), 7.83 (s, 1H), 7.74-7.25 (s, 1H), 4.05-3.94 (m, 2H), 3.85-3.70 (m, 1H), 3.53-3.51 (m, 2H), 3.14-3.10 (t, 4H), 2.67 (s, 3H), 1.92-1.58 (m, 11H). LCMS: 96.10%, m/z=520.4 (M+1)⁺. HPLC: 97.47%.

Example 125

2-(2-acetamidopyridin-4-yl)-N-(5-(4-hydroxypiperidin-1-yl)-2-morpholinothiazolo[4,5-b]pyridin-6-yl)oxazole-4-carboxamide

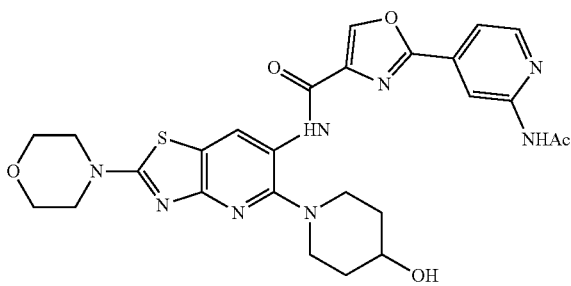 [SMILES: CC(=O)Nc1cc(-c2nc(C(=O)Nc3cc4sc(N5CCOCC5)nc4nc3N3CCC(O)CC3)co2)ccn1]

Using the same reaction conditions as described in example 45, 5-(4-((tert-butyldimethylsilyl)oxy)piperidin-1-yl)-2-morpholinothiazolo[4,5-b]pyridin-6-amine (product of step 3 of example 85) (155 mg, 0.3452 mmol), was coupled with 2-(2-acetamidopyridin-4-yl)oxazole-4-carboxylic acid (intermediate 20) (106 mg, 0.4315 mmol) using HATU (197 mg, 0.5188 mmol) and DIPEA (179 mg, 1.3835 mmol) in DMF (5 mL) to get the crude compound followed by deprotection using TBAF/THF (1/10 mL) to get the title compound (42 mg, 46%).

¹HNMR (CDCl₃, 300 MHz): δ 9.10 (s, 1H), 8.60 (s, 1H), 8.32-8.31 (d, 1H), 7.42-7.41 (d, 1H), 7.33-7.32 (d, 1H), 7.07-7.06 (d, 1H), 3.18 (s, 4H), 3.69-3.67 (m, 4H), 3.30-3.26 (m, 2H), 3.09-3.01 (t, 2H), 2.26 (s, 3H), 2.19-2.16 (m, 2H), 2.00-1.87 (m, 4H). LCMS: 96.40%, m/z=564.4 (M+1)⁺. HPLC: 96.95%.

Example 126

N-(2-(3-hydroxypiperidin-1-yl)-5-(4-hydroxypiperidin-1-yl)thiazolo[4,5-b]pyridin-6-yl)-2-(2-methylpyridin-4-yl)oxazole-4-carboxamide

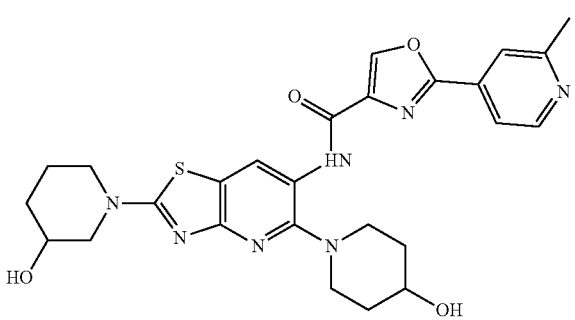 [SMILES: Cc1cc(-c2nc(C(=O)Nc3cc4sc(N5CCCC(O)C5)nc4nc3N3CCC(O)CC3)co2)ccn1]

Step 1: Preparation of 1-(2-(3-(benzyloxy)piperidin-1-yl)-6-bromothiazolo[4,5-b]pyridin-5-yl)piperidin-4-ol Using the same reaction conditions as described in step 1 of example 38, 2-(3-(benzyloxy)piperidin-1-yl)-6-bromo-5-(piperidin-1-yl)thiazolo[4,5-b]pyridine (product of step 3 of example 125) (200 mg, 0.456 mmol) was substituted with 4-hydroxypiperidine (56 mg, 0.547 mmol) using potassium carbonate (126 mg, 0.912 mmol) and DMF (5 mL) at 150° C. for 5 h to afford the crude product (250 mg). LCMS: m/z=505.3 (M+2)⁺.

Step 2: Preparation of 2-(3-(benzyloxy)piperidin-1-yl)-6-bromo-5-(4-((tert-butyldimethylsilyl)oxy)piperidin-1-yl)thiazolo[4,5-b]pyridine Using the same reaction conditions as described in step 2 of example 41, 1-(2-(3-(benzyloxy)piperidin-1-yl)-6-bromothiazolo[4,5-b]pyridin-5-yl)piperidin-4-ol (250 mg, 0.496 mmol) was protected using TBDMS chloride (149 mg, 0.992 mmol), imidazole (50 mg, 0.744 mmol) and DMAP (60 mg, 0.496 mmol) in DMF (5 mL) at RT for 2 h to get the crude product (306 mg).

Step 3: Preparation of N-(2-(3-(benzyloxy)piperidin-1-yl)-5-(4-((tert-butyldimethylsilyl)oxy)piperidin-1-yl)thiazolo[4,5-b]pyridin-6-yl)-2-(2-methylpyridin-4-yl)oxazole-4-carboxamide Using the same reaction conditions as described in step 5 of example 125, 2-(3-(benzyloxy)piperidin-1-yl)-6-bromo-5-(4-((tert-butyldimethylsilyl)oxy)piperidin-1-yl)thiazolo[4,5-b]pyridine (306 mg, 0.495 mmol) was coupled with 2-(2-methylpyridin-4-yl)oxazole-4-carboxamide (120 mg, 0.595 mmol) (intermediate 23) using potassium phosphate (314 mg, 1.485 mmol), copper iodide (10 mg, 0.049 mmol) and trans-N1,N2-dimethylcyclohexane-1,2-diamine (21 mg, 0.148 mmol) in 1,4-dioxane (5 mL) at 110° C. for 14 h and purified by 60-120 silica gel column chromatography using 2% methanol in DCM as eluent to obtain the title compound (300 mg, 84.2%).

Step 4: Preparation of N-(2-(3-(benzyloxy)piperidin-1-yl)-5-(4-hydroxypiperidin-1-yl)thiazolo[4,5-b]pyridin-6-yl)-2-(2-methylpyridin-4-yl)oxazole-4-carboxamide Using the same reaction conditions as described in step 8 of example 1, N-(2-(3-(benzyloxy)piperidin-1-yl)-5-(4-((tert-butyldimethylsilyl)oxy)piperidin-1-yl)thiazolo[4,5-b]pyridin-6-yl)-2-(2-methylpyridin-4-yl)oxazole-4-carboxamide (150 mg, 0.202 mmol) was deprotected using methanolic·HCl/methanol (1/1 mL) to get the crude compound (120 mg).

LCMS: m/z=626.4 (M+1)⁺.

Step 5: Preparation of N-(2-(3-hydroxypiperidin-1-yl)-5-(4-hydroxypiperidin-1-yl)thiazolo[4,5-b]pyridin-6-yl)-2-(2-methylpyridin-4-yl)oxazole-4-carboxamide Using the similar reaction conditions as described in step 8 of example 1, N-(2-(3-(benzyloxy)piperidin-1-yl)-5-(4-hydroxypiperidin-1-yl)thiazolo[4,5-b]pyridin-6-yl)-2-(2-methylpyridin-4-yl)oxazole-4-carboxamide (120 mg, 0.191 mmol) was deprotected using TFA (5 mL) and toluene (1 mL) at 110° C. for 1 h to afford the crude product. The resultant crude was purified by prep HPLC to obtain the title compound (40 mg, 39.2%).

¹HNMR (DMSO-d₆, 400 MHz): δ 9.76 (s, 1H), 9.08 (s, 1H), 8.91 (s, 1H), 8.70-8.69 (d, 1H), 7.89 (s, 1H), 7.79-7.77 (d, 1H), 5.09-5.08 (d, 1H), 4.90-4.89 (d, 1H), 3.88-3.86 (m,

1H), 3.73-3.62 (m, 3H), 3.21-3.11 (m, 4H), 2.89-2.86 (t, 2H), 2.67 (s, 3H), 2.02-1.99 (m, 2H), 1.90-1.77 (m, 4H), 1.53-1.23 (m, 2H). LCMS: 81.88%, m/z=536.3 (M+1)$^+$. HPLC: 98.31%.

Example 127

2-(2-acetamidopyridin-4-yl)-N-(5-(3-hydroxypiperidin-1-yl)-2-morpholinothiazolo[4,5-b]pyridin-6-yl)oxazole-4-carboxamide

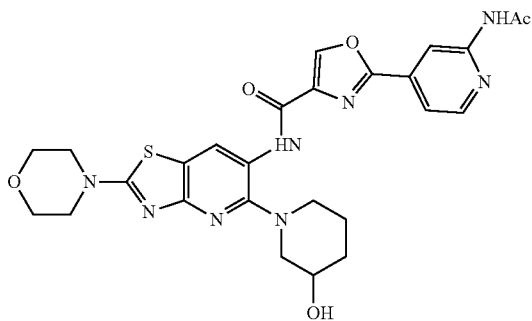 [SMILES: CC(=O)Nc1cc(-c2nc(C(=O)Nc3cc4sc(N5CCOCC5)nc4nc3N3CCCC(O)C3)co2)ccn1]

Step 1: Preparation of 1-(2-morpholino-6-nitrothiazolo[4,5-b]pyridin-5-yl)piperidin-3-ol Using the same reaction conditions as described in step 2 of example 43, 4-(5-chloro-6-nitrothiazolo[4,5-b]pyridin-2-yl)morpholine (product of step 4 of example 20) (500 mg, 1.66 mol) was substituted using piperidin-3-ol (202 mg, 1.99 mmol) using potassium carbonate (691 mg, 4.99 mmol) in DMF (5 mL) at RT for 2 h to obtain the title compound (500 mg, 83.33%). LCMS: m/z=366.2 (M+1)$^+$.

Step 2: Preparation of 4-(5-(3-((tert-butyldimethylsilyl)oxy)piperidin-1-yl)-6-nitrothiazolo[4,5-b]pyridin-2-yl)morpholine Using the same reaction conditions as described in step 2 of example 41, 1-(2-morpholino-6-nitrothiazolo[4,5-b]pyridin-5-yl)piperidin-3-ol (300 mg, 0.8219 mmol) was protected using TBDMS chloride (185 mg, 1.232 mmol) and imidazole (111 mg, 1.643 mmol) and DMAP (20 mg, 0.1643 mmol) in DMF (5 mL) at RT for 0.5 h to get the crude product. The resultant crude was purified by 60-120 silica gel column chromatography using 2% methanol in DCM as eluent to obtain the title compound (350 mg, 89.74%). LCMS: m/z=480.2 (M+1)$^+$.

Step 3: Preparation of 5-(3-((tert-butyldimethylsilyl)oxy)piperidin-1-yl)-2-morpholinothiazolo[4,5-b]pyridin-6-amine Using the same reaction conditions as described in step 2 of example 38, 4-(5-(3-((tert-butyldimethylsilyl)oxy)piperidin-1-yl)-6-nitrothiazolo[4,5-b]pyridin-2-yl)morpholine (400 mg, 0.8333 mmol) was reduced with zinc dust (435 mg, 6.66 mmol) and ammonium chloride (713 mg, 13.3 mmol) in THF/water (10/2 mL) to get the title compound (290 mg, 77.33%). LCMS: m/z=451.0 (M+1)$^+$.

Step 4: Preparation of 2-(2-acetamidopyridin-4-yl)-N-(5-(3-((tert-butyldimethylsilyl)oxy)piperidin-1-yl)-2-morpholinothiazolo[4,5-b]pyridin-6-yl)oxazole-4-carboxamide Using the same reaction conditions as described in step 6 of example 1, 5-(3-((tert-butyldimethylsilyl)oxy)piperidin-1-yl)-2-morpholinothiazolo[4,5-b]pyridin-6-amine (100 mg, 0.222 mmol), was coupled with 2-(2-acetamidopyridin-4-yl)oxazole-4-carboxylic acid (intermediate 20) (82 mg, 0.332 mmol) using HATU (108 mg, 0.288 mmol) and DIPEA (115 mg, 0.888 mmol) in DMF (5 mL) to get the crude title compound (132 mg, 88%). LCMS: m/z=679.5 (M+1)$^+$.

Step 5: Preparation of 2-(2-acetamidopyridin-4-yl)-N-(5-(3-hydroxypiperidin-1-yl)-2-morpholinothiazolo[4,5-b]pyridin-6-yl)oxazole-4-carboxamide Using the same reaction conditions as described in step 8 of example 12-(2-acetamidopyridin-4-yl)-N-(5-(3-((tert-butyldimethylsilyl)oxy)piperidin-1-yl)-2-morpholinothiazolo[4,5-b]pyridin-6-yl)oxazole-4-carboxamide (132 mg, 0.1946 mmol) was deprotected using methanolic HCl/methanol (3 mL) to get the title compound (20 mg, 18.34%).
$^1$HNMR (DMSO-d$_6$, 400 MHz): δ 10.81 (s, 1H), 9.61 (s, 1H), 9.07 (s, 1H), 8.93 (s, 1H), 8.79 (s, 1H), 8.56-8.55 (d, 1H), 7.66-7.65 (d, 1H), 4.81 (s, 1H), 3.88 (s, 1H), 3.74 (s, 4H), 3.58 (s, 4H), 3.30-3.20 (m, 1H), 3.14-3.11 (d, 1H), 2.72-2.60 (m, 3H), 2.15 (s, 3H), 2.05 (s, 1H), 1.86 (s, 1H), 1.40-1.20 (m, 1H). LCMS: 49.65%, m/z=565.4 (M+1)$^+$. HPLC: 95.43%.

Example 128

2-(2-aminopyridin-4-yl)-N-(5-(3-hydroxypiperidin-1-yl)-2-morpholinothiazolo[4,5-b]pyridin-6-yl)oxazole-4-carboxamide Hydrochloride

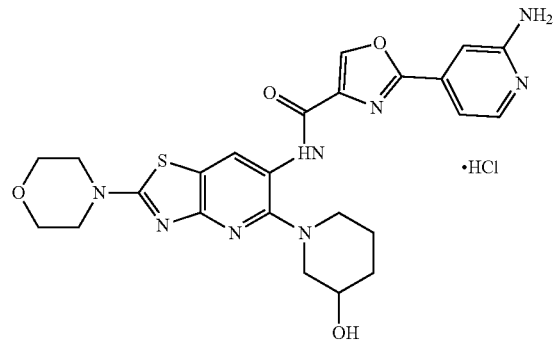 [SMILES: Nc1cc(-c2nc(C(=O)Nc3cc4sc(N5CCOCC5)nc4nc3N3CCCC(O)C3)co2)ccn1 ; Cl]

Step 1: Preparation of 2-(2-aminopyridin-4-yl)-N-(5-(3-((tert-butyldimethylsilyl)oxy)piperidin-1-yl)-2-morpholinothiazolo[4,5-b]pyridin-6-yl)oxazole-4-carboxamide Using the same reaction conditions as described in step 6 of example 1, 5-(3-((tert-butyldimethylsilyl)oxy)piperidin- 1-yl)-2-morpholinothiazolo[4,5-b]pyridin-6-amine (product of step 3 of example 128) (100 mg, 0.222 mmol), was coupled with 2-(2-aminopyridin-4-yl)oxazole-4-carboxylic acid (intermediate 21) (68 mg, 0.333 mmol) using HATU (109 mg, 0.288 mmol) and DIPEA (114 mg, 0.888 mmol) in DMF (5 mL) to get the title compound (120 mg, 85.71%). LCMS: m/z=637.4 (M+1)$^+$.

Step 2: Preparation of 2-(2-aminopyridin-4-yl)-N-(5-(3-hydroxypiperidin-1-yl)-2-morpholinothiazolo[4,5-b]pyridin-6-yl)oxazole-4-carboxamide Hydrochloride Using the same reaction conditions as described in step 8 of example 1, 2-(2-aminopyridin-4-yl)-N-(5-(3-((tert-butyldimethylsilyl)oxy)piperidin-1-yl)-2-morpholinothiazolo[4,5-b]pyridin-6-yl)oxazole-4-carboxamide (120 mg, 0.188 mmol) was deprotected using methanolic HCl/methanol (5/2 mL) to get the title compound (20 mg, 37.73%).

$^1$HNMR (DMSO-d$_6$, 400 MHz): δ 9.58 (s, 1H), 9.16 (s, 1H), 8.87 (s, 1H), 8.20-8.19 (d, 1H), 7.53 (s, 1H), 7.28-7.27 (d, 1H), 3.90-3.80 (m, 1H), 3.74 (s, 2H), 3.58 (s, 2H), 3.27-3.25 (m, 2H), 3.14-3.09 (m, 1H), 2.90-2.70 (m, 2H), 2.76-2.73 (m, 2H), 2.10-1.70 (m, 6H). LCMS: 93.20%, m/z=523.4 (M+1)$^+$. HPLC: 97.01%.

Example 129

5-(2-aminopyridin-4-yl)-N-(5-(4-hydroxypiperidin-1-yl)-2-morpholinothiazolo[4,5-b]pyridin-6-yl)furan-2-carboxamide Hydrochloride

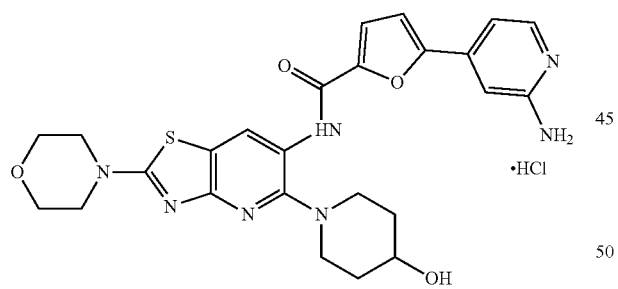

Using the same reaction conditions as described in example 45, 5-(4-((tert-butyldimethylsilyl)oxy)piperidin-1-yl)-2-morpholinothiazolo[4,5-b]pyridin-6-amine (product of step 3 of example 85) (155 mg, 0.3452 mmol), was coupled with 5-(2-acetamidopyridin-4-yl)furan-2-carboxylic acid (intermediate 22) (106 mg, 0.4315 mmol) using HATU (197 mg, 0.5188 mmol) and DIPEA (179 mg, 1.3835 mmol) in DMF (5 mL) to get the crude compound followed by deprotection using HCl/MeOH (5/5 mL) to get the title compound (50 mg, 55%).

$^1$HNMR (CD$_3$OD, 300 MHz): δ 8.58 (s, 1H), 7.93-7.91 (d, 1H), 7.55-7.52 (m, 2H), 7.48 (s, 1H), 7.41-7.38 (dd, 1H), 3.88-3.78 (m, 12H), 2.04-1.81 (m, 5H). LCMS: 99.14%, m/z=522.3 (M+1)$^+$. HPLC: 97.06%.

Example 130

2-(2-aminopyridin-4-yl)-N-(5-(4-hydroxypiperidin-1-yl)-2-morpholinothiazolo[4,5-b]pyridin-6-yl)oxazole-4-carboxamide Hydrochloride

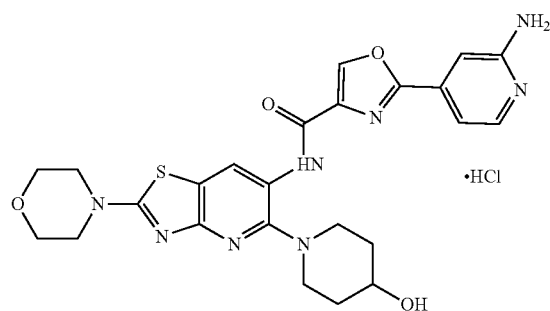 [SMILES: Nc1cc(-c2nc(C(=O)Nc3cc4sc(N5CCOCC5)nc4nc3N3CCC(O)CC3)co2)ccn1 ; Cl]

Using the same reaction conditions as described in example 45, 5-(4-((tert-butyldimethylsilyl)oxy)piperidin-1-yl)-2-morpholinothiazolo[4,5-b]pyridin-6-amine (product of step 3 of example 85) (100 mg, 0.222 mmol), was coupled with 2-(2-aminopyridin-4-yl)oxazole-4-carboxylic acid (intermediate 21) (50 mg, 0.244 mmol) using HATU (126 mg, 0.333 mmol) and DIPEA (114 mg, 0.888 mmol) in DMF (3 mL) to get the crude compound followed by deprotection using methanolic HCl/MeOH (2/1 mL) to get the crude compound. This was then purified by prep HPLC and treated with methanolic HCl to get the title compound (27 mg, 31%).

$^1$HNMR (CD$_3$OD, 300 MHz): δ 8.95 (s, 1H), 8.868-8.864 (d, 1H), 8.05-8.03 (d, 1H), 7.687-7.684 (d, 1H), 7.53-7.50 (dd, 1H), 3.87-3.84 (t, 4H), 3.73 (s, 4H), 3.54-3.33 (m, 2H), 3.12-3.07 (m, 3H), 2.12-2.09 (m, 2H), 1.90-1.87 (m, 2H). LCMS: 99.56%, m/z=523.2 (M+1)$^+$. HPLC: 97.24%.

Example 131

2-(2-aminopyridin-4-yl)-N-(5-(4-fluoropiperidin-1-yl)-2-morpholinothiazolo[4,5-b]pyridin-6-yl)oxazole-4-carboxamide Hydrochloride

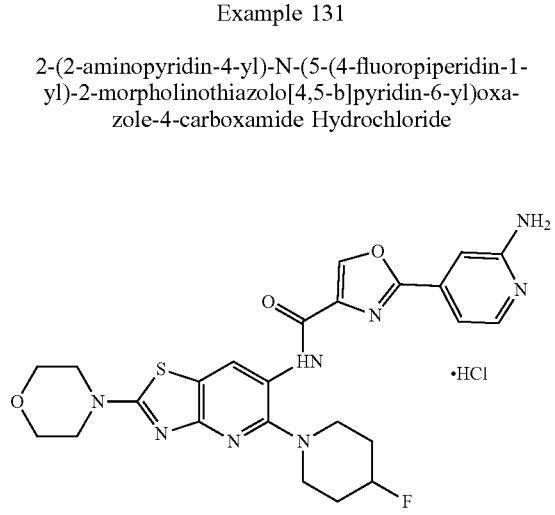

Using the same reaction conditions as described in example 45, 5-(4-fluoropiperidin-1-yl)-2-morpholinothiazolo[4,5-b]pyridin-6-amine (product of step 2 of example 98) (70 mg, 0.2 mmol) was coupled with 2-(2-acetamidopyridin-4-yl)oxazole-4-carboxylic acid (intermediate 20) (62 mg, 0.24 mmol) using HATU (100 mg, 0.27 mmol) and DIPEA (110 mg, 0.83 mmol) in DMF (0.3 mL) to afford the crude product followed by deprotection using HCl/MeOH (0.5/2 mL) to get the crude compound. This was then purified by prep HPLC and treated with methanol/ether HCl (0.5/0.5 mL) to get the title compound (30 mg).

$^1$HNMR (CD$_3$OD, 300 MHz): δ 8.90 (s, 1H), 8.86 (s, 1H), 8.03-8.02 (d, 1H), 7.64-7.63 (d, 1H), 7.50-7.06 (dd, 1H), 3.86-3.83 (m, 4H), 3.73-3.70 (t, 4H), 3.37-3.31 (m, 2H), 3.24-3.23 (m, 5H), 2.30-2.20 (m, 4H). LCMS: 58.28%, m/z=525.2 (M+1)$^+$. HPLC: 98.31%.

Example 132

N-(5-(2-fluoropyridin-4-yl)-2-morpholinothiazolo[4,5-b]pyridin-6-yl)-2-(2-methylpyridin-4-yl)oxazole-4-carboxamide

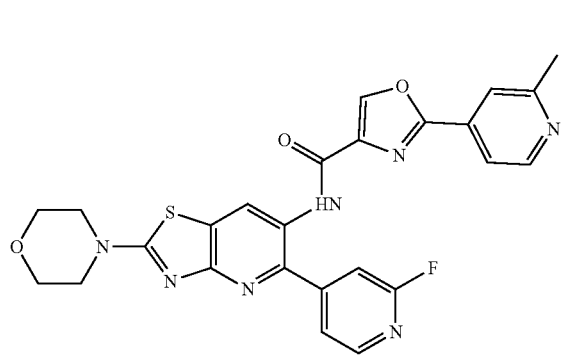 [SMILES: Cc1cc(-c2nc(C(=O)Nc3cc4sc(N5CCOCC5)nc4nc3-c3ccnc(F)c3)co2)ccn1]

Step 1: Preparation of 4-(5-(2-fluoropyridin-4-yl)-6-nitrothiazolo[4,5-b]pyridin-2-yl)morpholine Using the same reaction conditions as described in step 7 of example 1, 4-(5-chloro-6-nitrothiazolo[4,5-b]pyridin-2-yl)morpholine (product of step 4 of example 20) (200 mg, 0.666 mmol) was coupled with (2-fluoropyridin-4-yl)boronic acid (223 mg, 1 mmol) using sodium iodide (200 mg, 1.3 mmol), potassium carbonate (276 mg, 2 mmol) and Pd(dppf)Cl$_2$ (48 mg, 0.067 mmol) in 1,2-dimethoxyethane/water (1/0.2 mL) to get the title compound (100 mg).

Step 2: Preparation of 5-(2-fluoropyridin-4-yl)-2-morpholinothiazolo[4,5-b]pyridin-6-amine Using the same reaction conditions as described in step 5 of example 1, 4-(5-(2-fluoropyridin-4-yl)-6-nitrothiazolo[4,5-b]pyridin-2-yl)morpholine (90 mg, 0.25 mmol) was reduced with zinc dust (130 mg, 1.99 mmol) and ammonium chloride (212 mg, 3.98 mmol) in THF/water (2/1 mL) to get the title product (70 mg). LCMS: m/z=332.3 (M+1)$^+$.

Step 3: Preparation of N-(5-(2-fluoropyridin-4-yl)-2-morpholinothiazolo[4,5-b]pyridin-6-yl)-2-(2-methylpyridin-4-yl)oxazole-4-carboxamide Using the similar reaction conditions as described in step 6 of example 1, crude 5-(2-fluoropyridin-4-yl)-2-morpholinothiazolo[4,5-b]pyridin-6-amine (70 mg, 0.21 mmol), was coupled with 2-(2-methylpyridin-4-yl)oxazole-4-carboxylic acid (52 mg, 0.25 mmol) using HATU (104 mg, 0.27 mmol) and DIPEA (110 mg, 0.84 mmol) in DMF (0.3 mL) to get the title compound (100 mg).

$^1$HNMR (DMSO-d$_6$, 300 MHz): δ 10.40 (s, 1H), 8.92 (s, 1H), 8.67-8.65 (d, 1H), 8.44 (s, 1H), 8.28-8.26 (d, 1H), 7.81 (s, 1H), 7.73-7.71 (d, 1H), 7.63-7.61 (d, 1H), 7.44 (s, 1H), 3.75 (s, 4H), 3.65 (s, 4H), 2.56 (s, 3H). LCMS: 100%, m/z=518.4 (M+1)$^+$. HPLC: 96.41%.

Example 133

N-(5-(4-fluoropiperidin-1-yl)-2-(3-hydroxypiperidin-1-yl)thiazolo[4,5-b]pyridin-6-yl)-2-(2-methylpyridin-4-yl)oxazole-4-carboxamide

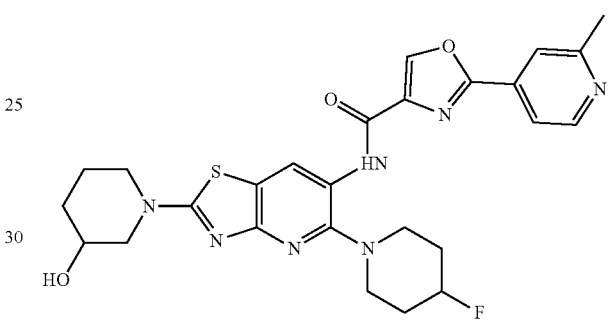

Step 1: Preparation of 1-(6-bromo-5-chlorothiazolo[4,5-b]pyridin-2-yl)piperidin-3-ol Using the same reaction conditions as described in step 1 of example 6, 6-bromo-5-chloro-2-(methylthio)thiazolo[4,5-b]pyridine (product of step 2 of example 125) (1 g, 3.370 mmol) was substituted using 3-hydroxypiperidine (510 mg, 5.06 mmol) in THF (10 mL) at 100° C. for 5 h to obtain the crude product (280 mg). The crude product was purified by using 60-120 silica-gel column chromatography and compound was eluted using 5% methanol in DCM as eluent to afford the title compound (1.1 g, 94%).

Step 2: Preparation of 6-bromo-2-(3-((tert-butyldimethylsilyl)oxy)piperidin-1-yl)-5-chlorothiazolo[4,5-b]pyridine Using the same reaction conditions as described in step 2 of example 41, 1-(6-bromo-5-chlorothiazolo[4,5-b]pyridin-2-yl)piperidin-3-ol (1 g, 2.865 mmol) was protected using TBDMS chloride (863 mg, 5.73 mmol), imidazole (292 mg, 4.297 mmol) and DMAP (350 mg, 2.865 mmol) in DMF (5 mL) at RT for 1 h to get the title compound (1.3 g, 100%). LCMS: m/z=464.2 (M+2)$^+$.

Step 3: Preparation of 1-(6-bromo-2-(3-((tert-butyldimethylsilyl)oxy)piperidin-1-yl)thiazolo[4,5-b]pyridin-5-yl)piperidin-4-ol Using the same reaction conditions as described in step 1 of example 38, 6-bromo-2-(3-((tert-butyldimethylsilyl)oxy)piperidin-1-yl)-5-chlorothiazolo[4,5-b]pyridine (500 mg, 1.082 mmol) was substituted with 4-hydroxypiperidine (162 mg, 1.623 mmol) using potassium carbonate (298 mg, 2.164 mmol) and DMF (1 mL) at 160° C. for 14 h to afford the crude product. The crude product was purified by using 60-120 silica-gel column chromatography and compound was eluted using 2% methanol in DCM as eluent to afford the title compound (200 mg, 35%). LCMS: m/z=527.2 (M+2)$^+$.

Step 4: Preparation of 6-bromo-2-(3-((tert-butyldimethylsilyl)oxy)piperidin-1-yl)-5-(4-fluoropiperidin-1-yl)thiazolo[4,5-b]pyridine Using the same reaction conditions as described in step 2 of example 59, 1-(6-bromo-2-(3-((tert-butyldimethylsilyl)oxy)piperidin-1-yl)thiazolo[4,5-b]pyridin-5-yl)piperidin-4-ol (200 mg, 0.378 mmol) was fluorinated using DAST (0.2 mL) in DCM (5 mL) at −20° C. for 1 h. The resultant crude was purified by 60-120 silica gel column chromatography using 50% ethyl acetate in hexane as eluent to obtain the title compound (120 mg). LCMS: m/z=529.3 (M)$^+$.

Step 5: Preparation of N-(2-(3-((tert-butyldimethylsilyl)oxy)piperidin-1-yl)-5-(4-fluoropiperidin-1-yl)thiazolo[4,5-b]pyridin-6-yl)-2-(2-methylpyridin-4-yl)oxazole-4-carboxamide Using the same reaction conditions as described in step 5 of example 125, 6-bromo-2-(3-((tert-butyldimethylsilyl)oxy)piperidin-1-yl)-5-(4-fluoropiperidin-1-yl)thiazolo[4,5-b]pyridine (120 mg, 0.226 mmol) was coupled with 2-(2-methylpyridin-4-yl)oxazole-4-carboxamide (60 mg, 0.294 mmol) (Intermediate 23) using potassium phosphate (143 mg, 0.678 mmol), copper iodide (4 mg, 0.022 mmol) and trans-N1,N2-dimethylcyclohexane-1,2-diamine (10 mg, 0.067 mmol) in 1,4-dioxane (5 mL) at 110° C. for 14 h and purified by 60-120 silica gel column chromatography using 2% methanol in DCM as eluent to obtain the crude compound (100 mg). LCMS: m/z=652.4 (M+1)$^+$.

Step 6: Preparation of N-(5-(4-fluoropiperidin-1-yl)-2-(3-hydroxypiperidin-1-yl)thiazolo[4,5-b]pyridin-6-yl)-2-(2-methylpyridin-4-yl)oxazole-4-carboxamide Using the similar reaction conditions as described in step 8 of example 1, N-(2-(3-((tert-butyldimethylsilyl)oxy)piperidin-1-yl)-5-(4-fluoropiperidin-1-yl)thiazolo[4,5-b]pyridin-6-yl)-2-(2-methylpyridin-4-yl)oxazole-4-carboxamide (100 mg, 0.153 mmol) was deprotected using methanolic HCl (5 mL) and methanol (1 mL) at RT for 0.5 h to afford the crude product. The resultant crude was purified by prep HPLC to obtain the title compound (24 mg, 29.2%).

$^1$HNMR (CDCl$_3$, 400 MHz): δ 9.83 (s, 1H), 9.02 (s, 1H), 8.71-8.69 (d, 1H), 8.41 (s, 1H), 7.83 (s, 1H), 7.72-7.70 (d, 1H), 5.00-4.75 (m, 1H), 3.97-3.94 (m, 2H), 3.85-3.75 (m, 1H), 3.54-3.50 (m, 2H), 3.40-3.30 (m, 2H), 3.13-3.11 (m, 2H), 2.68 (s, 3H), 2.24-2.20 (m, 4H), 2.00-1.99 (m, 3H), 1.69-1.64 (m, 2H). LCMS: 93.92%, m/z=538.4 (M+1)$^+$. HPLC: 95.18%.

Example 134

N-(5-(4-aminopiperidin-1-yl)-2-(3-hydroxypiperidin-1-yl)thiazolo[4,5-b]pyridin-6-yl)-2-(2-methylpyridin-4-yl)oxazole-4-carboxamide Hydrochloride

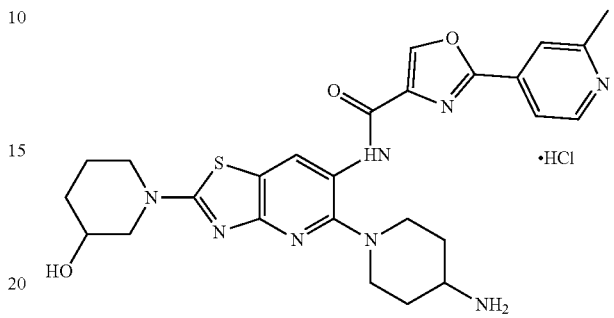

Step 1: Preparation of tert-butyl (1-(6-bromo-2-(3-((tert-butyldimethylsilyl)oxy)piperidin-1-yl)thiazolo[4,5-b]pyridin-5-yl)piperidin-4-yl)carbamate Using the same reaction conditions as described in step 1 of example 38, 6-bromo-2-(3-((tert-butyldimethylsilyl)oxy)piperidin-1-yl)-5-chlorothiazolo[4,5-b]pyridine (product of step 2 of example 134) (500 mg, 1.082 mmol) was substituted with tert-butyl piperidin-4-ylcarbamate (324 mg, 1.623 mmol) using potassium carbonate (298 mg, 2.164 mmol) and DMF (1 mL) at 150° C. for 14 h to afford the crude product. The crude product was purified by using 60-120 silica-gel column chromatography and compound was eluted using 50% ethyl acetate in hexane as eluent to afford the title compound (100 mg, 14.7%). LCMS: m/z=628.4 (M+2)$^+$.

Step 2: Preparation of tert-butyl (1-(2-(3-hydroxypiperidin-1-yl)-6-(2-(2-methylpyridin-4-yl)oxazole-4-carboxamido)thiazolo[4,5-b]pyridin-5-yl)piperidin-4-yl)carbamate Using the same reaction conditions as described in step 5 of example 125, tert-butyl (1-(6-bromo-2-(3-((tert-butyldimethylsilyl)oxy)piperidin-1-yl)thiazolo[4,5-b]pyridin-5-yl)piperidin-4-yl)carbamate (100 mg, 0.159 mmol) was coupled with 2-(2-methylpyridin-4-yl)oxazole-4-carboxamide (42 mg, 0.207 mmol) (Intermediate 23) using potassium phosphate (101 mg, 0.477 mmol), copper iodide (3 mg, 0.015 mmol) and trans-N1,N2-dimethylcyclohexane-1,2-diamine (7 mg, 0.047 mmol) in 1,4-dioxane (5 mL) at 110° C. for 14 h and purified by 60-120 silica gel column chromatography using 2% methanol in DCM as eluent to obtain the crude compound (100 mg).

Step 3: Preparation of N-(5-(4-aminopiperidin-1-yl)-2-(3-hydroxypiperidin-1-yl)thiazolo[4,5-b]pyridin-6-yl)-2-(2-methylpyridin-4-yl)oxazole-4-carboxamide Hydrochloride Using the similar reaction conditions as described in step 8 of example 1, tert-butyl (1-(2-(3-hydroxypiperidin-1-yl)-6-(2-(2-methylpyridin-4-yl)oxazole-4-carboxamido)thiazolo[4,5-b]pyridin-5-yl)piperidin-4-yl)carbamate (100 mg, 0.153 mmol) was deprotected using methanolic HCl (5 mL) and methanol (1 mL) at RT for 0.5 h to afford the crude product. The resultant crude was purified by prep HPLC to obtain the title compound (20 mg, 28.1%).

$^1$HNMR (CD$_3$OD, 300 MHz): δ 8.96-8.92 (m, 2H), 8.76 (s, 1H), 8.60-8.58 (m, 2H), 3.98-3.88 (m, 2H), 3.76-3.66 (m, 5H), 3.50-3.40 (m, 1H), 3.17-3.09 (t, 2H), 2.94 (s, 3H), 2.13-1.96 (m, 7H), 2.35-2.20 (m, 2H). LCMS: 98.18%, m/z=535.4 (M+1)$^+$. HPLC: 96.08%.

Example 135

N-(5-(2-hydroxypyridin-4-yl)-2-morpholinothiazolo [4,5-b]pyridin-6-yl)-2-(2-methylpyridin-4-yl)oxazole-4-carboxamide Hydrochloride

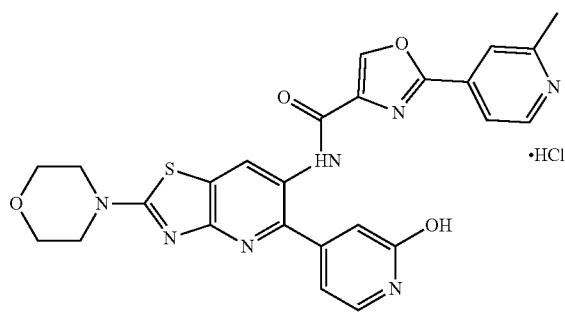 [SMILES: Cc1cc(-c2nc(C(=O)Nc3cc4sc(N5CCOCC5)nc4nc3-c3ccnc(O)c3)co2)ccn1 ; Cl]

The solution of N-(5-(2-fluoropyridin-4-yl)-2-morpholinothiazolo[4,5-b]pyridin-6-yl)-2-(2-methylpyridin-4-yl) oxazole-4-carboxamide (example 133) (100 mg, 0.19 mmol) in methanolic HCl (10 mL) was stirred at RT for 1 h and distilled out the solvent. The resultant crude was purified by prep HPLC and treated with methanolic HCl to obtain the title compound (50 mg).

$^1$HNMR (CD$_3$OD, 300 MHz): δ 8.91-8.88 (m, 2H), 8.78 (s, 1H), 8.56 (s, 1H), 8.48-8.46 (d, 1H), 7.83-7.80 (d, 1H), 7.12 (s, 1H), 7.97-7.95 (d, 1H), 3.88 (s, 8H), 2.91 (s, 3H). LCMS: 100%, m/z=516.2 (M+1)$^+$. HPLC: 98.02%.

IRAK-4 Biochemical Assay

Compounds were tested for their potential to inhibit IRAK-4 enzyme in a TR-FRET assay using recombinant IRAK-4 kinase from Millipore, USA. The assay buffer was 50 mM Tris-HCl pH 7.5, 20 mM MgCl$_2$, 1 mM EGTA, 2 mM DTT, 3 mM MnCl$_2$ and 0.01% Tween20. 5 ng of IRAK-4 kinase was used for the assay. After pre-incubation of enzyme with test compound for 30 minutes at room temperature, a substrate mix containing 100 nM Biotin Histone H3 (Millipore, USA) and 20 µM ATP (Sigma, USA) was added and the reaction was incubated for 30 minutes. Post incubation, the reaction was stopped by the addition of stop mix containing 40 mM EDTA, 1 nM of Europium-Anti-Phospho-Histone H3 (Ser10) antibody (Perkin Elmer, USA) and 20 nM Sure Light Allophycocyanin-Streptavidin (Perkin Elmer, USA). The fluorescence emission at 615 nm and 665 nm were measured at an excitation of 340 nm and the percent inhibition was estimated from the ratio of the fluorescence intensities [(F665/F615)*10000]. The compounds were initially screened at 1 µM and 10 µM concentrations and potent compounds (>50% inhibition at 1 µM) were taken for dose response studies. The IC$_{50}$ values were estimated by fitting the dose-response data to sigmoidal dose response (variable slope), curve fitting program using Graphpad Prism software Version 6.01.

The compounds of the present invention were screened in the above mentioned assay and the results (IC$_{50}$) are summarized in the table 1. The IC$_{50}$ values of the compounds of examples are set forth below wherein "A" refers to an IC$_{50}$ value of less than or equal to 50 nM, "B" refers to IC$_{50}$ value ranges from 50.01 nM to 100 nM and "C" refers to an IC50 value of greater than 100 nM.

TABLE 1

IC$_{50}$ values for IRAK4 activity of the selected compounds.

| Group | Example No |
|---|---|
| A | 3, 5, 7-8, 10-14, 16, 20-27, 29, 32-41, 43-45, 47, 50-67, 69-78, 80, 82-102, 104, 110-111, 113-131 and 133-134. |
| B | 4, 6, 9, 42, 68 and 79 |
| C | 17, 28, 30-31, 46, 48, 81, 103, 105-109 and 112 |

We claim:

1. A compound selected from

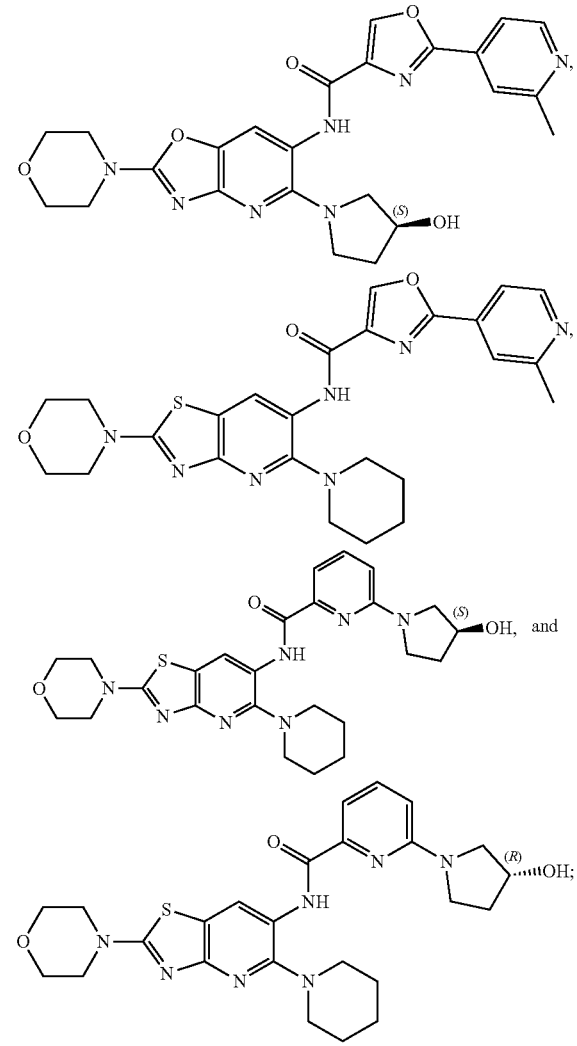

or a pharmaceutically acceptable salt thereof.

2. The compound of claim 1, wherein the compound is

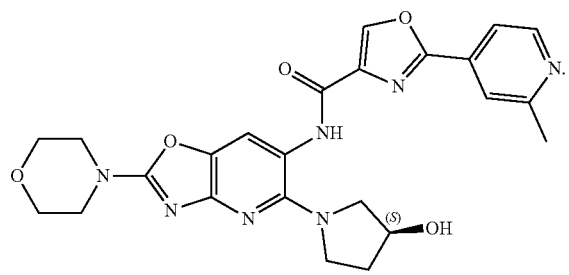

3. The compound of claim 1, wherein the compound is a pharmaceutically acceptable salt of

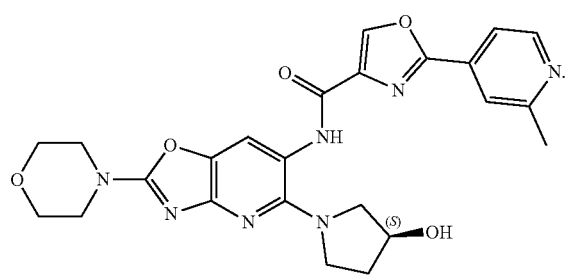

4. The compound of claim 1, wherein the compound is

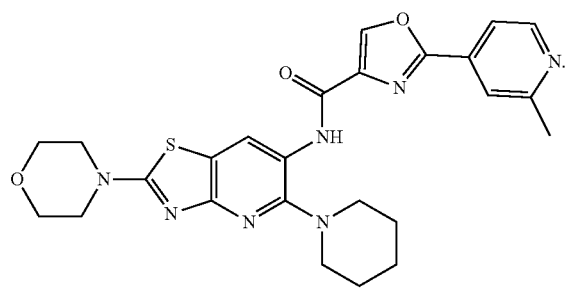 [SMILES: Cc1cc(-c2nc(C(=O)Nc3cc4sc(N5CCOCC5)nc4nc3N3CCCCC3)co2)ccn1]

5. The compound of claim 1, wherein the compound is a pharmaceutically acceptable salt of

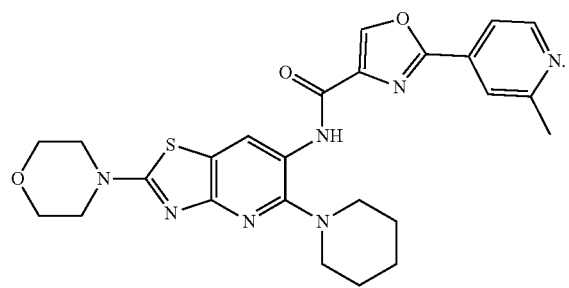 [SMILES: Cc1cc(-c2nc(C(=O)Nc3cc4sc(N5CCOCC5)nc4nc3N3CCCCC3)co2)ccn1]

6. The compound of claim 1, wherein the compound is

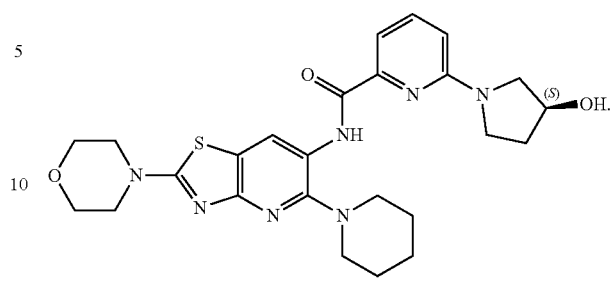

7. The compound of claim 1, wherein the compound is a pharmaceutically acceptable salt of

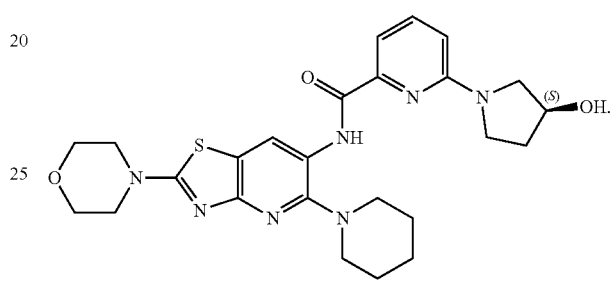

8. The compound of claim 1, wherein the compound is

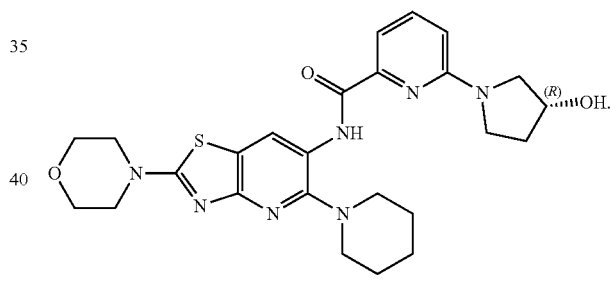

9. The compound of claim 1, wherein the compound is a pharmaceutically acceptable salt of

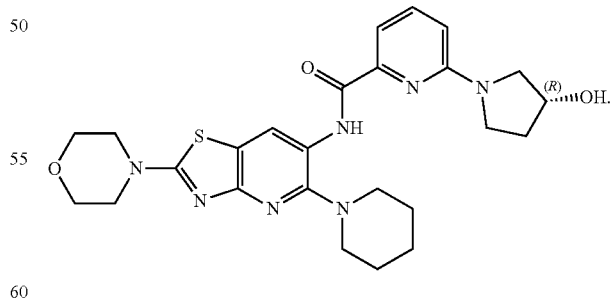

* * * * *